(12) United States Patent
Bader et al.

(10) Patent No.: US 10,251,952 B2
(45) Date of Patent: Apr. 9, 2019

(54) HUMANIZED ANTI-TAU(PS422) ANTIBODY BRAIN SHUTTLES AND USE THEREOF

(71) Applicant: Hoffmann-La Roche Inc., Little Falls, NJ (US)

(72) Inventors: Martin Bader, Penzberg (DE); Ulrich Goepfert, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/386,638

(22) Filed: Dec. 21, 2016

(65) Prior Publication Data

US 2017/0106084 A1  Apr. 20, 2017

Related U.S. Application Data

(63) Continuation of application No. PCT/EP2015/064321, filed on Jun. 25, 2015.

(30) Foreign Application Priority Data

Jun. 26, 2014 (EP) ..................................... 14174042

(51) Int. Cl.
  *A61K 39/395* (2006.01)
  *A61K 47/68* (2017.01)
  *A61K 39/00* (2006.01)
  *C07K 16/18* (2006.01)

(52) U.S. Cl.
  CPC ...... *A61K 39/3955* (2013.01); *A61K 47/6879* (2017.08); *A61K 47/6897* (2017.08); *C07K 16/18* (2013.01); *A61K 2039/507* (2013.01); *C07K 2317/24* (2013.01); *C07K 2317/31* (2013.01); *C07K 2317/56* (2013.01); *C07K 2317/92* (2013.01)

(58) Field of Classification Search
  None
  See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,500,362 A | 3/1996 | Robinson et al. |
| 5,571,894 A | 11/1996 | Wels et al. |
| 5,587,458 A | 12/1996 | King et al. |
| 5,624,821 A | 4/1997 | Winter et al. |
| 5,648,237 A | 7/1997 | Carter |
| 5,648,260 A | 7/1997 | Winter et al. |
| 5,731,168 A | 3/1998 | Carter et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,959,083 A | 9/1999 | Bosslet et al. |
| 5,959,177 A | 9/1999 | Hein et al. |
| 6,040,498 A | 3/2000 | Stomp et al. |
| 6,171,586 B1 | 1/2001 | Lam et al. |
| 6,194,551 B1 | 2/2001 | Idusogie et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,511,663 B1 | 1/2003 | King et al. |
| 6,737,056 B1 | 5/2004 | Presta |
| 6,897,044 B1 | 5/2005 | Braslawsky et al. |
| 6,982,321 B2 | 1/2006 | Winter |
| 7,087,409 B2 | 8/2006 | Barbas, III et al. |
| 7,125,978 B1 | 10/2006 | Vezina et al. |
| 7,129,330 B1 | 10/2006 | Little et al. |
| 7,332,581 B2 | 2/2008 | Presta |
| 7,371,826 B2 | 5/2008 | Presta |
| 7,446,180 B2 | 11/2008 | Novak |
| 7,521,541 B2 | 4/2009 | Eigenbrot et al. |
| 7,527,791 B2 | 5/2009 | Adams et al. |
| 2002/0086009 A1 | 7/2002 | Ishiguro et al. |
| 2002/0188106 A1 | 12/2002 | Mandelkow et al. |
| 2004/0166115 A1* | 8/2004 | Griffiths ................. A61K 45/06 424/178.1 |
| 2005/0014934 A1 | 1/2005 | Hinton et al. |
| 2005/0079170 A1 | 4/2005 | Le Gall et al. |
| 2005/0100543 A1 | 5/2005 | Hansen et al. |
| 2005/0163782 A1 | 7/2005 | Glaser et al. |
| 2005/0260186 A1 | 11/2005 | Bookbinder et al. |
| 2006/0025576 A1 | 2/2006 | Miller et al. |

(Continued)

FOREIGN PATENT DOCUMENTS

| | | |
|---|---|---|
| EP | 0404097 | 12/1990 |
| EP | 0 626 390 | 11/1994 |

(Continued)

OTHER PUBLICATIONS

Padlan, E.A., A possible procedure for reducing the immunogenicity of antibody variable domains while preserving their ligan-binding properties, Mol. Immuno., vol. 28, No. 4/5, pp. 489-498, (1991).
Dall'Acqua, W.F. et al., Antibody humanization by framework shuffling, Methods, 36 (2005), pp. 43-60.
Osbourne, J., et al., From rodent reagents to human therapeutics using antibody guided selection, Methods, 36 (2005), pp. 61-698.
Klimka, A., et al., Human anti-CD30 recombinant antibodies by guided phage antibody selection using cell panning, British Journal of Cancer (2000), pp. 253-260.
Sims, M.J., et al., A humanized CD18 antibody can block function without cell destruction, The Journal of Immuno., 151 (1993), pp. 2296-2308.
Carter, P., et al., Humanization of an anti-p185HER2 antibody for human cancer therapy, Proc. Natl. Acad. Sci., vol. 89, pp. 4285-4289, May 1992.

(Continued)

*Primary Examiner* — Adam Weidner
(74) *Attorney, Agent, or Firm* — Bryan Cave Leighton Paisner LLP

(57) ABSTRACT

Herein is reported a non-covalent complex of a haptenylated antibody that specifically binds to human tau(pS422) and an anti-blood brain barrier receptor/hapten bispecific antibody.

22 Claims, 23 Drawing Sheets

Specification includes a Sequence Listing.

(56) References Cited

U.S. PATENT DOCUMENTS

| | | | |
|---|---|---|---|
| 2006/0104968 A1 | 5/2006 | Bookbinder et al. | |
| 2007/0280935 A1 | 12/2007 | Bohrmann et al. | |
| 2008/0050383 A1 | 2/2008 | Sigurdsson et al. | |
| 2008/0069820 A1 | 3/2008 | Fuh et al. | |
| 2011/0059093 A1* | 3/2011 | Bohrmann | C07K 14/4711 424/139.1 |
| 2012/0276125 A1 | 11/2012 | Ast et al. | |
| 2014/0086921 A1* | 3/2014 | Griswold-Prenner | C07K 16/18 424/135.1 |

FOREIGN PATENT DOCUMENTS

| | | |
|---|---|---|
| EP | 1870459 A1 | 12/2007 |
| EP | 1876185 A1 | 1/2008 |
| EP | 2009104 A1 | 12/2008 |
| EP | 2 083 322 | 7/2009 |
| JP | H06239899 | 8/1994 |
| JP | 2003512019 | 4/2003 |
| JP | 200813566 | 1/2008 |
| JP | 2012529275 | 11/2012 |
| WO | 1993/01161 | 1/1991 |
| WO | 1991/06305 | 5/1991 |
| WO | 1992/004053 | 3/1992 |
| WO | 199308829 | 5/1993 |
| WO | 1993/016185 | 8/1993 |
| WO | WO 94/18560 | 8/1994 |
| WO | 1994029351 | 12/1994 |
| WO | 1995/009917 | 4/1995 |
| WO | 1996027011 | 9/1996 |
| WO | 1997/001580 | 1/1997 |
| WO | WO 97/034145 | 9/1997 |
| WO | 1998/22120 | 5/1998 |
| WO | 1998050431 | 11/1998 |
| WO | 1999/051642 | 10/1999 |
| WO | WO 00/42072 | 7/2000 |
| WO | 2001/55725 A1 | 8/2001 |
| WO | 2002/027017 A2 | 8/2001 |
| WO | 2001/077342 A1 | 10/2001 |
| WO | 2002/062851 A1 | 8/2002 |
| WO | 2004/016655 A1 | 2/2004 |
| WO | 2004/045642 A1 | 6/2004 |
| WO | 2004/050016 A2 | 6/2004 |
| WO | 2004/056312 | 7/2004 |
| WO | 2005/100402 | 10/2005 |
| WO | 2006/020258 A2 | 2/2006 |
| WO | 2006/029879 | 3/2006 |
| WO | 2006044908 A2 | 4/2006 |
| WO | 2006/055178 A2 | 5/2006 |
| WO | 2007/019273 A2 | 2/2007 |
| WO | 2007/024715 A2 | 3/2007 |
| WO | 2007/109254 | 9/2007 |
| WO | 2007/110205 A2 | 10/2007 |
| WO | 2007/147901 A1 | 12/2007 |
| WO | 2009/080251 A1 | 7/2009 |
| WO | 2009/080252 A1 | 7/2009 |
| WO | 2009/080253 A1 | 7/2009 |
| WO | 2009/080254 A1 | 7/2009 |
| WO | 2009/089004 A1 | 7/2009 |
| WO | 2010/037135 A2 | 4/2010 |
| WO | 2010/112193 A1 | 10/2010 |
| WO | 2010/115589 A1 | 10/2010 |
| WO | 2010/115843 A2 | 10/2010 |
| WO | 2010/129304 A2 | 11/2010 |
| WO | 2010/136172 A1 | 12/2010 |
| WO | 2010/142423 A2 | 12/2010 |
| WO | 2010/145792 A1 | 12/2010 |
| WO | 2010/145793 A1 | 12/2010 |
| WO | 2011003557 A1 | 1/2011 |
| WO | 2011003780 A1 | 1/2011 |
| WO | 2011/026031 A2 | 3/2011 |
| WO | 2011032022 A1 | 3/2011 |
| WO | 2011/053565 A2 | 5/2011 |
| WO | 2011/90754 A1 | 7/2011 |
| WO | 2011/090762 A1 | 7/2011 |
| WO | 2011/143545 A1 | 7/2011 |
| WO | 2012/045882 A2 | 4/2012 |
| WO | 2012/049570 A1 | 4/2012 |
| WO | 2012/058768 A1 | 5/2012 |
| WO | 2012075037 A1 | 6/2012 |
| WO | 2012093068 A1 | 7/2012 |
| WO | 2012/106363 A2 | 8/2012 |
| WO | 2012/149365 A2 | 11/2012 |
| WO | 2013007839 | 1/2013 |
| WO | 2013/096291 A2 | 6/2013 |
| WO | 2013/151762 A1 | 10/2013 |
| WO | 2013/157953 A1 | 10/2013 |
| WO | 2013/157954 A1 | 10/2013 |
| WO | 2014/016737 A1 | 1/2014 |
| WO | 2014006124 A1 | 1/2014 |
| WO | 2014028777 A2 | 2/2014 |
| WO | 2014/033074 A1 | 3/2014 |
| WO | 2015091656 A1 | 6/2015 |
| WO | 2015101586 A1 | 7/2015 |

OTHER PUBLICATIONS

Baca, M., et al., Antibody Humanization Using Monovalent Phage Display, the Journal of Biological Chemistry, vol. 272, No. 16, pp. 10678-10684 (1997).

Chowdhury, P.S., Engineering Hot Spots for Affinity Enhancement of Antibodies, Methods in Molecular Biology, vol. 207 (2008), pp. 179-196.

Hoogenboom, H.R., Antibody Phage-Display Technology and its Applications, vol. 178 (2002), pp. 1-37.

Cunningham, B., et al., High-Resolution Epitope Mapping of hGH-Receptor Interactions by Alanine-Scanning Mutagenesis., Science, 244 (1989) pp. 1081-1085.

Wright, A. et al., Effect of glycosylation on antibody function: implications for genetic engineering, TIBTECH 15 (1997), pp. 26-32.

Ravetch, J.V., et al., Fc Receptors, Annual Rev. Immunol. Table 3 on p. 464, (1991), vol. 9, pp. 457-492.

Hellstrom, I., et al., Antitumor effects of L6, an IgG2a antibody that reacts with most human carcinomas, Proc. Natl. Acad. Sci. USA vol. 83 (1986), pp. 7059-7063.

Hellstrom, I., et al., Strong antitumor activities of IgG3 antibodies to a human melanoma-associated ganglioside, Proc. Natl. Acad. Sci. USA, vol. 82 (1985), pp. 1499-1502.

Bruggemann, M., et al., Comparison of the Effector Functions of Human Immunoglobulins Using a Match Set of Chimeric Antobodies, J. Exp. Met 166 (1987), pp. 1351-1361.

Clynes, R., et al., Fc receptors are required in passive and active immunity to melanoma, Proc. Natl. Acad. Sci. USA, vol. 95, pp. 652-655, (1998).

Gazzano-Santoro, H., et al., A non-radioactive complement-dependent cytotoxicity array for anti-CD20 monoclonal antibody, J. of Immuno Methods, 202 (1997), pp. 163-171.

Cragg, M.S., et al., Complement-mediated lysis by anti-CD20 mAb correlates with segregation into lipid rafts, Blood 101 (2003), pp. 1045-1052.

Cragg, M.S., et al., Antibody specificty controls in vivo effector mechanisms of anti-CD20 reagents, Blood 103 (2003), pp. 1045-1052.

Petkova, S.B., et al., Enhanced half-life of genetically engineered human IgG1 antibodies in a humanized FcRn mouse model: pontential application in humorally mediated autoimmute disease, International Immunology, vol. 18, No. 12, pp. 1759-1769.

Shields, R.L., et al., High Resolution Mapping of the Binding Site on Human IgG1 for FcγRi, FcγRII, FcγRIII, and FcRn and Design of IgG1 variants with Improved Binding to the FcγR, The Journal of Biological Chemistry, 276 (2001), pp. 6591-6604.

Idusogie, E.E., et al., Mapping of the C1q Binding Site on Rituxan, a Chimeric Antibody with a Human IgG1 Fc, J. Immunol. 164 (2000), pp. 4178-4184.

Guyer, R.L., et al., Immunoglobulin Binding by Mouse Intestinal Epithelial Cell Receptors, The Journal of Immunol. vol. 117, No. 2, (1976), pp. 587-593.

(56) References Cited

OTHER PUBLICATIONS

Kim, J-K., et al., Localization of the site of the murine IgG1 molecule that is involved in binding to the murine intestinal Fc receptor, Eur. J. Immunol. 1994, 24: 2429-2434.

Duncan, A. R., The binding site for C1q on IgG, Nature 322 (1988), pp. 738-740.

Cam, N.W., et al., Carbon nanotubes as multifunctional biological transporters and near-infrared agents for selective cancer cell destruction, Proc., Natl. Acad. Sci. USA, 102 (2005) 11600-11605.

Charlton, K.A., et al., Expression and Isolation of Recombinant Antibody Fragments in E. coli, Methods in Molecular Biology, vol. 248, Humana Press, Totowa, NJ (2003), pp. 245-254.

Gerngross, T.U., Advances in the production of human therapeutic proteins in yeasts and filamentous fungi, Nature Biotechnology, 22 (2004), pp. 1409-1414.

Li, H., Optimization of humanized IgGs in glycoengineered Pichia pastoris, Nature Biotechnology, vol. 24, pp. 210-215 (2006).

Graham. F.L. et al., Characteristics of a Human Cell Line Transformed by DNA from Human Adenovirus Type 5 J. gen. Viral. (2977), 36, 59-7z.

Mather, J. P., Establishment and Characterization of two distinct mouse testicular epithelial cell lines, Biol. Reprod. 23, 243-252 (1980).

Mather J.P., Ceruloplasmin, a copper-transport protein, can act as a growth promoter for some cell lines in serum-free medium1, Annals. NY Acad. Sci. 383 (1982) 44-68.

Urlaub, G., et al., Isolation of Chinese hamster cell mutants deficient in dihydrofolate reductase activity. Proc. Natl. Acad. Sci. USA 1980, 77, 4216-4220, doi:10.1073/pnas.77.7.4216.

Yazaki, P. and Lo, B.K.C., (ed), Mammalian expression and hollow fiber bioreactor production of recombinant anti-CEA diabody and minibody for clinical applications, Methods in Molecular Biology, vol. 248, (2004) pp. 255-268, Humana Press, Totowa, NJ.

Tokuda, T., Detection of elevated levels of α-synuclein oligomers in CSF from patients with Parkinson disease, Neurology 75 (2010), pp. 1766-1772.

Dernick, G., et al., Multidimensional profi ling of plasma lipoproteins by size exclusion chromatography followed by reverse-phase protein arrays, J. Lipid Res. 52 (2011) pp. 2323-2331.

Towbin, H., et al., Electrophoretic transfer of proteins from polyacrylamide gels to nitrocellulose sheets: Procedure and some applications, Proc. Natl. Acad. Sci. USA, vol. 76, No. 9, pp. 4350-4354 (1979).

Emmanouilidou, E., et al., Cell-Produced a-Synuclein is Secreted in a Calcium-Dependent Manner by Exosomes and Impacts Neuronal Survival, J. Neurosci., vol. 30, pp. 6838-6851 (2010).

Remington's Pharmaceutical Sciences, 16th Ed., (1980).

Sambrook, J., et al., Molecular cloning: A laboratory manual, Cold Spring Harbor Laboratory Press, cold Spring Harbor, New York, 1989.

Zubler, R.H., Mutant EI-3 Thymoma Cells Polyclonally Activate Murine and Human B Cells via Direct Cell Interaction, The Journal of Immunology, vol. 134, No. 6 pp. 3662-3668 (1985).

Haun, R.S. et al., Rapid, reliable ligation-independent cloning of PCR products using modified plasmid vectors., Biotechniques. Oct. 1992;13(4):515-8.

Li, M.Z., et al. (2007), "Harnessing homologous recombination in vitro to generate recombinant DNA via SLIC", Nature Methods, 2007, 4 (3), 251-256.

Meissner, P., et al., Transient Gene Expression: Recombinant Protein Production with Suspension-Adapted HEK293-EBNA Cells, Biotechnology bioeng. 75 (2001), pp. 197-203.

Schraeml, M. et al., Kinetic Screening in the Antibody Development Process, Methods Mol. Biol., vol. 901 (2012), pp. 171,181.

Crepin, R., et al., Development of Human Single-Chain Antibodies to the Transferrin Receptor that Effectively Antagonize the Growth of Leukemias and Lymphomas, Therapeutics, Targets, and Chemical Biology (2010), American Association for Cancer Research.

Lesley, J. et al., Modulation of transferrin receptor expression and function by anti-transferrin receptor antibodies and antibody fragments, Exp Cell Res. May 1989;182(1):215-33.

Nygaard, R., The PP-Fold Solution Structure of Human Polypeptide YY and Human PYY3-36 As Determined by NMR, Biochemistry, 2006, 45 (27), pp. 8350-8357.

Hoffmann, E, et al., PK modulation of haptenylated peptides via non-covalent antibody complexation, Jounral of Cont. Rel., vol. 171, pp. 48-56 (2013).

Jolya, G., Biochemical Targets Of Plant Bioactive Compounds, CRC Press, New York (2003) p. 847.

Burnette, W.N., Western Blotting: Electrophoretic Transfer of Proteins form Sodium Dodecyl Sulfate-Polyacrylamide Gels to Unmodified Nitrocellulose and Radiographic Detection with Antibody and Radioiodinated Protein A, Analytical Biochemistry, vol. 112, pp. 195-203 (1981).

International Search Report and Written Opinion dated Dec. 30, 2015 to International Application No. PCT/EP2015/064321.

Reynolds, C.F., et al., Reactivating Kinase/p38 Phosphorylates 'r Protein in Vitro, J. of Neurochem. 69 (1997), 191-198.

Iqbal, K., et al, Tau pathology in Alzheimer disease and other tauopathies, Biochim. Biophys. Acta 1739 (2005), 198-210.

Hanger, D.P., et al., Novel Phosphorylation Sites in tau from Alzheimer Brain Support a Role for Casein Kinase 1 in Disease Pathogenesis, J. Biol. Chem., 282 (2007) 23645-23654.

Morishima-Kawashima, M. et al., Proline-directed and Non-proline-directed Phosphorylation of PHF-tau, J. Biol. Chem. vol. 270, No. 2 (Jan. 1995), 823-829.

Bussiere, T., et al., Phosphorylated serine422 on tau proteins is a pathological epitope found in several diseases with neurofibrillary degeneration, Acta Neuropathol. 97 (1999), 221-230.

Guillozet-Bongaarts, A., ] Pseudophosphorylation of tau at serine 422 inhibits caspase cleavage: in vitro evidence and implications for tangle formation in vivo, J. Neurochem. 97 (2006), 1005-1014.

Pei, J.J., et al., p70 S6 Kinase and Tau in Alzheimer's Disease, J. Alzheimer's Disease 14 2008), 385-392.

Augustinack, J.C., et al, Specific tau phosphorylation sites correlate with severity of neuronal cytopathology in Alzheimer's disease, Acta Neuropathol. 103, Issue 1, (2002) 26-35.

Deters, N. et al., Substrate-specific reduction of PP2A activity exaggerates tau pathology, Biochem. Biophys. Res. Commun. (2009) 379(2): 400-405.

Goetz, J., et al., Formation of neurofibrillary tangles in P301I tau transgenic mice induced by Abeta 42 fibrils, Science. Aug. 24, 2001;293(5534):1491-5.

Asuni, A.A., et al., Immunotherapy Targeting Pathological Tau Conformers in a Tangle Mouse Model Reduces Brain Pathology with Associated Functional Improvements, J. Neuroscience 27 (2007) 9115-9129.

Hasegawa, M., et al., Characterization of mAb AP422, a novel phosphorylation-dependent monoclonal antibody against tau protein, FEBS Lett. 384 (1996) 25-30.

Manich, G., et al., Study of the transcytosis of an anti-transferrin receptor antibody with a Fab' cargo across the blood-brain barrier in mice, Eur. J. Pharm. Sci. 49 (2013) 556-564.

Dufes, C., Applications of dentrimers for brain delivery and cancer therapy, Ther. Deliv. 4 (2013) 629-640.

Feng, J-M., Receptor-Mediated Transport of Drugs Across the BBB, Neurometh, 45 (2010) 15-34.

Partridge, W. R. Re-Engineering Biopharmaceuticals for Delivery to Brain with Molecular Trojan Horses, Bioconjug. Chem. 19 (2008) 1327-1338.

Ferrari, A., J., et al., Amyloid Induces Paired Helical Filament-like Tau Filaments in Tissue Culture, Biol. Chem. vol. 278, No. 41, Oct. 10, pp. 40162-40168 (2003).

Kabat, et al., Sequences of Proteins of Immunology Interest, 5th Ed., Public Health Service, national Institutes of Health, Bethesda, MDS 1991, pp. 647-660 and 661-723; NIH Publication 91/3242, vols. 1-3.

Chothia, C., et al., Canonical Structures for the Hypervariable Regions of Immunoglobulins, J. Mol. Biol. (1987) 196, 901-917.

(56) References Cited

OTHER PUBLICATIONS

MacCallum, R.M., et al., Antibody-antigen Interactions: Contact Analysis and Binding Site Topography, J. Mol. Biol. 262: 732-745, 1996.
Flatman, S., et al., Process analytics for purification of monoclonal antibodies, Journal of Chromatography B, vol. 848, Issue 1, Mar. 15, 2007, pp. 79-87.
Kindt, T.J., et al., Kuby Immunology, 6th Ed., W.H. Freeman and Co., NY (2007), p. 91.
Portolano, S., et al., Lack of promiscuity in autoantigen-specific H and L chain combinations as revealed by human H and L chain "roulette", J. Immunol. 150 (1993) 880-887.
Clackson, T., et al., Making antibody fragments using phage display libraries, Nature 352 (1991) 624-628.
Coloma, MJ, Nature Biotech, Design and production of novel tetravalent bispecific antibodies, 15 (1997) 159-163.
Morrison, S., et al., A new design for bispecific antibodies enables efficient production of stable molecules with good pharmacodynamic properties, Nature Biotech 25 (2007), pp. 1233-1234.
Holliger, P., et al., Engineered antibody fragments and the rise of single domains, Nature Biotechnology 23, 1126-1136 (2005).
Fischer, N., et al., Bispecific Antibodies: Molecules That Enable Novel Therapeutic Strategies, Pathobiology 74 (2007) 3-14.
Shen, J., et al., Single variable domain antibody as a versatile building block for the construction of IgG-like bispecific antibodies, Journal of Immunological Methods, vol. 318, Issues 1-2, 10, Jan. 2007, pp. 65-74.
Wu, C. Simultaneous targeting of multiple disease mediators by a dual-variable-domain immunoglobulin, Nature . Biotech 25 (2007) 1290-1297.
Milstein, C., et al., Hybrid hybridomas and their use in immunohistochemistry, Nature 305 (1983) 537-540 [Spec p. 51].
Traunecker, A.,et al., Bispecific single chain molecules (Janusins) target cytotoxic lymphocytes on HIV infected cells, EMBO J. 10 (1991), 3655-3659.
Brennan, M., et al., Preparation of bispecific antibodies by chemical recombiantion of monoclonal imunoglobulin G1 fragments, Science 229 (1985), 81-83.
Kostelny, S.A., et al., Formation of a bispecific antibody by the use of leucine zippers, The Journal of Immunology, 148 (1992), 1547-1553.
Holliger, Diabodies: Small bivalent and bispecific antibody fragments, Proc. Natl. Acad. Sci. USA 90 (1993) 6444-6448.
Gruber, M, et al., Efficient tumour cell lysis mediated by a bispecific single chain antibody expressed in *Escherichia coli*. J Immunol 152: 5368-5374, 1994.
Tutt, A., Trispecific F(ab')3 derivatives that use cooperative signaling via the TCR/CD3 complex and CD2 to activate and redirect resting cytotoxic T cells, J. Immunol. 147 (1991) 60-69.
Ridgeway, J.B., et al., Knobs-into-holes' engineering of antibody CH3 domains for heavy chain heterodimerization, Protein Eng. 1996, 9, 617-621.
Merchant, A.M., et al., An efficient route to human bispecific IgG, Nature Biotech, 16 (1998) 677-68.
Atwell, S., et al., "Stable heterodimers from remodeling the domain interface of a homodimer using a phage display library" J. Mol. Biol. 270 (1): 26-35 (1997).
Chen, Y., et al., Selection and Analysis of an Optimized Anti-VEGF antibody: Crystal Structure of an Affinity-matured Fab in Complex with Antigen, J. Mol. Biol. (1999) 293, 865-881.
Presta, L.G., et al., Humanization of an antibody directed against IgE, J. Immunol. (1993) 151: 2623-2632.
Hudson, P.J., et al., Engineered Antibodies, Nat Med. 9 (2003) 129-134.
Plueckthun, A., In: The Pharmacology of Monoclonal Antibodies, vol. 113, Rosenburg and Moore (eds.), Springer Verlad, New York, 1994), pp. 269-315.
Holliger, P., et al., Diabodies: Small bivalent and bispecific antibody fragments, Proc. Natl. Acad. Sci. USA, vol. 90, pp. 6444-6448, (1993).
Almagro, J.C. et al. Humanization of antibodies, J. Front Biosci. 13 (2008) 1619-1633.
Reichmann, L., et al., Reshaping human antibodies for therapy, Nature, vol. 332, pp. 323-329 (1988).
Queen, C., et al., A humanized antibody that binds to the interleukin 2 receptor, Proc. Natl. Aca. Sci. USA, vol. 86, pp. 10029-10033 (1989).
Kashmiri, S.V.S., et al., SDR grafting—a new approach to antibody humanization, Methods 36 (2005) pp. 25-34.
Rosok, M.J., A Combinatorial Library Strategy for the Rapid Humanization of Anticarcinoma BR96 Fab, J. Biol. Chem., 271 (1969), pp. 22611-22618.
Chen 1995 "enhancement and destruction of antibody function by somatic mutation: unequal occurrence is controlled by v gene combinatorial associations" EMBO 14(12):2784-2794.
The English translation of the Japanese Office Action, dated Mar. 1, 2016, in the related Japanese Patent Application No. 2012-514380.
Jose G. Vilches-Moure et al., "Comparison of rabbit monoclonal and mouse monoclonal antibodies in Immunohistochemistry in canine tissues," J Vet Diagn Invest 17:346-350 (2005) J Vet Diagn Invest 17:346-350 (2005).
Rossi et al., "A Comparative Study Between a Novel Category of Immunoreagents and the Corresponding Mouse Monoclonal Antibodies," Am J Clin Pathol 2005;124:295-302.
Foote et al., "Antibody Framework Residues Affecting the Conformation of the Hypervariable Loops," J. Mol. Biol. 224, 487-499. (1992).
The English translation of the Taiwanese Office Action, dated Aug. 10, 2015, in the related Taiwanese Patent Application No. 103144676.
The International Search Report and Written Opinion, dated Mar. 27, 2015, in the related PCT Appl. No. PCT/EP14/78234
The extended European search report, dated Jan. 19, 2016, in the related European Patent Application No. 15173511.5.
The International Search Report and Written Opinion, dated Aug. 22, 2016, in the related PCT Appl. No. PCT/EP16/64465.
JP Patent Application 2016-541620 Notification of Reasons for Rejection dated Sep. 4, 2018.
Barghorn Biochem (2002) vol. 41 pp. 14885-14896.
Barnes, Biotech. Bioeng. vol. 73 (2001) 261-270.
Barnes, Cytotechnology vol. 32 (2000) 109-123.
Durocher Nucl. Acids Res. vol. 30 2002 p. E9.
Geisse Protein Expr. Purif vol. 8 (1996) pp. 271-282.
Gong, Journal of biomedicine and biotechnology vol. 2006, Article ID 31825 pp. 1-11.
Hasegawa, M. et al., Neurobiology of Aging 17 (1996) S101, #403.
Johnson, Nucleic Acids Res. vol. 28 (2000) pp. 214-218.
Johnson, J. Neurochem. vol. 68 (1997) pp. 430-433.
Kaufman, R.J., Mol. Biotechnol. 16 (2000) 151-160.
Neuberger, Nature vol. 314 (1985) pp. 268-270.
Norderhaug, J. Immunol. Methods vol. 204 (1997) pp. 77-87.
Orlandi, Proc. Natl. Acad. Sci. USA vol. 86 (1989) pp. 3833-3837.
Ozmen, Neurodegen. Dis. vol. 61 (2008) pp. 29-36.
Richards, J.G. et al., J. Neurosci. 23 (2003) 8989-9003.
Rudikoff Proc Nat Acad. Sci USA vol. 79, pp. 1979-1983 Mar. 1982.
Schlaeger, E.-J., J. Immunol. Methods 194 (1996) 191-199.
Schlaeger, Cytotechnology vol. 30 (1999) pp. 71-83.
Schneider Neurotherapeutics 5(3):443-457 (Jul. 2008).
Tamura, J. Immunol vol. 164, No. 3 pp. 1432-1441 Feb. 2000.
The Canadian Office Action, dated May 1, 2014 in Canadian App. 2762594.
The International Search Report for Corres. Appl. PCT/EP2010/003437 dated Apr. 5, 2011.
European Search Report for Application EP 09 00 7656 dated Jul. 24, 2009.
Anti-phospha-tau, Internet Citation XP002453690 (2007).
Ausubel, F. et al. (eds.), Current Protocols in Molecular Biology, Greene Publishing and Wiley Interscience, New York (1987).
Gallyas, Acta Morphologica Acad. Sci. Hung. vol. 9 1971 pp. 1-8.
Huston, Methods in Enzymol vol. 203 (1991) pp. 46-96.
Makrides, Protein Expr. Purif. vol. 17 (1999( pp. 183-202.
Paul, W.E., Fundamental Immunology, 3rd edition (1993) 292-295.

(56) References Cited

OTHER PUBLICATIONS

The English translation of the Japanese Office Action, dated Sep. 10, 2013, in Japanese Patent No. 2012-514380.
The Search Report and Written Opinion dated Jan. 31, 2013 in Singapore Patent Application No. 201109113-9, pp. 16 (Jan. 31, 2013).
Werner, Drug Res. vol. 48 (1998) pp. 870-880.

\* cited by examiner

Figure 13
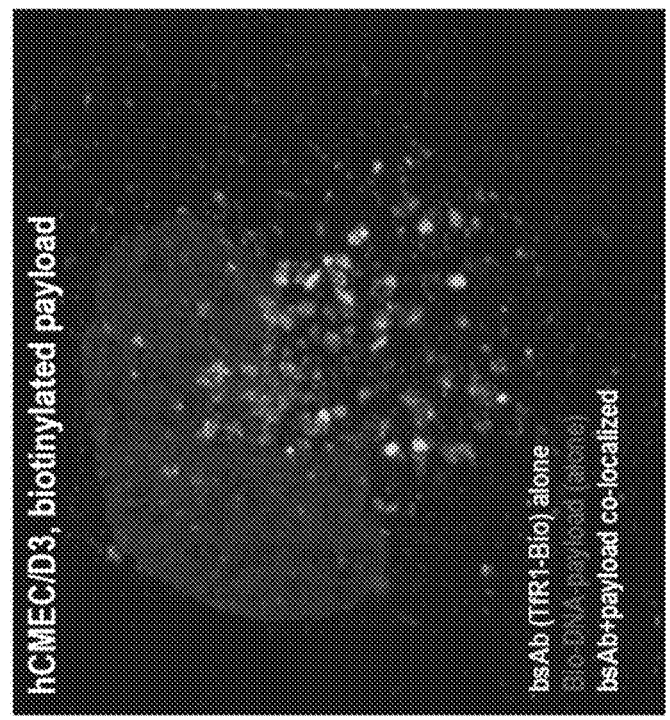
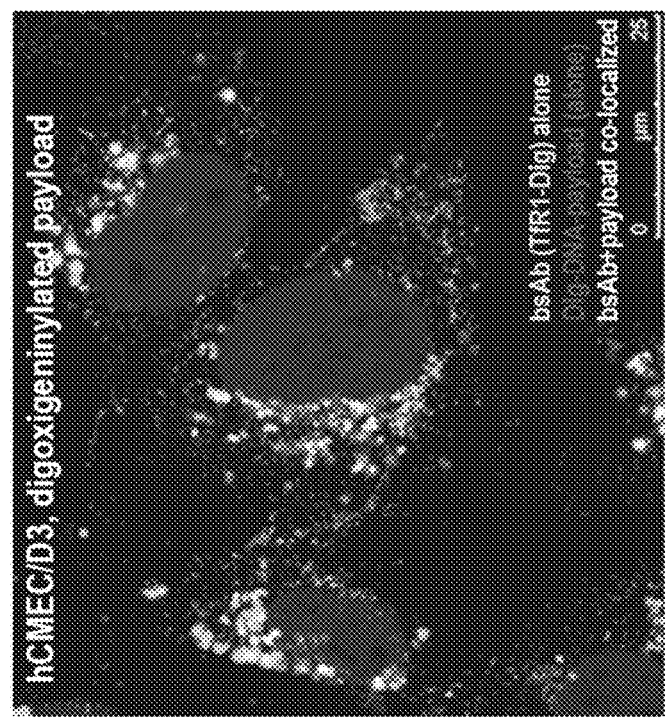

Figure 16 helical motif amino acid sequence cystein variant 1 containing Pseudomonas exotoxin antibody 0155 covalent conjugate

HUMANIZED ANTI-TAU(PS422) ANTIBODY BRAIN SHUTTLES AND USE THEREOF

CROSS REFERENCE TO RELATED APPLICATIONS

This application is a continuation of International Application No. PCT/EP2015/064321, filed on Jun. 25, 2015, which claims benefit of European Patent Application No. 14174042.3, filed on Jun. 26, 2014, both of which are herein incorporated by reference herein in their entireties.

FIELD OF THE INVENTION

The present invention relates to humanized anti-tau (pS422) antibody brain shuttle constructs which specifically bind to phosphorylated tau fragment of SEQ ID NO: 03 and their use for the treatment of brain diseases.

INCORPORATION BY REFERENCE OF SEQUENCE LISTING

This application contains references to amino acids and/or nucleic acid sequences that have been filed concurrently herewith as sequence listing text file "P32183-WO_12-May-2015_P32183-WO_ST251.txt", file size of 117 KB, created on May 12, 2015. The aforementioned sequence listing is hereby incorporated by reference in its entirety pursuant to 37 C.F.R. § 1.52(e)(5).

BACKGROUND OF THE INVENTION

Human tau (microtubule-associated protein tau (neurofibrillary tangle protein, paired helical filament-tau, PHF-tau)) is a neuronal microtubule-associated protein found predominantly in axons and functions to promote tubulin polymerization and to stabilize microtubules. Eight isoforms (isoform A, B, C, D, E, F, G, fetal-tau) are found in the human brain, the longest isoform comprising 441 amino acids (isoform F, Uniprot P10636-8). Tau and its properties are also described by Reynolds, C. H., et al., J. Neurochem. 69 (1997) 191-198.

Tau, in its hyperphosphorylated form, is the major component of paired helical filaments (PHF), the building block of neurofibrillary lesions in Alzheimer's disease (AD) brain. Tau can be phosphorylated at its serine or threonine residues by several different kinases including GSK3beta, cdk5, MARK and members of the MAP kinase family. Tauopathies are characterized by abnormal hyperphosphorylation of tau and are according to Iqbal, K., et al. (Biochim. Biophys. Acta 1739 (2005) 198-210):

Alzheimer disease, including tangle-only form of the disease
Down syndrome, adult cases
Guam parkinsonism dementia complex
Dementia pugilistica
Pick disease
Dementia with argyrophilic grains
Fronto-temporal dementia
Cortico-basal degeneration
Pallido-ponto-nigral degeneration
Progressive supranuclear palsy
Gerstmann-Sträussler-Scheinker disease with tangles.

So far nearly 40 serine (S)/threonine (T) phosphorylation sites have been found in tau from Alzheimer's disease brains (Hanger, D. P., et al., J. Biol. Chem. 282 (2007) 23645-23654). The development of tau pathology in Alzheimer's disease is related to its phosphorylation state. However, most of the 40 phosphorylation sites are not associated with disease pathology since they are also found in tau extracted from healthy, fetal brain tissue. Only a few phosphorylations are unique to the disease state and are presumably responsible for the abnormal, aggregation and characteristic insolubility that define tau in the PHFs of Alzheimer brain (Morishima-Kawashima, M., et al., J. Biol. Chem. 270 (1995) 823-829). According to Pei, J. J., et al. (J. Alzheimer's Disease 14 (2008) 385-392) the existing literature provides limited and unclear information about which of these sites are specific to AD brains. Pei used a list of phospho-specific antibodies to tau and measured their levels in homogenates of the medial temporal cortex from 22 AD patients and 10 controls.

Bussiere, T., et al. (Acta Neuropathol. 97 (1999) 221-230) described that phosphorylated serine 422 (pS422) on tau proteins is a pathological epitope found in several diseases with neurofibrillary degeneration. Augustinack, J. C., et al., (Acta Neuropathol. 103 (2002) 26-35) described pS422 as correlating with the severity of neuronal pathology in Alzheimer's disease. Guillozet-Bongaarts, A., (J. Neurochem. 97 (2006) 1005-1014) described the phosphorylation of tau at serine 422 as being part of the maturation process of PHFs. Tau pS422 is also found in association with developing pathology in various transgenic mouse models of Alzheimer's disease. Thus, Deters, N., et al., mentioned in Biochem. Biophys. Res. Commun. 379 (2009) 400-405 that double-transgenic Dom5/pR5 mice showed 7-fold increased numbers of hippocampal neurons that contain tau specifically phosphorylated the pathological S422 epitope. Goetz, J., et al., (Science 293 (2001) 1491-1495) reported the appearance of tau phosphorylated at S422 in the brains of tau P301L transgenic mice injected with Abeta42 fibrils.

EP 2 009 104 relates to epitopes of the tau protein which occur in a phosphorylated state in tau protein from Alzheimer's disease PHFs and to the use of said epitopes for the generation of antibodies specifically detecting Alzheimer tau protein. WO 2002/062851 and U.S. Pat. No. 7,446,180 relate to antibodies with a specificity to an abnormally truncated form of tau protein and diagnostic and therapeutic aspects in relation to Alzheimer's disease and related taupathies.

WO 1998/22120 relates to a method of treating a patient with Alzheimer's disease comprising the step of administering to the patient an antibody against phosphorylated tau fragment of amino acids about 207 to about 222, amino acids about 224 to about 240, and amino acids about 390 to about 408. Animal studies where the phosphorylated tau fragment 379-408 [P-Ser396,404] is used to vaccinate tau transgenic mice are mentioned in Asuni, A. A., et al., J. Neuroscience 27 (2007) 9115-9129. US 2008/0050383 relates to methods of treating and preventing Alzheimer's Disease or other taupathies in a subject by administering a tau protein fragment.

Hasegawa, M., et al. (FEBS Lett. 384 (1996) 25-30) report monoclonal antibody (AP422) specific for phosphoserine 422 in microtubule-associated protein tau.

In WO 2001/55725 an antibody that specifically recognizes tau and an antibody that specifically recognizes phospho-tau (181) for use in a method for the in vivo diagnosis of a tauopathy and/or for the in vivo differential diagnosis of a tauopathy versus a non-tauopathy is reported.

In WO 2002/027017 an antibody prepared from a polypeptide immunogen having a phosphorylated serine is reported. WO 2002/062851 relates to antibodies with a specificity to an abnormally truncated form of tau protein and diagnostic and therapeutic aspects in relation to Alzheimer's disease and related taupathies.

In WO 2004/016655 an antibody specific to a central nervous system (CNS) tau protein, wherein the antibody specifically recognizes a CNS tau protein but not a peripheral tau protein and wherein the antibody specifically recognizes an amino acid sequence of a connective portion between the amino acid sequence encoded by Exon 4 of a gene encoding a tau protein and the amino acid sequence encoded by Exon 5 thereof as an epitope is reported.

Monoclonal antibodies against tau (pS422) are described, for example, in EP 1 876 185. Polyclonal antibodies against tau (pS422) are commercially available (e.g. ProSci Inc. and Biosource International).

In WO 2006/055178 a method for inhibiting the phosphorylation of tau protein at Ser202/Thr205 comprising contacting a sample containing a tau protein with the antibody or antigen binding fragment that binds amyloid beta-derived diffusible ligands thereby inhibiting the phosphorylation of tau protein at Ser202/Thr205 is reported.

An antibody preparation that specifically binds to tau phosphorylated at tyr394 and/or tyr310 is reported in WO 2007/019273. Animal studies where the phosphorylated tau fragment 379-408 [P-Ser396,404] is used to vaccinate tau transgenic mice are mentioned in Asuni, A. A. et al., J. Neuroscience 27 (2007) 9115-9129.

EP 2 009 104 relates to epitopes of the tau protein which occur in a phosphorylated state in tau protein from Alzheimer's disease PHFs and to the use of said epitopes for the regeneration of antibodies specifically detecting Alzheimer tau protein.

US 2008/0050383 relates to methods of treating and preventing Alzheimer's Disease or other taupathies in a subject by administering a tau protein fragment.

In WO 2010/037135 an isolated, synthetic or recombinant polypeptide or peptide comprising a first domain comprising, or consisting of, a ligand for a blood brain barrier (BBB) receptor or equivalent and a second domain comprising, or consisting of an enzyme or composition that slows the rate of aggregation of a protein aggregate, inhibits the formation of a protein aggregate, or reverses, digests or dissolves a protein aggregate is reported. An antibody, particularly a monoclonal antibody or functional parts thereof, capable of recognizing and binding to a tau protein in vitro and/or in vivo is reported in WO 2010/115843.

In WO 2011/026031 a monoclonal antibody or its fragment that specifically binds tau oligomers and does not bind soluble tau or tau fibrils, useful for treating taupathy, e.g., Alzheimer's disease, progressive supranuclear palsy and corticobasal degeneration is reported. An isolated antibody that specifically binds human tau protein phosphorylated at one or more of Ser(238) and Thr(245) is reported in WO 2011/053565.

In WO 2012/045882 an antibody which specifically binds to a phospho-epitope on the mammalian tau protein, useful for treating neurodegenerative disorders such as tauopathies, and for treating or alleviating cognitive deficits is reported. A human monoclonal anti-tau antibody, or a tau binding fragment thereof is reported in WO 2012/049570. A method of preventing or treating Alzheimer's disease or other tauopathies in a subject, comprising administering antibodies to a human in need of therapy for Alzheimer's disease or other tauopathy, the antibodies having specificity to abnormal forms of tau protein, said antibody showing no binding and/or reactivity to a normal tau protein and being administered under conditions and in an amount(s) effective to prevent or treat Alzheimer's disease or other tauopathy is reported in WO 2012/106363.

In WO 2012/149365 an antibody which shows reactivity with aggregated tau and substantially no reactivity with non-aggregated tau, wherein the aggregated tau comprises at least two tau proteins cross-linked to each other, either directly or through a linker, at one or more cysteine residues is reported.

A composition useful in treating taupathy, e.g., Alzheimer disease comprises antibody binding to tau, phosphorylated serine modified compound at specific position specifically binding to specific phosphorylated tau and its fragment and carrier is reported in WO 2010/142423.

In EP 1 876 185 A an antibody which recognizes phosphorylated polypeptides is reported. In WO 2013/151762 a humanized tau antibody is reported. In WO 2014/016737 novel chicken monoclonal antibodies against human phosphorylated tau and uses thereof are reported.

In WO 2004/050016 the delivery of pharmaceutical agents via the human insulin receptor is reported. The study of the transcytosis of an anti-transferrin receptor antibody with a Fab' cargo across the blood brain barrier (BBB) in mice was reported by Manich, G., et al. (Eur. J Pharm. Sci. 49 (2013) 556-564). Dufes, C., et al. reported transferrin and the transferrin receptor for the targeted delivery of therapeutic agents to the brain and cancer cells (Ther. Deliv. 4 (2013) 629-640). Receptor-mediated transport of drugs across the BBB is reported by Feng, J-M., et al., Neurometh. 45 (2010) 15-34. Pardridge, W., et al. reported the re-engineering of biopharmaceuticals for delivery to brain with molecular Trojan horses (Bioconjug. Chem. 19 (2008) 1327-1338). In WO 2004/045642 the use of multi-specific, non-covalent complexes for targeted delivery of therapeutics is reported. Ferrari, A., et al. reported that beta-amyloid induces paired helical filament-like tau filaments in tissue culture (J. Biol. Chem. 278 (2003) 40162-40168). Substrate-specific reduction of PP2A activity exaggerates tau pathology is reported by Deters, N., et al., Biochem. Biophys. Res. 379 (2009) 400-405.

BRIEF SUMMARY OF THE INVENTION

The invention provides anti-human tau(pS422) antibody brain shuttle constructs and methods of using the same.

It has been found that covalent conjugates of an anti-human tau(pS422) antibody and a brain shuttle module, such as, e.g., a monovalent anti-human transferrin receptor antibody or antibody fragment, are less effective in reducing tau-related pathology compared to an anti-human tau (pS422) antibody not conjugated to a brain shuttle module. Furthermore the brain shuttle conjugate seems to be (neuro) toxic. Without being bound by this theory this might be due to the mode of action of the antibody and the cell-localization of the antibody's target.

Thus, herein is reported the use of a non-covalent complex as reported herein for transporting functional anti-tau (pS422) antibody across the blood brain barrier.

The construct as reported herein comprises a blood brain barrier-shuttle module (BBB-shuttle module) that is a bispecific antibody with a first binding specificity for a hapten and a second binding specificity for a blood brain barrier receptor (BBBR). Such a BBB-shuttle module recognizes a transcytoseable cell surface target on the blood brain barrier (such as transferrin receptor (TfR), low density lipoprotein receceptor-related proteins (LRPs) or other targets=BBBR) and simultaneously binds to haptenylated payloads.

It has been found that no further requirements with respect to binding valency, antibody format, BBBR binding affinities have to be met.

It has further been found that it is not required that the bispecific antibody-based shuttle module as reported herein is released as a whole, i.e. as a complex, from the endothelial cells of the blood brain barrier in order to mediate transcytosis of the haptenylated payload. Instead, the haptenylated payload, which is complexed by/non-covalently bound to the bispecific antibody-based shuttle module, i) is released from the bispecific antibody-based shuttle module within the BBB cell, i.e. after internalization in the intracellular vesicular system, ii) is separated from the shuttle module, and iii) subsequently is exocytosed from the BBB cell into the brain (leaving the bispecific antibody behind in the BBB cell).

The bispecific antibody-based shuttle module as reported herein is very variable regarding BBBR binding specificity valency as well as BBBR binding specific affinity. Simultaneously it enables payload release from the shuttle module.

One aspect as reported herein is a non-covalent complex of i) a haptenylated antibody that specifically binds to human tau(pS422), and ii) an anti-blood brain barrier receptor/hapten bispecific antibody.

The anti-blood-brain-barrier-receptor/hapten bispecific antibody is a bispecific antibody comprising a first binding specificity that specifically binds to a hapten, e.g. the hapten of the haptenylated antibody that specifically binds to human tau(pS422), and a second binding specificity that specifically binds to a blood brain barrier receptor.

One aspect as reported herein is a non-covalent complex of i) a bispecific antibody that specifically binds to human tau(pS422) and a hapten and ii) a haptenylated anti-blood brain barrier receptor antibody.

The antibody that specifically binds to human tau(pS422) and a hapten is a bispecific antibody comprising a first binding specificity that specifically binds to the hapten, e.g., of the haptenylated antibody that specifically binds to a blood brain barrier receptor, and a second binding specificity that specifically binds to human tau(pS422).

One aspect as reported herein is a non-covalent complex comprising i) a haptenylated antibody that specifically binds to human tau(pS422) and ii) a bispecific antibody, which has a first binding specificity that specifically binds to the hapten of the haptenylated antibody that specifically binds to human tau(pS422) and a second binding specificity that specifically binds to a blood brain barrier receptor, wherein the haptenylated antibody that specifically binds to human tau (pS422) is specifically bound by the first binding specificity of the bispecific antibody.

One aspect as reported herein is a non-covalent complex comprising i) a haptenylated antibody, which specifically binds to a blood brain barrier receptor, and ii) a bispecific antibody, which has a first binding specificity that specifically binds to human tau(pS422) and a second binding specificity that specifically binds to the hapten of the haptenylated antibody that specifically binds to a blood brain barrier receptor, wherein the haptenylated antibody that specifically binds to the blood brain barrier receptor is specifically bound by the second binding specificity of the bispecific antibody.

One aspect as reported herein is the use of a non-covalent complex of a haptenylated antibody that specifically binds to human tau(pS422) and an anti-blood brain barrier receptor/hapten bispecific antibody for the transport of the antibody that specifically binds to human tau(pS422) across the blood brain barrier.

One aspect as reported herein is the use of a non-covalent complex of a bispecific antibody that specifically binds to human tau(pS422) and a hapten, and a haptenylated anti-blood brain barrier receptor antibody for the transport of the antibody that specifically binds to human tau(pS422) across the blood brain barrier.

One aspect as reported herein is the use of a non-covalent complex comprising a haptenylated antibody that specifically binds to human tau(pS422) and bispecific antibody, which has a first binding specificity that specifically binds to the hapten of the haptenylated antibody that specifically binds to human tau(pS422) and a second binding specificity that specifically binds to a blood brain barrier receptor, wherein the haptenylated antibody that specifically binds to human tau(pS422) is specifically bound by the first binding specificity of the bispecific antibody, for the transport of the antibody that specifically binds to human tau(pS422) across the blood brain barrier.

One aspect as reported herein is the use of a non-covalent complex comprising a haptenylated antibody, which specifically binds to a blood brain barrier receptor, and a bispecific antibody, which has a first binding specificity that specifically binds to human tau(pS422) and a second binding specificity that specifically binds to the hapten of the haptenylated antibody that specifically binds to a blood brain barrier receptor, wherein the haptenylated antibody that specifically binds to the blood brain barrier receptor is specifically bound by the first binding specificity of the bispecific antibody, for the transport of the antibody that specifically binds to human tau(pS422) across the blood brain barrier.

In one embodiment the haptenylated antibody is selected from the group consisting of a biotinylated antibody, a theophyllinylated antibody, a digoxigenylated antibody, a carboranylated antibody, a fluoresceinylated antibody, a helicarylated antibody and a bromodeoxyuridinylated antibody. In one preferred embodiment the haptenylated antibody is a biotinylated antibody or a digoxigenylated antibody.

In one embodiment the haptenylated antibody that specifically binds to human tau(pS422) is selected from the group consisting of the biotinylated antibody that specifically binds to human tau(pS422), the theophyllinylated antibody that specifically binds to human tau(pS422), the digoxigenylated antibody that specifically binds to human tau(pS422), the carboranylated antibody that specifically binds to human tau(pS422), the fluoresceinylated antibody that specifically binds to human tau(pS422), the helicarylated antibody that specifically binds to human tau(pS422) and the bromodeoxyuridinylated antibody that specifically binds to human tau(pS422). In one preferred embodiment the haptenylated antibody that specifically binds to human tau(pS422) is a biotinylated antibody that specifically binds to human tau(pS422) or a digoxigenylated antibody that specifically binds to human tau(pS422).

In one embodiment the haptenylated antibody that specifically binds to a blood brain barrier receptor is selected from the group consisting of the biotinylated antibody that specifically binds to a blood brain barrier receptor, the theophyllinylated antibody that specifically binds to a blood brain barrier receptor, the digoxigenylated antibody that specifically binds to a blood brain barrier receptor, the carboranylated antibody that specifically binds to a blood brain barrier receptor, the fluoresceinylated antibody that specifically binds to a blood brain barrier receptor, the helicarylated antibody that specifically binds to a blood brain barrier receptor and the bromodeoxyuridinylated antibody that specifically binds to a blood brain barrier receptor. In one preferred embodiment the haptenylated antibody that specifically binds to a blood brain barrier receptor is a biotinylated antibody that specifically binds to a blood brain barrier receptor or a digoxigenylated antibody that specifically binds to a blood brain barrier receptor.

In one embodiment the blood brain barrier receptor is selected from the group consisting of the transferrin receptor (TfR), the insulin receptor, the insulin-like growth factor receptor (IGF receptor), the low density lipoprotein receptor-related protein 8 (LRP8), the low density lipoprotein receptor-related protein 1 (LRP1), and the heparin-binding epidermal growth factor-like growth factor (HB-EGF). In one preferred embodiment the blood brain barrier receptor is the transferrin receptor.

In one embodiment the bispecific antibody is a full length antibody comprising two binding sites.

In one embodiment the bispecific antibody is a full length antibody to which one or two scFvs or scFabs or CrossFabs or scCrossFabs have been fused and that comprises three or four binding sites.

In one embodiment the bispecific antibody is an antibody fragment. In one embodiment the antibody fragment is selected from F(ab')2 and diabodies.

In one embodiment the bispecific antibody is a humanized or a human antibody.

In one embodiment the bispecific antibody is free of effector function. In one embodiment the bispecific antibody has no functional Fc-region. In one embodiment the bispecific antibody has no Fc-region. In one embodiment the bispecific antibody has an Fc-region of the human IgG1 subclass with the mutations L234A, L235A and P329G, wherein the positions are determined according to the Fc-region numbering of Kabat (Kabat EU index). In one embodiment the bispecific antibody has an Fc-region of the human IgG4 subclass with the mutations S228P, L235E and P329G, wherein the positions are determined according to the Fc-region numbering of Kabat (Kabat EU index).

In one embodiment the bispecific antibody comprises
a) one binding site for the hapten of the haptenylated antibody and one binding site for the blood brain barrier receptor, or
b) two binding sites for the hapten of the haptenylated antibody and one binding site for the blood brain barrier receptor, or
c) one binding site for the hapten of the haptenylated antibody and two binding sites for the blood brain barrier receptor, or
d) two binding sites for the hapten of the haptenylated antibody and two binding sites for the blood brain barrier receptor.

In one embodiment the bispecific antibody comprises
a) one binding site for the hapten of the haptenylated antibody that specifically binds to human tau(pS422) and one binding site for the blood brain barrier receptor, or
b) two binding sites for the hapten of the haptenylated antibody that specifically binds to human tau(pS422) and one binding site for the blood brain barrier receptor, or
c) one binding site for the hapten of haptenylated antibody that specifically binds to human tau(pS422) and two binding sites for the blood brain barrier receptor, or
d) two binding sites for the hapten of the haptenylated antibody that specifically binds to human tau(pS422) and two binding sites for the blood brain barrier receptor.

In one embodiment the bispecific antibody comprises
a) one binding site for the hapten of the haptenylated antibody that specifically binds to a blood brain barrier receptor and one binding site for human tau(pS422), or
b) two binding sites for the hapten of the haptenylated antibody that specifically binds to a blood brain barrier receptor and one binding site for human tau(pS422), or
c) one binding site for the hapten of haptenylated antibody that specifically binds to a blood brain barrier receptor and two binding sites for human tau(pS422), or
d) two binding sites for the hapten of the haptenylated antibody that specifically binds to a blood brain barrier receptor and two binding sites for human tau(pS422).

In cases b) and c) of the previous embodiments one heavy chain of the bispecific antibody comprises a hole mutation and the respective other chain comprises a knob mutation.

In one preferred embodiment the bispecific antibody comprises two binding sites for the hapten of the haptenylated antibody that specifically binds to human tau (pS422) and two binding sites for the blood brain barrier receptor.

In one preferred embodiment the bispecific antibody comprises two binding sites for the hapten of the haptenylated antibody that specifically binds to a blood brain barrier receptor and two binding sites for human tau(pS422).

In one embodiment the bispecific antibody has two binding specificities that specifically bind to the hapten of the haptenylated antibody that specifically binds to human tau (pS422) (two anti-hapten binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment the bispecific antibody has two binding specificities that specifically bind to the hapten of the haptenylated antibody that specifically binds to the (human) transferrin receptor (two anti-hapten binding specificities) or to low density lipoprotein receptor-related protein 8 (two anti-hapten binding specificities) and two binding specificities that specifically bind to human tau(pS422).

In one embodiment the binding specificity that specifically binds to the digoxigenin of the digoxigenylated antibody that specifically binds to human tau(pS422) is a pair of an antibody heavy chain variable domain and an antibody light chain variable domain comprising (a) a heavy chain CDR1 comprising the amino acid sequence of SEQ ID NO: 65, (b) a heavy chain CDR2 comprising the amino acid sequence of SEQ ID NO: 66, (c) a heavy chain CDR3 comprising the amino acid sequence of SEQ ID NO: 67, (d) a light chain CDR1 comprising the amino acid sequence of SEQ ID NO: 69, (e) a light chain CDR2 comprising the amino acid sequence of SEQ ID NO: 70, and (f) a light chain CDR3 comprising the amino acid sequence of SEQ ID NO: 71.

In one embodiment the binding specificity that specifically binds to the digoxigenin of the digoxigenylated antibody that specifically binds to human tau(pS422) is a humanized binding specificity.

In one embodiment the binding specificity that specifically binds to the digoxigenin of the digoxigenylated antibody that specifically binds to human tau(pS422) comprises CDRs as in the above embodiment and an acceptor human framework (e.g. a human immunoglobulin framework or a human consensus framework).

In one embodiment the binding specificity that specifically binds to the digoxigenin of the digoxigenylated antibody that specifically binds to human tau(pS422) is a pair of an antibody heavy chain variable domain and an antibody light chain variable domain comprising (a) a heavy chain CDR1 comprising the amino acid sequence of SEQ ID NO: 73, (b) a heavy chain CDR2 comprising the amino acid sequence of SEQ ID NO: 74, (c) a heavy chain CDR3 comprising the amino acid sequence of SEQ ID NO: 75, (d) a light chain CDR1 comprising the amino acid sequence of SEQ ID NO: 77, (e) a light chain CDR2 comprising the amino acid sequence of SEQ ID NO: 78, and (f) a light chain CDR3 comprising the amino acid sequence of SEQ ID NO: 79.

In one embodiment the binding specificity that specifically binds to the digoxigenin of the digoxigenylated antibody that specifically binds to human tau(pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 68 or 76. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin. In certain embodiments, a total of 1 to 10 amino acids have been substituted, inserted and/or deleted in SEQ ID NO: 68 or 76. In certain embodiments, substitutions, insertions, or deletions occur in regions outside the CDRs (i.e., in the FRs). Optionally, the digoxigenin binding specificity comprises the VH sequence in SEQ ID NO: 68 or 76, including post-translational modifications of that sequence.

In one embodiment the binding specificity that specifically binds to the digoxigenin of the digoxigenylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 72 or 80. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin. In certain embodiments, a total of 1 to 10 amino acids have been substituted, inserted and/or deleted in SEQ ID NO: 72 or 80. In certain embodiments, the substitutions, insertions, or deletions occur in regions outside the CDRs (i.e., in the FRs). Optionally, the digoxigenin binding specificity comprises the VL sequence in SEQ ID NO: 72 or 80, including post-translational modifications of that sequence.

In one embodiment the bispecific antibody comprises a first binding specificity that specifically binds to the biotin of the biotinylated antibody that specifically binds to human tau(pS422) (anti-biotin binding specificity; anti-BI binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment the bispecific antibody has two binding specificities that specifically bind to the biotin of the biotinylated antibody that specifically binds to human tau (pS422) (two anti-biotin binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment the binding specificity that specifically binds to the biotin of the biotinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 81, (b) a heavy chain CDR2 comprising the amino acid sequence of SEQ ID NO: 82, (c) a heavy chain CDR3 comprising the amino acid sequence of SEQ ID NO: 83, (d) a light chain CDR1 comprising the amino acid sequence of SEQ ID NO: 85, (e) a light chain CDR2 comprising the amino acid sequence of SEQ ID NO: 86, and (f) a light chain CDR3 comprising the amino acid sequence of SEQ ID NO: 87.

In one embodiment the binding specificity that specifically binds to the biotin of the biotinylated antibody that specifically binds to human tau(pS422) is a humanized binding specificity.

In one embodiment the binding specificity that specifically binds to the biotin of the biotinylated antibody that specifically binds to human tau(pS422) comprises CDRs as in the above embodiment and an acceptor human framework (e.g. a human immunoglobulin framework or a human consensus framework).

In one embodiment the binding specificity that specifically binds to the biotin of the biotinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 89, (b) a heavy chain CDR2 comprising the amino acid sequence of SEQ ID NO: 90, (c) a heavy chain CDR3 comprising the amino acid sequence of SEQ ID NO: 91, (d) a light chain CDR1 comprising the amino acid sequence of SEQ ID NO: 93, (e) a light chain CDR2 comprising the amino acid sequence of SEQ ID NO: 94, and (f) a light chain CDR3 comprising the amino acid sequence of SEQ ID NO: 95.

In one embodiment the binding specificity that specifically binds to the biotin of the biotinylated antibody that specifically binds to human tau(pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 84 or 92. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin. In certain embodiments, a total of 1 to 10 amino acids have been substituted, inserted and/or deleted in SEQ ID NO: 84 or 92. In certain embodiments, substitutions, insertions, or deletions occur in regions outside the CDRs (i.e., in the FRs). Optionally, the biotin binding specificity comprises the VH sequence in SEQ ID NO: 84 or 92, including post-translational modifications of that sequence.

In one embodiment the binding specificity that specifically binds to the biotin of the biotinylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 88 or 96. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin. In certain embodiments, a total of 1 to 10 amino acids have been substituted, inserted and/or deleted in SEQ ID NO: 88 or 96. In certain embodiments, the substitutions, insertions, or deletions occur in regions outside the CDRs (i.e., in the FRs). Optionally, the biotin binding specificity comprises the VL sequence in SEQ ID NO: 88 or 96, including post-translational modifications of that sequence.

In one embodiment the bispecific antibody comprises a first binding specificity that specifically binds to the theophylline of the theophyllinylated antibody that specifically binds to human tau(pS422) (anti-theophylline binding specificity; anti-THEO binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment the bispecific antibody has two binding specificities that specifically bind to the theophylline of the theophyllinylated antibody that specifically binds to human tau(pS422) (two anti-theophylline binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment the binding specificity that specifically binds the theophylline of the theophyllinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 97, (b) a heavy chain CDR2 comprising the amino acid sequence of SEQ ID NO: 98, (c) a heavy chain CDR3 comprising the amino acid sequence of SEQ ID NO: 99, (d) a light chain CDR1 comprising the amino acid sequence of SEQ ID NO: 101, (e) a light chain CDR2 comprising the amino acid sequence of SEQ ID NO: 102, and (f) a light chain CDR3 comprising the amino acid sequence of SEQ ID NO: 103.

In one embodiment the binding specificity that specifically binds to the theophylline of the theophyllinylated antibody that specifically binds to human tau(pS422) is a humanized binding specificity.

In one embodiment the binding specificity that specifically binds to the theophylline of the theophyllinylated antibody that specifically binds to human tau(pS422) comprises CDRs as in the above embodiment and an acceptor human framework (e.g. a human immunoglobulin framework or a human consensus framework).

In one embodiment the binding specificity that specifically binds to the theophylline of the theophyllinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 105, (b) a heavy chain CDR2 comprising the amino acid sequence of SEQ ID NO: 106, (c) a heavy chain CDR3 comprising the amino acid sequence of SEQ ID NO: 107, (d) a light chain CDR1 comprising the amino acid sequence of SEQ ID NO: 109, (e) a light chain CDR2 comprising the amino acid sequence of SEQ ID NO: 110, and (f) a light chain CDR3 comprising the amino acid sequence of SEQ ID NO: 111.

In one embodiment the binding specificity that specifically binds to the theophylline of the theophyllinylated antibody that specifically binds to human tau(pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 100 or 108. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline. In certain embodiments, a total of 1 to 10 amino acids have been substituted, inserted and/or deleted in SEQ ID NO: 100 or 108. In certain embodiments, substitutions, insertions, or deletions occur in regions outside the CDRs (i.e., in the FRs). Optionally, the theophylline binding specificity comprises the VH sequence in SEQ ID NO: 100 or 108 including post-translational modifications of that sequence.

In one embodiment the binding specificity that specifically binds to the theophylline of the theophyllinylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 104 or 112. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline. In certain embodiments, a total of 1 to 10 amino acids have been substituted, inserted and/or deleted in SEQ ID NO: 104 or 112. In certain embodiments, the substitutions, insertions, or deletions occur in regions outside the CDRs (i.e., in the FRs). Optionally, the theophylline binding specificity comprises the VL sequence in SEQ ID NO: 104 or 112, including post-translational modifications of that sequence.

In one embodiment the bispecific antibody comprises a first binding specificity that specifically binds to the fluorescein of the fluoresceinylated antibody that specifically binds to human tau(pS422) (anti-fluorescein binding specificity; anti-FLUO binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment the bispecific antibody has two binding specificities that specifically bind to the the fluorescein of the fluoresceinylated antibody that specifically binds to human tau(pS422) (two anti-fluorescein binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment the binding specificity that specifically binds to the fluorescein of the fluoresceinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 113, (b) a heavy chain CDR2 comprising the amino acid sequence of SEQ ID NO: 114, (c) a heavy chain CDR3 comprising the amino acid sequence of SEQ ID NO: 115, (d) a light chain CDR1 comprising the amino acid sequence of SEQ ID NO: 117, (e) a light chain CDR2 comprising the amino acid sequence of SEQ ID NO: 118, and (f) a light chain CDR3 comprising the amino acid sequence of SEQ ID NO: 119.

In one embodiment the binding specificity that specifically binds to the fluorescein of the fluoresceinylated antibody that specifically binds to human tau(pS422) is a humanized binding specificity.

In one embodiment the binding specificity that specifically binds to the fluorescein of the fluoresceinylated antibody that specifically binds to human tau(pS422) comprises CDRs as in the above embodiment and an acceptor human framework (e.g. a human immunoglobulin framework or a human consensus framework).

In one embodiment the binding specificity that specifically binds to the fluorescein of the fluoresceinylated antibody that specifically binds to human tau(pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 116. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein. In certain embodiments, a total of 1 to 10 amino acids have been substituted, inserted and/or deleted in SEQ ID NO: 116. In certain embodiments, substitutions, insertions, or deletions occur in regions outside the CDRs (i.e., in the FRs). Optionally, the fluorescein binding specificity comprises the VH sequence in SEQ ID NO: 116, including post-translational modifications of that sequence.

In one embodiment the binding specificity that specifically binds to the fluorescein of the fluoresceinylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 120. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein. In certain embodiments, a total of 1 to 10 amino acids have been substituted, inserted and/or deleted in SEQ ID NO: 120. In certain embodiments, the substitutions, insertions, or deletions occur in regions outside the CDRs (i.e., in the FRs). Optionally, the fluorescein binding specificity comprises the VL sequence in SEQ ID NO: 120, including post-translational modifications of that sequence.

In one embodiment the bispecific antibody comprises a first binding specificity that specifically binds to a bromodeoxyuridinylated payload (anti-bromodeoxyuridine binding specificity; anti-BrdU binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

In one embodiment the bispecific antibody has two binding specificities that specifically bind to the bromodeoxyuridinylated payload (two anti-bromodeoxyuridine binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

In one embodiment the binding specificity that specifically binds to the bromodeoxyuridine of the bromodeoxyuridinylated antibody that specifically binds to human tau (pS422) is a pair of an antibody heavy chain variable domain and an antibody light chain variable domain comprising (a) a heavy chain CDR1 comprising the amino acid sequence of SEQ ID NO: 121, (b) a heavy chain CDR2 comprising the amino acid sequence of SEQ ID NO: 123, (c) a heavy chain CDR3 comprising the amino acid sequence of SEQ ID NO: 125, (d) a light chain CDR1 comprising the amino acid sequence of SEQ ID NO: 126, (e) a light chain CDR2 comprising the amino acid sequence of SEQ ID NO: 127, and (f) a light chain CDR3 comprising the amino acid sequence of SEQ ID NO: 128.

In one embodiment the binding specificity that specifically binds to the bromodeoxyuridine of the bromodeoxyuridinylated antibody that specifically binds to human tau (pS422) is a humanized binding specificity.

In one embodiment the binding specificity that specifically binds to the bromodeoxyuridine of the bromodeoxyuridinylated antibody that specifically binds to human tau (pS422) comprises CDRs as in the above embodiment and an acceptor human framework (e.g. a human immunoglobulin framework or a human consensus framework).

In one embodiment the binding specificity that specifically binds to the bromodeoxyuridine of the bromodeoxyuridinylated antibody that specifically binds to human tau (pS422) is a pair of an antibody heavy chain variable domain and an antibody light chain variable domain comprising (a) a heavy chain CDR1 comprising the amino acid sequence of SEQ ID NO: 121 or 122, (b) a heavy chain CDR2 comprising the amino acid sequence of SEQ ID NO: 123 or 124, (c) a heavy chain CDR3 comprising the amino acid sequence of SEQ ID NO: 125, (d) a light chain CDR1 comprising the amino acid sequence of SEQ ID NO: 126, (e) a light chain CDR2 comprising the amino acid sequence of SEQ ID NO: 127, and (f) a light chain CDR3 comprising the amino acid sequence of SEQ ID NO: 128.

In one embodiment the binding specificity that specifically binds to the bromodeoxyuridine of the bromodeoxyuridinylated antibody that specifically binds to human tau (pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 129 or 131. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine. In certain embodiments, a total of 1 to 10 amino acids have been substituted, inserted and/or deleted in SEQ ID NO: 129 or 131. In certain embodiments, substitutions, insertions, or deletions occur in regions outside the CDRs (i.e., in the FRs). Optionally, the bromodeoxyuridine binding specificity comprises the VH sequence in SEQ ID NO: 129 or 131, including post-translational modifications of that sequence.

In one embodiment the binding specificity that specifically binds to the bromodeoxyuridine of the bromodeoxyuridinylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 130 or 132. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine. In certain embodiments, a total of 1 to 10 amino acids have been substituted, inserted and/or deleted in SEQ ID NO: 130 or 132. In certain embodiments, the substitutions, insertions, or deletions occur in regions outside the CDRs (i.e., in the FRs). Optionally, the bromodeoxyuridine binding specificity comprises the VL sequence in SEQ ID NO: 130 or 132, including post-translational modifications of that sequence.

In one embodiment the haptenylated antibody that specifically binds to human tau(pS422) comprises between the hapten and the antibody that specifically binds to human tau(pS422) a linker. In one embodiment the linker is a peptidic linker. In one embodiment the linker is a chemical linker (non-peptidic linker).

In one embodiment the antibody that specifically binds to human tau(pS422) is a full length antibody.

In one embodiment the antibody that specifically binds to human tau(pS422)
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to human tau that has the amino acid sequence of SEQ ID NO: 01 and that has the amino acid mutation S422A.

The antibodies that specifically binds to human tau (pS422) as reported herein show a selectivity with respect to human tau phosphorylated at the serine at position 422 with respect to not-phosphorylated wild-type human tau and the tau mutant S422A. The not-phosphorylated wild-type human tau and the tau mutant S422A are not bound at all or with a lower affinity, respectively.

In one embodiment the antibody that specifically binds to human tau(pS422) comprises
  a) in the heavy chain variable domain the HVRs of SEQ ID NO: 08, 18 and 10, or
  b) in the heavy chain variable domain the HVRs of SEQ ID NO: 08, 09 and 10.

In one embodiment the antibody that specifically binds to human tau(pS422) further comprises
  a) in the light chain variable domain the HVRs of SEQ ID NO: 13, 14 and 15, or
  b) in the light chain variable domain the HVRs of SEQ ID NO: 12, 05 and 15.

In one embodiment the antibody that specifically binds to human tau(pS422) comprises
  a) in the heavy chain variable domain the HVRs of SEQ ID NO: 08, 18 and 10, and in the light chain variable domain the HVRs of SEQ ID NO: 13, 14 and 15, or
  b) in the heavy chain variable domain the HVRs of SEQ ID NO: 08, 09 and 10, and in the light chain variable domain the HVRs of SEQ ID NO: 12, 05 and 15, or
  c) in the heavy chain variable domain the HVRs of SEQ ID NO: 08, 09 and 10, and in the light chain variable domain the HVRs of SEQ ID NO: 13, 14 and 15.

In one embodiment the antibody that specifically binds to human tau(pS422) comprises
  a) a heavy chain variable domain of SEQ ID NO: 20 and a light chain variable domain of SEQ ID NO: 17, or
  b) a heavy chain variable domain of SEQ ID NO: 19 and a light chain variable domain of SEQ ID NO: 16, or
  c) a heavy chain variable domain of SEQ ID NO: 19 and a light chain variable domain of SEQ ID NO: 17, or
  d) a heavy chain variable domain of SEQ ID NO: 21 and a light chain variable domain of SEQ ID NO: 17.

In one embodiment the non-covalent complex is for use in the treatment of Alzheimer's Disease.

In one embodiment both antibodies in the complex are effector function silent. In one embodiment both antibodies of the complex have no effector function.

In one embodiment the antibody that specifically binds to human tau(pS422)
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02).

In one embodiment the antibody that specifically binds to human tau(pS422) has an $EC_{50}$ value for
  a) the human tau(pS422) fragment that has the amino acid sequence of SEQ ID NO: 03 of 6 ng/mL or less, and/or
  b) the full length human tau(pS422) that has the amino acid sequence of SEQ ID NO: 02 of 4.5 ng/mL or less, and/or
  c) aggregates of human tau(pS422) that has the amino acid sequence of SEQ ID NO: 02 of 30 ng/mL or less, and/or
  d) the human tau that has the amino acid sequence of SEQ ID NO: 01 and that has the amino acid mutation S422A of 125 ng/mL or less.

In one embodiment the antibody that specifically binds to human tau(pS422) (SEQ ID NO: 02) does not bind to human tau (SEQ ID NO: 01).

In one embodiment the antibody that specifically binds to human tau(pS422) is a monoclonal antibody.

In one embodiment the antibody that specifically binds to human tau(pS422) is an antibody fragment that binds to human tau(pS422) and
  i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human tau(pS422) fragment that has the amino acid sequence of SEQ ID NO: 03 of 6 ng/mL or less, and/or
  vii) has an $EC_{50}$ value for the full length human tau (pS422) that has the amino acid sequence of SEQ ID NO: 02 of 4.5 ng/mL or less, and/or
  viii) has an $EC_{50}$ value for aggregates of human tau (pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

In one embodiment the antibody that specifically binds to human tau(pS422) is
  a) a full length antibody of the human subclass IgG1, or
  b) a full length antibody of the human subclass IgG4, or
  c) a full length antibody of the human subclass IgG1 with the mutations L234A, L235A and P329G,
  d) a full length antibody of the human subclass IgG4 with the mutations S228P, L235E and P329G,
  e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
  f) a full length antibody of the human subclass IgG4 with the mutations S228P and P329G in both heavy chains and the mutations T366W and S354C in one heavy chain and the mutations T366S, L368A, Y407V and Y349C in the respective other heavy chain.

In one embodiment antibody that specifically binds to human tau(pS422)
  a) comprises two antibody heavy chains each comprising a heavy chain variable domain and a heavy chain constant region, wherein
    i) the variable domain comprises the HVRs of SEQ ID NO: 08, SEQ ID NO: 18 and SEQ ID NO: 10,
    ii) the constant region is a human IgG1 constant region, wherein the C-terminal lysine residue can be present or absent, and
    iii) the constant region comprises the amino acid changes L234A, L235A and P329G,
  b) comprises two antibody light chains each comprising a light chain variable domain and a light chain constant domain, wherein
    i) the variable domain comprises the HVRs of SEQ ID NO: 13, SEQ ID NO: 14 and SEQ ID NO: 15,
    ii) the constant region is a human kappa light chain constant region or a human lambda light chain constant region, and
  c) i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human tau(pS422) fragment that has the amino acid sequence of SEQ ID NO: 03 of 6 ng/mL or less, and/or
    vii) has an $EC_{50}$ value for the full length human tau(pS422) that has the amino acid sequence of SEQ ID NO: 02 of 4.5 ng/mL or less, and/or
    viii) has an $EC_{50}$ value for aggregates of human tau (pS422) that has the amino acid sequence of SEQ ID NO: 02 of 30 ng/mL or less, and/or
    ix) has an $EC_{50}$ value for the human tau that has the amino acid sequence of SEQ ID NO: 01 and that has the amino acid mutation S422A of 125 ng/mL or less.

In one embodiment the antibody that specifically binds to human tau(pS422)
  a) comprises two antibody heavy chains each comprising a heavy chain variable domain and a heavy chain constant region, wherein
    i) the variable domain comprises the HVRs of SEQ ID NO: 08, SEQ ID NO: 09 and SEQ ID NO: 10,
    ii) the constant region is a human IgG1 constant region, wherein the C-terminal lysine residue can be present or absent, and
    iii) the constant region comprises the amino acid changes L234A, L235A and P329G,
  b) comprises two antibody light chains each comprising a light chain variable domain and a light chain constant domain, wherein
    i) the variable domain comprises the HVRs of SEQ ID NO: 12, SEQ ID NO: 05 and SEQ ID NO: 15,
    ii) the constant region is a human kappa light chain constant region or a human lambda light chain constant region, and
  c) i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human tau(pS422) fragment that has the amino acid sequence of SEQ ID NO: 03 of 6 ng/mL or less, and/or
    vii) has an $EC_{50}$ value for the full length human tau(pS422) that has the amino acid sequence of SEQ ID NO: 02 of 4.5 ng/mL or less, and/or viii) has an $EC_{50}$ value for aggregates of human tau (pS422) that has the amino acid sequence of SEQ ID NO: 02 of 30 ng/mL or less, and/or ix) has an $EC_{50}$ value for the human tau that has the amino acid sequence of SEQ ID NO: 01 and that has the amino acid mutation S422A of 125 ng/mL or less.

In one embodiment the antibody that specifically binds to human tau(pS422)
a) comprises two antibody heavy chains each comprising a heavy chain variable domain and a heavy chain constant region, wherein
  i) the variable domain comprises the HVRs of SEQ ID NO: 08, SEQ ID NO: 09 and SEQ ID NO: 10,
  ii) the constant region is a human IgG1 constant region, wherein the C-terminal lysine residue can be present or absent, and
  iii) the constant region comprises the amino acid changes L234A, L235A and P329G,
b) comprises two antibody light chains each comprising a light chain variable domain and a light chain constant domain, wherein
  i) the variable domain comprises the HVRs of SEQ ID NO: 13, SEQ ID NO: 14 and SEQ ID NO: 15,
  ii) the constant region is a human kappa light chain constant region or a human lambda light chain constant region, and
c) i) specifically binds to a polypeptide that has the amino acid sequence of SEQ ID NO: 03, and/or
  ii) does not bind to full length human tau (SEQ ID NO: 01) at 1 μg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human tau(pS422) fragment that has the amino acid sequence of SEQ ID NO: 03 of 6 ng/mL or less, and/or
  vii) has an $EC_{50}$ value for the full length human tau(pS422) that has the amino acid sequence of SEQ ID NO: 02 of 4.5 ng/mL or less, and/or
  viii) has an $EC_{50}$ value for aggregates of human tau (pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

In one embodiment the antibody that specifically binds to human tau(pS422)
a) comprises two antibody heavy chains each comprising a heavy chain variable domain and a heavy chain constant region, wherein
  i) the variable domain has the amino acid sequence of SEQ ID NO: 20,
  ii) the constant region is a human IgG1 constant region, wherein the C-terminal lysine residue can be present or absent, and
  iii) the constant region comprises the amino acid changes L234A, L235A and P329G,
b) comprises two antibody light chains each comprising a light chain variable domain and a light chain constant domain, wherein
  i) the variable domain has the amino acid sequence of SEQ ID NO: 17,
  ii) the constant region is a human kappa light chain constant region or a human lambda light chain constant region, and
c) i) specifically binds to a polypeptide that has the amino acid sequence of SEQ ID NO: 03, and/or
  ii) does not bind to full length human tau (SEQ ID NO: 01) at 1 μg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human tau(pS422) fragment that has the amino acid sequence of SEQ ID NO: 03 of 6 ng/mL or less, and/or
  vii) has an $EC_{50}$ value for the full length human tau(pS422) that has the amino acid sequence of SEQ ID NO: 02 of 4.5 ng/mL or less, and/or
  viii) has an $EC_{50}$ value for aggregates of human tau (pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

In one embodiment the antibody that specifically binds to human tau(pS422)
a) comprises two antibody heavy chains each comprising a heavy chain variable domain and a heavy chain constant region, wherein
  i) the variable domain has the amino acid sequence of SEQ ID NO: 19,
  ii) the constant region is a human IgG1 constant region, wherein the C-terminal lysine residue can be present or absent, and
  iii) the constant region comprises the amino acid changes L234A, L235A and P329G,
b) comprises two antibody light chains each comprising a light chain variable domain and a light chain constant domain, wherein
  i) the variable domain has the amino acid sequence of SEQ ID NO: 16,
  ii) the constant region is a human kappa light chain constant region or a human lambda light chain constant region, and
c) i) specifically binds to a polypeptide that has the amino acid sequence of SEQ ID NO: 03, and/or
  ii) does not bind to full length human tau (SEQ ID NO: 01) at 1 μg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or vi) has an $EC_{50}$ value for the human tau(pS422) fragment that has the amino acid sequence of SEQ ID NO: 03 of 6 ng/mL or less, and/or vii) has an $EC_{50}$ value for the full length human tau(pS422) that has the amino acid sequence of SEQ ID NO: 02 of 4.5 ng/mL or less, and/or viii) has an $EC_{50}$ value for aggregates of human tau (pS422) that has the amino acid sequence of SEQ ID NO: 02 of 30 ng/mL or less, and/or ix) has an $EC_{50}$ value for the human tau that has the amino acid sequence of SEQ ID NO: 01 and that has the amino acid mutation S422A of 125 ng/mL or less.

In one embodiment the antibody that specifically binds to human tau(pS422)
a) comprises two antibody heavy chains each comprising a heavy chain variable domain and a heavy chain constant region, wherein
   i) the variable domain has the amino acid sequence of SEQ ID NO: 19,
   ii) the constant region is a human IgG1 constant region, wherein the C-terminal lysine residue can be present or absent, and
   iii) the constant region comprises the amino acid changes L234A, L235A and P329G,
b) comprises two antibody light chains each comprising a light chain variable domain and a light chain constant domain, wherein
   i) the variable domain has the amino acid sequence of SEQ ID NO: 17,
   ii) the constant region is a human kappa light chain constant region or a human lambda light chain constant region, and
c) i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human tau(pS422) fragment that has the amino acid sequence of SEQ ID NO: 03 of 6 ng/mL or less, and/or
   vii) has an $EC_{50}$ value for the full length human tau(pS422) that has the amino acid sequence of SEQ ID NO: 02 of 4.5 ng/mL or less, and/or
   viii) has an $EC_{50}$ value for aggregates of human tau (pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.

In one embodiment the antibody that specifically binds to human tau(pS422)
a) comprises two antibody heavy chains each comprising a heavy chain variable domain and a heavy chain constant region, wherein
   i) the variable domain has the amino acid sequence of SEQ ID NO: 21,
   ii) the constant region is a human IgG1 constant region, wherein the C-terminal lysine residue can be present or absent, and
   iii) the constant region comprises the amino acid changes L234A, L235A and P329G,
b) comprises two antibody light chains each comprising a light chain variable domain and a light chain constant domain, wherein
   i) the variable domain has the amino acid sequence of SEQ ID NO: 17,
   ii) the constant region is a human kappa light chain constant region or a human lambda light chain constant region, and
c) i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human tau(pS422) fragment that has the amino acid sequence of SEQ ID NO: 03 of 6 ng/mL or less, and/or
   vii) has an $EC_{50}$ value for the full length human tau(pS422) that has the amino acid sequence of SEQ ID NO: 02 of 4.5 ng/mL or less, and/or
   viii) has an $EC_{50}$ value for aggregates of human tau (pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.

In one preferred embodiment of all aspects the antibody that specifically binds to human tau(pS422) has in the heavy chain variable domain at positions 4, 24 and 78 a valine residue.

In one preferred embodiment of all aspects the antibody that specifically binds to human tau(pS422) has in the heavy chain variable domain at position 71 an arginine residue.

One aspect as reported herein is a pharmaceutical formulation comprising the non-covalent complex as reported herein and a pharmaceutically acceptable carrier.

In one embodiment the pharmaceutical formulation further comprises an additional therapeutic agent.

In one embodiment the additional therapeutic agent is an anti-amyloid therapeutic agent. In one embodiment the anti-amyloid therapeutic agent is an anti-human alpha-synuclein antibody or an anti-Abeta antibody. In one embodiment the anti-human alpha-synuclein antibody or the anti-Abeta antibody is haptenylated. In one embodiment the anti-human alpha-synuclein antibody or the anti-Abeta antibody is in a complex with an anti-blood brain barrier receptor/hapten bispecific antibody.

One aspect as reported herein is the non-covalent complex as reported herein for use as a medicament.

One aspect as reported herein is the non-covalent complex as reported herein for use in treating Alzheimer's Disease.

One aspect as reported herein is the non-covalent complex as reported herein for use in treating prodromal Alzheimer's Disease.

One aspect as reported herein is the non-covalent complex as reported herein for use in treating mild Alzheimer's Disease.

One aspect as reported herein is the non-covalent complex as reported herein for use in reducing tau(pS422)-induced neurodegeneration.

One aspect as reported herein is the non-covalent complex as reported herein for use in maintaining cognition and function.

One aspect as reported herein is the non-covalent complex as reported herein for use in slowing the rate of cognitive and functional decline.

One aspect as reported herein is the use of the non-covalent complex as reported herein in the manufacture of a medicament.

In one embodiment the medicament is for treatment of Alzheimer's Disease.

In one embodiment the medicament is for treatment of prodromal Alzheimer's Disease.

In one embodiment the medicament is for treatment of mild Alzheimer's Disease.

In one embodiment the medicament is for reducing tau (pS422) induced neurodegeneration.

In one embodiment the medicament is for maintaining cognition and function.

In one embodiment the medicament is for slowing the rate of cognitive and functional decline.

One aspect as reported herein is a method of treating an individual having Alzheimer's Disease comprising administering to the individual an effective amount of the non-covalent complex as reported herein.

One aspect as reported herein is a method of reducing tau(pS422) induced neurodegeneration in an individual comprising administering to the individual an effective amount of the non-covalent complex as reported herein to reduce tau(pS422) induced neurodegeneration.

One aspect as reported herein is a method of maintaining cognition and function in an individual comprising administering to the individual an effective amount of the non-covalent complex as reported herein to maintain cognition and function.

One aspect as reported herein is a method of slowing the rate of cognitive and functional decline in an individual comprising administering to the individual an effective amount of the non-covalent complex as reported herein to slow the rate of cognitive and functional decline.

One aspect as reported herein is the use of the non-covalent complex as reported herein in the reduction of tau(pS422) induced neurodegeneration.

One aspect as reported herein is the use of the non-covalent complex as reported herein in maintaining cognition and function.

One aspect as reported herein is the use of the non-covalent complex as reported herein in slowing the rate of cognitive and functional decline.

The non-covalent complex as reported herein can be used in the treatment of Alzheimer's disease.

With the non-covalent complex as reported herein inhibition/reduction of progression of Alzheimer's disease and neuropathology can be effected.

The non-covalent complex as reported herein can be used to protect from development of Alzheimer's Disease or even used to stop the progression of Alzheimer's Disease.

In one embodiment the non-covalent complex as reported herein i) binds to tau(pS422) on brain sections of tau(pS422) transgenic mice and Alzheimer's Disease patients; and/or labels tau(pS422) in tau(pS422) transgenic cells.

One aspect as reported herein is the non-covalent complex that specifically binds to the amino acid sequence of SEQ ID NO: 03 in human tau(pS422).

The non-covalent complex as reported herein specifically bind to/recognize early and late stage disease-relevant forms of human tau(pS422).

One aspect as reported herein is the use of the non-covalent complex as reported herein for the prevention of human tau(pS422)-related Alzheimer's Disease spread.

One aspect as reported herein is the use of the non-covalent complex as reported herein for the reduction of lysosomal membrane disintegration.

One aspect as reported herein is the use of the non-covalent complex as reported herein for the stabilization of lysosome membrane against human tau(pS422) induced destabilization and/or disintegration.

One aspect as reported herein is the use of the non-covalent complex as reported herein for the prevention of Alzheimer's Disease progression.

The non-covalent complex as reported herein functions by antibody mediated inhibition of human tau(pS422) seeding and spreading between cells.

The non-covalent complex as reported herein protected lysosomes from fibrillar damage by binding to human tau (pS422).

BRIEF DESCRIPTION OF THE DRAWINGS

FIG. 1 shows sequence alignment of rabbit and humanized light chain variable domains; CDRs are enboxed.

FIG. 2 shows sequence alignment of rabbit and humanized heavy chain variable domains; CDRs are enboxed.

SEQUENCE CORRESPONDENCE TABLE

Figure 3:
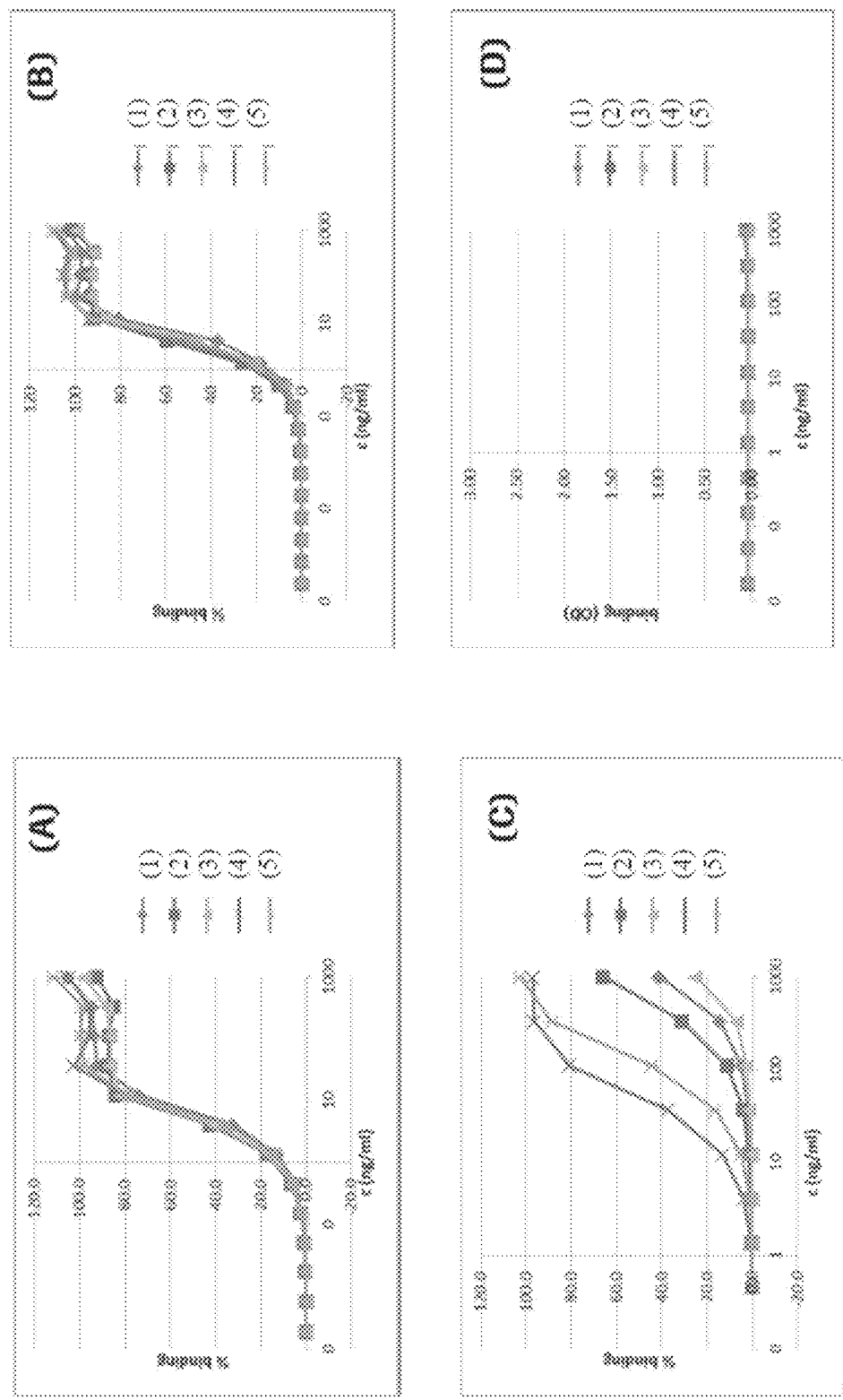
FIG. 3 shows biochemical binding of different combinations of humanized VH and VL to (A) phosphorylated tau peptide, (B) phosphorylated full-length human tau, (C) not-phosphorylated tau peptide, (D) not-phosphorylated full-length human tau; (1)=VH00/VL00, (2)=VH32/VL21, (3)=VH20/VL22, (4)=VH32/VL22, (5)=VH33/VL22; coating concentrations: phosphorylated tau peptide: 50 ng/ml, all other targets: 1 µg/ml; (comparable results are obtained if phosphorylated tau peptide is coated with 1 µg/ml (data not shown)).

| variable domain | CDR1 | CDR2 | CDR3 | complete sequence |
|---|---|---|---|---|
| VH32 | 08 | 09 | 10 | 19 |
| VH33 | 08 | 09 | 10 | 21 |

DETAILED DESCRIPTION OF THE INVENTION

I. Definitions

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype and the Kabat EU index numbering system (see pages 661-723) is used for the constant heavy chain domains (CH1, Hinge, CH2 and CH3).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-human tau(pS422) antibody" and "an antibody that specifically binds to human tau(pS422)" refer to an antibody that is capable of binding human tau(pS422) with sufficient affinity such that the antibody is useful as a diagnostic and/or therapeutic agent in targeting human tau (pS422). In one embodiment, the extent of binding of an anti-human tau(pS422) antibody to an unrelated, non-human tau(pS422) protein is less than about 10% of the binding of the antibody to human tau(p S422) as measured, e.g., by a radioimmunoassay (MA).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); CrossFabs; and multispecific antibodies formed from antibody fragments.

The term "biotin", short "BI", denotes 5-[(3aS,4S,6aR)-2-oxohexahydro-1H-thieno[3,4-d]imidazol-4-yl]pentanoic acid. Biotin is also known as vitamin H or coenzyme R.

The term "biotinylated antibody that specifically binds to human tau(pS422)" denotes a conjugated entity comprising a biotin moiety, optionally a linker and an antibody that specifically binds to human tau(pS422). The linker can be any linker, such as e.g. a peptidic linker or a chemical linker.

The term "bispecific antibody" denotes an antibody that has two different (antigen/hapten) binding specificities. In one embodiment a bispecific antibody is specific for two different antigens, i.e. a hapten and a non-hapten antigen.

The term "bromodeoxyuridine", short "BrdU", denotes 5-bromo-2'-desoxyuridine. Bromodeoxyuridine is also known as broxuridine, BudR, BrdUrd.

The term "bromodeoxyuridinylated antibody that specifically binds to human tau(pS422)" denotes a conjugated entity comprising a bromodeoxyuridine moiety, optionally a linker and an antibody that specifically binds to human tau(pS422). The linker can be any linker, such as e.g. a peptidic linker or a chemical linker.

The term "digoxigenin", short "DIG", denotes 3-[(3S,5R,8R,9S,10S,12R,13S,14S,17R)-3,12,14-trihydroxy-10,13-dimethyl-1,2,3,4,5,6,7,8,9,11,12,15,16,17-tetradecahydro-cyclopenta[a]-phenanthren-17-yl]-2H-furan-5-one (CAS number 1672-46-4). Digoxigenin (DIG) is a steroid found exclusively in the flowers and leaves of the plants *Digitalis purpurea, Digitalis orientalis* and *Digitalis lanata* (foxgloves) (Polya, G., Biochemical targets of plant bioactive compounds, CRC Press, New York (2003) p. 847).

The term "digoxigenylated antibody that specifically binds to human tau(pS422)" denotes a conjugated entity comprising a digoxigenin moiety, optionally a linker and an antibody that specifically binds to human tau(pS422). The linker can be any linker, such as e.g. a peptidic linker or a chemical linker.

The term "fluorescein", short "FLUO", denotes 6-hydroxy-9-(2-carboxyphenyl)-(3H)-xanthen-3-on, alternatively 2-(6-hydroxy-3-oxo-(3H)-xanthen-9-yl)-benzoic acid. Fluorescein is also known as resorcinolphthalein, C.I. 45350, solvent yellow 94, D & C yellow no. 7, angiofluor, Japan yellow 201, or soap yellow.

The term "fluoresceinylated antibody that specifically binds to human tau(pS422)" denotes a conjugated entity comprising a fluorescein moiety, optionally a linker and an antibody that specifically binds to human tau(pS422). The linker can be any linker, such as e.g. a peptidic linker or a chemical linker.

The term "theophylline", short "THEO", denotes 1,3-dimethyl-7H-purine-2,6-dione. Theophylline is also known as dimethylxanthine.

The term "theophyllinylated antibody that specifically binds to human tau(pS422)" denotes a conjugated entity comprising a theophylline moiety, optionally a linker and an antibody that specifically binds to human tau(pS422). The linker can be any linker, such as e.g. a peptidic linker or a chemical linker.

The term "hapten" denotes a small molecule that can elicit an immune response only when attached to a large carrier such as a protein. Exemplary haptens are aniline, o-, m-, and p-aminobenzoic acid, quinone, histamine-succinyl-glycine (HSG), hydralazine, halothane, indium-DTPA, fluorescein, biotin, digoxigenin, theophylline, bromodeoxyuridine and dinitrophenol. In one embodiment the hapten is biotin or digoxigenin or theophylline or fluorescein or bromodeoxyuridine.

The term "haptenylated antibody that specifically binds to human tau(pS422)" denotes a hapten which is (covalently) conjugated to an antibody that specifically binds to human tau(pS422). Activated hapten derivatives can be used as starting materials for the formation of such conjugates. In one embodiment the hapten is conjugated (in one embodiment via its 3-hydroxy group) to the antibody that specifically binds to human tau(pS422) via a linker. In one embodiment the linker comprises a) one or more (in one embodiment three to six) methylene-carboxy-methyl groups (—CH2-C(O)—), and/or b) from 1 to 10 (in one embodiment from 1 to 5) amino acid residues (in one embodiment selected from glycine, serine, glutamate, β-alanine, γ-aminobutyric acid, ε-aminocaproic acid or lysine), and/or c) one or more (in one embodiment one or two) compounds having the structural formula NH2-[(CH2)nO]xCH2-CH2-COOH in which n is 2 or 3 and x is 1 to 10, in one embodiment 1 to 7. The last element results (at least partly) in a linker (part) of the formula —NH—[(CH2)nO]xCH2-CH2-C(O)—. One example of such a compound is e.g. 12-amino-4,7,10-trioxadodecanoic acid (results in a TEG (triethylenglycol) linker). In one embodiment the linker further comprises a maleimido group. In addition the linker can sterically facilitate the binding of the anti-hapten antibody to the hapten of the haptenylated antibody that specifically binds to human tau(pS422). In one embodiment the linker is conjugated to a side chain of an amino acid of the antibody that specifically binds to human tau(pS422) (e.g. conjugated to a lysine or cysteine side chain via an amino or thiol group). In one embodiment the linker is conjugated to the amino terminus or the carboxy terminus of the antibody that specifically binds to human tau(pS422). The conjugation position of the linker to the antibody that specifically binds to human tau(pS422) is typically chosen to be in a region where the conjugation to the linker does not affect the biological activity of the antibody that specifically binds to human tau(pS422). Therefore the attachment position of the linker depends on the relevant structure elements which are responsible for the biological activity of the antibody that specifically binds to human tau(pS422). The biological activity of the antibody that specifically binds to human tau(pS422) to which the hapten attached can be tested before and after conjugation in an in vitro assay.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain.

However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc-region as defined herein. The term "full length antibody" denotes a multimeric polypeptide consisting of two antibody light chain polypeptides and two antibody heavy chain polypeptides linked by disulfide bonds wherein in the two antibody heavy chain polypeptides the C-terminal lysine residue (K) can be present or not.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence ("complementarity determining regions" or "CDRs") and form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs herein include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s).

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-human tau(pS422) antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "human tau(pS422)", as used herein, refers to native human tau(pS422) (UniProt P37840). The term encompasses "full-length", unprocessed human tau(pS422) as well as any form of human tau(pS422) that results from processing in the cell. The term also encompasses naturally occurring variants of human tau(pS422), e.g., mutants, splice variants or allelic variants. The amino acid sequence of human tau(pS422) is shown in SEQ ID NO: 02.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "x-valent", e.g. "mono-valent" or "bi-valent" or "tri-valent" or "tetra-valent", denotes the presence of a specified number of binding sites, i.e. "x", in an antibody molecule. As such, the terms "bivalent", "tetravalent", and "hexavalent" denote the presence of two binding site, four binding sites, and six binding sites, respectively, in an antibody molecule. Bispecific antibodies are at least "bivalent" and may be "trivalent" or "multivalent" (e.g. "tetravalent" or "hexavalent"). In one embodiment the bispecific antibody is bivalent, trivalent, or tetravalent. In one embodiment the bispecific antibody is bivalent. In one embodiment the bispecific antibody is trivalent. In one embodiment the bispecific antibody is tetravalent.

Bispecific antibodies may be bispecific even in cases where there are more than two binding sites (i.e. that the antibody is trivalent or multivalent). The term bispecific antibodies includes, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2,) are linked via one or more peptide-linkers. The antibodies can be full length from a single species, or be chimerized or humanized. For an antibody with more than two antigen binding sites, some binding sites may be identical, so long as the antibody has binding sites for two different antigens. That is, whereas a first binding site is specific for a hapten, a second binding site is specific for a non-hapten antigen, and vice versa.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S. et al., J. Immunol. 150 (1993) 880-887; Clackson, T. et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

A. Blood Brain Barrier Shuttles as Reported Herein

One part of the non-covalent complex as reported herein is a blood brain barrier-shuttle module (BBB-shuttle module) that is a bispecific antibody with a first binding specificity for a hapten and a second binding specificity for a blood brain barrier receptor (BBBR). Such a BBB-shuttle module recognizes a transcytoseable cell surface target on the blood brain barrier (such as TfR, LRPs or other targets, BBBR) and simultaneously binds to a haptenylated payload.

It has been found that no further requirements with respect to binding valency, antibody format, BBBR binding affinity have to be met.

It has further been found that it is not required that the bispecific antibody-based shuttle module as reported herein is released from the endothelial cells of the blood brain barrier in order to mediate transcytosis of the haptenylated payload. Instead, the haptenylated payload, which is complexed by/bound to the bispecific antibody-based shuttle module upon binding to the BBBR, is released from the bispecific antibody-based shuttle module within the BBB cell, i.e. in the intracellular vesicular system, is separated from the shuttle module, and subsequently is exocytosed from the BBB cell into the brain leaving the bispecific antibody behind in the BBB cell.

The bispecific antibody-based shuttle module as reported herein is very variable in terms of binding specificity valency as well as affinity of the BBBR binding specificity. Simultaneously it enables payload release from the shuttle module.

Multispecific Antibodies

A wide variety of recombinant antibody formats have been developed, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Léger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N. and Léger, O., Pathobiology 74 (2007) 3-14) or CrossFabs. It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent FV antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking. Oligomeric monoclonal antibodies with high avidity for antigen are reported in WO 1991/06305 reports that oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

In certain embodiments, an antibody provided herein or the antibody in a conjugate as reported herein is a multispecific antibody, e.g. a bispecific antibody. Multispecific antibodies are monoclonal antibodies that have binding specificities for at least two different sites. In certain embodiments, one of the binding specificities is for a hapten and the other is for any other (non-hapten) antigen. Bispecific antibodies may also be used to localize cytotoxic agents to cells. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (scFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

In one embodiment the CH3 domains of the heavy chains of the bispecific antibody are altered by the "knob-into-holes" technology which is described in detail with several examples in e.g. WO 96/027011, WO 98/050431, Ridgway J. B., et al., Protein Eng. 9 (1996) 617-621, Merchant, A. M., et al., Nat Biotechnol 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge stabilizes the heterodimers (Merchant, A. M, et al., Nature Biotech 16 (1998) 677-681, Atwell, S., et al. J. Mol. Biol. 270 (1997) 26-35) and increases the yield.

In one embodiment of all aspects the bispecific antibody is characterized in that
the CH3 domain of one heavy chain and the CH3 domain of the other heavy chain each meet at an interface which comprises an original interface between the antibody CH3 domains,
wherein said interface is altered to promote the formation of the bispecific antibody, wherein the alteration is characterized in that
a) the CH3 domain of one heavy chain is altered,
so that within the original interface the CH3 domain of one heavy chain that meets the original interface of the CH3 domain of the other heavy chain within the bispecific antibody,
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and
b) the CH3 domain of the other heavy chain is altered,
so that within the original interface of the second CH3 domain that meets the original interface of the first CH3 domain within the bispecific antibody
an amino acid residue is replaced with an amino acid residue having a smaller side chain volume, thereby generating a cavity within the interface of the second CH3 domain within which a protuberance within the interface of the first CH3 domain is positionable.

Thus, the antibodies as reported herein are in one embodiment characterized in that
the CH3 domain of the first heavy chain of the full length antibody and the CH3 domain of the second heavy chain of the full length antibody each meet at an interface which comprises an alteration in the original interface between the antibody CH3 domains,
wherein i) in the CH3 domain of the first heavy chain
an amino acid residue is replaced with an amino acid residue having a larger side chain volume, thereby generating a protuberance within the interface of the CH3 domain of one heavy chain which is positionable in a cavity within the interface of the CH3 domain of the other heavy chain
and wherein ii) in the CH3 domain of the second heavy chain
an amino acid residue is replaced with an amino acid residue having a smaller side chain volume, thereby generating a cavity within the interface of the second CH3 domain within which a protuberance within the interface of the first CH3 domain is positionable.

In one embodiment the amino acid residue having a larger side chain volume is selected from the group consisting of arginine (R), phenylalanine (F), tyrosine (Y), and tryptophan (W).

In one embodiment the amino acid residue having a smaller side chain volume is selected from the group consisting of alanine (A), serine (S), threonine (T), and valine (V).

In one embodiment both CH3 domains are further altered by the introduction of cysteine (C) as amino acid in the corresponding positions of each CH3 domain such that a disulfide bridge between both CH3 domains can be formed.

In one preferred embodiment, the multispecific antibody comprises the amino acid T366W mutation in the first CH3 domain of the "knobs chain" and the amino acid T366S, L368A, Y407V mutations in the second CH3 domain of the "hole chain". An additional interchain disulfide bridge between the CH3 domains can also be used (Merchant, A. M., et al., Nature Biotech. 16 (1998) 677-681), e.g., by introducing the amino acid Y349C mutation into the CH3 domain of the "hole chain" and the amino acid E356C mutation or the amino acid S354C mutation into the CH3 domain of the "knobs chain".

In one embodiment the bispecific antibody comprises Y349C, T366W mutations in one of the two CH3 domains and E356C, T366S, L368A, Y407V mutations in the other of the two CH3 domains. In one embodiment the bispecific antibody comprises Y349C, T366W mutations in one of the two CH3 domains and S354C, T366S, L368A, Y407V mutations in the other of the two CH3 domains (the additional Y349C mutation in one CH3 domain and the additional E356C or S354C mutation in the other CH3 domain forming a interchain disulfide bridge) (numbering according to EU index of Kabat; (Kabat, E. A., et al., Sequences of Proteins of Immunological Interest, 5th ed., Public Health Service, National Institutes of Health, Bethesda, Md. (1991))). Further knobs-in-holes technologies as described by EP 1 870 459 A1, can be used alternatively or additionally. Thus another example for the bispecific antibody are R409D, K370E mutations in the CH3 domain of the "knobs chain" and D399K, E357K mutations in the CH3 domain of the "hole chain" (numbering according to EU index of Kabat; (Kabat, E. A., et al., Sequences of Proteins of Immunological Interest, 5th ed., Public Health Service, National Institutes of Health, Bethesda, Md. (1991)).

In one embodiment the bispecific antibody comprises a T366W mutation in the CH3 domain of the "knobs chain" and T366S, L368A, Y407V mutations in the CH3 domain of the "hole chain" and additionally R409D, K370E mutations in the CH3 domain of the "knobs chain" and D399K, E357K mutations in the CH3 domain of the "hole chain".

In one embodiment the bispecific antibody comprises Y349C, T366W mutations in one of the two CH3 domains and S354C, T366S, L368A, Y407V mutations in the other of the two CH3 domains or the bispecific antibody comprises Y349C, T366W mutations in one of the two CH3 domains and S354C, T366S, L368A, Y407V mutations in the other of the two CH3 domains and additionally R409D, K370E mutations in the CH3 domain of the "knobs chain" and D399K, E357K mutations in the CH3 domain of the "hole chain". Such knob and hole mutations in the CH3 domain are typically used in human heavy chain constant regions of SEQ ID NO: 58 (human IgG1 subclass allotypes (Caucasian and Afro-American or mutants L234A/L235A, and L234A/L235A/P329G) (numbering according to the EU index of Kabat et al., Sequences of Proteins of Immunological Interest, 5th ed., Public Health Service, National Institutes of Health, Bethesda, Md. (1991).

In one embodiment the bispecific antibody comprises human heavy chain constant regions of SEQ ID NO: 58 further including such "knob" and "hole" mutations in the CH3 domain (e.g. Y349C, T366W mutations in one of the two CH3 domains and S354C, T366S, L368A, Y407V mutations in the other of the two CH3 domains) (numbering according to the EU index of Kabat et al., Sequences of Proteins of Immunological Interest, 5th ed., Public Health Service, National Institutes of Health, Bethesda, Md. (1991).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to a hapten as well as another, different antigen (see US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

In one preferred embodiment, the multispecific antibody (which comprises a CH3 domain in each heavy chain) comprises the amino acid S354C, T366W mutations in one of the two CH3 domains and the amino acid Y349C, T366S, L368A, Y407V mutations in the other of the two CH3 domains (the additional amino acid S354C mutation in one CH3 domain and the additional amino acid Y349C mutation in the other CH3 domain forming an interchain disulfide bridge) (numbering according to Kabat).

Other techniques for CH3-modifications to enforcing the heterodimerization are contemplated as alternatives and described e.g. in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment the heterodimerization approach described in EP 1 870 459 A1, is used. This approach is based on the introduction of substitutions/mutations of charged amino acids with the opposite charge at specific amino acid positions in the CH3/CH3 domain interface between both heavy chains. In one preferred embodiment the multispecific antibody comprises the amino acid R409D, K370E mutations in the CH3 domain of the first heavy chain (of the multispecific antibody) and the amino acid D399K, E357K mutations in the seconds CH3 domain of the second heavy chain (of the multispecific antibody) (numbering according to Kabat).

In another embodiment the multispecific antibody comprises the amino acid T366W mutation in the CH3 domain of the "knobs chain" and the amino acid T366S, L368A, Y407V mutations in the CH3 domain of the "hole chain" and additionally the amino acid R409D, K370E mutations in the CH3 domain of the "knobs chain" and the amino acid D399K, E357K mutations in the CH3 domain of the "hole chain".

In another embodiment the multispecific antibody comprises the amino acid S354C, T366W mutations in one of the two CH3 domains and the amino acid Y349C, T366S, L368A, Y407V mutations in the other of the two CH3 domains or the multispecific antibody comprises the amino acid Y349C, T366W mutations in one of the two CH3 domains and the amino acid S354C, T366S, L368A, Y407V mutations in the other of the two CH3 domains and additionally the amino acid R409D, K370E mutations in the CH3 domain of the "knobs chain" and the amino acid D399K, E357K mutations in the CH3 domain of the "hole chain".

In one embodiment the heterodimerization approach described in WO 2013/157953 is used. In one embodiment the first CH3 domain comprises the amino acid T366K mutation and the second CH3 domain comprises the amino acid L351D mutation. In a further embodiment the first CH3 domain further comprises the amino acid L351K mutation. In a further embodiment the second CH3 domain further comprises an amino acid mutation selected from Y349E, Y349D and L368E (preferably L368E).

In one embodiment the heterodimerization approach described in WO 2012/058768 is used. In one embodiment the first CH3 domain comprises the amino acid L351Y, Y407A mutations and the second CH3 domain comprises the amino acid T366A, K409F mutations. In a further embodiment the second CH3 domain comprises a further amino acid mutation at position T411, D399, S400, F405, N390 or K392 e.g. selected from a) T411N, T411R, T411Q, T411K, T411D, T411E or T411W, b) D399R, D399W, D399Y or D399K, c) S400E, S400D, S400R or S400K, F405I, F405M, F405T, F405S, F405V or F405W, N390R, N390K or N390D, K392V, K392M, K392R, K392L, K392F or K392E. In a further embodiment the first CH3 domain comprises the amino acid L351Y, Y407A mutations and the second CH3 domain comprises the amino acid T366V, K409F mutations. In a further embodiment the first CH3 domain comprises the amino acid Y407A mutation and the second CH3 domain comprises the amino acid T366A, K409F mutations. In a further embodiment the second CH3 domain further comprises the amino acid K392E, T411E, D399R and S400R mutations.

In one embodiment the heterodimerization approach described in WO 2011/143545 is used e.g. with the amino acid modification at a position selected from the group consisting of 368 and 409.

In one embodiment the heterodimerization approach described in WO 2011/090762 is used, which also uses the knobs-into-holes technology described above. In one embodiment the first CH3 domain comprises the amino acid T366W mutation and the second CH3 domain comprises the amino acid Y407A mutation. In one embodiment the first CH3 domain comprises the amino acid T366Y mutation and the second CH3 domain comprises the amino acid Y407T mutation.

In one embodiment the multispecific antibody is of IgG2 isotype and the heterodimerization approach described in WO 2010/129304 is used.

In one embodiment the heterodimerization approach described in WO 2009/089004 is used. In one embodiment the first CH3 domain comprises the substitution of the amino acid residue K392 or N392 with a negative-charged amino acid (e.g. glutamic acid (E), or aspartic acid (D), preferably K392D or N392D) and the second CH3 domain comprises the substitution of the amino acid residue D399, E356, D356 or E357 with a positive-charged amino acid (e.g. Lysine (K) or arginine (R), preferably D399K, E356K, D356K, or E357K and more preferably D399K and E356K). In a further embodiment the first CH3 domain further comprises substitution of the amino acid residue K409 or R409 with a negative-charged amino acid (e.g. glutamic acid (E), or aspartic acid (D), preferably K409D or R409D). In a further embodiment the first CH3 domain further or alternatively comprises substitution of the amino acid residue K439 and/or K370 with a negative-charged amino acid (e.g. glutamic acid (E), or aspartic acid (D)).

In one embodiment the heterodimerization approach described in WO 2007/147901 is used. In one embodiment the first CH3 domain comprises the amino acid K253E, D282K, and K322D mutations and the second CH3 domain comprises the amino acid D239K, E240K, and K292D mutations.

In one embodiment the heterodimerization approach described in WO 2007/110205 is used.

B. Non-Covalent Complexes as Reported Herein

The blood brain barrier shuttle as reported herein is used as an antibody that specifically binds to human tau(pS422) delivery vehicle. The antibody that specifically binds to human tau(pS422) is conjugated with the hapten and thus complexed by the hapten-binding site of the blood brain barrier shuttle. This complex is defined and stable and specifically delivers the haptenylated antibody that specifically binds to human tau(pS422) over the blood brain barrier. Since the haptenylated antibody that specifically binds to human tau(pS422) is complexed in a non-covalent manner by the blood brain barrier shuttle, the haptenylated antibody that specifically binds to human tau(pS422) is on the one hand bound to its delivery vehicle (=blood brain barrier shuttle=bispecific antibody) during its time in the circulation but can also on the other hand be efficiently released after transcytosis. The conjugation with the hapten can be effected without interfering with the activity of the antibody that specifically binds to human tau(pS422). The blood brain barrier shuttle does not contain an unusual covalent addition and therefore obviates any risk of immunogenicity. Complexes of haptenylated antibody that specifically binds to human tau(pS422) with the bispecific antibody as reported herein containing hapten-specific binding sites confer benign biophysical behavior to the antibody that specifically binds to human tau(pS422). Furthermore, such complexes are capable to target the load to cells or tissues which display the antigen that is recognized by the bispecific antibody's second binding specificity.

The antibody that specifically binds to human tau(pS422) retains its functionality despite being haptenylated, as well as while being complexed by the blood brain barrier shuttle (=bispecific antibody). In addition, the blood brain barrier receptor binding site of the bispecific antibody retains its binding specificity and affinity in the presence of complexed haptenylated antibody that specifically binds to human tau (pS422). The complexes of haptenylated antibody that specifically binds to human tau(pS422) with the bispecific antibody as reported herein can be used to target the antibody that specifically binds to human tau(pS422) specifically to cells that express the blood brain barrier receptor. Since the haptenylated antibody that specifically binds to human tau(pS422) is coupled in a non-covalent manner to the bispecific antibody the antibody that specifically binds to human tau(pS422) can be released after internalization or transcytosis.

Due to their chemical and physical properties, such as molecular weight and domain architecture including secondary modifications, the downstream processing of antibodies is very complicated. For example, not only for formulated drugs but also for intermediates in downstream processing (DSP) concentrated solutions are required to achieve low volumes for economic handling and application storage.

With increasing concentration of antibodies a tendency to form aggregates can be observed. These aggregated antibodies have impaired characteristics compared to the isolated antibody. Aggregation of the complexes as reported herein can be reduced by the introduction of disulfide bonds between the heavy and light chain variable domains of the single chain antibodies of the blood brain barrier shuttle module. This improved stability is not only useful during the production process but also for the storage of the complexes.

In one embodiment the disulfide bond between the variable domains of the single chain antibodies comprised in the bispecific antibody is independently for each single chain antibody selected from:
  i) heavy chain variable domain position 44 to light chain variable domain position 100,
  ii) heavy chain variable domain position 105 to light chain variable domain position 43, or
  iii) heavy chain variable domain position 101 to light chain variable domain position 100.

In one embodiment the disulfide bond between the variable domains of the single chain antibodies comprised in the bispecific antibody is between heavy chain variable domain position 44 and light chain variable domain position 100.

In one embodiment the disulfide bond between the variable domains of the single chain antibodies comprised in the bispecific antibody is between heavy chain variable domain position 105 and light chain variable domain position 43.

C. Exemplary Antibodies that Specifically Bind to Human Tau(pS422)

The humanized antibodies that specifically bind to human tau(pS422) of the non-covalent complex as reported herein were not available by standard humanization methods. It was required to introduce non-standard mutations in the amino acid sequence in order to obtain a humanized antibody with comparable binding characteristics as the parent rabbit antibody. This is especially important as the antibodies as reported herein are intended to cross the human blood-brain-barrier and to be effective within the human brain. Thus, the generally applied criteria for the selection of humanized antibodies are not sufficiently stringent in order to be applied directly in the current case.

It has been found that in order to obtain a suitable and developable humanized antibody two cysteines forming a disulfide-bridge in the CDRL3 (light chain CDR3) had to be replaced by serine and isoleucine, respectively. In addition to ensure proper orientation of the same CDRL3 an isoleucine residue present in the middle of the rabbit CDRL3 was deleted resulting in a humanized CDRL3 that is one amino acid residue smaller than the parent rabbit CDRL3.

Is has further been found that it is advantageous to maintain three valine amino acid residues in the heavy chain at positions 4, 24 and 78. Without being bound by this theory it is assumed that these residues are required to ensure proper presentation of the antigen binding loops of the heavy chain variable region. Additionally the presence of an arginine residue at position 71 is advantageous.

Figure 1:
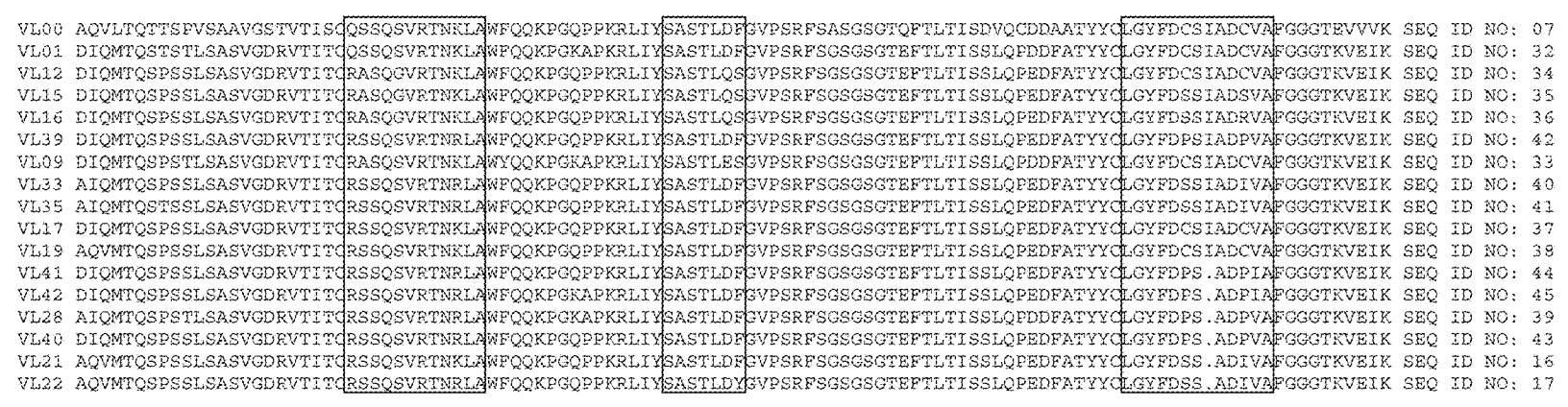

A sequence alignment of different humanized light chain variable domains is shown in FIG. 1. A sequence alignment of different humanized heavy chain variable domains is shown in FIG. 2. All numbering as used herein is based on the Kabat variable domain numbering scheme.

In the following Table characteristics of the different humanized variants of the rabbit light chain variable domain in combination with the humanized heavy chain variable domains VH14 and VH20, respectively, are shown. Binding partner was human tau(pS422).

|  | ka [1/Ms] | kd [1/s] | KD [M] | t/2 diss [min] | T [° C.] |
| --- | --- | --- | --- | --- | --- |
| VH14 with |  |  |  |  |  |
| VL00 |  | 1.04E−03 |  | 11 | 25 |
| VL01 |  | 3.82E−03 |  | 3 | 25 |
| VL09 |  | 2.35E−03. |  | 5 | 25 |
| VL12 |  | 2.48E−03 |  | 5 | 25 |
| VL15 |  | 3.63E−03 |  | 3 | 25 |
| VL16 |  | n.d. |  |  |  |
| VL17 |  | 2.39E−03 |  | 5 | 25 |
| VL17 |  | 3.03E−03 |  | 4 | 25 |
| VL19 |  | 1.98E−03 |  | 6 | 25 |
| VL21 |  | 2.93E−03 |  | 4 | 25 |
| VL22 |  | 3.30E−03 |  | 4 | 25 |
| VL28 |  | 3.84E−03 |  | 3 | 25 |
| VL33 |  | 1.02E−02 |  | 1 | 25 |
| VL35 |  | 1.10E−02 |  | 1 | 25 |
| VL39 |  | 5.22E−03 |  | 2 | 25 |
| VL40 |  | 3.01E−03 |  | 4 | 25 |
| VL41 |  | n.d. |  |  |  |
| VL42 |  | n.d. |  |  |  |
| VH20 with |  |  |  |  |  |
| VL00 |  | n.d. |  |  |  |
| VL01 |  | n.d. |  |  |  |
| VL09 |  | 2.14E−03 |  | 5 | 25 |
| VL12 |  | n.d. |  |  |  |
| VL15 |  | n.d. |  |  |  |
| VL16 |  | n.d. |  |  |  |
| VL17 |  | 5.35E−04 |  | 22 | 25 |
| VL19 |  | 3.66E−04 |  | 32 | 25 |
| VL19 | 1.94E+04 | 1.13E−03 | 5.84E−8 | 10.2 | 37 |
| VL21 |  | 7.88E−04 |  | 15 | 25 |
| VL21 | 3.03E+04 | 2.10E−03 | 6.95E−08 | 5.5 | 37 |
| VL22 |  | 8.39E−04 |  | 14 | 25 |
| VL22 | 3.44E+04 | 2.37E−03 | 6.90E−08 | 4.9 | 37 |
| VL28 |  | 1.27E−03 |  | 9 | 25 |
| VL28 | 2.50E+04 | 3.61E−03 | 1.45E−07 | 3.2 | 37 |
| VL33 |  | 1.61E−03 |  | 7 | 25 |
| VL35 |  | 1.59E−03 |  | 7 | 25 |
| VL39 |  | 1.91E−03 |  | 6 | 25 |
| VL40 |  | 9.98E−04 |  | 12 | 25 |
| VL41 |  | 4.29E−03 |  | 3 | 25 |
| VL42 |  | 4.57E−03 |  | 3 | 25 |

Reference values VH00 with VL00 (rabbit antibody):
25° C.: kd = 2.6E−04; t/2 = 44 minutes
37° C.: ka = 3.7E+04, kd = 5.25E−03, KD = 1.4E−08, t/2 = 22 minutes In the following Table characteristics of the different humanized variants of the rabbit light chain variable domain in combination with the humanized light chain variable domains VL17 and VL19, respectively, are shown.

|  | ka [1/Ms] | kd [1/s] | KD [M] | t/2 diss [min] | T [° C.] |
| --- | --- | --- | --- | --- | --- |
| VL17 with |  |  |  |  |  |
| VH00 |  | 4.98E−04 |  | 23 | 25 |
| VH01 |  | 2.3E−03 |  | 5 | 25 |
| VH02 |  | 3.71E−03 |  | 3 | 25 |
| VH03 |  | 3.93E−03 |  | 3 | 25 |
| VH04 |  | 4.16E−03 |  | 3 | 25 |
| VH14 |  | 3.0E−03 |  | 4 | 25 |
| VH15 |  | 3.26E−03 |  | 4 | 25 |
| VH18 |  | 2.3E−03 |  | 5 | 25 |
| VH19 |  | n.d. |  |  |  |
| VH20 |  | 5.4E−04 |  | 22 | 25 |
| VH22 |  | 2.0E−03 |  | 6 | 25 |
| VH23 |  | 7.0E−04 |  | 17 | 25 |
| VH24 |  | 7.9E−04 |  | 15 | 25 |
| VH31 |  | n.d. |  |  |  |
| VH32 |  | n.d. |  |  |  |
| VH33 |  | n.d. |  |  |  |
| VL19 with |  |  |  |  |  |
| VH00 |  | n.d. |  |  |  |
| VH01 |  | 1.9E−03 |  | 6 | 25 |
| VH02 |  | n.d. |  |  |  |
| VH03 |  | n.d. |  |  |  |
| VH04 |  | n.d. |  |  |  |
| VH14 |  | 2.0E−03 |  | 6 | 25 |
| VH15 |  | n.d. |  |  |  |
| VH18 |  | 1.9E−03 |  | 6 | 25 |
| VH19 |  | 2.0E−03 |  | 6 | 25 |
| VH20 |  | 3.7E−04 |  | 32 | 25 |
| VH20 | 1.94E+04 | 1.13E−03 | 5.84E−08 | 10.2 | 37 |
| VH22 |  | 2.1E−03 |  | 6 | 25 |
| VH23 |  | 5.7E−04 |  | 20 | 25 |
| VH24 |  | 6.3E−04 |  | 18 | 25 |
| VH31 |  | n.d. |  |  |  |
| VH32 |  | n.d. |  |  |  |
| VH33 |  | n.d. |  |  |  |

Reference values VH00 with VL00 (rabbit antibody):
25° C.: kd = 2.6E−04; t/2 = 44 minutes
37° C.: ka = 3.7E+04, kd = 5.25E−03, KD = 1.4E−08, t/2 = 22 minutes In the following Table the kinetic constants for different VH/VL combinations are shown.

| VH/VL combination | KD 25° C. [nM] | t/2diss 25° C. [min] | MR | KD 37° C. [nM] | t/2diss 37° C. [min] | MR |
| --- | --- | --- | --- | --- | --- | --- |
| VH00/VL00 | 8 | 54 | 0.6 | 12 | 24 | 0.8 |
| VH20/VL22 | 37 | 16 | 0.4 | 68 | 5 | 0.5 |
| VH32/VL21 | 18 | 26 | 0.5 | 32 | 9 | 0.6 |
| VH32/VL22 | 14 | 29 | 0.5 | 31 | 8 | 0.6 |
| VH33/VL22 | 20 | 25 | 0.4 | 39 | 8 | 0.5 |

Figure 4:
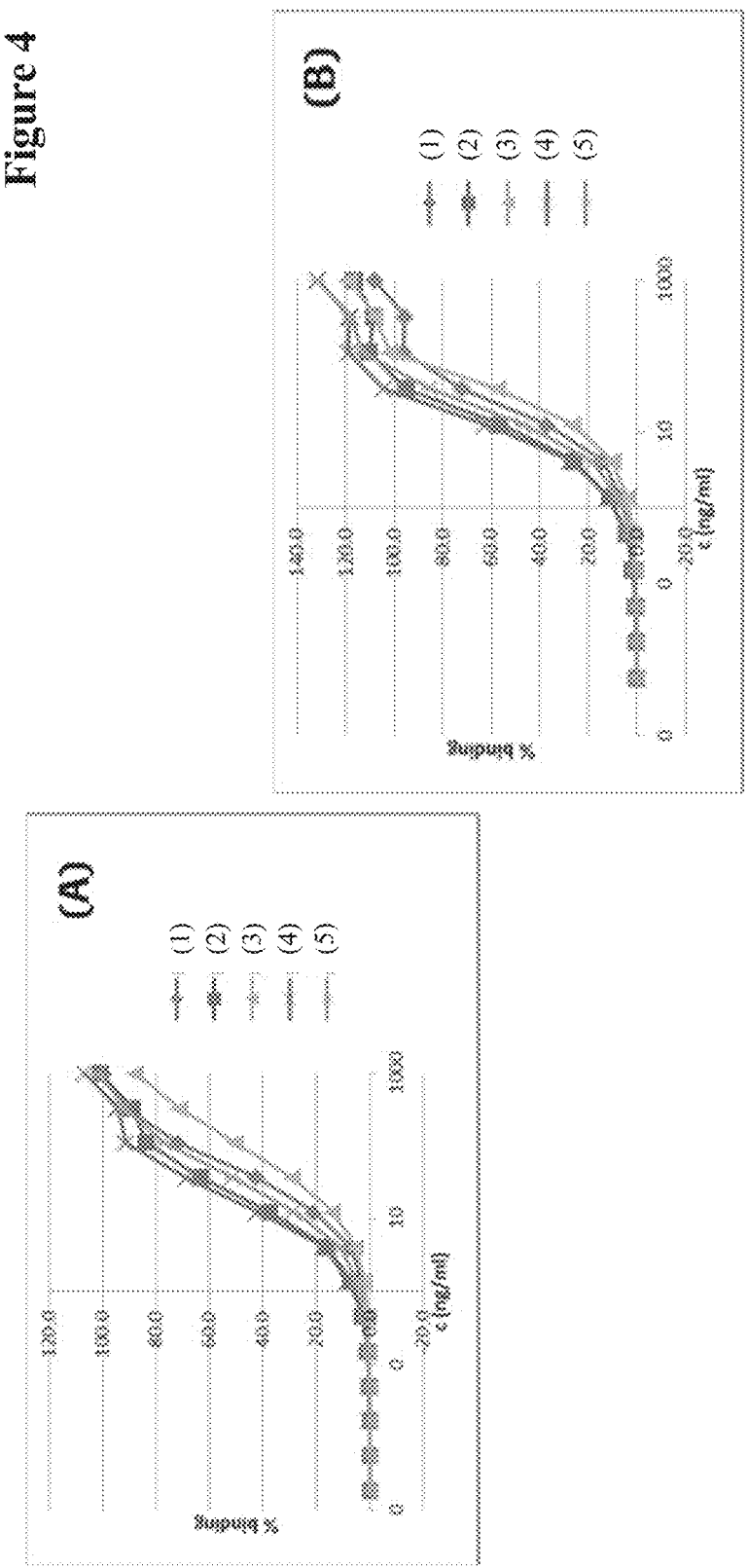
FIG. 4 shows biochemical binding of different combinations of humanized VH and VL to (A)=full length human tau S422A mutant, (B)=aggregated human Tau(pS422); (1)=VH00/VL00, (2)=VH32/VL21, (3)=VH20/VL22, (4)=VH32/VL22, (5)=VH33/VL22; coating concentrations: phosphorylated tau peptide: 50 ng/ml, all other targets: 1 µg/ml; (comparable results are obtained if phosphorylated tau peptide is coated with 1 µg/ml (data not shown)).

The biochemical binding of different combinations of humanized VH and VL is shown in FIGS. 3 and 4.

In the following Table the binding specificity for different VH/VL combinations are shown (EC50 values in [ng/ml]).

| VH/VL combination | tau(pS422) fragment SEQ ID NO: 03 | full length tau(pS422) SEQ ID NO: 02 | tau(pS422) aggregates | full length tau SEQ ID NO: 01 | tau peptide residues 416 to 430 of SEQ ID NO: 01 | micro-tubuli associated tau | S422A tau mutant S422A SEQ ID NO: 01 |
|---|---|---|---|---|---|---|---|
| VH00/VL00 | 6.3 | 5.2 | 18.1 | no binding | >1000 | no binding | 47.9 |
| VH20/VL22 | 4.8 | 4.0 | 27.2 | no binding | >1000 | no binding | 110.6 |
| VH32/VL21 | 4.4 | 2.9 | 9.4 | no binding | 634 | no binding | 21.5 |
| VH32/VL22 | 5.6 | 3.5 | 8.3 | no binding | 48 | no binding | 17.4 |
| VH33/VL22 | 5.6 | 3.8 | 13.5 | no binding | 120 | no binding | 34.5 |

Figure 5:
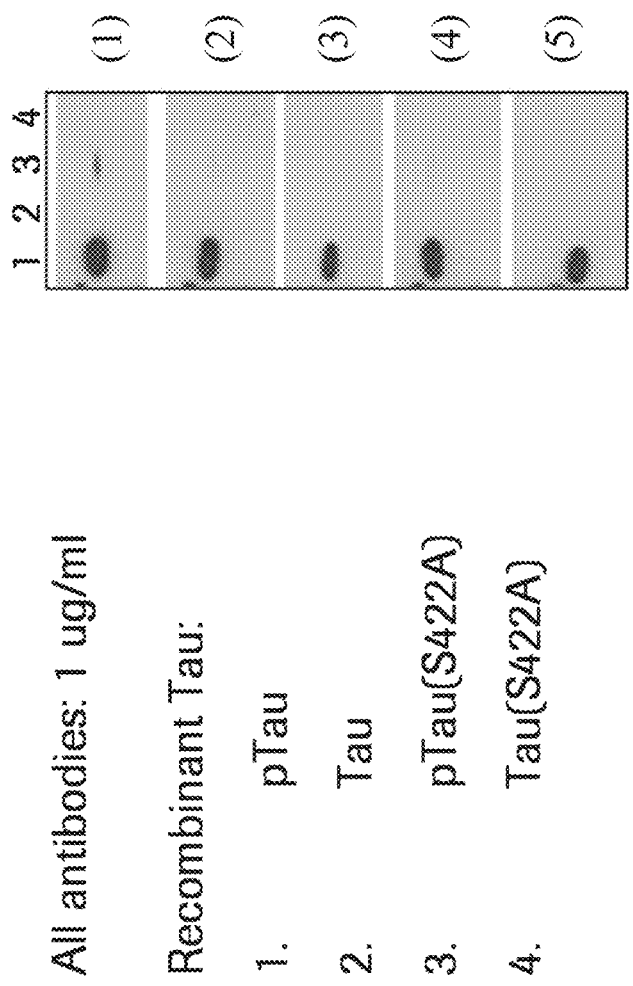
FIG. 5 is a Western Blot showing the selectivity of selected humanized VH/VL combinations; (1)=VH00/VL00, (2)=VH32/VL21, (3)=VH20/VL22, (4)=VH32/VL22, (5)=VH33/VL22.

The sensitivity of selected humanized VH/VL combinations to the human tau mutant S422A can be seen from the Western Blots shown in FIG. 5. All humanized variants selectively bind to human tau phosphorylated at S422. There is low level x-reactivity to non-S422 phosphoepitopes of the parent rabbit antibody but the humanized variants shown are less cross-reactive in this respect than the parental rabbit antibody.

Figure 6:
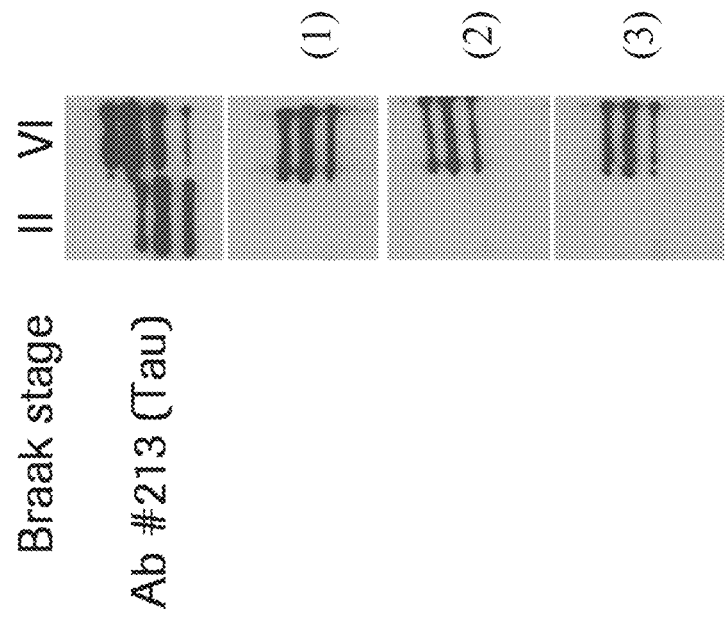
FIG. 6 shows binding to hyperphosphorylated tau in brain extracts of Alzheimer's disease patients; (1)=VH00/VL00, (2)=VH32/VL21, (3)=VH32/VL22.

In FIG. 6 the binding to PHF-tau in brain extracts of Alzheimer's disease patients for the parental rabbit antibody and for selected humanized anti-human tau(pS422) antibodies is shown.

The following table summarizes the biological properties of selected humanized VH/VL combinations.

| VH/VL combination | BIAcore | ELISA potency | ELISA specificity | WB | IHC | in vivo | developability |
|---|---|---|---|---|---|---|---|
| VH20/VL22 | 4 | + | ++ | 4 | 3 | + | ++ |
| VH32/VL21 | 2 | +(+) | + | 2 | 3 | + | ++ |
| VH32/VL22 | 1 | +(+) | + | 1 | 1 | + | ++ |
| VH33/VL22 | 3 | + | + | 3 | 2 | + | ++ |

In one embodiment the antibody that specifically binds to human tau(pS422) comprises at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 18; (c) HVR-H3 comprising the amino acid sequence of SEQ ID NO: 10; (d) HVR-L1 comprising the amino acid sequence of SEQ ID NO: 13; (e) HVR-L2 comprising the amino acid sequence of SEQ ID NO: 14; and (f) HVR-L3 comprising the amino acid sequence of SEQ ID NO: 15.

In one embodiment the antibody that specifically binds to human tau(pS422) comprises at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 12; (e) HVR-L2 comprising the amino acid sequence of SEQ ID NO: 05; and (f) HVR-L3 comprising the amino acid sequence of SEQ ID NO: 15.

In one embodiment the antibody that specifically binds to human tau(pS422) comprises at least one, or two, or three, or four, or five, or six HVRs selected from (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 13; (e) HVR-L2 comprising the amino acid sequence of SEQ ID NO: 14; and (f) HVR-L3 comprising the amino acid sequence of SEQ ID NO: 15.

In one embodiment the antibody that specifically binds to human tau(pS422) comprises at least one, at least two, or all three VH HVR sequences selected from i) (a) HVR-H1 comprising the amino acid sequence of SEQ ID NO: 08; (b) HVR-H2 comprising the amino acid sequence of SEQ ID NO: 18; and (c) HVR-H3 comprising the amino acid sequence of SEQ ID NO: 10; or ii) (a) HVR-H1 comprising the amino acid sequence of SEQ ID NO: 08; (b) HVR-H2 comprising the amino acid sequence of SEQ ID NO: 09; and (c) HVR-H3 comprising the amino acid sequence of SEQ ID NO: 10.

In one embodiment, the antibody that specifically binds to human tau(pS422) comprises i) (a) HVR-H1 comprising the amino acid sequence of SEQ ID NO: 08; (b) HVR-H2 comprising the amino acid sequence of SEQ ID NO: 18; and (c) HVR-H3 comprising the amino acid sequence of SEQ ID NO: 10; or ii) (a) HVR-H1 comprising the amino acid sequence of SEQ ID NO: 08; (b) HVR-H2 comprising the amino acid sequence of SEQ ID NO: 09; and (c) HVR-H3 comprising the amino acid sequence of SEQ ID NO: 10.

In another embodiment the antibody that specifically binds to human tau(pS422) further comprises at least one, at least two, or all three VL HVR sequences selected from i) (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15; or ii) (a) HVR-L1 comprising the amino acid sequence of SEQ ID NO: 12; (b) HVR-L2 comprising the amino acid sequence of SEQ ID NO: 05; and (c) HVR-L3 comprising the amino acid sequence of SEQ ID NO: 15.

In a further embodiment, the antibody that specifically binds to human tau(pS422) comprises i) (a) HVR-L1 comprising the amino acid sequence of SEQ ID NO: 13; (b) HVR-L2 comprising the amino acid sequence of SEQ ID NO: 14; and (c) HVR-L3 comprising the amino acid sequence of SEQ ID NO: 15; or ii) (a) HVR-L1 comprising the amino acid sequence of SEQ ID NO: 12; (b) HVR-L2 comprising the amino acid sequence of SEQ ID NO: 05; and (c) HVR-L3 comprising the amino acid sequence of SEQ ID NO: 15.

In one embodiment the antibody that specifically binds to human tau(pS422) comprises i) (a) HVR-H1 comprising the amino acid sequence of SEQ ID NO: 08; (b) HVR-H2 comprising the amino acid sequence of SEQ ID NO: 18; (c) HVR-H3 comprising the amino acid sequence of SEQ ID NO: 10; (d) HVR-L1 comprising the amino acid sequence of SEQ ID NO: 13; (e) HVR-L2 comprising the amino acid sequence of SEQ ID NO: 14; and (f) HVR-L3 comprising the amino acid sequence of SEQ ID NO: 15, or ii) (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 12; (e) HVR-L2 comprising the amino acid sequence of SEQ ID NO: 05; and (f) HVR-L3 comprising the amino acid sequence of SEQ ID NO: 15, or iii) (a) HVR-H1 comprising the amino acid sequence of SEQ ID NO: 08; (b) HVR-H2 comprising the amino acid sequence of SEQ ID NO: 09; (c) HVR-H3 comprising the amino acid sequence of SEQ ID NO: 10; (d) HVR-L1 comprising the amino acid sequence of SEQ ID NO: 13; (e) HVR-L2 comprising the amino acid sequence of SEQ ID NO: 14; and (f) HVR-L3 comprising the amino acid sequence of SEQ ID NO: 15.

In another embodiment the VH or VL of the antibody that specifically binds to human tau(pS422) contains substitutions (e.g. conservative substitutions), insertions, or deletions relative to the reference sequence, but an anti-human tau(pS422) antibody comprising that sequence retains the ability to bind to human tau(pS422).

In a further embodiment the antibody that specifically binds to human tau(pS422) is a monoclonal antibody, including a chimeric, humanized or human antibody. In one embodiment, the antibody that specifically binds to human tau(pS422) is an antibody fragment, e.g., an Fv, Fab, Fab', scFv, CrossFab, scCrossFab, diabody, or F(ab')$_2$ fragment. In another embodiment, the antibody that specifically binds to human tau(pS422) is a full length antibody, e.g., an intact IgG1 or IgG 4 antibody or other antibody class or isotype as defined herein.

In a further embodiment the antibody that specifically binds to human tau(pS422) according to any of the above embodiments may incorporate any of the features, singly or in combination, as described in Sections 1-5 below:

1. Antibody Affinity

In certain embodiments, an antibody provided herein has a dissociation constant (KD) of ≤100 nM, ≤50 nM, or between 1 nM and 100 nM (e.g., $10^{-7}$M or less, e.g., from $10^{-7}$M to $10^{-9}$M).

In one embodiment, Kd is measured by a radiolabeled antigen binding assay (MA). In one embodiment, an MA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, Y. et al., J. Mol. Biol. 293 (1999) 865-881). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta, L. G. et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at 25° C. at a flow rate of approximately 25 µl/minute. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (see, e.g., Chen, Y. et al., J. Mol. Biol. 293 (1999) 865-881). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, CrossFab, scCrossFab, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. No. 5,571,894 and U.S. Pat. No. 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J. et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. E. coli or phage), as described herein.

3. Humanized Antibodies

Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of or a full length human constant region. In some embodiments, some FR residues in a humanized antibody are substituted with corresponding residues from a non-human antibody (e.g. the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. No. 5,821,337, U.S. Pat. No. 7,527,791, U.S. Pat. No. 6,982,321, and U.S. Pat. No. 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

4. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for human tau(pS422) and the other is for any other antigen. In certain embodiments, bispecific antibodies may bind to two different epitopes of human tau(pS422). Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g., Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g., US 2006/0025576).

The antibody or fragment herein also includes a "Dual Acting Fab" or "DAF" comprising an antigen binding site that binds to human tau(pS422) as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

5. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.
a) Substitution, Insertion and Deletion Variants In certain embodiments, antibody variants having one or more amino acid substitutions are provided. Sites of interest for substitutional mutagenesis include the HVRs and FRs. Conservative substitutions are shown in the following Table under the heading of "preferred substitutions". More substantial changes are provided in the following Table under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE

| Original Residue | Exemplary Substitutions | Conservative Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized antibody). Generally, the resulting variant(s) selected for further study will have modifications (e.g. improvements) in certain biological properties (e.g. increased affinity, reduced immunogenicity) relative to the parent antibody and/or will have substantially retained certain biological properties of the parent antibody. An exemplary substitutional variant is an affinity matured antibody, which may be conveniently generated, e.g. using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g., a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g., Hellstrom, I. et al., Proc. Natl. Acad. Sci. USA 83 (1986) 7059-7063; and Hellstrom, I. et al., Proc. Natl. Acad. Sci. USA 82 (1985) 1499-1502; U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc-region mutants include Fc-region mutants with substitutions at two or more of amino acid positions 265, 269, 270, 297 and 327, including the so-called "DANA" Fc-region mutant with substitution of residues 265 and 297 to alanine (U.S. Pat. No. 7,332,581).

Certain antibody variants with improved or diminished binding to FcRs are described (see, e.g., U.S. Pat. No. 6,737,056; WO 2004/056312, and Shields, R. L. et al., J. Biol. Chem. 276 (2001) 6591-6604).

In some embodiments, alterations are made in the Fc-region that result in altered (i.e., diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc-region variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. No. 5,648,260; U.S. Pat. No. 5,624,821; and WO 94/29351 concerning other examples of Fc-region variants.

d) Cysteine Engineered Antibody Variants

In certain embodiments, it may be desirable to create cysteine engineered antibodies, e.g., "thiomAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g. glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

D. Recombinant Methods and Compositions

Antibodies may be produced using recombinant methods and compositions, e.g., as described in U.S. Pat. No. 4,816,567. In one embodiment, isolated nucleic acid encoding an anti-human tau(pS422) antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-human tau(pS422) antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-human tau(pS422) antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. No. 5,648,237, U.S. Pat. No. 5,789,199, and U.S. Pat. No. 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in E. coli.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. No. 5,959,177, U.S. Pat. No. 6,040,498, U.S. Pat. No. 6,420,548, U.S. Pat. No. 7,125,978, and U.S. Pat. No. 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TM cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR⁻ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

E. Assays

Anti-human tau(pS422) antibodies of the non-covalent complex as reported herein may be identified, screened for, or characterized for their physical/chemical properties and/or biological activities by various assays known in the art.

1. Binding Assays and Other Assays

An antibody that specifically binds to human tau(pS422) is tested for its antigen binding activity, e.g., by known methods such as ELISA, alphaLISA, Western blot, antibody or reverse phase array, etc.

In an exemplary ELISA or alphaLISA assay, tau(pS422) in solution (e.g., in cell supernatant, cell or tissue lysates, body fluids, etc.) is bound by a capture antibody, which specifically binds to a first epitope on tau(pS422), or tau(pS422) in a certain conformation and a detection antibody coupled to a detection entity, which specifically binds to a second epitope or conformation of tau(pS422). The readout is based on the detection entity (chemiluminescence, fluorescence, energy transfer induced luminescence, etc.). In some instances the same antibody can be used in the same assay as capture and detection antibody to detect aggregated forms of tau(pS422) (see e.g. Tokuda, T. et al., Neurology 75 (2010) 1766-1772).

In the case of antibody array, antibodies are spotted onto glass or nitrocellulose chips. The slides are blocked and incubated with tau(pS422) containing solution, washed to remove unbound antibodies and bound antibodies are detected with a fluorescently labeled corresponding secondary antibody. The fluorescence signal is measured by a fluorescence slide scanner. Similarly for a reverse phase array, recombinant tau(pS422), cell supernatant, cell or tissue lysates, body fluids etc. are spotted onto glass or nitrocellulose chips. The slides are blocked and individual arrays are incubated with an antibody against a specific epitope on tau(pS422). Unbound antibodies are washed off and bound antibodies are detected with a fluorescently labeled corresponding secondary antibody. The fluorescence signal is measured by a fluorescence slide scanner (Dernick, G., et al., J. Lipid Res. 52 (2011) 2323-2331).

In the example of Western blot, aggregated recombinant tau(pS422) or tau(pS422) derived, e.g., from cell supernatant, cell or tissue lysates, body fluids etc. is separated by molecular weight in SDS PAGE or native gel conditions and blotted onto a nitrocellulose or PVDF membrane. After blocking the membrane is incubated with antibodies specific to amino acid sequence or conformations of tau(pS422). Thereafter the membrane is washed to remove unbound antibody. Bound antibodies are detected by corresponding secondary antibodies coupled to detection entities for chemiluminescence or fluorescence or other means of detection. Antibodies specific to amino acid sequences of tau(pS422) will bind to tau(pS422) in various aggregated forms and hence molecular weights as long as the epitope is not masked by the aggregation. On the other hand, conformation specific antibodies will detect only certain aggregated forms of tau(pS422) revealing only bands at specific molecular weights (see, e.g., Towbin, H., et al., Proc. Natl. Acad. Sci. USA 76 (1979) 4350-4353; Burnette, W. N., Anal. Biochem. 112 (1981) 195-203).

2. Activity Assays

In one aspect, assays are provided for identifying anti-human tau(pS422) antibodies thereof having biological activity. Biological activity may include, e.g., protection from/reduction of/inhibition of tau(pS422)-induced cytotoxicity, and/or protection from/reduction of/inhibition of cell-to-cell transmission of oligomeric human tau(pS422), and/or reduction of tau(pS422)-induced caspase activity in LUHMES cells. Antibodies having such biological activity in vivo and/or in vitro are also provided.

In certain embodiments, an antibody of the invention is tested for such biological activity.

The protective biological activity can be assessed by adding conditioned medium containing secreted tau(pS422), which causes cell death on recipient neuronal cells. This toxicity can be reversed by adding protective antibodies as described herein. The toxic nature of secreted tau(pS422) has been established previously (Emmanouilidou, E., et al., J. Neurosci., 30 (2010) 6838-6851).

F. Pharmaceutical Formulations

Pharmaceutical formulations of a non-covalent complex as described herein are prepared by mixing such non-covalent complex having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US 2005/0260186 and US 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredient as necessary for the particular indication being treated, preferably those with complementary activities that do not adversely affect each other. For example, where the indication being treated is Alzheimer's disease or prodromal Alzheimer's disease, the pharmaceutical formulation may also contain one or more additional active ingredients such as donepezil, memantine, rivastigmine, galantamine, ergoloid mesylates, an anti-Abeta antibody and an anti-alpha-synuclein antibody. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the non-covalent complexes as reported herein may be used in therapeutic methods.

In one aspect, a non-covalent complex as reported herein for use as a medicament is provided. In further aspects, a non-covalent complex as reported herein for use in treating Alzheimer's Disease is provided. In certain embodiments, a non-covalent complex as reported herein for use in a method of treatment is provided. In certain embodiments, the invention provides a non-covalent complex as reported herein for use in a method of treating an individual having Alzheimer's Disease comprising administering to the individual an effective amount of the non-covalent complex. In one such embodiment, the method further comprises administering to the individual an effective amount of at least one additional therapeutic agent, e.g., as described below. In further embodiments, the invention provides a non-covalent complex for use in inhibiting tau(pS422)-induced cytotoxicity in human neurons and glia cells. In certain embodiments, the invention provides a non-covalent complex for use in a method of inhibiting tau(pS422)-induced cytotoxicity in human neurons and glia cells in an individual comprising administering to the individual an effective of the non-covalent complex to inhibit tau(pS422) induced cytotoxicity in human neurons and glia cells. An "individual" according to any of the above embodiments is preferably a human.

In a further aspect, the invention provides for the use of a non-covalent complex as reported herein in the manufacture or preparation of a medicament. In one embodiment, the medicament is for treatment of Alzheimer's Disease. In a further embodiment, the medicament is for use in a method of treating Alzheimer's Disease comprising administering to an individual having Alzheimer's Disease an effective amount of the medicament. In one such embodiment, the method further comprises administering to the individual an effective amount of at least one additional therapeutic agent. In a further embodiment, the medicament is for inhibiting tau(pS422)-induced cytotoxicity in human neurons and glia cells. In a further embodiment, the medicament is for use in a method of inhibiting tau(pS422)-induced cytotoxicity in human neurons and glia cells in an individual comprising administering to the individual an amount effective of the medicament to inhibit tau(pS422)-induced cytotoxicity in human neurons and glia cells. An "individual" according to any of the above embodiments may be a human.

In a further aspect, the invention provides a method for treating Alzheimer's Disease. In one embodiment, the method comprises administering to an individual having such Alzheimer's Disease an effective amount of a non-covalent complex as reported herein. In one such embodiment, the method further comprises administering to the individual an effective amount of at least one additional therapeutic agent. An "individual" according to any of the above embodiments may be a human.

In a further aspect, the invention provides a method for inhibiting tau(pS422) induced cytotoxicity in human neurons and glia cells in an individual. In one embodiment, the method comprises administering to the individual an effective amount of a non-covalent complex as reported herein to inhibit tau(pS422) induced cytotoxicity in human neurons and glia cells. In one embodiment, an "individual" is a human.

In a further aspect, the invention provides pharmaceutical formulations comprising any of the non-covalent complexes as reported herein, e.g., for use in any of the above therapeutic methods. In one embodiment, a pharmaceutical formulation comprises any of the non-covalent complexes as reported herein and a pharmaceutically acceptable carrier. In another embodiment, a pharmaceutical formulation comprises any of the non-covalent complexes as reported herein and at least one additional therapeutic agent.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the non-covalent complex and administration of an additional therapeutic agent occur within about one month, or within about one, two or three weeks, or within about one, two, three, four, five, or six days, of each other.

A non-covalent complex as reported herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Non-covalent complexes as reported herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The non-covalent complex need not be, but is optionally formulated with one or more agents currently used to prevent or treat the disorder in question. The effective amount of such other agents depends on the amount of non-covalent complex present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a non-covalent complex as reported herein (when used alone or in combination with one or more other additional therapeutic agents) will depend on the type of disease to be treated, the type of non-covalent complex, the severity and course of the disease, whether the non-covalent complex is administered for preventive or therapeutic purposes, previous therapy, the patient's clinical history and response to the antibody, and the discretion of the attending physician. The non-covalent complex is suitably administered to the patient at one time or over a series of treatments. Depending on the type and severity of the disease, about 1 µg/kg to 15 mg/kg (e.g. 0.5 mg/kg-10 mg/kg) of non-covalent complex can be an initial candidate dosage for administration to the patient, whether, for example, by one or more separate administrations, or by continuous infusion.

One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the non-covalent complex would be in the range from about 0.05 mg/kg to about 50 mg/kg. Thus, one or more doses of about 0.5 mg/kg, 2.0 mg/kg, 4.0 mg/kg, 15 mg/kg, 25 mg/mg or 50 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to a non-covalent complex.

III. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-human tau(pS422) antibody.

IV. Specific Embodiments

1. A non-covalent complex of a haptenylated antibody that specifically binds to human tau(pS422) and an anti-blood brain barrier receptor/hapten bispecific antibody.

2. A non-covalent complex comprising a haptenylated antibody that specifically binds to human tau(pS422) and a bispecific antibody, which has a first binding specificity that specifically binds to the hapten of the haptenylated antibody that specifically binds to human tau(pS422) and a second binding specificity that specifically binds to a blood brain barrier receptor, wherein the haptenylated antibody that specifically binds to human tau(pS422) is specifically bound by the first binding specificity of the bispecific antibody.

3. The non-covalent complex according to any one of embodiments 1 to 2, wherein the haptenylated antibody that specifically binds to human tau(pS422) is selected from the group consisting of the biotinylated antibody that specifically binds to human tau(pS422), the theophyllinylated antibody that specifically binds to human tau (pS422), the digoxigenylated antibody that specifically binds to human tau(pS422), the carboranylated antibody that specifically binds to human tau(pS422), the fluoresceinylated antibody that specifically binds to human tau (pS422), the helicarylated antibody that specifically binds to human tau(pS422) and the bromodeoxyuridinylated antibody that specifically binds to human tau(pS422).

4. The non-covalent complex according to any one of embodiments 1 to 3, wherein the blood brain barrier receptor is selected from the group consisting of the transferrin receptor (TfR), the insulin receptor, the insulin-like growth factor receptor (IGF receptor), the low density lipoprotein receptor-related protein 8 (LRP8), the low density lipoprotein receptor-related protein 1 (LRP1), and the heparin-binding epidermal growth factor-like growth factor (HB-EGF).

5. The non-covalent complex according to any one of embodiments 1 to 4, wherein the bispecific antibody is a full length antibody comprising two binding sites.

6. The non-covalent complex according to any one of embodiments 1 to 5, wherein the bispecific antibody is a full length antibody to which one or two scFvs or scFabs or CrossFabs or scCrossFabs have been fused and that comprises three or four binding sites.

7. The non-covalent complex according to any one of embodiments 1 to 6, wherein the bispecific antibody is selected from an antibody fragment, F(ab')2 and diabodies.

8. The non-covalent complex according to any one of embodiments 1 to 7, wherein the bispecific antibody is a humanized or a human antibody.

9. The non-covalent complex according to any one of embodiments 1 to 8, wherein the bispecific antibody is free of effector function.

10. The non-covalent complex according to any one of embodiments 1 to 9, wherein embodiment the bispecific antibody has no functional Fc-region.

11. The non-covalent complex according to any one of embodiments 1 to 10, wherein the bispecific antibody has no Fc-region.

12. The non-covalent complex according to any one of embodiments 1 to 12, wherein the bispecific antibody has an Fc-region of the human IgG1 subclass with the mutations L234A, L235A and P329G, wherein the positions are determined according to the Fc-region numbering of Kabat (Kabat EU index).

13. The non-covalent complex according to any one of embodiments 1 to 12, wherein the bispecific antibody has an Fc-region of the human IgG4 subclass with the mutations S228P, L235E and P329G, wherein the positions are determined according to the Fc-region numbering of Kabat (Kabat EU index).

14. The non-covalent complex according to any one of embodiments 1 to 13, wherein the bispecific antibody comprises
   a) one binding site for the hapten of the haptenylated antibody that specifically binds to human tau(pS422) and one binding site for the blood brain barrier receptor, or
   b) two binding sites for the hapten of the haptenylated antibody that specifically binds to human tau(pS422) and one binding site for the blood brain barrier receptor, or
   c) one binding site for the hapten of haptenylated antibody that specifically binds to human tau(pS422) and two binding sites for the blood brain barrier receptor, or
   d) two binding sites for the hapten of the haptenylated antibody that specifically binds to human tau(pS422) and two binding sites for the blood brain barrier receptor, wherein in cases b) and c) one heavy chain of the bispecific antibody comprises a hole mutation and the respective other chain comprises a knob mutation.

15. The non-covalent complex according to any one of embodiments 1 to 14, wherein the bispecific antibody comprises two binding sites for the hapten of the haptenylated antibody that specifically binds to human tau (pS422) and two binding sites for the blood brain barrier receptor.

16. The non-covalent complex according to any one of embodiments 1 to 15, wherein the bispecific antibody has two binding specificities that specifically bind to the hapten of the haptenylated antibody that specifically binds to human tau(pS422) (two anti-hapten binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

17. The non-covalent complex according to any one of embodiments 1 to 16, wherein the binding specificity that specifically binds to the digoxigenin of the digoxigenylated antibody that specifically binds to human tau (pS422) is a pair of an antibody heavy chain variable domain and an antibody light chain variable domain comprising (a) a heavy chain CDR1 comprising the amino acid sequence of SEQ ID NO: 65, (b) a heavy chain CDR2 comprising the amino acid sequence of SEQ ID NO: 66, (c) a heavy chain CDR3 comprising the amino acid sequence of SEQ ID NO: 67, (d) a light chain CDR1 comprising the amino acid sequence of SEQ ID NO: 69, (e) a light chain CDR2 comprising the amino acid sequence of SEQ ID NO: 70, and (f) a light chain CDR3 comprising the amino acid sequence of SEQ ID NO: 71.

18. The non-covalent complex according to any one of embodiments 1 to 17, wherein the binding specificity that specifically binds to the digoxigenin of the digoxigenylated antibody that specifically binds to human tau (pS422) is a humanized binding specificity.

19. The non-covalent complex according to any one of embodiments 1 to 18, wherein the binding specificity that specifically binds to the digoxigenin of the digoxigenylated antibody that specifically binds to human tau (pS422) comprises CDRs as in embodiment 17 and an acceptor human framework (e.g. a human immunoglobulin framework or a human consensus framework).

20. The non-covalent complex according to any one of embodiments 1 to 19, wherein the binding specificity that specifically binds to the digoxigenin of the digoxigenylated antibody that specifically binds to human tau (pS422) is a pair of an antibody heavy chain variable domain and an antibody light chain variable domain comprising (a) a heavy chain CDR1 comprising the amino acid sequence of SEQ ID NO: 73, (b) a heavy chain CDR2 comprising the amino acid sequence of SEQ ID NO: 74, (c) a heavy chain CDR3 comprising the amino acid sequence of SEQ ID NO: 75, (d) a light chain CDR1 comprising the amino acid sequence of SEQ ID NO: 77, (e) a light chain CDR2 comprising the amino acid sequence of SEQ ID NO: 78, and (f) a light chain CDR3 comprising the amino acid sequence of SEQ ID NO: 79.

21. The non-covalent complex according to any one of embodiments 1 to 20, wherein the binding specificity that specifically binds to the digoxigenin of the digoxigenylated antibody that specifically binds to human tau (pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 68 or 76.

22. The non-covalent complex according to any one of embodiments 1 to 21, wherein, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin. In certain embodiments, a total of 1 to 10 amino acids have been substituted, inserted and/or deleted in SEQ ID NO: 68 or 76.

23. The non-covalent complex according to any one of embodiments 1 to 22, wherein, substitutions, insertions, or deletions occur in regions outside the CDRs (i.e., in the FRs).

24. The non-covalent complex according to any one of embodiments 1 to 23, wherein the digoxigenin binding specificity comprises the VH sequence in SEQ ID NO: 68 or 76, including post-translational modifications of that sequence.

25. The non-covalent complex according to any one of embodiments 1 to 24, wherein the binding specificity that specifically binds to the digoxigenin of the digoxigenylated antibody that specifically binds to human tau (pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 72 or 80.

26. The non-covalent complex according to any one of embodiments 1 to 25, wherein, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin. In certain embodiments, a total of 1 to 10 amino acids have been substituted, inserted and/or deleted in SEQ ID NO: 72 or 80.

27. The non-covalent complex according to any one of embodiments 1 to 26, wherein, the substitutions, insertions, or deletions occur in regions outside the CDRs (i.e., in the FRs).

28. The non-covalent complex according to any one of embodiments 1 to 27, wherein the digoxigenin binding specificity comprises the VL sequence in SEQ ID NO: 72 or 80, including post-translational modifications of that sequence.

29. The non-covalent complex according to any one of embodiments 1 to 16, wherein the bispecific antibody comprises a first binding specificity that specifically binds to the biotin of the biotinylated antibody that specifically binds to human tau(pS422) (anti-biotin binding specificity; anti-BI binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

30. The non-covalent complex according to any one of embodiments 1 to 16 and 29, wherein the bispecific antibody has two binding specificities that specifically bind to the biotinylated payload (two anti-biotin binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

31. The non-covalent complex according to any one of embodiments 1 to 16 and 29 to 30, wherein the binding specificity that specifically binds to the biotin of the biotinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 81, (b) a heavy chain CDR2 comprising the amino acid sequence of SEQ ID NO: 82, (c) a heavy chain CDR3 comprising the amino acid sequence of SEQ ID NO: 83, (d) a light chain CDR1 comprising the amino acid sequence of SEQ ID NO: 85, (e) a light chain CDR2 comprising the amino acid sequence of SEQ ID NO: 86, and (f) a light chain CDR3 comprising the amino acid sequence of SEQ ID NO: 87.

32. The non-covalent complex according to any one of embodiments 1 to 16 and 29 to 31, wherein the binding specificity that specifically binds to the biotin of the biotinylated antibody that specifically binds to human tau(pS422) is a humanized binding specificity.

33. The non-covalent complex according to any one of embodiments 1 to 16 and 29 to 32, wherein the binding specificity that specifically binds to the biotin of the biotinylated antibody that specifically binds to human tau(pS422) comprises CDRs as in the embodiment 31 and an acceptor human framework (e.g., a human immunoglobulin framework or a human consensus framework).

34. The non-covalent complex according to any one of embodiments 1 to 16 and 29 to 33, wherein the binding specificity that specifically binds to the biotin in the biotinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 89, (b) a heavy chain CDR2 comprising the amino acid sequence of SEQ ID NO: 90, (c) a heavy chain CDR3 comprising the amino acid sequence of SEQ ID NO: 91, (d) a light chain CDR1 comprising the amino acid sequence of SEQ ID NO: 93, (e) a light chain CDR2 comprising the amino acid sequence of SEQ ID NO: 94, and (f) a light chain CDR3 comprising the amino acid sequence of SEQ ID NO: 95.

35. The non-covalent complex according to any one of embodiments 1 to 16 and 29 to 34, wherein the binding specificity that specifically binds to the biotin of the biotinylated antibody that specifically binds to human tau(pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 84 or 92.

36. The non-covalent complex according to any one of embodiments 1 to 16 and 29 to 35, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin.

37. The non-covalent complex according to any one of embodiments 1 to 16 and 29 to 36, wherein a total of 1 to 10 amino acids have been substituted, inserted and/or deleted in SEQ ID NO: 84 or 92.

38. The non-covalent complex according to any one of embodiments 1 to 16 and 29 to 37, wherein substitutions, insertions, or deletions occur in regions outside the CDRs (i.e., in the FRs).

39. The non-covalent complex according to any one of embodiments 1 to 16 and 29 to 38, wherein the biotin binding specificity comprises the VH sequence in SEQ ID NO: 84 or 92, including post-translational modifications of that sequence.

40. The non-covalent complex according to any one of embodiments 1 to 16 and 29 to 39, wherein the binding specificity that specifically binds to the biotin of the biotinylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 88 or 96.

41. The non-covalent complex according to any one of embodiments 1 to 16 and 29 to 40, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin.

42. The non-covalent complex according to any one of embodiments 1 to 16 and 29 to 41, wherein a total of 1 to 10 amino acids have been substituted, inserted and/or deleted in SEQ ID NO: 88 or 96.

43. The non-covalent complex according to any one of embodiments 1 to 16 and 29 to 42, wherein the substitutions, insertions, or deletions occur in regions outside the CDRs (i.e., in the FRs).

44. The non-covalent complex according to any one of embodiments 1 to 16 and 29 to 43, wherein the biotin binding specificity comprises the VL sequence in SEQ ID NO: 88 or 96, including post-translational modifications of that sequence.

45. The non-covalent complex according to any one of embodiments 1 to 16, wherein the bispecific antibody comprises a first binding specificity that specifically binds to a theophyllinylated payload (anti-theophylline binding specificity; anti-THEO binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

46. The non-covalent complex according to any one of embodiments 1 to 16 and 45, wherein the bispecific antibody has two binding specificities that specifically bind to the theophyllinylated payload (two anti-theophylline binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

47. The non-covalent complex according to any one of embodiments 1 to 16 and 45 to 46, wherein the binding specificity that specifically binds the theophylline of the theophyllinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 97, (b) a heavy chain CDR2 comprising the amino acid sequence of SEQ ID NO: 98, (c) a heavy chain CDR3 comprising the amino acid sequence of SEQ ID NO: 99, (d) a light chain CDR1 comprising the amino acid sequence of SEQ ID NO: 101, (e) a light chain CDR2 comprising the amino acid sequence of SEQ ID NO: 102, and (f) a light chain CDR3 comprising the amino acid sequence of SEQ ID NO: 103.

48. The non-covalent complex according to any one of embodiments 1 to 16 and 45 to 47, wherein the binding specificity that specifically binds to the theophylline of the theophyllinylated antibody that specifically binds to human tau(pS422) is a humanized binding specificity.

49. The non-covalent complex according to any one of embodiments 1 to 16 and 45 to 48, wherein the binding specificity that specifically binds to the theophylline of the theophyllinylated antibody that specifically binds to human tau(pS422) comprises CDRs as in the embodiment 47 and an acceptor human framework (e.g., a human immunoglobulin framework or a human consensus framework).

50. The non-covalent complex according to any one of embodiments 1 to 16 and 45 to 49, wherein the binding specificity that specifically binds to the theophylline of the theophyllinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 105, (b) a heavy chain CDR2 comprising the amino acid sequence of SEQ ID NO: 106, (c) a heavy chain CDR3 comprising the amino acid sequence of SEQ ID NO: 107, (d) a light chain CDR1 comprising the amino acid sequence of SEQ ID NO: 109, (e) a light chain CDR2 comprising the amino acid sequence of SEQ ID NO: 110, and (f) a light chain CDR3 comprising the amino acid sequence of SEQ ID NO: 111.

51. The non-covalent complex according to any one of embodiments 1 to 16 and 45 to 50, wherein the binding specificity that specifically binds to the theophylline of the theophyllinylated antibody that specifically binds to human tau(pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 100 or 108.

52. The non-covalent complex according to any one of embodiments 1 to 16 and 45 to 51, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline.

53. The non-covalent complex according to any one of embodiments 1 to 16 and 45 to 52, wherein a total of 1 to 10 amino acids have been substituted, inserted and/or deleted in SEQ ID NO: 100 or 108.

54. The non-covalent complex according to any one of embodiments 1 to 16 and 45 to 53, wherein substitutions, insertions, or deletions occur in regions outside the CDRs (i.e., in the FRs).

55. The non-covalent complex according to any one of embodiments 1 to 16 and 45 to 54, wherein the theophylline binding specificity comprises the VH sequence in SEQ ID NO: 100 or 108 including post-translational modifications of that sequence.

56. The non-covalent complex according to any one of embodiments 1 to 16 and 45 to 55, wherein the binding specificity that specifically binds to the theophylline of the theophyllinylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 104 or 112.

57. The non-covalent complex according to any one of embodiments 1 to 16 and 45 to 56, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline.

58. The non-covalent complex according to any one of embodiments 1 to 16 and 45 to 57, wherein a total of 1 to 10 amino acids have been substituted, inserted and/or deleted in SEQ ID NO: 104 or 112.

59. The non-covalent complex according to any one of embodiments 1 to 16 and 45 to 58, wherein the substitutions, insertions, or deletions occur in regions outside the CDRs (i.e., in the FRs).

60. The non-covalent complex according to any one of embodiments 1 to 16 and 45 to 59, wherein the theophylline binding specificity comprises the VL sequence in SEQ ID NO: 104 or 112, including post-translational modifications of that sequence.

61. The non-covalent complex according to any one of embodiments 1 to 16, wherein the bispecific antibody comprises a first binding specificity that specifically binds to a fluoresceinylated payload (anti-fluorescein binding specificity; anti-FLUO binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

62. The non-covalent complex according to any one of embodiments 1 to 16 and 61, wherein the bispecific antibody has two binding specificities that specifically bind to the fluoresceinylated payload (two anti-fluorescein binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

63. The non-covalent complex according to any one of embodiments 1 to 16 and 61 to 62, wherein the binding specificity that specifically binds to the fluorescein of the fluoresceinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 113, (b) a heavy chain CDR2 comprising the amino acid sequence of SEQ ID NO: 114, (c) a heavy chain CDR3 comprising the amino acid sequence of SEQ ID NO: 115, (d) a light chain CDR1 comprising the amino acid sequence of SEQ ID NO: 117, (e) a light chain CDR2 comprising the amino acid sequence of SEQ ID NO: 118, and (f) a light chain CDR3 comprising the amino acid sequence of SEQ ID NO: 119.

64. The non-covalent complex according to any one of embodiments 1 to 16 and 61 to 63, wherein the binding specificity that specifically binds to the fluorescein of the fluoresceinylated antibody that specifically binds to human tau(pS422) is a humanized binding specificity.

65. The non-covalent complex according to any one of embodiments 1 to 16 and 61 to 64, wherein the binding specificity that specifically binds to the fluorescein of the fluoresceinylated antibody that specifically binds to human tau(pS422) comprises CDRs as in embodiment 63 and an acceptor human framework (e.g. a human immunoglobulin framework or a human consensus framework).

66. The non-covalent complex according to any one of embodiments 1 to 16 and 61 to 65, wherein the binding specificity that specifically binds to the fluorescein of the fluoresceinylated antibody that specifically binds to human tau(pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 116.

67. The non-covalent complex according to any one of embodiments 1 to 16 and 61 to 66, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein.

68. The non-covalent complex according to any one of embodiments 1 to 16 and 61 to 67, wherein a total of 1 to 10 amino acids have been substituted, inserted and/or deleted in SEQ ID NO: 116.

69. The non-covalent complex according to any one of embodiments 1 to 16 and 61 to 68, wherein substitutions, insertions, or deletions occur in regions outside the CDRs (i.e., in the FRs).

70. The non-covalent complex according to any one of embodiments 1 to 16 and 61 to 69, wherein the fluorescein binding specificity comprises the VH sequence in SEQ ID NO: 116, including post-translational modifications of that sequence.

71. The non-covalent complex according to any one of embodiments 1 to 16 and 61 to 70, wherein the binding specificity that specifically binds to the fluorescein of the fluoresceinylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 120.

72. The non-covalent complex according to any one of embodiments 1 to 16 and 61 to 71, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein.

73. The non-covalent complex according to any one of embodiments 1 to 16 and 61 to 72, wherein a total of 1 to 10 amino acids have been substituted, inserted and/or deleted in SEQ ID NO: 120.

74. The non-covalent complex according to any one of embodiments 1 to 16 and 61 to 73, wherein the substitutions, insertions, or deletions occur in regions outside the CDRs (i.e., in the FRs).

75. The non-covalent complex according to any one of embodiments 1 to 16 and 61 to 74, wherein the fluorescein binding specificity comprises the VL sequence in SEQ ID NO: 120, including post-translational modifications of that sequence.

76. The non-covalent complex according to any one of embodiments 1 to 16, wherein the bispecific antibody comprises a first binding specificity that specifically binds to a bromodeoxyuridinylated payload (anti-bromodeoxyuridine binding specificity; anti-BrdU binding specificity) and a second binding specificity that specifically binds to the (human) transferrin receptor (anti-(human) transferrin receptor binding specificity; anti-(h)TfR binding specificity) or to low density lipoprotein receptor-related protein 8 (anti-low density lipoprotein receptor-related protein 8 binding specificity; anti-LRP8 binding specificity).

77. The non-covalent complex according to any one of embodiments 1 to 16 and 76, wherein the bispecific antibody has two binding specificities that specifically bind to the bromodeoxyuridinylated payload (two anti-bromodeoxyuridine binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

78. The non-covalent complex according to any one of embodiments 1 to 16 and 76 to 77, wherein the binding specificity that specifically binds to the bromodeoxyuridine of the bromodeoxyuridinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 121, (b) a heavy chain CDR2 comprising the amino acid sequence of SEQ ID NO: 123, (c) a heavy chain CDR3 comprising the amino acid sequence of SEQ ID NO: 125, (d) a light chain CDR1 comprising the amino acid sequence of SEQ ID NO: 126, (e) a light chain CDR2 comprising the amino acid sequence of SEQ ID NO: 127, and (f) a light chain CDR3 comprising the amino acid sequence of SEQ ID NO: 128.

79. The non-covalent complex according to any one of embodiments 1 to 16 and 76 to 78, wherein the binding specificity that specifically binds to the bromodeoxyuridine of the bromodeoxyuridinylated antibody that specifically binds to human tau(pS422) is a humanized binding specificity.

80. The non-covalent complex according to any one of embodiments 1 to 16 and 76 to 79, wherein the binding specificity that specifically binds to the bromodeoxyuridine of the bromodeoxyuridinylated antibody that specifically binds to human tau(pS422) comprises CDRs as in the above embodiment and an acceptor human framework (e.g. a human immunoglobulin framework or a human consensus framework).

81. The non-covalent complex according to any one of embodiments 1 to 16 and 76 to 80, wherein the binding specificity that specifically binds to the bromodeoxyuridine of the bromodeoxyuridinylated antibody that specifically binds to human tau(pS422) is a pair of an antibody heavy chain variable domain and an antibody light chain variable domain comprising (a) a heavy chain CDR1 comprising the amino acid sequence of SEQ ID NO: 121 or 122, (b) a heavy chain CDR2 comprising the amino acid sequence of SEQ ID NO: 123 or 124, (c) a heavy chain CDR3 comprising the amino acid sequence of SEQ ID NO: 125, (d) a light chain CDR1 comprising the amino acid sequence of SEQ ID NO: 126, (e) a light chain CDR2 comprising the amino acid sequence of SEQ ID NO: 127, and (f) a light chain CDR3 comprising the amino acid sequence of SEQ ID NO: 128.

82. The non-covalent complex according to any one of embodiments 1 to 16 and 76 to 81, wherein the binding specificity that specifically binds to the bromodeoxyuridine of the bromodeoxyuridinylated antibody that specifically binds to human tau(pS422) is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 129 or 131.

83. The non-covalent complex according to any one of embodiments 1 to 16 and 76 to 82, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine.

84. The non-covalent complex according to any one of embodiments 1 to 16 and 76 to 83, wherein a total of 1 to 10 amino acids have been substituted, inserted and/or deleted in SEQ ID NO: 129 or 131.

85. The non-covalent complex according to any one of embodiments 1 to 16 and 76 to 84, wherein substitutions, insertions, or deletions occur in regions outside the CDRs (i.e., in the FRs).

86. The non-covalent complex according to any one of embodiments 1 to 16 and 76 to 85, wherein the bromodeoxyuridine binding specificity comprises the VH sequence in SEQ ID NO: 129 or 131, including post-translational modifications of that sequence.

87. The non-covalent complex according to any one of embodiments 1 to 16 and 76 to 86, wherein the binding specificity that specifically binds to the bromodeoxyuridine of the bromodeoxyuridinylated antibody that specifically binds to human tau(pS422) is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 130 or 132.

88. The non-covalent complex according to any one of embodiments 1 to 16 and 76 to 87, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine.

89. The non-covalent complex according to any one of embodiments 1 to 16 and 76 to 88, wherein a total of 1 to 10 amino acids have been substituted, inserted and/or deleted in SEQ ID NO: 130 or 132.

90. The non-covalent complex according to any one of embodiments 1 to 16 and 76 to 89, wherein the substitutions, insertions, or deletions occur in regions outside the CDRs (i.e., in the FRs).

91. The non-covalent complex according to any one of embodiments 1 to 16 and 76 to 90, wherein the bromodeoxyuridine binding specificity comprises the VL sequence in SEQ ID NO: 130 or 132, including post-translational modifications of that sequence.

92. The non-covalent complex according to any one of embodiments 1 to 91, wherein the haptenylated antibody that specifically binds to human tau(pS422) comprises between the hapten and the antibody that specifically binds to human tau(pS422) a linker.

93. The non-covalent complex according to embodiment 92, wherein the linker is a peptidic linker.

94. The non-covalent complex according to embodiment 92, wherein the linker is a chemical linker (non-peptidic linker).

95. The non-covalent complex according to any one of embodiments 1 to 94, wherein the antibody that specifically binds to human tau(pS422) is a full length antibody.

96. The non-covalent complex according to any one of embodiments 1 to 95, wherein the antibody that specifically binds to human tau(pS422)
   i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or v) specifically binds to human tau that has the amino acid sequence of SEQ ID NO: 01 and that has the amino acid mutation S422A.
97. The non-covalent complex according to any one of embodiments 1 to 96, wherein the antibody that specifically binds to human tau(pS422) comprises
   a) in the heavy chain variable domain the HVRs of SEQ ID NO: 08, 18 and 10, or
   b) in the heavy chain variable domain the HVRs of SEQ ID NO: 08, 09 and 10.
98. The non-covalent complex according to any one of embodiments 1 to 97, wherein the antibody that specifically binds to human tau(pS422) further comprises
   a) in the light chain variable domain the HVRs of SEQ ID NO: 13, 14 and 15, or
   b) in the light chain variable domain the HVRs of SEQ ID NO: 12, 05 and 15.
99. The non-covalent complex according to any one of embodiments 1 to 98, wherein the antibody that specifically binds to human tau(pS422) comprises
   a) in the heavy chain variable domain the HVRs of SEQ ID NO: 08, 18 and 10, and in the light chain variable domain the HVRs of SEQ ID NO: 13, 14 and 15, or
   b) in the heavy chain variable domain the HVRs of SEQ ID NO: 08, 09 and 10, and in the light chain variable domain the HVRs of SEQ ID NO: 12, 05 and 15, or
   c) in the heavy chain variable domain the HVRs of SEQ ID NO: 08, 09 and 10, and in the light chain variable domain the HVRs of SEQ ID NO: 13, 14 and 15.
100. The non-covalent complex according to any one of embodiments 1 to 99, wherein the antibody that specifically binds to human tau(pS422) comprises
   a) a heavy chain variable domain of SEQ ID NO: 20 and a light chain variable domain of SEQ ID NO: 17, or
   b) a heavy chain variable domain of SEQ ID NO: 19 and a light chain variable domain of SEQ ID NO: 16, or
   c) a heavy chain variable domain of SEQ ID NO: 19 and a light chain variable domain of SEQ ID NO: 17, or
   d) a heavy chain variable domain of SEQ ID NO: 21 and a light chain variable domain of SEQ ID NO: 17.
101. The non-covalent complex according to any one of embodiments 1 to 100, wherein the non-covalent complex is for use in the treatment of Alzheimer's Disease.
102. The non-covalent complex according to any one of embodiments 1 to 101, wherein both antibodies in the complex are effector function silent.
103. The non-covalent complex according to any one of embodiments 1 to 102, wherein both antibodies of the complex have no effector function.
104. The non-covalent complex according to any one of embodiments 1 to 103, wherein the antibody that specifically binds to human tau(pS422)
   i) specifically binds to a polypeptide that has the amino acid sequence of SEQ ID NO: 03, and/or
   ii) does not bind to full length human tau (SEQ ID NO: 01) at 1 μg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02).
105. The non-covalent complex according to any one of embodiments 1 to 104, wherein the antibody that specifically binds to human tau(pS422) has an $EC_{50}$ value for
   a) the human tau(pS422) fragment that has the amino acid sequence of SEQ ID NO: 03 of 6 ng/mL or less, and/or
   b) the full length human tau(pS422) that has the amino acid sequence of SEQ ID NO: 02 of 4.5 ng/mL or less, and/or
   c) aggregates of human tau(pS422) that has the amino acid sequence of SEQ ID NO: 02 of 30 ng/mL or less, and/or
   d) the human tau that has the amino acid sequence of SEQ ID NO: 01 and that has the amino acid mutation S422A of 125 ng/mL or less.
106. The non-covalent complex according to any one of embodiments 1 to 105, wherein the antibody that specifically binds to human tau(pS422) (SEQ ID NO: 02) and does not bind to human tau (SEQ ID NO: 01).
107. The non-covalent complex according to any one of embodiments 1 to 106, wherein the antibody that specifically binds to human tau(pS422) is a monoclonal antibody.
108. The non-covalent complex according to any one of embodiments 1 to 107, wherein the antibody that specifically binds to human tau(pS422) is an antibody fragment that binds to human tau(pS422) and
   i) specifically binds to a polypeptide that has the amino acid sequence of SEQ ID NO: 03, and/or
   ii) does not bind to full length human tau (SEQ ID NO: 01) at 1 μg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human tau(pS422) fragment that has the amino acid sequence of SEQ ID NO: 03 of 6 ng/mL or less, and/or
   vii) has an $EC_{50}$ value for the full length human tau (pS422) that has the amino acid sequence of SEQ ID NO: 02 of 4.5 ng/mL or less, and/or
   viii) has an $EC_{50}$ value for aggregates of human tau (pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.
109. The non-covalent complex according to any one of embodiments 1 to 108, wherein the antibody that specifically binds to human tau(pS422) is
   a) a full length antibody of the human subclass IgG1, or
   b) a full length antibody of the human subclass IgG4, or
   c) a full length antibody of the human subclass IgG1 with the mutations L234A, L235A and P329G,
   d) a full length antibody of the human subclass IgG4 with the mutations S228P, L235E and P329G,
   e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
   f) a full length antibody of the human subclass IgG4 with the mutations S228P and P329G in both heavy chains and the mutations T366W and S354C in one heavy chain and the mutations T366S, L368A, Y407V and Y349C in the respective other heavy chain.

110. The non-covalent complex according to any one of embodiments 1 to 109, wherein the antibody that specifically binds to human tau(pS422)
a) comprises two antibody heavy chains each comprising a heavy chain variable domain and a heavy chain constant region, wherein
    i) the variable domain comprises the HVRs of SEQ ID NO: 08, SEQ ID NO: 18 and SEQ ID NO: 10,
    ii) the constant region is a human IgG1 constant region, wherein the C-terminal lysine residue can be present or absent, and
    iii) the constant region comprises the amino acid changes L234A, L235A and P329G,
b) comprises two antibody light chains each comprising a light chain variable domain and a light chain constant domain, wherein
    i) the variable domain comprises the HVRs of SEQ ID NO: 13, SEQ ID NO: 14 and SEQ ID NO: 15,
    ii) the constant region is a human kappa light chain constant region or a human lambda light chain constant region, and
c) i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human tau(pS422) fragment that has the amino acid sequence of SEQ ID NO: 03 of 6 ng/mL or less, and/or
    vii) has an $EC_{50}$ value for the full length human tau(pS422) that has the amino acid sequence of SEQ ID NO: 02 of 4.5 ng/mL or less, and/or
    viii) has an $EC_{50}$ value for aggregates of human tau (pS422) that has the amino acid sequence of SEQ ID NO: 02 of 30 ng/mL or less, and/or
    ix) has an $EC_{50}$ value for the human tau that has the amino acid sequence of SEQ ID NO: 01 and that has the amino acid mutation S422A of 125 ng/mL or less.

111. The non-covalent complex according to any one of embodiments 1 to 110, wherein the antibody that specifically binds to human tau(pS422)
a) comprises two antibody heavy chains each comprising a heavy chain variable domain and a heavy chain constant region, wherein
    i) the variable domain comprises the HVRs of SEQ ID NO: 08, SEQ ID NO: 09 and SEQ ID NO: 10,
    ii) the constant region is a human IgG1 constant region, wherein the C-terminal lysine residue can be present or absent, and
    iii) the constant region comprises the amino acid changes L234A, L235A and P329G,
b) comprises two antibody light chains each comprising a light chain variable domain and a light chain constant domain, wherein
    i) the variable domain comprises the HVRs of SEQ ID NO: 12, SEQ ID NO: 05 and SEQ ID NO: 15,
    ii) the constant region is a human kappa light chain constant region or a human lambda light chain constant region, and
c) i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human tau(pS422) fragment that has the amino acid sequence of SEQ ID NO: 03 of 6 ng/mL or less, and/or
    vii) has an $EC_{50}$ value for the full length human tau(pS422) that has the amino acid sequence of SEQ ID NO: 02 of 4.5 ng/mL or less, and/or
    viii) has an $EC_{50}$ value for aggregates of human tau (pS422) that has the amino acid sequence of SEQ ID NO: 02 of 30 ng/mL or less, and/or
    ix) has an $EC_{50}$ value for the human tau that has the amino acid sequence of SEQ ID NO: 01 and that has the amino acid mutation S422A of 125 ng/mL or less.

112. The non-covalent complex according to any one of embodiments 1 to 111, wherein the antibody that specifically binds to human tau(pS422)
a) comprises two antibody heavy chains each comprising a heavy chain variable domain and a heavy chain constant region, wherein
    i) the variable domain comprises the HVRs of SEQ ID NO: 08, SEQ ID NO: 09 and SEQ ID NO: 10,
    ii) the constant region is a human IgG1 constant region, wherein the C-terminal lysine residue can be present or absent, and
    iii) the constant region comprises the amino acid changes L234A, L235A and P329G,
b) comprises two antibody light chains each comprising a light chain variable domain and a light chain constant domain, wherein
    i) the variable domain comprises the HVRs of SEQ ID NO: 13, SEQ ID NO: 14 and SEQ ID NO: 15,
    ii) the constant region is a human kappa light chain constant region or a human lambda light chain constant region, and
c) i) specifically binds to a polypeptide that has the amino acid sequence of SEQ ID NO: 03, and/or
    ii) does not bind to full length human tau (SEQ ID NO: 01) at 1 µg/mL, and/or
    iii) specifically binds to full length human tau phosphorylated at the serine at position 422 (SEQ ID NO: 02), and/or
    iv) specifically binds to aggregates of human tau phosphorylated at the serine at position 422 (SEQ ID NO: 02), and/or
    v) specifically binds to full length human tau that has the amino acid sequence of SEQ ID NO: 01 and that has the amino acid mutation S422A, and/or
    vi) has an $EC_{50}$ value for the human tau(pS422) fragment that has the amino acid sequence of SEQ ID NO: 03 of 6 ng/mL or less, and/or
    vii) has an $EC_{50}$ value for the full length human tau(pS422) that has the amino acid sequence of SEQ ID NO: 02 of 4.5 ng/mL or less, and/or viii) has an $EC_{50}$ value for aggregates of human tau (pS422) that has the amino acid sequence of SEQ ID NO: 02 of 30 ng/mL or less, and/or ix) has an $EC_{50}$ value for the human tau that has the amino acid sequence of SEQ ID NO: 01 and that has the amino acid mutation S422A of 125 ng/mL or less.

113. The non-covalent complex according to any one of embodiments 1 to 112, wherein the antibody that specifically binds to human tau(pS422)
   a) comprises two antibody heavy chains each comprising a heavy chain variable domain and a heavy chain constant region, wherein
      i) the variable domain has the amino acid sequence of SEQ ID NO: 20,
      ii) the constant region is a human IgG1 constant region, wherein the C-terminal lysine residue can be present or absent, and
      iii) the constant region comprises the amino acid changes L234A, L235A and P329G,
   b) comprises two antibody light chains each comprising a light chain variable domain and a light chain constant domain, wherein
      i) the variable domain has the amino acid sequence of SEQ ID NO: 17,
      ii) the constant region is a human kappa light chain constant region or a human lambda light chain constant region, and
   c) i) specifically binds to a polypeptide that has the amino acid sequence of SEQ ID NO: 03, and/or
      ii) does not bind to full length human tau (SEQ ID NO: 01) at 1 µg/mL, and/or
      iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or
      vi) has an $EC_{50}$ value for the human tau(pS422) fragment that has the amino acid sequence of SEQ ID NO: 03 of 6 ng/mL or less, and/or
      vii) has an $EC_{50}$ value for the full length human tau(pS422) that has the amino acid sequence of SEQ ID NO: 02 of 4.5 ng/mL or less, and/or
      viii) has an $EC_{50}$ value for aggregates of human tau (pS422) that has the amino acid sequence of SEQ ID NO: 02 of 30 ng/mL or less, and/or
      ix) has an $EC_{50}$ value for the human tau that has the amino acid sequence of SEQ ID NO: 01 and that has the amino acid mutation S422A of 125 ng/mL or less.

114. The non-covalent complex according to any one of embodiments 1 to 113, wherein the antibody that specifically binds to human tau(pS422)
   a) comprises two antibody heavy chains each comprising a heavy chain variable domain and a heavy chain constant region, wherein
      i) the variable domain has the amino acid sequence of SEQ ID NO: 19,
      ii) the constant region is a human IgG1 constant region, wherein the C-terminal lysine residue can be present or absent, and
      iii) the constant region comprises the amino acid changes L234A, L235A and P329G,
   b) comprises two antibody light chains each comprising a light chain variable domain and a light chain constant domain, wherein
      i) the variable domain has the amino acid sequence of SEQ ID NO: 16,
      ii) the constant region is a human kappa light chain constant region or a human lambda light chain constant region, and
   c) i) specifically binds to a polypeptide that has the amino acid sequence of SEQ ID NO: 03, and/or
      ii) does not bind to full length human tau (SEQ ID NO: 01) at 1 µg/mL, and/or
      iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or
      vi) has an $EC_{50}$ value for the human tau(pS422) fragment that has the amino acid sequence of SEQ ID NO: 03 of 6 ng/mL or less, and/or
      vii) has an $EC_{50}$ value for the full length human tau(pS422) that has the amino acid sequence of SEQ ID NO: 02 of 4.5 ng/mL or less, and/or
      viii) has an $EC_{50}$ value for aggregates of human tau (pS422) that has the amino acid sequence of SEQ ID NO: 02 of 30 ng/mL or less, and/or
      ix) has an $EC_{50}$ value for the human tau that has the amino acid sequence of SEQ ID NO: 01 and that has the amino acid mutation S422A of 125 ng/mL or less.

115. The non-covalent complex according to any one of embodiments 1 to 114, wherein the antibody that specifically binds to human tau(pS422)
   a) comprises two antibody heavy chains each comprising a heavy chain variable domain and a heavy chain constant region, wherein
      i) the variable domain has the amino acid sequence of SEQ ID NO: 19,
      ii) the constant region is a human IgG1 constant region, wherein the C-terminal lysine residue can be present or absent, and
      iii) the constant region comprises the amino acid changes L234A, L235A and P329G,
   b) comprises two antibody light chains each comprising a light chain variable domain and a light chain constant domain, wherein
      i) the variable domain has the amino acid sequence of SEQ ID NO: 17,
      ii) the constant region is a human kappa light chain constant region or a human lambda light chain constant region, and
   c) i) specifically binds to a polypeptide that has the amino acid sequence of SEQ ID NO: 03, and/or
      ii) does not bind to full length human tau (SEQ ID NO: 01) at 1 µg/mL, and/or iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or vi) has an $EC_{50}$ value for the human tau(pS422) fragment that has the amino acid sequence of SEQ ID NO: 03 of 6 ng/mL or less, and/or vii) has an $EC_{50}$ value for the full length human tau(pS422) that has the amino acid sequence of SEQ ID NO: 02 of 4.5 ng/mL or less, and/or viii) has an $EC_{50}$ value for aggregates of human tau (pS422) that has the amino acid sequence of SEQ ID NO: 02 of 30 ng/mL or less, and/or ix) has an $EC_{50}$ value for the human tau that has the amino acid sequence of SEQ ID NO: 01 and that has the amino acid mutation S422A of 125 ng/mL or less.

116. The non-covalent complex according to any one of embodiments 1 to 115, wherein the antibody that specifically binds to human tau(pS422)

a) comprises two antibody heavy chains each comprising a heavy chain variable domain and a heavy chain constant region, wherein
  i) the variable domain has the amino acid sequence of SEQ ID NO: 21,
  ii) the constant region is a human IgG1 constant region, wherein the C-terminal lysine residue can be present or absent, and
  iii) the constant region comprises the amino acid changes L234A, L235A and P329G, b) comprises two antibody light chains each comprising a light chain variable domain and a light chain constant domain, wherein
  i) the variable domain has the amino acid sequence of SEQ ID NO: 17,
  ii) the constant region is a human kappa light chain constant region or a human lambda light chain constant region, and c) i) specifically binds to a polypeptide that has the amino acid sequence of SEQ ID NO: 03, and/or
  ii) does not bind to full length human tau (SEQ ID NO: 01) at 1 µg/mL, and/or
  iii) specifically binds to full length human tau phosphorylated at the serine at position 422 (SEQ ID NO: 02), and/or
  iv) specifically binds to aggregates of human tau phosphorylated at the serine at position 422 (SEQ ID NO: 02), and/or
  v) specifically binds to full length human tau that has the amino acid sequence of SEQ ID NO: 01 and that has the amino acid mutation S422A, and/or
  vi) has an $EC_{50}$ value for the human tau(pS422) fragment that has the amino acid sequence of SEQ ID NO: 03 of 6 ng/mL or less, and/or
  vii) has an $EC_{50}$ value for the full length human tau(pS422) that has the amino acid sequence of SEQ ID NO: 02 of 4.5 ng/mL or less, and/or
  viii) has an $EC_{50}$ value for aggregates of human tau (pS422) that has the amino acid sequence of SEQ ID NO: 02 of 30 ng/mL or less, and/or
  ix) has an $EC_{50}$ value for the human tau that has the amino acid sequence of SEQ ID NO: 01 and that has the amino acid mutation S422A of 125 ng/mL or less.

117. The non-covalent complex according to any one of embodiments 1 to 116, wherein the antibody that specifically binds to human tau(pS422) has in the heavy chain variable domain at positions 4, 24 and 78 a valine residue.

118. The non-covalent complex according to any one of embodiments 1 to 117, wherein the antibody that specifically binds to human tau(pS422) has in the heavy chain variable domain at position 71 an arginine residue.

119. A non-covalent complex of a haptenylated antibody that specifically binds to a blood brain barrier receptor and an anti-human tau(pS422)/hapten bispecific antibody.

120. A non-covalent complex comprising a haptenylated antibody that specifically binds to a blood brain barrier receptor and bispecific antibody, which has a first binding specificity that specifically binds to the hapten of the haptenylated antibody that specifically binds to a blood brain barrier receptor and a second binding specificity that specifically binds to human tau(pS422), wherein the haptenylated antibody that specifically binds to the blood brain barrier receptor is specifically bound by the first binding specificity of the bispecific antibody.

121. The non-covalent complex according to any one of embodiments 119 to 120, wherein the haptenylated antibody that specifically binds to a blood brain barrier receptor is selected from the group consisting of the biotinylated antibody that specifically binds to a blood brain barrier receptor, the theophyllinylated antibody that specifically binds to a blood brain barrier receptor, the digoxigenylated antibody that specifically binds to a blood brain barrier receptor, the carboranylated antibody that specifically binds to a blood brain barrier receptor, the fluoresceinylated antibody that specifically binds to a blood brain barrier receptor, the helicarylated antibody that specifically binds to a blood brain barrier receptor and the bromodeoxyuridinylated antibody that specifically binds to a blood brain barrier receptor.

122. The non-covalent complex according to any one of embodiments 119 to 121, wherein the blood brain barrier receptor is selected from the group consisting of the transferrin receptor (TfR), the insulin receptor, the insulin-like growth factor receptor (IGF receptor), the low density lipoprotein receptor-related protein 8 (LRP8), the low density lipoprotein receptor-related protein 1 (LRP1), and the heparin-binding epidermal growth factor-like growth factor (HB-EGF).

123. The non-covalent complex according to any one of embodiments 119 to 122, wherein the bispecific antibody is a full length antibody comprising two binding sites.

124. The non-covalent complex according to any one of embodiments 119 to 123, wherein the bispecific antibody is a full length antibody to which one or two scFvs or scFabs or CrossFabs or scCrossFabs have been fused and that comprises three or four binding sites.

125. The non-covalent complex according to any one of embodiments 119 to 124, wherein the bispecific antibody is selected from an antibody fragment, F(ab')2 and diabodies.

126. The non-covalent complex according to any one of embodiments 119 to 125, wherein the bispecific antibody is a humanized or a human antibody.

127. The non-covalent complex according to any one of embodiments 119 to 126, wherein the bispecific antibody is free of effector function.

128. The non-covalent complex according to any one of embodiments 119 to 127, wherein embodiment the bispecific antibody has no functional Fc-region.

129. The non-covalent complex according to any one of embodiments 119 to 128, wherein the bispecific antibody has no Fc-region.

130. The non-covalent complex according to any one of embodiments 119 to 129, wherein the bispecific antibody has an Fc-region of the human IgG1 subclass with the mutations L234A, L235A and P329G, wherein the posi- 131. The non-covalent complex according to any one of embodiments 119 to 129, wherein the bispecific antibody has an Fc-region of the human IgG4 subclass with the mutations S228P, L235E and P329G, wherein the positions are determined according to the Fc-region numbering of Kabat (Kabat EU index).
132. The non-covalent complex according to any one of embodiments 119 to 131, wherein the bispecific antibody comprises
   a) one binding site for the hapten of the haptenylated antibody that specifically binds to a blood brain barrier receptor and one binding site for human tau(pS422), or
   b) two binding sites for the hapten of the haptenylated antibody that specifically binds to a blood brain barrier receptor and one binding site for human tau(pS422), or
   c) one binding site for the hapten of haptenylated antibody that specifically binds to a blood brain barrier receptor and two binding sites for human tau(pS422), or
   d) two binding sites for the hapten of the haptenylated antibody that specifically binds to a blood brain barrier receptor and two binding sites for human tau(p S422),
   wherein in cases b) and c) one heavy chain of the bispecific antibody comprises a hole mutation and the respective other chain comprises a knob mutation.
133. The non-covalent complex according to any one of embodiments 119 to 132, wherein the bispecific antibody comprises two binding sites for the hapten of the haptenylated antibody that specifically binds to the blood brain barrier receptor and two binding sites for human tau (pS422).
134. The non-covalent complex according to any one of embodiments 119 to 133, wherein the bispecific antibody has two binding specificities that specifically bind to the hapten of the haptenylated antibody that specifically binds to the (human) transferrin receptor or to low density lipoprotein receptor-related protein 8 (anti-hapten binding specificity).
135. The non-covalent complex according to any one of embodiments 119 to 134, wherein the binding specificity that specifically binds to the digoxigenin of the digoxigenylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 65, (b) a heavy chain CDR2 comprising the amino acid sequence of SEQ ID NO: 66, (c) a heavy chain CDR3 comprising the amino acid sequence of SEQ ID NO: 67, (d) a light chain CDR1 comprising the amino acid sequence of SEQ ID NO: 69, (e) a light chain CDR2 comprising the amino acid sequence of SEQ ID NO: 70, and (f) a light chain CDR3 comprising the amino acid sequence of SEQ ID NO: 71.
136. The non-covalent complex according to any one of embodiments 119 to 135, wherein the binding specificity that specifically binds to the digoxigenin of the digoxigenylated antibody that specifically binds to a blood brain barrier receptor is a humanized binding specificity.
137. The non-covalent complex according to any one of embodiments 119 to 136, wherein the binding specificity that specifically binds to the digoxigenin of the digoxigenylated antibody that specifically binds to a blood brain barrier receptor comprises CDRs as in embodiment 17 and an acceptor human framework (e.g., a human immunoglobulin framework or a human consensus framework).
138. The non-covalent complex according to any one of embodiments 119 to 137, wherein the binding specificity that specifically binds to the digoxigenin of the digoxigenylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 73, (b) a heavy chain CDR2 comprising the amino acid sequence of SEQ ID NO: 74, (c) a heavy chain CDR3 comprising the amino acid sequence of SEQ ID NO: 75, (d) a light chain CDR1 comprising the amino acid sequence of SEQ ID NO: 77, (e) a light chain CDR2 comprising the amino acid sequence of SEQ ID NO: 78, and (f) a light chain CDR3 comprising the amino acid sequence of SEQ ID NO: 79.
139. The non-covalent complex according to any one of embodiments 119 to 138, wherein the binding specificity that specifically binds to the digoxigenin of the digoxigenylated antibody that specifically binds to a blood brain barrier receptor is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 68 or 76.
140. The non-covalent complex according to any one of embodiments 119 to 139, wherein, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin. In certain embodiments, a total of 119 to 10 amino acids have been substituted, inserted and/or deleted in SEQ ID NO: 68 or 76.
141. The non-covalent complex according to any one of embodiments 119 to 140, wherein, substitutions, insertions, or deletions occur in regions outside the CDRs (i.e., in the FRs).
142. The non-covalent complex according to any one of embodiments 119 to 141, wherein the digoxigenin binding specificity comprises the VH sequence in SEQ ID NO: 68 or 76, including post-translational modifications of that sequence.
143. The non-covalent complex according to any one of embodiments 119 to 142, wherein the binding specificity that specifically binds to the digoxigenin of the digoxigenylated antibody that specifically binds to a blood brain barrier receptor is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 72 or 80.
144. The non-covalent complex according to any one of embodiments 119 to 143, wherein, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-digoxigenin antibody comprising that sequence retains the ability to bind to digoxigenin. In certain embodiments, a total of 119 to 10 amino acids have been substituted, inserted and/or deleted in SEQ ID NO: 72 or 80.

145. The non-covalent complex according to any one of embodiments 119 to 144, wherein, the substitutions, insertions, or deletions occur in regions outside the CDRs (i.e., in the FRs).

146. The non-covalent complex according to any one of embodiments 119 to 145, wherein the digoxigenin binding specificity comprises the VL sequence in SEQ ID NO: 72 or 80, including post-translational modifications of that sequence.

147. The non-covalent complex according to any one of embodiments 119 to 134, wherein the bispecific antibody comprises a first binding specificity that specifically binds to the biotin of the biotinylated antibody that specifically binds to a blood brain barrier receptor and a second binding specificity that specifically binds to human tau (pS422).

148. The non-covalent complex according to any one of embodiments 119 to 134 and 147, wherein the bispecific antibody has two binding specificities that specifically bind to the biotinylated antibody that specifically binds to the (human) transferrin receptor or the biotinylated antibody that specifically binds to low density lipoprotein receptor-related protein 8 (two anti-biotin binding specificities) and two binding specificities that specifically bind to human tau(pS422).

149. The non-covalent complex according to any one of embodiments 119 to 134 and 147 to 148, wherein the binding specificity that specifically binds to the biotin of the biotinylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 81, (b) a heavy chain CDR2 comprising the amino acid sequence of SEQ ID NO: 82, (c) a heavy chain CDR3 comprising the amino acid sequence of SEQ ID NO: 83, (d) a light chain CDR1 comprising the amino acid sequence of SEQ ID NO: 85, (e) a light chain CDR2 comprising the amino acid sequence of SEQ ID NO: 86, and (f) a light chain CDR3 comprising the amino acid sequence of SEQ ID NO: 87.

150. The non-covalent complex according to any one of embodiments 119 to 134 and 147 to 149, wherein the binding specificity that specifically binds to the biotin of the biotinylated antibody that specifically binds to a blood brain barrier receptor is a humanized binding specificity.

151. The non-covalent complex according to any one of embodiments 119 to 134 and 147 to 150, wherein the binding specificity that specifically binds to the biotin of the biotinylated antibody that specifically binds to a blood brain barrier receptor comprises CDRs as in the embodiment 149 and an acceptor human framework (e.g., a human immunoglobulin framework or a human consensus framework).

152. The non-covalent complex according to any one of embodiments 119 to 134 and 147 to 151, wherein the binding specificity that specifically binds to the biotin in the biotinylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 89, (b) a heavy chain CDR2 comprising the amino acid sequence of SEQ ID NO: 90, (c) a heavy chain CDR3 comprising the amino acid sequence of SEQ ID NO: 91, (d) a light chain CDR1 comprising the amino acid sequence of SEQ ID NO: 93, (e) a light chain CDR2 comprising the amino acid sequence of SEQ ID NO: 94, and (f) a light chain CDR3 comprising the amino acid sequence of SEQ ID NO: 95.

153. The non-covalent complex according to any one of embodiments 119 to 134 and 147 to 152, wherein the binding specificity that specifically binds to the biotin of the biotinylated antibody that specifically binds to a blood brain barrier receptor is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 84 or 92.

154. The non-covalent complex according to any one of embodiments 119 to 134 and 147 to 153, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin.

155. The non-covalent complex according to any one of embodiments 119 to 134 and 147 to 154, wherein a total of 119 to 10 amino acids have been substituted, inserted and/or deleted in SEQ ID NO: 84 or 92.

156. The non-covalent complex according to any one of embodiments 119 to 134 and 147 to 155, wherein substitutions, insertions, or deletions occur in regions outside the CDRs (i.e., in the FRs).

157. The non-covalent complex according to any one of embodiments 119 to 134 and 147 to 156, wherein the biotin binding specificity comprises the VH sequence in SEQ ID NO: 84 or 92, including post-translational modifications of that sequence.

158. The non-covalent complex according to any one of embodiments 119 to 134 and 147 to 157, wherein the binding specificity that specifically binds to the biotin of the biotinylated antibody that specifically binds to a blood brain barrier receptor is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 88 or 96.

159. The non-covalent complex according to any one of embodiments 119 to 134 and 147 to 158, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-biotin antibody comprising that sequence retains the ability to bind to biotin.

160. The non-covalent complex according to any one of embodiments 119 to 134 and 147 to 159, wherein a total of 119 to 10 amino acids have been substituted, inserted and/or deleted in SEQ ID NO: 88 or 96.

161. The non-covalent complex according to any one of embodiments 119 to 134 and 147 to 160, wherein the substitutions, insertions, or deletions occur in regions outside the CDRs (i.e., in the FRs).

162. The non-covalent complex according to any one of embodiments 119 to 134 and 147 to 161, wherein the biotin binding specificity comprises the VL sequence in SEQ ID NO: 88 or 96, including post-translational modifications of that sequence.

163. The non-covalent complex according to any one of embodiments 119 to 133, wherein the bispecific antibody comprises a first binding specificity that specifically binds to a theophyllinylated antibody that specifically binds to a blood brain barrier receptor and a second binding specificity that specifically binds to human tau(pS422).

164. The non-covalent complex according to any one of embodiments 119 to 134 and 45, wherein the bispecific antibody has two binding specificities that specifically bind to the theophyllinylated antibody that specifically binds to the (human) transferrin receptor or antibody that specifically binds to low density lipoprotein receptor-related protein 8 (two anti-theophylline binding specificities) and two binding specificities that specifically bind to human tau(pS422).

165. The non-covalent complex according to any one of embodiments 119 to 134 and 163 to 164, wherein the binding specificity that specifically binds the theophylline of the theophyllinylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 97, (b) a heavy chain CDR2 comprising the amino acid sequence of SEQ ID NO: 98, (c) a heavy chain CDR3 comprising the amino acid sequence of SEQ ID NO: 99, (d) a light chain CDR1 comprising the amino acid sequence of SEQ ID NO: 101, (e) a light chain CDR2 comprising the amino acid sequence of SEQ ID NO: 102, and (f) a light chain CDR3 comprising the amino acid sequence of SEQ ID NO: 103.

166. The non-covalent complex according to any one of embodiments 119 to 134 and 163 to 165, wherein the binding specificity that specifically binds to the theophylline of the theophyllinylated antibody that specifically binds to a blood brain barrier receptor is a humanized binding specificity.

167. The non-covalent complex according to any one of embodiments 119 to 134 and 163 to 166, wherein the binding specificity that specifically binds to the theophylline of the theophyllinylated antibody that specifically binds to a blood brain barrier receptor comprises CDRs as in the embodiment 165 and an acceptor human framework (e.g., a human immunoglobulin framework or a human consensus framework).

168. The non-covalent complex according to any one of embodiments 119 to 134 and 163 to 167, wherein the binding specificity that specifically binds to the theophylline of the theophyllinylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 105, (b) a heavy chain CDR2 comprising the amino acid sequence of SEQ ID NO: 106, (c) a heavy chain CDR3 comprising the amino acid sequence of SEQ ID NO: 107, (d) a light chain CDR1 comprising the amino acid sequence of SEQ ID NO: 109, (e) a light chain CDR2 comprising the amino acid sequence of SEQ ID NO: 110, and (f) a light chain CDR3 comprising the amino acid sequence of SEQ ID NO: 111.

169. The non-covalent complex according to any one of embodiments 119 to 134 and 163 to 168, wherein the binding specificity that specifically binds to the theophylline of the theophyllinylated antibody that specifically binds to a blood brain barrier receptor is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 100 or 108.

170. The non-covalent complex according to any one of embodiments 119 to 134 and 163 to 169, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline.

171. The non-covalent complex according to any one of embodiments 119 to 134 and 163 to 170, wherein a total of 119 to 10 amino acids have been substituted, inserted and/or deleted in SEQ ID NO: 100 or 108.

172. The non-covalent complex according to any one of embodiments 119 to 134 and 163 to 171, wherein substitutions, insertions, or deletions occur in regions outside the CDRs (i.e., in the FRs).

173. The non-covalent complex according to any one of embodiments 119 to 134 and 163 to 172, wherein the theophylline binding specificity comprises the VH sequence in SEQ ID NO: 100 or 108 including post-translational modifications of that sequence.

174. The non-covalent complex according to any one of embodiments 119 to 134 and 163 to 173, wherein the binding specificity that specifically binds to the theophylline of the theophyllinylated antibody that specifically binds to a blood brain barrier receptor is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 104 or 112.

175. The non-covalent complex according to any one of embodiments 119 to 134 and 163 to 174, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-theophylline antibody comprising that sequence retains the ability to bind to theophylline.

176. The non-covalent complex according to any one of embodiments 119 to 134 and 163 to 175, wherein a total of 119 to 10 amino acids have been substituted, inserted and/or deleted in SEQ ID NO: 104 or 112.

177. The non-covalent complex according to any one of embodiments 119 to 134 and 163 to 176, wherein the substitutions, insertions, or deletions occur in regions outside the CDRs (i.e., in the FRs).

178. The non-covalent complex according to any one of embodiments 119 to 134 and 163 to 177, wherein the theophylline binding specificity comprises the VL sequence in SEQ ID NO: 104 or 112, including post-translational modifications of that sequence.

179. The non-covalent complex according to any one of embodiments 119 to 133, wherein the bispecific antibody comprises a first binding specificity that specifically binds to a fluoresceinylated antibody that specifically binds to a blood brain barrier receptor (anti-fluorescein binding specificity; anti-FLUO binding specificity) and a second binding specificity that specifically binds to human tau (pS422).

180. The non-covalent complex according to any one of embodiments 119 to 134 and 179, wherein the bispecific antibody has two binding specificities that specifically bind to the fluoresceinylated antibody that specifically binds to the (human) transferrin receptor or the antibody that specifically binds to low density lipoprotein receptor-related protein 8 and a second binding specificity that specifically binds to human tau(pS422).

181. The non-covalent complex according to any one of embodiments 119 to 134 and 179 to 180, wherein the binding specificity that specifically binds to the fluorescein of the fluoresceinylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 113, (b) a heavy chain CDR2 comprising the amino acid sequence of SEQ ID NO: 114, (c) a heavy chain CDR3 comprising the amino acid sequence of SEQ ID NO: 115, (d) a light chain CDR1 comprising the amino acid sequence of SEQ ID NO: 117, (e) a light chain CDR2 comprising the amino acid sequence of SEQ ID NO: 118, and (f) a light chain CDR3 comprising the amino acid sequence of SEQ ID NO: 119.

182. The non-covalent complex according to any one of embodiments 119 to 134 and 179 to 181, wherein the binding specificity that specifically binds to the fluorescein of the fluoresceinylated antibody that specifically binds to a blood brain barrier receptor is a humanized binding specificity.

183. The non-covalent complex according to any one of embodiments 119 to 134 and 179 to 182, wherein the binding specificity that specifically binds to the fluorescein of the fluoresceinylated antibody that specifically binds to a blood brain barrier receptor comprises CDRs as in embodiment 63 and an acceptor human framework (e.g., a human immunoglobulin framework or a human consensus framework).

184. The non-covalent complex according to any one of embodiments 119 to 134 and 179 to 183, wherein the binding specificity that specifically binds to the fluorescein of the fluoresceinylated antibody that specifically binds to a blood brain barrier receptor is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 116.

185. The non-covalent complex according to any one of embodiments 119 to 134 and 179 to 184, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein.

186. The non-covalent complex according to any one of embodiments 119 to 134 and 179 to 185, wherein a total of 119 to 10 amino acids have been substituted, inserted and/or deleted in SEQ ID NO: 116.

187. The non-covalent complex according to any one of embodiments 119 to 134 and 179 to 186, wherein substitutions, insertions, or deletions occur in regions outside the CDRs (i.e., in the FRs).

188. The non-covalent complex according to any one of embodiments 119 to 134 and 179 to 187, wherein the fluorescein binding specificity comprises the VH sequence in SEQ ID NO: 116, including post-translational modifications of that sequence.

189. The non-covalent complex according to any one of embodiments 119 to 134 and 179 to 188, wherein the binding specificity that specifically binds to the fluorescein of the fluoresceinylated antibody that specifically binds to a blood brain barrier receptor is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 120.

190. The non-covalent complex according to any one of embodiments 119 to 134 and 179 to 189, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-fluorescein antibody comprising that sequence retains the ability to bind to fluorescein.

191. The non-covalent complex according to any one of embodiments 119 to 134 and 179 to 190, wherein a total of 119 to 10 amino acids have been substituted, inserted and/or deleted in SEQ ID NO: 120.

192. The non-covalent complex according to any one of embodiments 119 to 134 and 179 to 191, wherein the substitutions, insertions, or deletions occur in regions outside the CDRs (i.e., in the FRs).

193. The non-covalent complex according to any one of embodiments 119 to 134 and 179 to 192, wherein the fluorescein binding specificity comprises the VL sequence in SEQ ID NO: 120, including post-translational modifications of that sequence.

194. The non-covalent complex according to any one of embodiments 119 to 133, wherein the bispecific antibody comprises a first binding specificity that specifically binds to a bromodeoxyuridinylated antibody that specifically binds to a blood brain barrier receptor and a second binding specificity that specifically binds to human tau (pS422).

195. The non-covalent complex according to any one of embodiments 119 to 134 and 194, wherein the bispecific antibody has two binding specificities that specifically bind to the bromodeoxyuridinylated antibody that that specifically bind to the (human) transferrin receptor or antibody that specifically binds to low density lipoprotein receptor-related protein 8 and a second binding specificity that specifically binds to human tau(pS422).

196. The non-covalent complex according to any one of embodiments 119 to 134 and 194 to 195, wherein the binding specificity that specifically binds to the bromodeoxyuridine of the bromodeoxyuridinylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 121, (b) a heavy chain CDR2 comprising the amino acid sequence of SEQ ID NO: 123, (c) a heavy chain CDR3 comprising the amino acid sequence of SEQ ID NO: 125, (d) a light chain CDR1 comprising the amino acid sequence of SEQ ID NO: 126, (e) a light chain CDR2 comprising the amino acid sequence of SEQ ID NO: 127, and (f) a light chain CDR3 comprising the amino acid sequence of SEQ ID NO: 128.

197. The non-covalent complex according to any one of embodiments 119 to 134 and 194 to 196, wherein the binding specificity that specifically binds to the bromodeoxyuridine of the bromodeoxyuridinylated antibody that specifically binds to a blood brain barrier receptor is a humanized binding specificity.

198. The non-covalent complex according to any one of embodiments 119 to 134 and 194 to 197, wherein the binding specificity that specifically binds to the bromodeoxyuridine of the bromodeoxyuridinylated antibody that specifically binds to a blood brain barrier receptor comprises CDRs as in the above embodiment and an acceptor human framework (e.g. a human immunoglobulin framework or a human consensus framework).

199. The non-covalent complex according to any one of embodiments 119 to 134 and 194 to 198, wherein the binding specificity that specifically binds to the bromodeoxyuridine of the bromodeoxyuridinylated antibody that specifically binds to a blood brain barrier receptor is a pair of an antibody heavy chain variable domain and an antibody light chain variable domain comprising (a) a heavy chain CDR1 comprising the amino acid sequence of SEQ ID NO: 121 or 122, (b) a heavy chain CDR2 comprising the amino acid sequence of SEQ ID NO: 123 or 124, (c) a heavy chain CDR3 comprising the amino acid sequence of SEQ ID NO: 125, (d) a light chain CDR1 comprising the amino acid sequence of SEQ ID NO: 126, (e) a light chain CDR2 comprising the amino acid sequence of SEQ ID NO: 127, and (f) a light chain CDR3 comprising the amino acid sequence of SEQ ID NO: 128.

200. The non-covalent complex according to any one of embodiments 119 to 134 and 194 to 199, wherein the binding specificity that specifically binds to the bromodeoxyuridine of the bromodeoxyuridinylated antibody that specifically binds to a blood brain barrier receptor is a pair of an antibody heavy chain variable domain and an antibody light chain variable domain comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 129 or 131.

201. The non-covalent complex according to any one of embodiments 119 to 134 and 194 to 200, wherein a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine.

202. The non-covalent complex according to any one of embodiments 119 to 134 and 194 to 201, wherein a total of 119 to 10 amino acids have been substituted, inserted and/or deleted in SEQ ID NO: 129 or 131.

203. The non-covalent complex according to any one of embodiments 119 to 134 and 194 to 202, wherein substitutions, insertions, or deletions occur in regions outside the CDRs (i.e., in the FRs).

204. The non-covalent complex according to any one of embodiments 119 to 134 and 194 to 203, wherein the bromodeoxyuridine binding specificity comprises the VH sequence in SEQ ID NO: 129 or 131, including post-translational modifications of that sequence.

205. The non-covalent complex according to any one of embodiments 119 to 134 and 194 to 204, wherein the binding specificity that specifically binds to the bromodeoxyuridine of the bromodeoxyuridinylated antibody that specifically binds to a blood brain barrier receptor is a pair of an antibody heavy chain variable domain and an antibody light chain variable domain further comprising a light chain variable domain (VL) having at least 90%, 91%, 92%, 93%, 94%, 95%, 96%, 97%, 98%, 99%, or 100% sequence identity to the amino acid sequence of SEQ ID NO: 130 or 132.

206. The non-covalent complex according to any one of embodiments 119 to 134 and 194 to 205, wherein a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-bromodeoxyuridine antibody comprising that sequence retains the ability to bind to bromodeoxyuridine.

207. The non-covalent complex according to any one of embodiments 119 to 134 and 194 to 206, wherein a total of 119 to 10 amino acids have been substituted, inserted and/or deleted in SEQ ID NO: 130 or 132.

208. The non-covalent complex according to any one of embodiments 119 to 134 and 194 to 207, wherein the substitutions, insertions, or deletions occur in regions outside the CDRs (i.e., in the FRs).

209. The non-covalent complex according to any one of embodiments 119 to 134 and 194 to 208, wherein the bromodeoxyuridine binding specificity comprises the VL sequence in SEQ ID NO: 130 or 132, including post-translational modifications of that sequence.

210. The non-covalent complex according to any one of embodiments 119 to 208, wherein the haptenylated antibody that specifically binds to a blood brain barrier receptor comprises between the hapten and the antibody that specifically binds to a blood brain barrier receptor a linker.

211. The non-covalent complex according to embodiment 210, wherein the linker is a peptidic linker.

212. The non-covalent complex according to embodiment 210, wherein the linker is a chemical linker (non-peptidic linker).

213. The non-covalent complex according to any one of embodiments 119 to 212, wherein the antibody that specifically binds to a blood brain barrier receptor is a full length antibody.

214. The non-covalent complex according to any one of embodiments 119 to 213, wherein the antibody that specifically binds to human tau(pS422)
 i) specifically binds to a polypeptide that has the amino acid sequence of SEQ ID NO: 03, and/or
 ii) does not bind to full length human tau (SEQ ID NO: 01) at 1 µg/mL, and/or
 iii) specifically binds to full length human tau phosphorylated at the serine at position 422 (SEQ ID NO: 02), and/or
 iv) specifically binds to aggregates of human tau phosphorylated at the serine at position 422 (SEQ ID NO: 02), and/or
 v) specifically binds to human tau that has the amino acid sequence of SEQ ID NO: 01 and that has the amino acid mutation S422A.

215. The non-covalent complex according to any one of embodiments 119 to 214, wherein the antibody that specifically binds to human tau(pS422) comprises
 a) in the heavy chain variable domain the HVRs of SEQ ID NO: 08, 18 and 10, or
 b) in the heavy chain variable domain the HVRs of SEQ ID NO: 08, 09 and 10.

216. The non-covalent complex according to any one of embodiments 119 to 215, wherein the antibody that specifically binds to human tau(pS422) further comprises
 a) in the light chain variable domain the HVRs of SEQ ID NO: 13, 14 and 15, or b) in the light chain variable domain the HVRs of SEQ ID NO: 12, 05 and 15.
217. The non-covalent complex according to any one of embodiments 119 to 216, wherein the antibody that specifically binds to human tau(pS422) comprises
   a) in the heavy chain variable domain the HVRs of SEQ ID NO: 08, 18 and 10, and in the light chain variable domain the HVRs of SEQ ID NO: 13, 14 and 15, or
   b) in the heavy chain variable domain the HVRs of SEQ ID NO: 08, 09 and 10, and in the light chain variable domain the HVRs of SEQ ID NO: 12, 05 and 15, or
   c) in the heavy chain variable domain the HVRs of SEQ ID NO: 08, 09 and 10, and in the light chain variable domain the HVRs of SEQ ID NO: 13, 14 and 15.
218. The non-covalent complex according to any one of embodiments 119 to 217, wherein the antibody that specifically binds to human tau(pS422) comprises
   a) a heavy chain variable domain of SEQ ID NO: 20 and a light chain variable domain of SEQ ID NO: 17, or
   b) a heavy chain variable domain of SEQ ID NO: 19 and a light chain variable domain of SEQ ID NO: 16, or
   c) a heavy chain variable domain of SEQ ID NO: 19 and a light chain variable domain of SEQ ID NO: 17, or
   d) a heavy chain variable domain of SEQ ID NO: 21 and a light chain variable domain of SEQ ID NO: 17.
219. The non-covalent complex according to any one of embodiments 119 to 218, wherein the non-covalent complex is for use in the treatment of Alzheimer's Disease.
220. The non-covalent complex according to any one of embodiments 119 to 219, wherein both antibodies in the complex are effector function silent.
221. The non-covalent complex according to any one of embodiments 119 to 220, wherein both antibodies of the complex have no effector function.
222. The non-covalent complex according to any one of embodiments 119 to 221, wherein the antibody that specifically binds to human tau(pS422)
   i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02).
223. The non-covalent complex according to any one of embodiments 119 to 222, wherein the antibody that specifically binds to human tau(pS422) has an $EC_{50}$ value for
   a) the human tau(pS422) fragment that has the amino acid sequence of SEQ ID NO: 03 of 6 ng/mL or less, and/or
   b) the full length human tau(pS422) that has the amino acid sequence of SEQ ID NO: 02 of 4.5 ng/mL or less, and/or
   c) aggregates of human tau(pS422) that has the amino acid sequence of SEQ ID NO: 02 of 30 ng/mL or less, and/or
   d) the human tau that has the amino acid sequence of SEQ ID NO: 01 and that has the amino acid mutation S422A of 125 ng/mL or less.
224. The non-covalent complex according to any one of embodiments 119 to 223, wherein the antibody that specifically binds to human tau(pS422) (SEQ ID NO: 02) and does not bind to human tau (SEQ ID NO: 01).
225. The non-covalent complex according to any one of embodiments 119 to 224, wherein the antibody that specifically binds to a blood brain barrier receptor is a monoclonal antibody.
226. The non-covalent complex according to any one of embodiments 119 to 225, wherein the antibody that specifically binds to human tau(pS422) is an antibody fragment that binds to human tau(pS422) and
   i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human tau(pS422) fragment that has the amino acid sequence of SEQ ID NO: 03 of 6 ng/mL or less, and/or
   vii) has an $EC_{50}$ value for the full length human tau (pS422) that has the amino acid sequence of SEQ ID NO: 02 of 4.5 ng/mL or less, and/or
   viii) has an $EC_{50}$ value for aggregates of human tau (pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.
227. The non-covalent complex according to any one of embodiments 119 to 226, wherein the antibody that specifically binds to a blood brain barrier receptor is
   a) a full length antibody of the human subclass IgG1, or
   b) a full length antibody of the human subclass IgG4, or
   c) a full length antibody of the human subclass IgG1 with the mutations L234A, L235A and P329G,
   d) a full length antibody of the human subclass IgG4 with the mutations S228P, L235E and P329G,
   e) a full length antibody of the human subclass IgG1 with the mutations L234A, L235A and P329G in both heavy chains and the mutations T366W and S354C in one heavy chain and the mutations T366S, L368A, Y407V and Y349C in the respective other heavy chain, or
   f) a full length antibody of the human subclass IgG4 with the mutations S228P, L235E and P329G in both heavy chains and the mutations T366W and S354C in one heavy chain and the mutations T366S, L368A, Y407V and Y349C in the respective other heavy chain, or
   g) a full length antibody of the human subclass IgG1 with the mutations L234A, L235A and P329G in both heavy chains and the mutations T366W and Y349C in one heavy chain and the mutations T366S, L368A, Y407V and S354C in the respective other heavy chain, or
   h) a full length antibody of the human subclass IgG4 with the mutations S228P, L235E and P329G in both heavy chains and the mutations T366W and Y349C in one heavy chain and the mutations T366S, L368A, Y407V and S354C in the respective other heavy chain.
228. The non-covalent complex according to any one of embodiments 119 to 227, wherein the antibody that specifically binds to human tau(pS422)

a) comprises two antibody heavy chains each comprising a heavy chain variable domain and a heavy chain constant region, wherein
   i) the variable domain comprises the HVRs of SEQ ID NO: 08, SEQ ID NO: 18 and SEQ ID NO: 10,
   ii) the constant region is a human IgG1 constant region, wherein the C-terminal lysine residue can be present or absent, and
   iii) the constant region comprises the amino acid changes L234A, L235A and P329G,
b) comprises two antibody light chains each comprising a light chain variable domain and a light chain constant domain, wherein
   i) the variable domain comprises the HVRs of SEQ ID NO: 13, SEQ ID NO: 14 and SEQ ID NO: 15,
   ii) the constant region is a human kappa light chain constant region or a human lambda light chain constant region, and
c) i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human tau(pS422) fragment that has the amino acid sequence of SEQ ID NO: 03 of 6 ng/mL or less, and/or
   vii) has an $EC_{50}$ value for the full length human tau(pS422) that has the amino acid sequence of SEQ ID NO: 02 of 4.5 ng/mL or less, and/or
   viii) has an $EC_{50}$ value for aggregates of human tau (pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.

229. The non-covalent complex according to any one of embodiments 119 to 228, wherein the antibody that specifically binds to human tau(pS422)
a) comprises two antibody heavy chains each comprising a heavy chain variable domain and a heavy chain constant region, wherein
   i) the variable domain comprises the HVRs of SEQ ID NO: 08, SEQ ID NO: 09 and SEQ ID NO: 10,
   ii) the constant region is a human IgG1 constant region, wherein the C-terminal lysine residue can be present or absent, and
   iii) the constant region comprises the amino acid changes L234A, L235A and P329G,
b) comprises two antibody light chains each comprising a light chain variable domain and a light chain constant domain, wherein
   i) the variable domain comprises the HVRs of SEQ ID NO: 12, SEQ ID NO: 05 and SEQ ID NO: 15,
   ii) the constant region is a human kappa light chain constant region or a human lambda light chain constant region, and
c) i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human tau(pS422) fragment that has the amino acid sequence of SEQ ID NO: 03 of 6 ng/mL or less, and/or
   vii) has an $EC_{50}$ value for the full length human tau(pS422) that has the amino acid sequence of SEQ ID NO: 02 of 4.5 ng/mL or less, and/or
   viii) has an $EC_{50}$ value for aggregates of human tau (pS422) that has the amino acid sequence of SEQ ID NO: 02 of 30 ng/mL or less, and/or
   ix) has an $EC_{50}$ value for the human tau that has the amino acid sequence of SEQ ID NO: 01 and that has the amino acid mutation S422A of 125 ng/mL or less.

230. The non-covalent complex according to any one of embodiments 119 to 229, wherein the antibody that specifically binds to human tau(pS422)
a) comprises two antibody heavy chains each comprising a heavy chain variable domain and a heavy chain constant region, wherein
   i) the variable domain comprises the HVRs of SEQ ID NO: 08, SEQ ID NO: 09 and SEQ ID NO: 10,
   ii) the constant region is a human IgG1 constant region, wherein the C-terminal lysine residue can be present or absent, and
   iii) the constant region comprises the amino acid changes L234A, L235A and P329G,
b) comprises two antibody light chains each comprising a light chain variable domain and a light chain constant domain, wherein
   i) the variable domain comprises the HVRs of SEQ ID NO: 13, SEQ ID NO: 14 and SEQ ID NO: 15,
   ii) the constant region is a human kappa light chain constant region or a human lambda light chain constant region, and
c) i) specifically binds to a polypeptide that has the amino acid sequence of SEQ ID NO: 03, and/or
   ii) does not bind to full length human tau (SEQ ID NO: 01) at 1 µg/mL, and/or
   iii) specifically binds to full length human tau phosphorylated at the serine at position 422 (SEQ ID NO: 02), and/or
   iv) specifically binds to aggregates of human tau phosphorylated at the serine at position 422 (SEQ ID NO: 02), and/or
   v) specifically binds to full length human tau that has the amino acid sequence of SEQ ID NO: 01 and that has the amino acid mutation S422A, and/or
   vi) has an $EC_{50}$ value for the human tau(pS422) fragment that has the amino acid sequence of SEQ ID NO: 03 of 6 ng/mL or less, and/or
   vii) has an $EC_{50}$ value for the full length human tau(pS422) that has the amino acid sequence of SEQ ID NO: 02 of 4.5 ng/mL or less, and/or
   viii) has an $EC_{50}$ value for aggregates of human tau (pS422) that has the amino acid sequence of SEQ ID NO: 02 of 30 ng/mL or less, and/or ix) has an $EC_{50}$ value for the human tau that has the amino acid sequence of SEQ ID NO: 01 and that has the amino acid mutation S422A of 125 ng/mL or less.
231. The non-covalent complex according to any one of embodiments 119 to 230, wherein the antibody that specifically binds to human tau(pS422)
   a) comprises two antibody heavy chains each comprising a heavy chain variable domain and a heavy chain constant region, wherein
      i) the variable domain has the amino acid sequence of SEQ ID NO: 20,
      ii) the constant region is a human IgG1 constant region, wherein the C-terminal lysine residue can be present or absent, and
      iii) the constant region comprises the amino acid changes L234A, L235A and P329G,
   b) comprises two antibody light chains each comprising a light chain variable domain and a light chain constant domain, wherein
      i) the variable domain has the amino acid sequence of SEQ ID NO: 17,
      ii) the constant region is a human kappa light chain constant region or a human lambda light chain constant region, and
   c) i) specifically binds to a polypeptide that has the amino acid sequence of SEQ ID NO: 03, and/or
      ii) does not bind to full length human tau (SEQ ID NO: 01) at 1 µg/mL, and/or
      iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or
      vi) has an $EC_{50}$ value for the human tau(pS422) fragment that has the amino acid sequence of SEQ ID NO: 03 of 6 ng/mL or less, and/or
      vii) has an $EC_{50}$ value for the full length human tau(pS422) that has the amino acid sequence of SEQ ID NO: 02 of 4.5 ng/mL or less, and/or
      viii) has an $EC_{50}$ value for aggregates of human tau (pS422) that has the amino acid sequence of SEQ ID NO: 02 of 30 ng/mL or less, and/or
      ix) has an $EC_{50}$ value for the human tau that has the amino acid sequence of SEQ ID NO: 01 and that has the amino acid mutation S422A of 125 ng/mL or less.
232. The non-covalent complex according to any one of embodiments 119 to 231, wherein the antibody that specifically binds to human tau(pS422)
   a) comprises two antibody heavy chains each comprising a heavy chain variable domain and a heavy chain constant region, wherein
      i) the variable domain has the amino acid sequence of SEQ ID NO: 19,
      ii) the constant region is a human IgG1 constant region, wherein the C-terminal lysine residue can be present or absent, and
      iii) the constant region comprises the amino acid changes L234A, L235A and P329G,
   b) comprises two antibody light chains each comprising a light chain variable domain and a light chain constant domain, wherein
      i) the variable domain has the amino acid sequence of SEQ ID NO: 16,
      ii) the constant region is a human kappa light chain constant region or a human lambda light chain constant region, and
   c) i) specifically binds to a polypeptide that has the amino acid sequence of SEQ ID NO: 03, and/or
      ii) does not bind to full length human tau (SEQ ID NO: 01) at 1 µg/mL, and/or
      iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or
      vi) has an $EC_{50}$ value for the human tau(pS422) fragment that has the amino acid sequence of SEQ ID NO: 03 of 6 ng/mL or less, and/or
      vii) has an $EC_{50}$ value for the full length human tau(pS422) that has the amino acid sequence of SEQ ID NO: 02 of 4.5 ng/mL or less, and/or
      viii) has an $EC_{50}$ value for aggregates of human tau (pS422) that has the amino acid sequence of SEQ ID NO: 02 of 30 ng/mL or less, and/or
      ix) has an $EC_{50}$ value for the human tau that has the amino acid sequence of SEQ ID NO: 01 and that has the amino acid mutation S422A of 125 ng/mL or less.
233. The non-covalent complex according to any one of embodiments 119 to 232, wherein the antibody that specifically binds to human tau(pS422)
   a) comprises two antibody heavy chains each comprising a heavy chain variable domain and a heavy chain constant region, wherein
      i) the variable domain has the amino acid sequence of SEQ ID NO: 19,
      ii) the constant region is a human IgG1 constant region, wherein the C-terminal lysine residue can be present or absent, and
      iii) the constant region comprises the amino acid changes L234A, L235A and P329G,
   b) comprises two antibody light chains each comprising a light chain variable domain and a light chain constant domain, wherein
      i) the variable domain has the amino acid sequence of SEQ ID NO: 17,
      ii) the constant region is a human kappa light chain constant region or a human lambda light chain constant region, and
   c) i) specifically binds to a polypeptide that has the amino acid sequence of SEQ ID NO: 03, and/or
      ii) does not bind to full length human tau (SEQ ID NO: 01) at 1 µg/mL, and/or
      iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or vi) has an $EC_{50}$ value for the human tau(pS422) fragment that has the amino acid sequence of SEQ ID NO: 03 of 6 ng/mL or less, and/or vii) has an $EC_{50}$ value for the full length human tau(pS422) that has the amino acid sequence of SEQ ID NO: 02 of 4.5 ng/mL or less, and/or viii) has an $EC_{50}$ value for aggregates of human tau (pS422) that has the amino acid sequence of SEQ ID NO: 02 of 30 ng/mL or less, and/or ix) has an $EC_{50}$ value for the human tau that has the amino acid sequence of SEQ ID NO: 01 and that has the amino acid mutation S422A of 125 ng/mL or less.

234. The non-covalent complex according to any one of embodiments 119 to 233, wherein the antibody that specifically binds to human tau(pS422)
   a) comprises two antibody heavy chains each comprising a heavy chain variable domain and a heavy chain constant region, wherein
      i) the variable domain has the amino acid sequence of SEQ ID NO: 21,
      ii) the constant region is a human IgG1 constant region, wherein the C-terminal lysine residue can be present or absent, and
      iii) the constant region comprises the amino acid changes L234A, L235A and P329G,
   b) comprises two antibody light chains each comprising a light chain variable domain and a light chain constant domain, wherein
      i) the variable domain has the amino acid sequence of SEQ ID NO: 17,
      ii) the constant region is a human kappa light chain constant region or a human lambda light chain constant region, and
   c) i) specifically binds to a polypeptide that has the amino acid sequence of SEQ ID NO: 03, and/or
      ii) does not bind to full length human tau (SEQ ID NO: 01) at 1 µg/mL, and/or
      iii) specifically binds to full length human tau phosphorylated at the serine at position 422 (SEQ ID NO: 02), and/or
      iv) specifically binds to aggregates of human tau phosphorylated at the serine at position 422 (SEQ ID NO: 02), and/or
      v) specifically binds to full length human tau that has the amino acid sequence of SEQ ID NO: 01 and that has the amino acid mutation S422A, and/or
      vi) has an $EC_{50}$ value for the human tau(pS422) fragment that has the amino acid sequence of SEQ ID NO: 03 of 6 ng/mL or less, and/or
      vii) has an $EC_{50}$ value for the full length human tau(pS422) that has the amino acid sequence of SEQ ID NO: 02 of 4.5 ng/mL or less, and/or
      viii) has an $EC_{50}$ value for aggregates of human tau (pS422) that has the amino acid sequence of SEQ ID NO: 02 of 30 ng/mL or less, and/or
      ix) has an $EC_{50}$ value for the human tau that has the amino acid sequence of SEQ ID NO: 01 and that has the amino acid mutation S422A of 125 ng/mL or less.

235. The non-covalent complex according to any one of embodiments 119 to 234, wherein the antibody that specifically binds to human tau(pS422) has in the heavy chain variable domain at positions 4, 24 and 78 a valine residue.

236. The non-covalent complex according to any one of embodiments 119 to 235, wherein the antibody that specifically binds to human tau(pS422) has in the heavy chain variable domain at position 71 an arginine residue.

237. A pharmaceutical formulation comprising the non-covalent complex according to any one of embodiments 1 to 236 and a pharmaceutically acceptable carrier.

238. The pharmaceutical formulation according to embodiment 237, wherein the pharmaceutical formulation further comprises an additional therapeutic agent.

239. The pharmaceutical formulation according to embodiment 238, wherein the additional therapeutic agent is an anti-amyloid therapeutic agent.

240. The pharmaceutical formulation according to embodiment 239, wherein the anti-amyloid therapeutic agent is an anti-human alpha-synuclein antibody or an anti-Abeta antibody.

241. The pharmaceutical formulation according to any one of embodiments 239 to 122, wherein the anti-human alpha-synuclein antibody or the anti-Abeta antibody is haptenylated.

242. The pharmaceutical formulation according to any one of embodiments 239 to 123, wherein the anti-human alpha-synuclein antibody or the anti-Abeta antibody is in a complex with an anti-blood brain barrier receptor/hapten bispecific antibody.

243. The non-covalent complex according to any one of embodiments 1 to 236 for use as a medicament.

244. The non-covalent complex according to any one of embodiments 1 to 236 for use in treating Alzheimer's Disease.

245. The non-covalent complex according to any one of embodiments 1 to 236 for use in treating prodromal Alzheimer's Disease.

246. The non-covalent complex according to any one of embodiments 1 to 236 for use in treating mild Alzheimer's Disease.

247. The non-covalent complex according to any one of embodiments 1 to 236 for use in reducing tau(pS422)-induced neurodegeneration.

248. The non-covalent complex according to any one of embodiments 1 to 236 for use in maintaining cognition and function.

249. The non-covalent complex according to any one of embodiments 1 to 236 for use in slowing the rate of cognitive and functional decline.

250. Use of the non-covalent complex according to any one of embodiments 1 to 236 in the manufacture of a medicament.

251. The use according to embodiment 250, wherein the medicament is for treatment of Alzheimer's Disease.

252. The use according to any one of embodiments 250 to 251, wherein the medicament is for treatment of prodromal Alzheimer's Disease.

253. The use according to any one of embodiments 250 to 251, wherein the medicament is for treatment of mild Alzheimer's Disease.

254. The use according to any one of embodiments 250 to 251, wherein the medicament is for reducing tau(pS422)-induced neurodegeneration.

255. The use according to any one of embodiments 250 to 251, wherein the medicament is for maintaining cognition and function.

256. The use according to any one of embodiments 250 to 251, wherein the medicament is for slowing the rate of cognitive and functional decline.

257. A method of treating an individual having Alzheimer's Disease comprising administering to the individual an effective amount of the non-covalent complex according to any one of embodiments 1 to 236.

258. A method of reducing tau(pS422)-induced neurodegeneration in an individual comprising administering to the individual an effective amount of the non-covalent complex according to any one of embodiments 1 to 236 to reduce tau(pS422)-induced neurodegeneration.

259. A method of maintaining cognition and function in an individual comprising administering to the individual an effective amount of the non-covalent complex according to any one of embodiments 1 to 236 to maintain cognition and function.

260. A method of slowing the rate of cognitive and functional decline in an individual comprising administering to the individual an effective amount of the non-covalent complex according to any one of embodiments 1 to 236 to slow the rate of cognitive and functional decline.

261. Use of the non-covalent complex according to any one of embodiments 1 to 236 in the reduction of tau(pS422)-induced neurodegeneration.

262. Use of the non-covalent complex according to any one of embodiments 1 to 236 in maintaining cognition and function.

263. Use of the non-covalent complex according to any one of embodiments 1 to 236 in slowing the rate of cognitive and functional decline.

264. Use of the non-covalent complex according to any one of embodiments 1 to 236 in the treatment of Alzheimer's disease.

265. Use of the non-covalent complex according to any one of embodiments 1 to 236 to protect from development of Alzheimer's Disease.

266. Use of the non-covalent complex according to any one of embodiments 1 to 236 to stop the progression of Alzheimer's Disease.

267. The use of the non-covalent complex according to any one of embodiments 1 to 236 for the prevention of human tau (pS422)-related Alzheimer's Disease spread.

268. The use of the non-covalent complex according to any one of embodiments 1 to 236 for the reduction of lysosomal membrane disintegration.

269. The use of the non-covalent complex according to any one of embodiments 1 to 236 for the stabilization of lysosome membrane against human tau(pS422)-induced destabilization and/or disintegration.

270. The use of the non-covalent complex according to any one of embodiments 1 to 236 for the prevention of Alzheimer's Disease progression.

V. Examples

The following are examples of methods and compositions of the invention. It is understood that various other embodiments may be practiced, given the general description provided above.

Materials and Methods

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene and Oligonucleotide Synthesis

Desired gene segments were prepared by chemical synthesis at Geneart GmbH (Regensburg, Germany). The synthesized gene fragments were cloned into an E. coli plasmid for propagation/amplification. The DNA sequences of subcloned gene fragments were verified by DNA sequencing. Alternatively, short synthetic DNA fragments were assembled by annealing chemically synthesized oligonucleotides or via PCR. The respective oligonucleotides were prepared by metabion GmbH (Planegg-Martinsried, Germany).

Reagents

All commercial chemicals, antibodies and kits were used as provided according to the manufacturer's protocol if not stated otherwise.

Example 1

Preparation and Purification of Rabbit Antibodies

Immunization

New Zealand White (NZW) rabbits from Charles River Laboratories International, Inc. were used for immunization. Phosphopeptide tau (416-430)[pS422] coupled on keyhole limpet hemocyanin (KLH) was solved in $K_3PO_4$ puffer, pH 7.0 at a concentration of 1 mg/ml and mixed (1:1) with complete Freund's adjuvant (CFA) till generation of stabile emulsion. Three rabbits received an intra-dermal (i.d.) injection of 2 ml of emulsion followed by a second intra muscular (i.m.) and third subcutaneous (s.c.) injection each with 1 ml in one week interval. The fourth i.m. injection of 1 ml was performed two weeks later followed by two further s.c. injections of 1 ml in four weeks interval. 10 ml peripheral whole blood samples of each animal was collected 4-6 days after third, fourth, fifth and sixth injection and used for single cell sorting in FACS. An additional 0.5 ml serum of each animal was collected at the same time and used for the determination of tau (416-463)[pS422] specific antibody response.

Antibody Response

The antibody response to the immunization was determined by serial dilution of sera using an ELISA, in which 30 ng per well of biotinylated tau (416-430)[pS422] was incubated in 1×PBS at 4° C. overnight on streptavidin pre-coated 96-well microtiter plates (MC1347, Micro Coat Biotechnologie GmbH, Bernried, Germany). For detection, goat anti-rabbit IgG linked to a horseradish peroxidase (The Jackson laboratory) was used at 1:16,000 dilution. BM Blue POD Substrate, precipitating tetramethyl benzidine (TMB), ready-to-use solution from Roche Diagnostics GmbH was used for visualization. Reaction was stopped via 1N HCl and measured in Tecan Infinite by 450/690 nm.

B-cell Cloning

Coating of Plates

Sterile streptavidin-coated 6-well plates (cell culture grade) were incubated with either a mixture of 3 biotinylated control peptides (non-phosphorylated tau (416-430), MCAK_Human (88-102)[95-pSer] and MAP2_Human (1802-1816)[pSer-1802]) or with the biotinylated phosphopeptide tau (416-430)[pS422] each in a concentration at 0.5-1 µg/ml in PBS at room temperature for 1 hour. Plates were washed in sterile PBS three times before use. Cell culture 6-well plates were coated with 2 µg/ml KLH (key hole limpet hemocyanin) in carbonate buffer (0.1 M sodium bicarbonate, 34 mM Disodiumhydrogencarbonate, pH 9.55) overnight at 4° C. Plates were washed in sterile PBS three times before use.

Isolation of Rabbit Peripheral Blood Mononuclear Cells (PBMC)

EDTA containing whole blood was diluted twofold with 1×PBS before density centrifugation on lympholyte mammal (Cedarlane Laboratories) which was performed to isolate rabbit PBMC. PBMCs were washed twice before staining with antibodies.

EL-4 B5 Medium

RPMI 1640 (Pan Biotech, Aidenbach, Germany) supplemented with 10% FCS (Hyclone, Logan, Utah, USA), 2 mM glutamine, 1% penicillin/streptomycin solution (PAA, Pasching, Austria), 2 mM sodium pyruvate, 10 mM HEPES (PAN Biotech, Aidenbach, Germany) and 0.05 mM beta-mercaptoethanol (Gibco, Paisley, Scotland)

Depletion of Macrophages/Monocytes

Sterile 6-well plates (cell culture grade) were used to deplete macrophages and monocytes through unspecific adhesion. Wells were either coated with KLH (key hole limpet hemocyanin) or with streptavidin and the control peptides. Each well was filled with at maximum 4 ml medium and up to $6 \times 10^6$ peripheral blood mononuclear cells from the immunized rabbit and allowed to bind for 1 hour at 37° C. in the incubator. 50% of the cells in the supernatant were used for the panning step; the remaining 50% of cells were directly subjected to immune fluorescence staining and single cell sorting.

Panning B-Cells on Peptides 6-well tissue culture plates coated with streptavidin and the biotinylated peptide tau (416-430)[pS422] were seeded with up to $6 \times 10^6$ cells per 4 ml medium and allowed to bind for 1 hour at 37° C. in the incubator. Non-adherent cells were removed by carefully washing the wells 1-2 times with 1×PBS. The remaining sticky cells were detached by trypsin for 10 minutes at 37° C. in the incubator and then washed twice in media. The cells were kept on ice until the immune fluorescence staining.

Immune Fluorescent Staining and Single Cell Sorting

Anti-rabbit IgG FITC used for single cell sorting was from AbD Serotec (STAR121F, Dusseldorf, Germany). For surface staining, cells from the depletion and panning step were incubated with anti-rabbit IgG FITC antibody in PBS for 30 minutes rolling in the cold room at 4° C. in the dark. Following centrifugation, the supernatants were removed by aspiration. The PBMCs were subjected to 2 cycles of centrifugation and washing with ice cold PBS. Finally the PBMCs were resuspended in ice cold PBS and immediately subjected to the FACS analysis. Propidium iodide at a concentration of 5 µg/ml (BD Pharmingen, San Diego, Calif., USA) was added prior to the FACS analyses to discriminate between dead and live cells. FACS was performed using a Becton Dickinson FACSAria equipped the FACSDiva software (BD Biosciences, USA) and single, FITC-labeled, live cells were deposited in 96-well plates.

B-Cell Culture

B-cell cultures were prepared by a method similar to that described by Zubler, R. H. et al., J. Immunol. 134 (1985) 3662-3668. Briefly, single sorted B cells were cultured in 96-well plates with 210 µl/well EL-4 B5 medium with Pansorbin Cells (1:20000) (Calbiochem (Merck), Darmstadt, Deutschland), 5% rabbit thymocyte supernatant and gamma-irradiated EL-4-B5 murine thymoma cells ($2 \times 10^4$/well) for 7 days at 37° C. in an atmosphere of 5% $CO_2$ in the incubator. B cell culture supernatants were removed for screening and the cells harvested immediately for variable region gene cloning or frozen at −80° C. in 100 µl RLT buffer (Qiagen, Hilden, Germany).

B-Cell Clone Screening

B-cell culture supernatants were screened for binding to biotinylated tau (416-430)[pS422] by ELISA. Non-phosphorylated tau (416-430), KLH (key hole limpet hemocyanin) and the unrelated phospho-peptide MCAK_Human (88-102)[95-pSer] were used as control antigens. For the preparation of ELISA plates, streptavidin pre-coated microtiter plates were incubated with biotinylated tau (415-430) [pS422] at 50 ng/ml for 1 hour at room temperature. Coating with KLH or control peptides was performed at 1 µg/ml. B cell supernatants were diluted 1:5 to 1:10 and were incubated in the antigen coated microtiter plates for 60 minutes. After intensive washing, the binding of the rabbit antibodies was detected using a sheep anti-rabbit IgG digoxigenin conjugated detection antibody (Chemicon AQ301D). After incubation with TMB at room temperature, absorbance at 370 nm-492 nm was measured. B-cell clones yielding signals above background with biotinylated tau (416-430) [pS422] but not with KLH and MCAK_Human (88-102) [95-pSer] were further considered and subjected to variable region gene cloning.

PCR Amplification of V-Domains and Sequencing

Total RNA was prepared using the NucleoSpin® 8/96 RNA kit (Macherey&Nagel; 740709.4, 740698) according to manufacturer's protocol. All steps were done on an epMotion 5075 liquid handling system (Eppendorf). RNA was eluted with 60 µl RNAse free water. 6 µl of RNA was used to generate cDNA by reverse transcriptase reaction using the Superscript III First-Strand Synthesis SuperMix (Invitrogen 18080-400) and an oligo dT-primer according to the manufacturer's instructions. 4 µl of cDNA were used to amplify the immunoglobulin heavy and light chain variable regions (VH and VL) with the AccuPrime SuperMix (Invitrogen 12344-040) in a final volume of 50 µl using the primers rbHCfinal.up and rbHCfinal.do for the heavy chain and rbLCfinal.up and rbLCfinal.do for the light chain (see Table below). The PCR conditions were as follows: Hot start at 94° C. for 5 minutes; 35 cycles of 20 seconds at 94° C., 20 seconds at 70° C., 45 seconds at 68° C., and a final extension at 68° C. for 7 minutes.

TABLE

| | |
|---|---|
| rbHCfinal.up (SEQ ID NO: 61) | AAGCTTGCCACCATGGAGACTGGGCTGCGCTGGC TTC |
| rbHCfinal.do (SEQ ID NO: 62) | CCATTGGTGAGGGTGCCCGAG |
| rbLCfinal.up (SEQ ID NO: 63) | AAGCTTGCCACCATGGACAYGAGGGCCCCCACTC |
| rbLCfinal.do (SEQ ID NO: 64) | CAGAGTRCTGCTGAGGTTGTAGGTAC |

8 µl of the 50 µl PCR solution were loaded on a 48 E-Gel 2% (Invitrogen G8008-02). Positive PCR reactions were cleaned using the NucleoSpin® Extract II kit (Macherey&Nagel; 740609250) according to manufacturer's protocol and eluted in 50 µl elution buffer. 12 µl of purified PCR products were sequenced directly in both directions using the rbHCfinal.up and rbHCfinal.do for heavy chains and rbLCfinal.up and rbLCfinal.do for light chains (see Table above).

Recombinant Expression of Rabbit Monoclonal Antibodies and Rabbit/Mouse Chimeric Antibodies For recombinant expression of rabbit monoclonal antibodies, PCR-products coding for VH or VL were cloned as cDNA into expression vectors by the overhang cloning method (Haun, R. S. et al., BioTechniques 13 (1992) 515-518; Li, M. Z., et al., Nature Methods 4 (2007) 251-256). Linearized expression plasmids coding for the rabbit kappa or gamma constant region and VL of VH inserts were amplified by PCR using overlapping primers. Purified PCR products were incubated with T4 DNA-polymerase which generated single-strand overhangs. The reaction was stopped by dCTP addition. In the next step, plasmid and insert were combined and incubated with RecA which induced site specific recombination. The recombined plasmids were transformed into E. coli. The next day the grown colonies were picked and tested for correct recombined plasmid by plasmid preparation, restriction analysis and DNA-sequencing. For antibody expression, the isolated HC and LC plasmids were transiently co-transfected into HEK293 cells and the supernatants were harvested after 1 week. For cloning and expression of rabbit mouse chimeric antibodies, the VH and VL regions were amplified by PCR and sub-cloned into expression vectors containing the mouse constant kappa or mouse constant gamma 1 region. The rabbit/mouse chimeric HC and LC plasmids were isolated, tested by restriction analysis and DNA-sequencing for correct insertion and transiently co-transfected into HEK293 cells. Supernatants were harvested one week after transfection.

Antibody Purification

Recombinantly expressed rabbit antibodies were purified from cell culture supernatants on MabSelectSuRe™ columns (GE Healthcare). Prior to sample loading the column was equilibrated with 25 mmol/L Tris-HCl, 25 mmol/L NaCl, pH 7.4. Elution of the antibody was achieved with 50 mmol/L acetate pH 3.14. The eluted sample was immediately loaded onto a desalting column (Sephadex G25, GE Healthcare) and eluted in 20 mmol/L His-HCl, 140 mmol/L NaCl pH 6.0. This buffer was also used for the storage of purified antibody. General storage temperature was 4° C., room temperature during the purification process and −80° C. after aliquotation. Recombinantly expressed rabbit/mouse chimaeras antibodies from cell culture supernatants were purified on MabSelectSuRe™ columns (GE Healthcare). Prior to sample loading the column was equilibrated with 1×PBS, pH 7.4. Elution of the antibodies was achieved with 100 mmol/L citrate pH 3.0. The eluted sample was immediately neutralized with 2 mol/L Tris/HCl pH 9.0. Afterwards the antibodies were loaded onto a size exclusion column (Superdex 200, GE Healthcare) and eluted in 20 mmol/L His-HCl, 140 mmol/L NaCl pH 6.0. This buffer was also used for the storage of purified antibodies. General storage temperature was 4° C., room temperature during the purification process and −80° C. after aliquotation.

Example 2

Anti-Tau (pS422) Monoclonal Rabbit Antibodies are Highly Selective for Tau Phosphorylated at pS422 and Bind to Fibrillary Aggregates of Tau (pS422)

ELISA

Rabbit monoclonal antibodies were recombinantly expressed in HEK 293 cells. Cell culture supernatants or purified rabbit antibodies were tested for binding to biotinylated tau (416-430)[pS422], non-phosphorylated tau (416-430), KLH and the unrelated phospho-peptide MCAK_Human (88-102)[95-pSer] by ELISA. For preparation of ELISA plates, streptavidin pre-coated microtiter plates were incubated with biotinylated tau (415-430) [pS422] at 50 ng/ml for 1 hour at room temperature. Coating with KLH or control peptides was performed at 1 µg/ml. Rabbit anti-tau (pS422) antibody (Abcam AB51071) or rabbit antibody containing supernatants were incubated in the antigen labeled microtiter plates for 60 minutes at various concentrations. After intensive washing, the binding of the rabbit antibodies was detected using a sheep anti-rabbit IgG digoxigenin conjugated detection antibody (Chemicon AQ301D). After incubation with TMB at room temperature absorbance at 370 nm-492 nm was measured. The antibody binding was characterized by its EC50 values. Antibody binding to biotinylated tau (416-430)[pS422] and non-phosphorylated tau (416-430) peptides was characterized by its EC50 values. Cross-reactivity with KLH or MCAK phosphopeptide was estimated by single-point measurement at high concentrations, i.e. at 1:5 dilution of the cell culture supernatants. Results are shown in the Table below. EC50 values of binding to tau phosphopeptide were found to be more than 100 times lower than EC50 values of binding to tau peptide, indicating at least 100 fold selectivity for phosphorylated tau fragment compared to non-phosphorylated tau peptide. Binding to KLH and MCAK control phosphopeptide was at background level with all antibodies, which is about 1 to 3% of the maximal value measures with tau phosphopeptide.

TABLE

|  | $EC_{50}$ phosphorylated tau peptide (µg/ml) | $EC_{50}$ non-phosphorylated tau peptide (µg/ml) | IgG titer of supernatant (µg/ml) | OD 1:5 dilution of supernatant | |
| --- | --- | --- | --- | --- | --- |
|  |  |  |  | KLH (mE) | MCAK (mE) |
| mAb 005 | <0.003 | 3.727 | 5.818 | 0.026 | 0.067 |
| mAb 019 | <0.003 | 1.076 | 6.958 | 0.026 | 0.023 |
| mAb 020 | 0.002 | >3.369 | 3.369 | 0.016 | 0.010 |
| mAb 085 | 0.0009 | 0.146 | 6.46 | 0.029 | 0.062 |
| mAb 086 | 0.0011 | 0.266 | 8.84 | 0.046 | 0.104 |
| mAb 097 | 0.0013 | 1.281 | 19.87 | 0.042 | 0.029 |

Specificity for soluble and aggregated full-length tau (pS422) was also tested. Fibrillary aggregates of tau (pS422) (300 µg/ml) were coated on a polystyrene based Maxisorb microtiter plate (Nunc) overnight at room temperature. In similar manner, soluble full-length tau and tau (pS422) were coated on a Maxisorb microtiter plate. Rabbit anti-tau (pS422) antibody control (Abcam AB51071), or purified rabbit antibodies were added and incubated for 60 minutes in concentrations up to 1000 ng/ml. After intensive washing, the binding of the rabbit antibodies was detected using a sheep anti-rabbit IgG digoxigenin conjugated detection antibody (Chemicon AQ301D). After incubation with TMB at room temperature absorbance at 370 nm-492 nm was measured. The antibody binding was characterized by its EC50 values. Results are shown in the following Table.

TABLE

| Rabbit mAb | $EC_{50}$ tau (pS422) protein (µg/ml) | $EC_{50}$ tau protein (µg/ml) | $EC_{50}$ fibrillary tau (pS422) (µg/ml) |
| --- | --- | --- | --- |
| mAb 005 | 0.00034 | no binding | 0.00755 |
| mAb 019 | 0.00038 | no binding | 0.00059 |
| mAb 020 | 0.00036 | no binding | 0.00042 |
| mAb 085 | 0.00025 | no binding | 0.00074 |
| mAb 086 | 0.00023 | no binding | 0.00048 |
| mAb 097 | 0.00040 | no binding | 0.01358 |

Rabbit monoclonal antibodies bound to tau(pS422) protein with EC50 values below 1 ng/ml. Fibrillary tau (pS422) was detected with EC50 values ranging from 0.4 ng/ml to 14 ng/ml. Signals for binding to non-phosphorylated full-lengths tau protein were indistinguishable from background levels. Therefore it was estimated that each of the antibodies binds to tau (pS422) and fibrillary tau (pS422) with a selectivity of at least 100-fold compared to tau.

BIAcore™

Binding to fibrillary tau (pS422) aggregates was further investigated and confirmed by BIAcore™ analysis. Measurements were performed using the BIAcore 3000 instrument at 37° C. The system and sample buffer was HBS-EP (10 mM HEPES, 150 mM NaCl, 3.4 mM EDTA, 0.005% Polysorbate 20 (v/v)). A BIAcore™ CM5 sensor chip was subjected to a preconditioning procedure. Sequentially 0.1% SDS, 50 mM NaOH, 10 mM HCl and 100 mM $H_3PO_4$ were injected for 30 seconds over the flow cells FC1, FC2, FC3 and FC4. The amine coupling procedure was done according to the manufacturer's instructions using the BIAcore 3000™ wizard v. 4.1. After an EDC/NHS activation of the sensor surface, a non-phosphoselective anti-tau antibody mAb <TAU>M-4/53-IgG was immobilized on sensor flow cells FC2, FC3 and FC4. As a control, an antibody against CK-MM (creatine kinase isotype), recognizing an irrelevant antigen, was captured on the FC1 flow cell. mAb <TAU>M-4/53-IgG and the antibody against CK-MM were diluted at 30 μg/ml in 10 mM NaAc pH 5.0 and were injected at 10 μl/min for 7 minutes contact time to immobilize 10,000 RU of the antibody capturing system. The surface was deactivated by saturation with 1 M ethanolamine. The sensor was conditioned by 5 cycles with phosphorylated filamentous tau protein (stock 0.3 mg/ml diluted 1:100 in HBS-EP) as analyte in solution at 10 μl/min for 2 minutes. Regeneration was performed with 10 mM glycine pH 2.5 at 30 μl/min for 3 minutes. It was assumed, that the analyte binding to mAb 4/53 does not dissociate the ptau filaments, because no dissociation of ptau filaments from the mAb 4/53 could be observed. For all further measurement cycles, 0.3 mg/ml ptau filaments were diluted 1:100 in HBS-EP buffer and were injected at 10 μl/min for 1 minute in order to present ptau to the respective antibody analytes in a heterogeneous sandwich-mode. The antibody analytes were diluted in HBS-EP buffer to a concentration of 100 nM and were injected into the system at 20 μl/min for 3 minutes. After 3 minutes of dissociation, the sensor surface was regenerated by 2 injections of a 10 mM glycine pH 2.5 for 1 minute at 100 followed by a HBS-wash for 15 seconds at 100 μl/minute. The association and dissociation phase of the interactions were monitored. Since the antibody analyte in solution is bivalent, the avidity-burdened antibody-ptau kinetics were characterized by a biphasic dissociation model, consisting of a fast affinity-based early dissociation step followed by an avidity-stabilized, but rate-limiting kinetic step in the latter complex dissociation. 10 seconds (early) and 50 seconds (late) after analyte injection end, the kd and t/2 diss were quantified, where possible. The kinetic measurements were evaluated using a double referencing procedure. First the signal from the FC1 reference was subtracted to correct the buffer bulk effect and unspecific binding. Second the 0 nM analyte injection was subtracted to correct the dissociation of the primary antibodies from the respective capturing system. The kinetic rates were evaluated using a Langmuir 1.1 dissociation fit model according to the BIAcore™ evaluation software v.4.1. The antigen/antibody complex stability halftime (min) was calculated according to the formula ln(2)/60*kd.

Results are summarized in the following Table.

TABLE

| Clone | early (10 s) | | late (50 s) | |
|---|---|---|---|---|
| | kd (1/s) | t/2 diss (min) | kd (1/s) | t/2 diss (min) |
| mAb 005 | 2.19E−03 | 5.3 | $3.12 \times 10^{-3}$ | 4 |
| mAb 019 | 1.43E−02 | 0.8 | $6.17 \times 10^{-4}$ | 19 |
| mAb 020 | 3.28E−03 | 3.5 | $4.08 \times 10^{-4}$ | 28 |
| mAb 085 | n.d. | n.d. | $6.60 \times 10^{-4}$ | 18 |
| mAb 086 | 1.62E−03 | 7.2 | $3.68 \times 10^{-4}$ | 32 |
| mAb 097 | n.d. | n.d. | n.d. | n.d. |

Example 3

Binding of Anti-Tau (pS422) Monoclonal Rabbit Antibodies to Intracellular Ptau in Brain Sections of Alzheimer's Disease Patients The specific and sensitive immunohistochemical detection of ptau pathology in Alzheimer's disease brain tissue by monoclonal rabbit anti-tau (pS422) antibodies was investigated by immunofluorescence staining experiments using cryosections of human brain tissue from AD patients. Rabbit IgGs were detected by goat anti-rabbit Alexa Fluor488® conjugated secondary antibodies (Invitrogen/Molecular Probes A11034). Specific and sensitive staining of ptau deposits and filaments was evident for clones mAb 005, mAb 019, mAb 020, mAb 085, mAb 086 and mAb 097. Intracellular ptau deposits, like large neurofibrillary tangles and elongated neutrophil threads, were noticeable. A minimal effective concentration ranging between 0.08 and 0.016 μg/ml was determined for all clones investigated, which indicates highly sensitive binding to genuine human ptau deposits.

Example 4

Humanization of Rabbit Anti-Human Tau(pS422) Antibodies

The "variable domain" (variable domain of a light chain (VL), variable domain of a heavy chain (VH)) as used herein denotes each of the pair of light and heavy chain domains which are involved directly in binding the antibody to the tau(p S422) antigen. The variable light and heavy chain domains have the same general structure and each domain comprises four framework (FR) regions whose sequences are widely conserved, connected by three "hypervariable regions".

The structures of the VH and the VL domain of the rabbit antibody mAb 086 were analyzed in silico and compared to a structural database of human VH and VL domains (IMGT). A panel of structurally most similar V domains were chosen for grafting the CDRs of the rabbit antibody onto the chosen human VH and VL domains. In addition, similarities in the primary sequence were taken into account to narrow down the choice of the human V domains by aligning the primary sequence of the VH and VL domain of the rabbit antibody to the human V domain repertoire. Backmutations within the human framework regions to rabbit parent residues were introduced in some humanization variants. Similarly, mutations in the CDRs were introduced in some variants where appropriate to potentially increase the affinity to the antigen, to maintain the CDR tertiary structure, and to remove non-wanted features like cysteine residues or residues that can undergo modification after antibody purification.

The heavy and light chain vectors containing each of the humanized variant were co-transfected into HEK293 suspension cells in microtiter culture plates in a matrix manner to obtain cell cultures expressing full size IgG of all possible light/heavy chain combinations. After 5 days cultivation at 37° C., the supernatants were harvested and purified by protein A affinity chromatography in the microtiter scale.

Example 5

Generation of Recombinant Expression Vectors
a) Generation of Vectors for the Expression of Immunoglobulin Heavy Chains Using the Human IgG1 Constant Region The humanized heavy chain encoding fusion gene comprising the human IgG1 constant region (CH1, hinge, CH2, CH3) and a humanized anti-human tau(pS422) antibody VH domain derived from rabbit antibody mAb 086 was assembled by fusing a DNA fragment coding for the respective anti-human tau(pS422)-specific antibody VH domain to a sequence element coding the human IgG1 constant region.

The human IgG1 constant region has the following amino acid sequence:

```
                                              (SEQ ID NO: 58)
ASTKGPSVFP LAPSSKSTSG GTAALGCLVK DYFPEPVTVS

WNSGALTSGV HTFPAVLQSS GLYSLSSVVT VPSSSLGTQT

YICNVNHKPS NTKVDKKVEP KSCDKTHTCP PCPAPELLGG

PSVFLFPPKP KDTLMISRTP EVTCVVVDVS HEDPEVKFNW

YVDGVEVHNA KTKPREEQYN STYRVVSVLT VLHQDWLNGK

EYKCKVSNKA LPAPIEKTIS KAKGQPREPQ VYTLPPSRDE

LTKNQVSLTC LVKGFYPSDI AVEWESNGQP ENNYKTTPPV

LDSDGSFFLY SKLTVDKSRW QQGNVFSCSV MHEALHNHYT

QKSLSLSPGK.
```

The expression vector also comprised an origin of replication from the vector pUC18, which allows replication of this plasmid in *E. coli*, and a beta-lactamase gene which confers ampicillin resistance in *E. coli*.

The transcription unit of the antibody heavy chain comprises the following functional elements in 5' to 3' direction:
the immediate early enhancer and promoter from the human cytomegalovirus (P-CMV) including intron A,
a human heavy chain immunoglobulin 5'-untranslated region (5'UTR),
a murine immunoglobulin heavy chain signal sequence,
a heavy chain variable (VH) domain encoding nucleic acid,
a human IgG1 constant region encoding nucleic acid, and
the bovine growth hormone polyadenylation sequence (BGH pA).

b) Generation of Vectors for the Expression of Immunoglobulin Light Chains Using the Human Ig-Kappa Constant Region The humanized kappa light chain encoding fusion gene comprising the human Ig-kappa constant region (CL-kappa) and an anti-human tau(pS422) antibody VL (kappa) domain derived from rabbit antibody mAb 086 was assembled by fusing a DNA fragment coding for the respective anti-human tau(pS422) antibody VL (kappa) domain to a sequence element coding for the human Ig-kappa constant region.

The human Ig-kappa constant region has the following amino acid sequence:

```
                                              (SEQ ID NO: 59)
RTVAAPSVFI FPPSDEQLKS GTASVVCLLN NFYPREAKVQ

WKVDNALQSG NSQESVTEQD SKDSTYSLSS TLTLSKADYE

KHKVYACEVT HQGLSSPVTK SFNRGEC.
```

The expression vector also comprised an origin of replication from the vector pUC18, which allows replication of this plasmid in *E. coli*, and a beta-lactamase gene which confers ampicillin resistance in *E. coli*.

The transcription unit of the antibody kappa light chain comprises the following functional elements in 5' to 3' direction:
the immediate early enhancer and promoter from the human cytomegalovirus (P-CMV) including intron A,
a human heavy chain immunoglobulin 5'-untranslated region (5'UTR),
a murine immunoglobulin heavy chain signal sequence,
a light chain variable (VL) domain encoding nucleic acid,
a human Ig-kappa constant region encoding nucleic acid, and
the bovine growth hormone polyadenylation sequence (BGH pA).

c) Generation of Vectors for the Expression of Immunoglobulin Light Chains Using the Human Ig-Lambda Constant Region The humanized lambda light chain encoding fusion gene comprising the human Ig-lambda constant region (CL-lambda) and an anti-human tau(pS422) antibody VL (lambda) domain derived from rabbit antibody mAb 086 was assembled by fusing a DNA fragment coding for the respective anti-human tau(pS422) antibody VL (lambda) domain to a sequence element coding for the human Ig-lambda constant region.

The human Ig-lambda constant region has the following amino acid sequence:

```
                                              (SEQ ID NO: 60)
GQPKAAPSVT LFPPSSEELQ ANKATLVCLI SDFYPGAVTV

AWKADSSPVK AGVETTTPSK QSNNKYAASS YLSLTPEQWK

SHRSYSCQVT HEGSTVEKTV APTECS.
```

The expression vector also comprised an origin of replication from the vector pUC18, which allows replication of this plasmid in *E. coli*, and a beta-lactamase gene which confers ampicillin resistance in *E. coli*.

The transcription unit of the antibody lambda light chain comprises the following functional elements in 5' to 3' direction:
the immediate early enhancer and promoter from the human cytomegalovirus (P-CMV) including intron A,
a human heavy chain immunoglobulin 5'-untranslated region (5'UTR),
a murine immunoglobulin heavy chain signal sequence,
a variable light chain (VL) domain encoding nucleic acid,
a human Ig-lambda constant region encoding nucleic acid, and
the bovine growth hormone polyadenylation sequence (BGH pA).

d) Generation of Vectors for the Expression of Immunoglobulin Kappa Light Chains Using the Human Ig-Kappa Constant Region The human Ig-kappa light chain encoding fusion gene comprising the human Ig-kappa constant region (CL-kappa) and an anti-human tau(S422) antibody VL (kappa) domain derived from rabbit antibody mAb 086 was assembled by fusing a DNA fragment coding for the respective anti-human tau(pS422)-antibody VL (kappa) domain to a sequence element coding for the human Ig-kappa constant region. The construct was in a genomic organization, i.e. introns were present in the signal peptide and between the VL (kappa) and the CL-kappa domains.

The expression vector also comprised an origin of replication from the vector pUC18, which allows replication of this plasmid in E. coli, and a beta-lactamase gene which confers ampicillin resistance in E. coli.

The transcription unit of the antibody kappa light chain comprises the following functional elements in 5' to 3' direction:
- the immediate early enhancer and promoter from the human cytomegalovirus (P-CMV)
- a human heavy chain immunoglobulin 5'-untranslated region (5'UTR),
- a murine immunoglobulin heavy chain signal sequence,
- a light chain variable (VL) domain encoding nucleic acid,
- a human IgG kappa constant region, and
- the bovine growth hormone polyadenylation sequence (BGH pA).

e) Generation of Vectors for the Expression of Immunoglobulin Lambda Light Chains Using the Human Ig-Lambda Constant Region The human Ig-lambda light chain encoding fusion gene comprising the human Ig-lambda constant region (CL-lambda) and an anti-human tau(S422) antibody VL (lambda) domain derived from rabbit antibody mAb 086 was assembled by fusing a DNA fragment coding for the respective anti-human tau(pS422)-antibody VL (lambda) domain to a sequence element coding for the human Ig-lambda constant region. The construct was in a genomic organization, i.e. introns were present in the signal peptide and between the VL (lambda) and the CL-lambda domains.

The expression vector also comprised an origin of replication from the vector pUC18, which allows replication of this plasmid in E. coli, and a beta-lactamase gene which confers ampicillin resistance in E. coli.

The transcription unit of the antibody lambda light chain comprises the following functional elements in 5' to 3' direction:
- the immediate early enhancer and promoter from the human cytomegalovirus (P-CMV)
- a human heavy chain immunoglobulin 5'-untranslated region (5'UTR),
- a murine immunoglobulin heavy chain signal sequence,
- a light chain variable (VL) domain encoding nucleic acid,
- a human IgG lambda constant region, and
- the bovine growth hormone polyadenylation sequence (BGH pA).

Example 6

Recombinant Production of Anti-Human Tau(pS422) Antibodies

Antibodies were produced in transiently transfected HEK293 cells (human embryonic kidney cell line 293-derived) cultivated in F17 Medium (Invitrogen Corp.). For transfection of the respective vectors as described in Example 5 "293-Free" Transfection Reagent (Novagen) was used. The antibodies were expressed from individual expression plasmids. Transfections were performed as specified in the manufacturer's instructions. Recombinant antibody-containing cell culture supernatants were harvested three to seven days after transfection. Supernatants were stored at reduced temperature (e.g. −80° C.) until purification.

General information regarding the recombinant expression of human immunoglobulins in e.g. HEK293 cells is given in: Meissner, P. et al., Biotechnol. Bioeng. 75 (2001) 197-203.

Example 7

Purification of Recombinant Anti-Human Tau(pS422) Antibodies

The antibody-containing culture supernatants were filtered and purified by two chromatographic steps.

The antibodies were captured by affinity chromatography using HiTrap MabSelectSuRe (GE Healthcare) equilibrated with PBS (1 mM $KH_2PO_4$, 10 mM $Na_2HPO_4$, 137 mM NaCl, 2.7 mM KCl), pH 7.4. Unbound proteins were removed by washing with equilibration buffer, and the antibody was recovered with 25 mM citrate buffer, pH 3.1, which was immediately after elution adjusted to pH 6.0 with 1 M Tris-base, pH 9.0.

Size exclusion chromatography on Superdex 200™ (GE Healthcare) was used as second purification step. The size exclusion chromatography was performed in 20 mM histidine buffer, 0.14 M NaCl, pH 6.0. The antibody containing solutions were concentrated with an Ultrafree-CL centrifugal filter unit equipped with a Biomax-SK membrane (Millipore, Billerica, Mass., USA) and stored at −80° C.

Example 8

Kinetic Screening

Kinetic screening was performed according to Schraeml et al. (Schraeml, M. and M. Biehl, Methods Mol. Biol. 901 (2012) 171-181) on a BIAcore 4000 instrument, mounted with a BIAcore CM5 sensor. The BIAcore 4000 instrument was under the control of the software version V1.1. A BIAcore CM5 series S chip was mounted into the instrument and was hydrodynamically addressed and preconditioned according to the manufacturer's instructions. The instrument buffer was HBS-EP buffer (10 mM HEPES (pH 7.4), 150 mM NaCl, 1 mM EDTA, 0.05% (w/v) P20). An antibody capture system was prepared on the sensor surface. A polyclonal goat anti-human antibody with human IgG-Fc specificity (Jackson Lab.) was immobilized at 30 µg/ml in 10 mM sodium acetate buffer (pH 5) to spots 1, 2, 4 and 5 in the instrument's flow cells 1, 2, 3 and 4 at 10,000 RU using NHS/EDC chemistry. In each flow cell the antibodies were captured on spot 1 and spot 5. Spot 2 and spot 4 were used as reference spots. The sensor was deactivated with a 1 M ethanolamine solution. Humanized antibody derivatives were applied at concentrations between 44 nM and 70 nM in instrument buffer supplemented with 1 mg/ml CMD (carboxymethyldextrane). The antibodies were injected at a flow rate of 30 µl/min for 2 minutes. The capture level (CL) of the surface-presented antibodies was measured in rel. response units (RU). The analytes in solution, phosphorylated human tau protein, non-phosphorylated human tau protein and the phosphorylated human tau mutant protein T422S were injected at 300 nM for 3 minutes at a flow rate of 30 µl/minute. The dissociation was monitored for 5 minutes. The capture system was regenerated by a 1 minute injection of 10 mM glycine buffer, pH 1.7 at 30 µL/minute over all flow cells. Two report points, the recorded signal shortly before the end of the analyte injection, denoted as binding late (BL) and the recorded signal shortly before the end of the dissociation time, stability late (SL), were used to characterize the kinetic screening performance. Furthermore, the dissociation rate constant kd (1/s) was calculated according to a Langmuir model and the antibody/antigen complex half-life was calculated in minutes according to the formula ln(2)/(60*kd). The molar ratio (MR) was calculated according to the formula MR=(Binding Late (RU))/(Capture level (RU))*(MW(antibody)/(MW(antigen)). In case the sensor was configured with a suitable amount of antibody ligand capture level, each antibody should be able to functionally bind at least to one analyte in solution, which is represented by a molar ratio of MR=1.0. Then, the molar ratio is also an indicator for the valence mode of analyte binding. The maximum valence can be MR=2 for an antibody binding two analytes, one with each Fab valence.

In another embodiment, kinetic rates were determined at 25° C. and 37° C. using the same experimental setup, but using multiple concentration series of each analyte in solution at 0 nM (buffer), 1.2 nM, 3.7 nM, 11.1 nM, 33.3 nM, 100 nM and 300 nM. From the concentration-dependent binding behavior the kinetic data was calculated using the BIAcore evaluation software according to the manufacturer's instructions and a Langmuir 1.1 model with RMAX global.

Example 9

ELISA

Non-biotinylated peptide/protein/aggregate was added to non-coated Maxisorb plates, biotinylated peptide/protein/aggregate in PBS was added to streptavidin-coated Maxisorb plates, and plates were incubated over-night. The supernatant was discarded and the wells washed three times with 90 µl wash buffer (lx PBS/0.1% Tween 20). Remaining reactive spots were blocked with blocking buffer (lx PBS/2% BSA (Bovine Serum Albumin Fraction V, fatty acid free, Roche, Cat. No.: 10735078001)/0.05% Tween 20) by incubating for one hour. The supernatant was discarded and the wells washed three times with 90 µl wash buffer. Samples and control antibody were prepared in 12 dilutions (1:2) in ELISA buffer (lx PBS/0.5% BSA (Bovine Serum Albumin Fraction V, fatty acid free, Roche, Cat. No.: 10735078001)/0.05% Tween 20) with a start concentration of 500 ng/ml. The incubation time was 60 minutes at room temperature on a shaker. The supernatant was discarded and the wells washed three times with 90 µl wash buffer. Solutions of secondary antibody were prepared in ELISA buffer. A total of 25 µl antibody-mix was transferred to all wells of the assay plate and the plate was thereafter incubated on shaker for 60 minutes at room temperature. The supernatant was discarded and the wells were washed three times with 90 µl wash buffer. 25 µl of ABTS solution was added to all wells. The absorbance was read at 405 nm-492 nm.

Example 10

Binding of Recombinant Humanized Anti-Biotin Antibody to Biotin-Labeled Compound (Haptenylated Compound)

In order to determine whether the humanization procedure and the subsequent introduction of cysteine mutations resulted in derivatives that had retained full binding activity the following experiments were performed.

The binding properties of the recombinant anti-biotin antibody derivatives were analyzed by biolayer interferometry (BLI) technology using an Octet QK instrument (ForteBio Inc.). This system is well established for the study of molecule interactions. BLI technology is based on the measurement of the interference pattern of white light reflected from the surface of a biosensor tip and an internal reference. Binding of molecules to the biosensor tip is resulting in a shift of the interference pattern which can be measured. To analyze if the humanization procedure described above diminished the ability of the anti-biotin antibody to bind to biotin, the properties of the chimeric and the humanized versions of the antibody in their ability to bind to a biotinylated protein were compared directly. Binding studies were performed by capturing anti-biotin antibody on anti-hIgG Fc antibody Capture (AHC) Biosensors (ForteBio Inc.). First, biosensors were incubated in an antibody solution with a concentration of 0.5 mg/ml in 20 mM histidine, 140 mM NaCl, pH 6.0 for 1 minute. Thereafter, the biosensors were incubated for 1 minute in 1xPBS pH 7.4 to reach a stable baseline. Binding was measured by incubating the antibody-coated biosensors in a solution containing biotinylated protein with a concentration of 0.06 mg/ml in 20 mM histidine, 140 mM NaCl, pH 6.0 for 5 minutes. Dissociation was monitored for 5 minutes in 1xPBS pH 7.4. The resulting binding curves for chimeric and humanized anti-biotin antibodies were compared directly.

The humanized version of the antibody showed equal or even better binding of the biotinylated antigen than the chimeric antibody. The biotinylated protein showed residual unspecific binding to the biosensors which was reduced when the biosensors were coated with Herceptin, which does not bind biotin. Thus, the functionality of the anti-biotin antibody was retained in its humanized variant (which is defined by the sequences as depicted in SEQ ID NO: 92 and 96).

Surface Plasmon Resonance

Surface plasmon resonance measurement was performed on a BIACORE® T200 instrument (GE Healthcare Biosciences AB, Sweden) at 25° C. Around 4300 resonance units (RU) of the capturing system (10 µg/ml Anti-human Capture (IgG Fc) from Human Antibody Capture Kit, BR-1008-39, GE Healthcare Biosciences AB, Sweden) were coupled on a CM3 chip (GE Healthcare, BR-1005-36) at pH 5.0 by using the standard amine coupling kit supplied by GE Healthcare (BR-1000-50). The running buffer for amine coupling was HBS-N(10 mM HEPES, pH 7.4, 150 mM NaCl, GE Healthcare, BR-1006-70). Running and dilution buffer for the followed binding study was PBS-T (10 mM phosphate buffered saline including 0.05% Tween 20) pH 7.4. The humanized anti-biotin antibody was captured by injecting a 2 nM solution for 60 seconds at a flow rate of 5 µl/minute. Biotinylated siRNA was diluted with PBS-T at concentrations of 0.14-100 nM (1:3 dilution series). Binding was measured by injecting each concentration for 180 sec at a flow rate of 30 µl/min, dissociation time 600 seconds. The surface was regenerated by 30 second washing with a 3 M $MgCl_2$ solution at a flow rate of 5 µl/minute. The data were evaluated using BIAevaluation software (GE Healthcare Biosciences AB, Sweden). Bulk refractive index differences were corrected by subtracting the response obtained from an anti-human IgG Fc surface. Blank injections were also subtracted (=double referencing). For calculation of $K_D$ and kinetic parameters the Langmuir 1:1 model was used.

Kinetic binding analysis by surface plasmon resonance (SPR) was carried out for humanized anti-biotin antibody SEQ ID NO: 92 and 96. Anti-biotin antibodies at a concentration of 2 nM were captured by anti-human IgG Fc antibody which was bound to a CM3 sensor chip. Binding of biotinylated siRNA (Mw: 13868 Da) was recorded at the concentrations 0.41, 1.23, 3.7, 11.1, 33.3, 100 and 300 nM. Measurements were carried out in duplicates. The calculated $K_D$ for humanized anti-biotin antibody was 0.633 nM.

Example 11

Generation of Non-Covalent Complexes of Haptenylated Compounds with Anti-Hapten Antibodies
General Method:

The generation of complexes of anti-hapten antibodies with haptenylated compounds (=haptens conjugated to a payload) shall result in defined complexes and it shall be assure that the compound (=payload) in these complexes retains its activity. For the generation of complexes of haptenylated compounds with the respective anti-hapten antibody the haptenylated compound was dissolved in $H_2O$ to a final concentration of 1 mg/ml. The antibody was concentrated to a final concentration of 1 mg/ml (4.85 µM) in 20 mM histidine buffer, 140 mM NaCl, pH=6.0. Haptenylated payload and antibody were mixed to a 2:1 molar ratio (compound to antibody) by pipetting up and down and incubated for 15 minutes at RT.

Alternatively, the haptenylated compound was dissolved in 100% DMF to a final concentration of 10 mg/ml. The antibody was concentrated to a final concentration of 10 mg/ml in 50 mM Tris-HCl, 1 mM EDTA, pH=8.2. Haptenylated compound and antibody were mixed to a 2.5:1 molar ratio (compound to antibody) by pipetting up and down and incubated for 60 minutes at room temperature RT and 350 rpm.

Exemplary Method for the Formation of Complexes of Haptenylated Polypeptides and Anti-Hapten Antibodies—Digoxigenin-PYY(3-36)/Anti-Digoxigenin Antibody Complex For the generation of non-covalent complexes of digoxigenylated polypeptides with an anti-digoxigenin antibody the murine hybridoma-derived antibody (lyophilisate from 10 mM $KPO_4$, 70 mM NaCl; pH 7.5) was dissolved in 12 ml water and dialyzed against a solution comprising 20 mM histidine, 140 mM NaCl, pH 6.0 to yield 300 mg ($2 \times 10^{-6}$ mol) in 11 ml buffer (c=27.3 mg/ml). Digoxigenin-PYY(3-36) conjugate (11.57 mg, $4 \times 10^{-6}$ mol, 2 eq.) was added in 4 portions of 2.85 mg within 1 hour and incubated for another hour at room temperature. After completion of the complexation reaction, the complexes were purified by size exclusion chromatography via a Superdex 200 26/60 GL column (320 ml) in 20 mM histidine, 140 mM NaCl, at pH 6.0 at a flow rate of 2.5 ml/minute. The eluted complex was collected in 4 ml fractions, pooled and sterilized over a 0.2 µm filter to give 234 mg of the complex at a concentration of 14.3 mg/ml. In a similar manner, for generation of complexes of the humanized anti-digoxigenin antibody the antibody was adjusted to a concentration of 10.6 mg/ml (9.81 mg, $6.5 \times 10^{-8}$ mol in 0.93 ml) in 20 mM histidine, 140 mM NaCl, pH 6.0. 0.57 mg=$1.97 \times 10^{-7}$ mol=3.03 eq. of the digoxigenylated polypeptide (DIG-PYY) were added to the antibody solution as lyophilisate. Polypeptide and antibody were incubated for 1.5 hours at room temperature. The excess of polypeptide was removed by size exclusion chromatography via a Superose 6 10/300 GL column in 20 mM histidine, 140 mM NaCl, at pH 6.0 at a flow rate of 0.5 ml/min. The eluted complex was collected in 0.5 ml fractions, pooled and sterilized over a 0.2 µm filter to give 4.7 mg of the complex at a concentration of 1.86 mg/ml.

The resulting haptenylated polypeptide-anti-hapten antibody complex was defined as monomeric IgG-like molecule via the occurrence of a single peak in a size exclusion chromatography. The resulting complex was defined as monomeric IgG-like molecule, carrying two digoxigenin-PYY derivatives per antibody molecule. The defined composition of these peptide complexes was confirmed by size exclusion chromatography, which also indicated the absence of protein aggregates. The defined composition (and 2:1 polypeptide to protein ratio) of these bispecific peptide complexes was further confirmed by SEC-MALS (Size exclusion chromatography-Multi Angle Light Scattering). For SEC-MALS analysis, 100-500 µg of the respective sample was applied to a Superdex 200 10/300 GL size exclusion column with a flow rate of 0.25-0.5 ml/minute with 1×PBS pH 7.4 as mobile phase. Light scattering was detected with a Wyatt MiniDawn TREOS/QELS detector, the refractive index was measured with a Wyatt Optilab rEX-detector. Resulting data was analyzed using the software ASTRA (version 5.3.4.14). The results of SEC-MALLS analyses provide information about the mass, radius and size of the complex. These data were then compared with those of the corresponding non-complexed antibody. The results of these experiments demonstrate that exposure of digoxigenylated-PYY to the anti-digoxigenin antibody results in complexes that contain two digoxigenin-PYY derivatives per one antibody molecule. Thus, digoxigenylated PYY can be complexed with the anti-digoxigenin antibody at defined sites (binding region) and with a defined stoichiometry.

Characterization of the complex by surface plasmon resonance studies provided additional evidence that the complexation reaction generated defined and completely complexed molecules. The anti-digoxigenin antibody can be bound to the SPR chip which results in signal increases. Subsequent addition of digoxigenin-PYY conjugate results in further signal increases until all binding sites are completely occupied. At these conditions, addition of more digoxigenin-PYY does not increase the signal further. This indicates that the complexing reaction is specific and that the signals are not caused by non-specific stickiness of the digoxigenylated polypeptide.

Exemplary Method for the Formation of Complexes of Haptenylated Polypeptides and Anti-Hapten Antibodies—Ac-PYY-PEG3-Cys-PEG2-Biot)/Chimeric Anti-Biotin Antibody Complex For the generation of non-covalent complexes of biotinylated-PYY-polypeptide containing a cysteinylated linker, 0.16 mg of Ac-PYY-PEG3-Cys-PEG2-Biot were dissolved in 100% DMF to a concentration of 10 mg/ml. The antibody was used in a concentration of 10.7 mg/ml (about 73 µM) in a buffer composed of 50 mM Tris-HCl, 1 mM EDTA, pH 8.2. Ac-PYY-PEG3-Cys-PEG2-Biot and antibody were mixed at a 2.5:1 molar ratio (Ac-PYY-PEG3-Cys-PEG2-Biot to antibody) and incubated for 60 minutes at room temperature and 350 rpm. The resulting complex was defined as 63% monomeric IgG-like molecule and 37% dimeric soluble aggregates via size exclusion chromatography. The resulting complex was further analyzed by SDS-PAGE and subsequent Western Blot analysis. 10 µg of the complex were mixed with 4×LDS sample buffer (Invitrogen) and incubated at 95° C. for 5 minutes. The sample was applied to a 4-12% Bis-Tris polyacrylamide-gel (NuPAGE, Invitrogen) which was run for 35 min at 200V and 120 mA. Molecules that were separated in the polyacrylamide-gel were transferred to a PVDF membrane (0.2 µm pore size, Invitrogen) for 40 minutes at 25V and 160 mA. The membrane was blocked in 1% (w/v) skim milk in 1×PBST (1×PBS+0.1% Tween20) for 1 hour at room temperature. The membrane was washed 3× for 5 min in 1×PBST and subsequently incubated with a streptavidin-POD-conjugate (2900 U/ml, Roche) which was used in a 1:2000 dilution. Detection of streptavidin-POD bound to biotin on the membrane was carried out using Lumi-Light Western Blotting Substrate (Roche).

Exemplary Method for the Formation of Complexes of Haptenylated Polypeptides and Anti-Hapten Antibodies— Ac-PYY(PEG3-Cys-PEG2-5-Fluo)/Chimeric Anti-Fluorescein Antibody Complex For the generation of non-covalent complexes of fluorescein-conjugated-PYY-polypeptide containing a cysteinylated linker, 0.33 mg of Ac-PYY(PEG3-Cys-PEG2-5-Fluo were dissolved in 100% DMF to a concentration of 10 mg/ml. The antibody was used in a concentration of 9.99 mg/ml (about 68 µM) in a buffer composed of 50 mM Tris-HCl, 1 mM EDTA, pH 8.2. Ac-PYY(PEG3-Cys-PEG2-5-Fluo and antibody were mixed at a 2.5:1 molar ratio (Ac-PYY(PEG3-Cys-PEG2-5-Fluo) to antibody) and incubated for 60 minutes at room temperature and 350 rpm. The resulting complex was defined as 76% monomeric IgG-like molecule and 24% dimeric soluble aggregates via size exclusion chromatography. The resulting complex was further analyzed by SDS-PAGE and subsequent detection of fluorescein-related fluorescence in the polyacrylamide-gel. 8 µg of the complex were mixed with 4×LDS sample buffer (Invitrogen) and incubated at 95° C. for 5 minutes. Fluorescein-related fluorescence was recorded using a LumiImager F1 device (Roche) at an excitation wavelength of 645 nm.

Example 12

Polypeptides in Conjugates and in Complexes with Anti-Hapten Antibody Retain Functionality It has previously been shown that polypeptides which are part of non-covalent hapten-polypeptide conjugates and in complexes with anti-hapten antibodies retain functionality (WO2011/003557, WO 2011/003780 and PCT/EP2011/074273).

Example 13

Engineering of Blood Brain Barrier-Shuttle Modules

Figure 7:
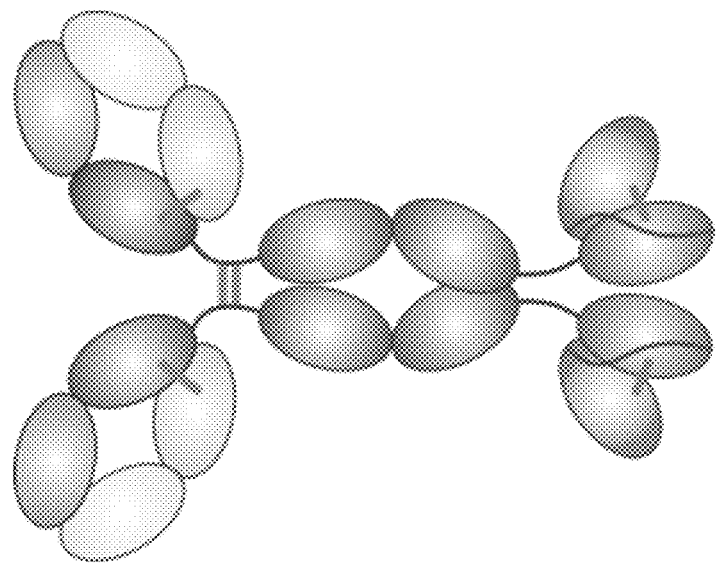
FIG. 7 shows a scheme of blood brain barrier-shuttle module composition.

Hapten-binding bispecific blood brain barrier-shuttle modules were generated by fusing disulfide-stabilized hapten-binding single-chain Fvs to the C-termini of the CH3 domains of anti-TfR antibodies. Similar designs and technologies were applied as previously described (see e.g. WO 2014/006124). An example for the composition of these blood brain barrier-shuttle modules is shown in FIG. 7.

The blood brain barrier-shuttle modules recognize transcytoseable cell surface targets on endothelial cells of the blood brain barrier (blood brain barrier receptor). Exemplarily, we used two different antibodies that bind the transferrin receptor with different affinities. Antibody TfR1 binds to the transferrin receptor with high affinity and antibody TfR2 binds to the transferrin receptor with reduced affinity (see e.g. WO 2012/075037). The TfR-binding sites derived from these anti-TfR antibodies were set as unaltered Fab arms into a bispecific antibody to obtain a bivalent full-length IgG module. Disulfide-stabilized hapten-binding single-chain Fvs were fused via short GS-linker to the C-termini of the CH3 domain of the generated bispecific antibody. Exemplarily, as anti-hapten binding sites previously described entities that bind derivatives of digoxigenin (Dig) or Biotin (Bio) were used (for sequences see above).

Examples for the sequence composition of these shuttle vehicles are listed as SEQ ID NO: 134 (LC anti-TfR1 antibody), SEQ ID NO: 135 (HC anti-TfR1 antibody conjugated to scFv anti-digoxigenin antibody fragment), SEQ ID NO: 136 (HC anti-TfR1 antibody conjugated to scFv anti-biotin antibody fragment), SEQ ID NO: 137 (LC anti-TfR2 antibody), SEQ ID NO: 138 (HC anti-TfR2 antibody conjugated to scFv anti-digoxigenin antibody fragment), SEQ ID NO: 139 (HC anti-TfR2 antibody conjugated to scFv anti-biotin antibody fragment).

Example 14

Expression and Purification of Bispecific Antibodies (Blood Brain Barrier-Shuttle Modules)

The blood brain barrier-shuttle module bispecific antibodies were produced in mammalian cells in defined serum free media as previously described (see above). HEK293 suspension cells were transiently transfected with L- and H-chain encoding expression plasmids to generate cultures that express the blood brain barrier-shuttle module bispecific antibody.

To generate digoxigenylated payload binding blood brain barrier-shuttle modules that bind TfR with high affinity, expression plasmids containing SEQ ID NO: 134 encoding nucleic acid/expression cassette were co-transfected with expression plasmids containing SEQ ID NO: 135 encoding nucleic acid/expression cassette.

To generate digoxigenylated payload binding blood brain barrier-shuttle modules that bind TfR with high affinity, expression plasmids containing SEQ ID NO: 134 encoding nucleic acid/expression cassette were co-transfected with expression plasmids containing SEQ ID NO: 136 encoding nucleic acid/expression cassette.

To generate digoxigenylated payload binding blood brain barrier-shuttle modules that bind TfR with reduced affinity, expression plasmids containing SEQ ID NO: 137 encoding nucleic acid/expression cassette were co-transfected with expression plasmids containing SEQ ID NO: 138 encoding nucleic acid/expression cassette.

To generate digoxigenylated payload binding blood brain barrier-shuttle modules that bind TfR with reduced affinity, expression plasmids containing SEQ ID NO: 137 encoding nucleic acid/expression cassette were co-transfected with expression plasmids containing SEQ ID NO: 139 encoding nucleic acid/expression cassette.

Figure 8:
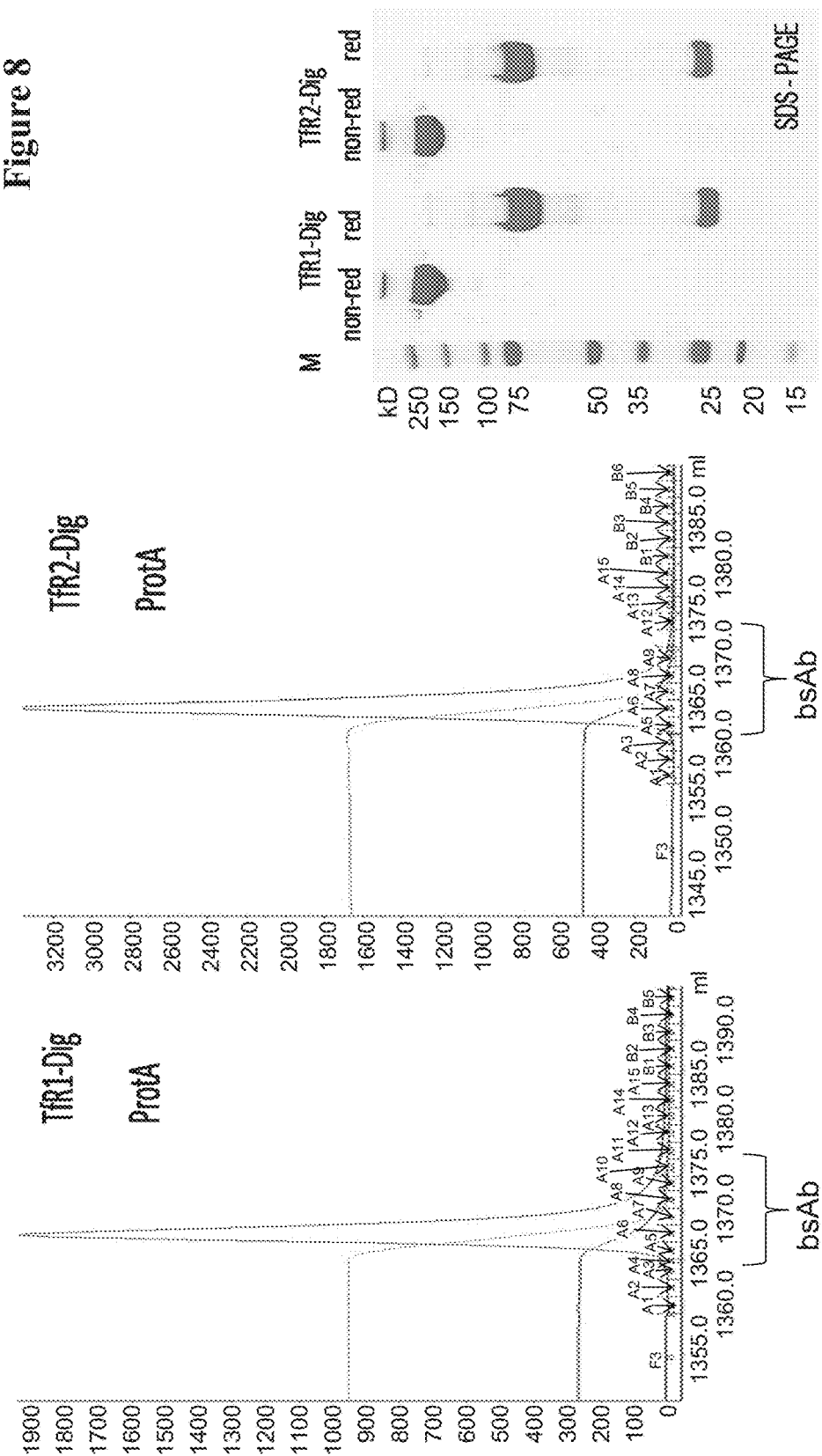
FIG. 8 shows SEC profiles and SDS PAGE of blood brain barrier-shuttle modules as produced in Example 14.

Bispecific antibodies were purified from supernatants of HEK293 suspension cells that were transiently transfected with L- and H-chain encoding expression plasmids by protein A chromatography (see above). Subsequently, size exclusion chromatography (SEC) was applied to obtain bispecific antibodies free of aggregates or contaminants. Examples for the purity and composition of the purified blood brain barrier-shuttle modules are shown as SEC profiles and SDS PAGE in FIG. 8.

Example 15

Bispecific Hapten-Binding Blood Brain Barrier-Shuttle Modules Simultaneously Bind Haptenylated Payloads and Blood Brain Barrier Receptor To enable blood brain barrier-shuttle functionality of the bispecific antibodies, they must simultaneously bind to the blood brain barrier receptor on endothelial cells of the blood brain barrier, and to the haptenylated payloads to be shuttled.

Figure 9:
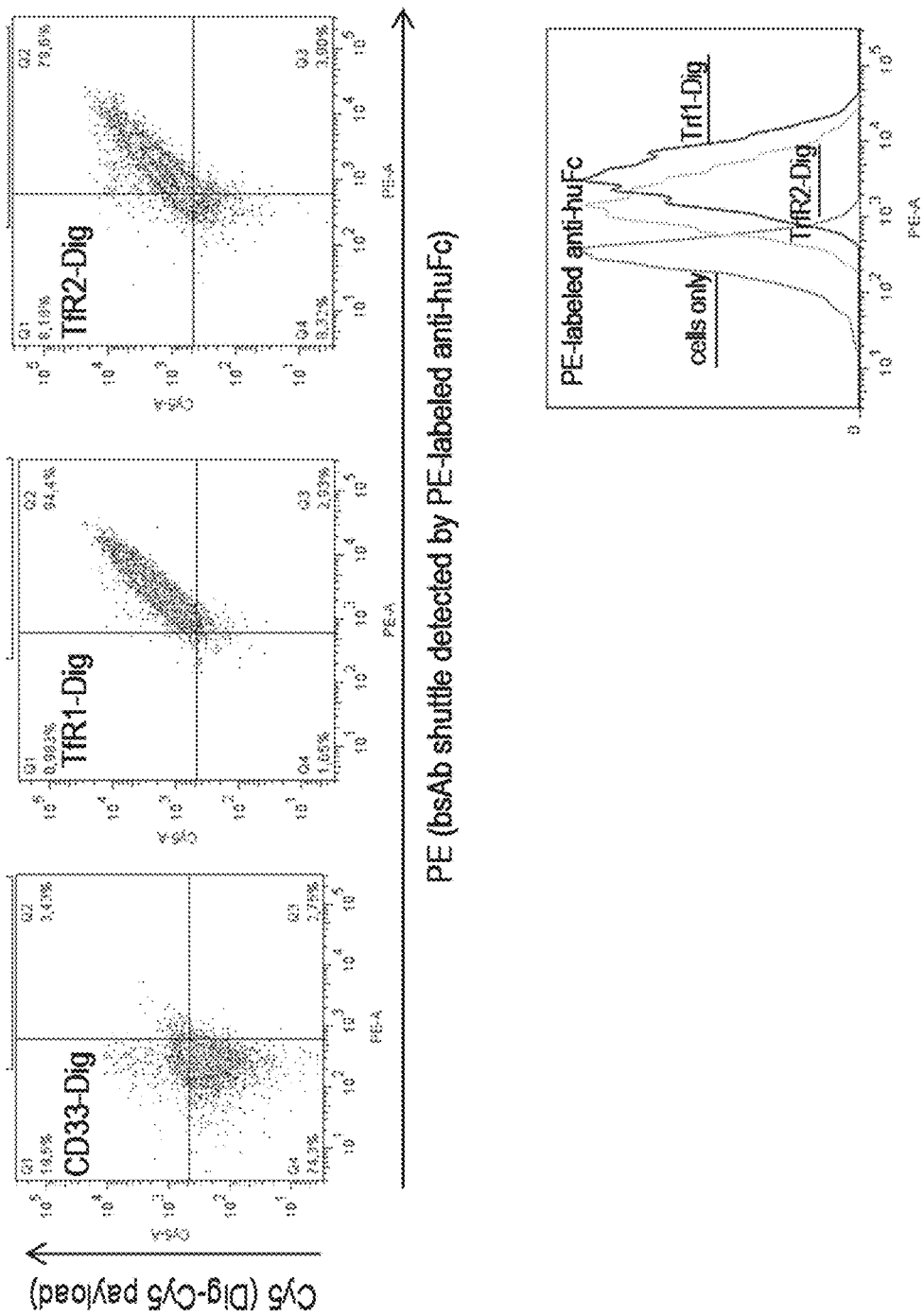
FIG. 9 shows results of the FACS analysis, using hCMEC/D3 cells as TfR expressing BBB-derived cell line and Dig-Cy5 as fluorescent payload.

To evaluate this functionality of the hapten-binding bispecific antibodies as reported herein, simultaneous cell surface and payload binding was addressed by FACS analyses. For these analyses, cell binding of the blood brain barrier-shuttle module (=bispecific antibody) was detected by phytoerythrin-labeled IgG recognizing secondary antibodies. Simultaneous payload binding was detected by application of a haptenylated fluorescent payload (digoxigenylated Cy5; DIG-Cy5). The results of the FACS analysis, using hCMEC/D3 cells as TfR expressing BBB-derived cell line and Dig-Cy5 as fluorescent payload are shown in FIG. 9: both transferrin receptor binding bispecific antibodies bind to hCMEC/D3 as shown by the anti-IgG-PE associated signals. Similarly, both bispecific antibodies also and simultaneously bind Dig-Cy5 as shown by cell-associated Cy5 attributable signals. A comparison of signal intensities between the (high affinity) TfR1 bispecific antibody and the (reduced affinity) TfR2 bispecific antibody indicates (as expected) higher signal intensity on cells with the high affinity compared to medium affinity bispecific antibody. A control bispecific antibody which recognizes an antigen that is not present in detectable amounts on hCMEC/D3 (CD33-Dig) does (as expected) not generate relevant signals with anti-IgG antibody nor with Dig-Cy5.

These results show that bispecific hapten-binding blood brain barrier-shuttle modules specifically bind to their targets on the surface of endothelial cells. Furthermore, these bispecific antibodies simultaneously bind haptenylated payloads and thereby can direct them to endothelial cells of the blood brain barrier.

Example 16

Figure 10:
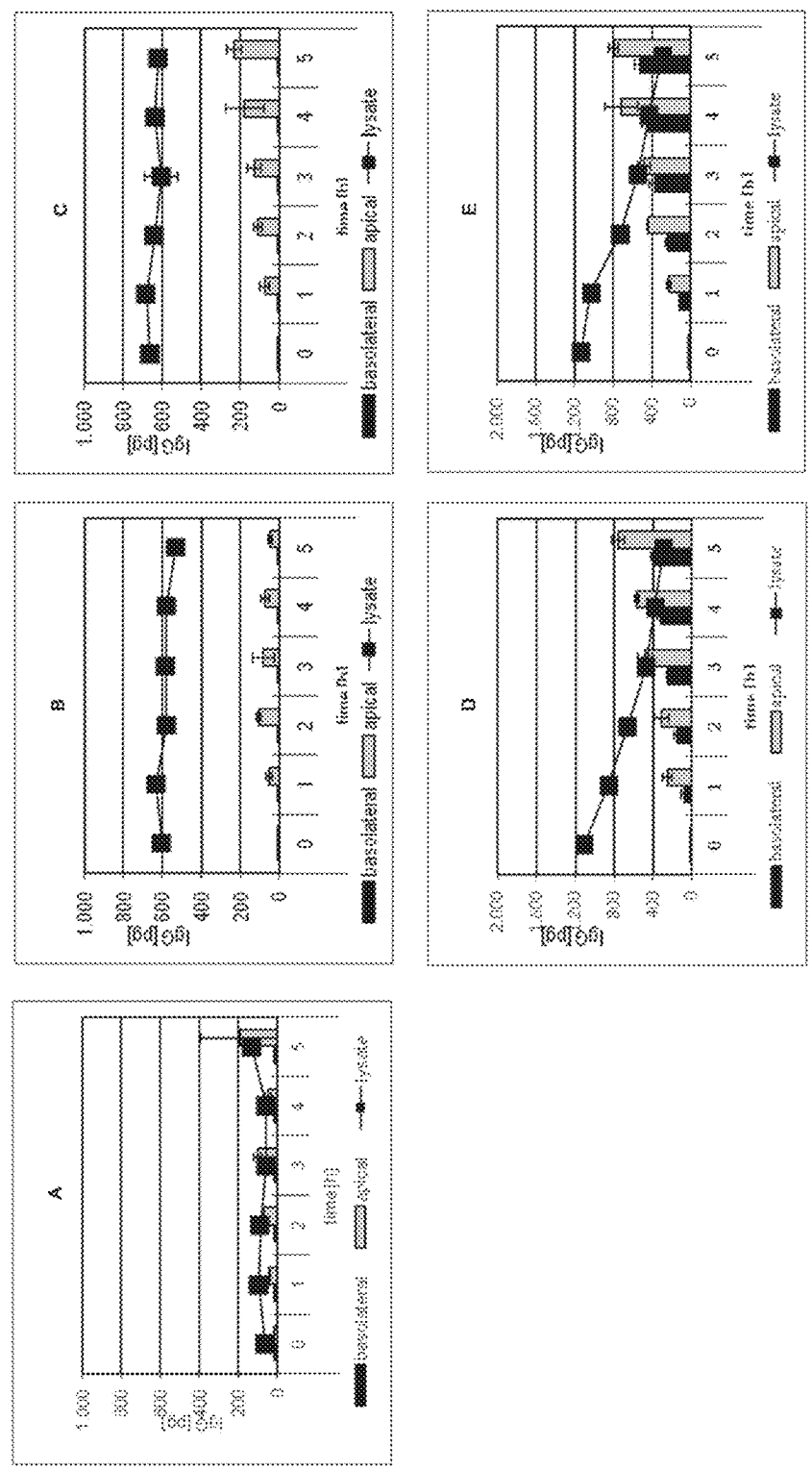
FIG. 10 shows transcytosis and release from endothelial cells of hapten-binding bispecific antibody blood brain barrier-shuttle modules; A: anti-CD33-dig antibody transwell assay, huFc ELISA; B: anti-TfR1 antibody transwell assay, huFc ELISA; C: anti-TfR1 antibody-Dig transwell assay, huFc ELISA; D: anti-TfR2 antibody transwell assay, huFc ELISA, E: anti-TfR2-antibody Dig transwell assay, huFc ELISA.

Receptor Binding Mode of the Blood Brain Barrier-Shuttle Module Influences Release from Brain Endothelial Cells We used brain endothelial cells (hCMEC/D3) to investigate cell binding and transcytosis of the shuttle modules as reported herein. Previous studies (Crepin et al., 2010; Lesley et al., 1989, WO 2012/075037, WO 2014/033074) reported that valency and affinity of TfR binding antibodies influence efficacy of binding to, transcytosis though, and release from endothelial cells of the blood brain barrier. To investigate cell binding and transcytosis in hCMEC/D3, hCMEC/D3 cells cultured on filter inserts were incubated apically with the bispecific antibody or parent antibody (without hapten-binding scFvs as controls) for 1 hour at 37° C. Cell monolayers were washed at room temperature in serum-free medium apically (400 µl) and basolaterally (1600 µl) three times for 3-5 minutes each. All wash volumes were collected to monitor efficiency of removal of the unbound ligand or antibody. Pre-warmed medium was added to the apical chamber and the filters transferred to a fresh 12 well plate (blocked overnight with PBS containing 1% BSA) containing 1600 µl pre-warmed medium. At this point, cells were lysed in 500 µl RIPA buffer (Sigma, Munich, Germany, #R0278) in order to determine specific uptakes. The remaining filters were incubated at 37° C. and samples collected at various time points to determine apical and/or basolateral release. The content of antibody in the samples was quantified using a highly sensitive IgG ELISA. The results of these analyses are shown in FIG. 10: high affinity bivalent anti-TfR antibodies (TfR1) become efficiently bound to the cells, but are not released to apical or basolateral compartments. In the same manner, bispecific antibodies that contain the high affinity TfR binding sites (TfR1-Dig, TfR1-Bio) become efficiently bound to the cells, but are not released to apical or basolateral compartments. In contrast, bivalent anti-TfR antibodies with reduced affinity (TfR2) become efficiently bound to the cells, and become subsequently released over time to apical or basolateral compartments. Bispecific antibodies that contain the reduced affinity bivalent TfR binding sites (TfR2-Dig, TfR2-Bio) become also efficiently bound to the cells and are released to apical or basolateral compartments to the same degree as the parent antibody. Control bispecific antibodies (CD33-Dig, CD33-Bio) that bind an antigen that is not present on hCMEC/D3 do not bind to these cells and are therefore also not released over time into apical or basolateral compartments.

Example 17

Figure 11A:
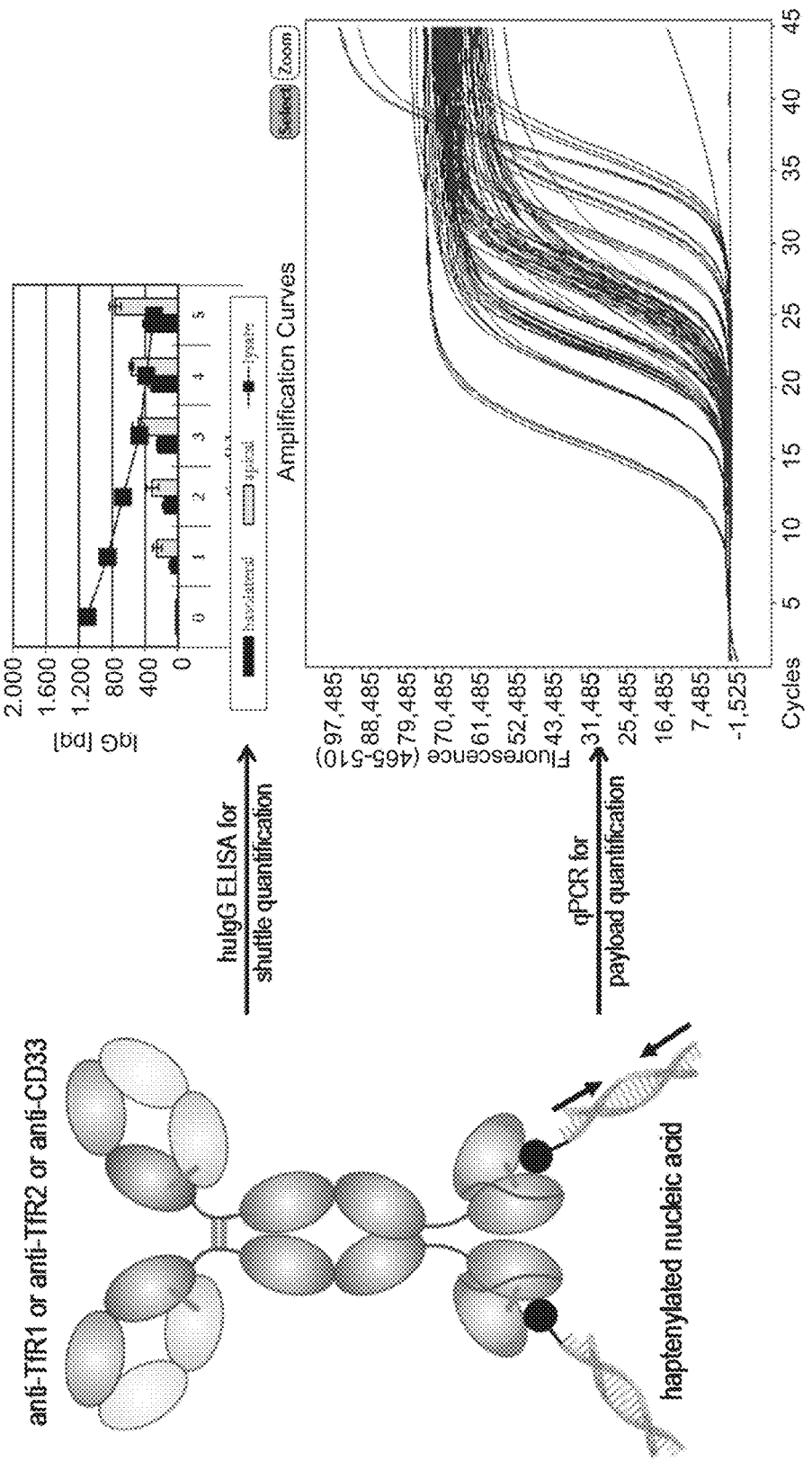
FIG. 11A shows composition and quantification of bispecific antibody-haptenylated payload non-covalent complexes
Figure 11B:
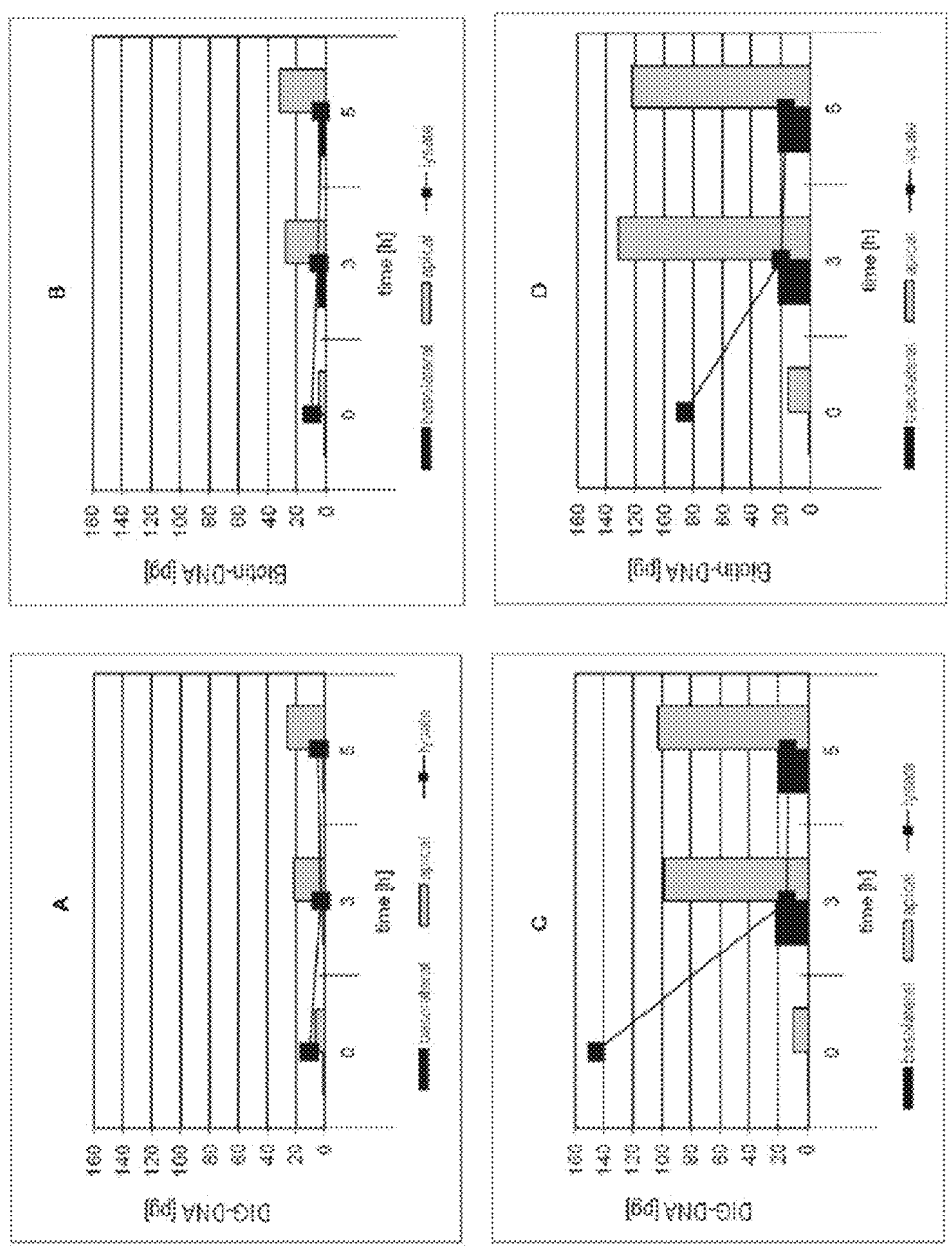
FIG. 11B shows transcytosis and release from endothelial cells of haptenylated payloads using bispecific antibodies with reduced affinity towards TfR (A: anti-CD33-Dig+Dig-DNA transwell assay, qPCR; B: anti-CD33-Bio+Bio-DNA transwell assay, qPCR, C: anti-TfR2-Dig+Dig-DNA transwell assay, qPCR, D: anti-TfR2-Bio+Bio-DNA transwell assay, qPCR).

Blood Brain Barrier-Shuttle Modules with Reduced Affinity Towards TfR Shuttle Across Endothelial Cells and Support Transcytosis and Release of Haptenylated Payload Brain endothelial cells (hCMEC/D3) were used to investigate cell binding and transcytosis of haptenylated payloads that form non-covalent complexes with hapten-binding blood brain barrier-shuttle modules. To evaluate if payload transcytosis can be achieved via hapten-binding blood brain barrier-shuttle modules (bispecific antibodies) as reported herein for non-covalently complexed payloads, hCMEC/D3 cells in a trans-well system were exposed to haptenylated payload complexed by the bispecific antibody as reported herein (see previous examples for exemplary constructs) for one hour to allow TfR binding. Following removal of shuttle and payloads by washing (see Example 15), bound molecules, internalization, intracellular sorting, transcytosis and release of payload were monitored over time (0 to 5 hours after start of the experiment=washing step) in a similar manner as described in Example 15 for the shuttle modules. The payload that was used in the current example was mono-haptenylated DNA, which becomes upon incubation with bispecific antibodies as reported herein non-covalently complexed in a 2:1 (molar) ratio, as shown in FIG. 11A. Presence of the payload can be detected and quantified in cell extracts, apical and basolateral compartments by qPCR. Exemplarily, terminally mono-biotinylated or mono-digoxigenylated double-stranded DNA 50 mer (SEQ ID NO: 140) as payload and two PCR primers PrFor (SEQ ID NO: 141) and PrRev (SEQ ID NO: 142) for payload quantification on a Roche LightCycler as shown in FIG. 11A. The results of these analyses (FIG. 11B) demonstrate that the non-covalent attached haptenylated payload binds to cells, is internalized and subsequently becomes released into apical and basolateral compartments. Binding and subsequent release is mediated by the TfR-binding blood brain barrier-shuttle module neither binding to cells nor release is detected if a CD33-binding control bispecific antibody is applied. Furthermore, neither binding to cells nor release is detected in cases where haptenylated payload without bispecific antibody is applied. Transcytosis of non-covalently complexed payload was observed for digoxigenin binding sites as well as for biotin binding sites comprising bispecific antibodies and the corresponding haptenylated payloads. This shows that different haptens can be used to design a non-covalent bispecific antibody blood brain barrier-shuttle module. Thus, payload transcytosis across the blood brain barrier can be achieved using hapten-binding bispecific antibodies for non-covalently complexed haptenylated payloads.

Example 18

Blood Brain Barrier-Shuttle Modules with Binding Sites with High Affinity Towards TfR Bind to but are not Released from Endothelial Cells, but Still Support Transcytosis and Release of Haptenylated Payload Brain endothelial cells (hCMEC/D3) were used to investigate cell binding and transcytosis of haptenylated payloads that can form non-covalent complexes with hapten-binding blood brain barrier-shuttle modules in the same manner as described in previous Example 17. HCMEC/D3 cells in a trans-well system were exposed to haptenylated payload complexed by the blood brain barrier-shuttle module (bispecific antibody) for 1 hour to allow TfR binding, internalization and intracellular sorting, and transcytosis. The payload was mono-haptenylated DNA, which becomes upon incubation with the bispecific antibody non-covalently complexed in a 2:1 (molar) ratio, as shown in FIG. 11A. Presence of mono-biotinylated or mono-digoxigenylated double-stranded DNA 50 mer payload (SEQ ID NO: 140) was quantified by qPCR in cell extracts, apical and basolateral compartments as described in previous Example 17.

Figure 12:
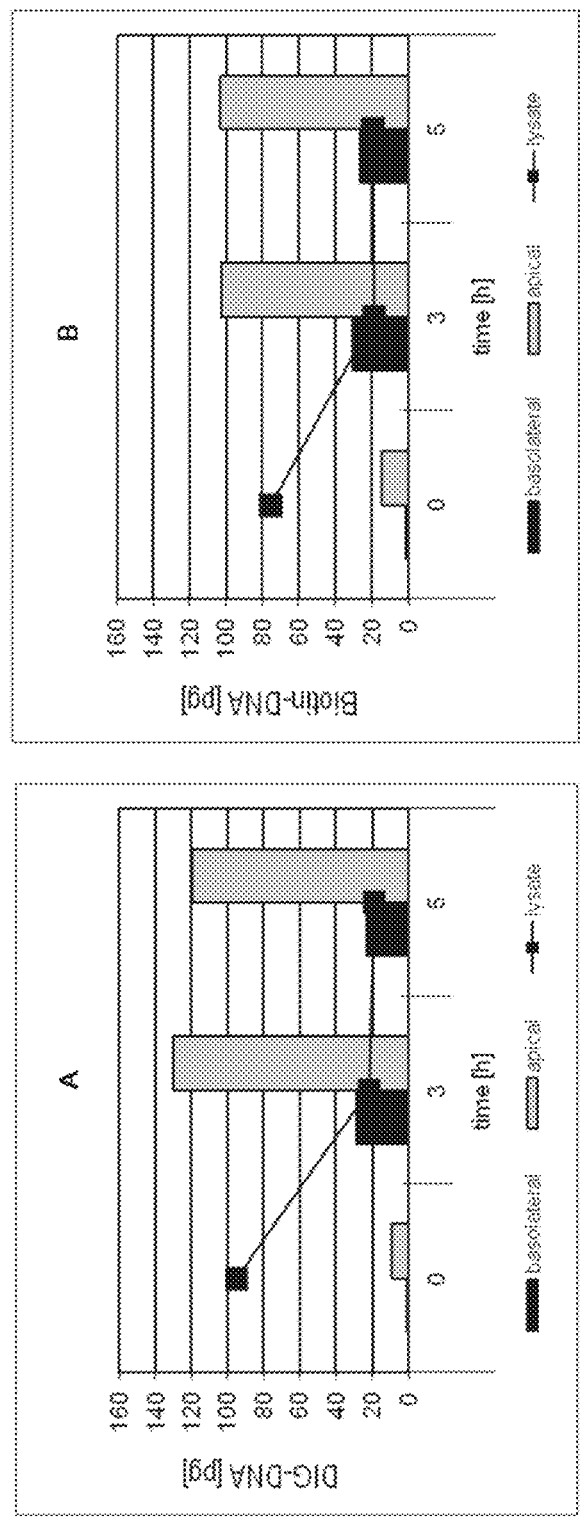
FIG. 12 shows transcytosis and release from endothelial cells of haptenylated payloads applying non-releasable blood brain barrier-shuttle modules with high affinity towards TfR; A: anti-TrF1-Dig+Dig-DNA transwell assay, qPCR, B: anti-TfR1 antibody- -continued

The results of these analyses (FIG. 12) demonstrate that the non-covalent complexed haptenylated payload binds to cells, is internalized and subsequently becomes released into apical and basolateral compartments. This was a surprising finding since the bivalent high affinity shuttle module by itself is not released from the cells. Binding and subsequent payload release is mediated by the TfR-binding bispecific antibody blood brain barrier-shuttle module because neither binding to cells nor release is detected if a CD33-binding control bispecific antibody is applied. Furthermore, neither binding to cells nor release is detected in cases where haptenylated payload without bispecific antibody blood brain barrier-shuttle module is applied. Transcytosis and release of non-covalently complexed payload was observed for digoxigenin binding sites as well as biotin binding sites comprising bispecific antibodies and the corresponding haptenylated payloads. This indicates that different haptens can be used to design non-covalent complexes of haptenylated payload with bispecific antibody blood brain barrier-shuttle module. Payload transcytosis across cells that comprise the blood brain barrier can be achieved via haptenylated payloads non-covalently complexed by blood brain barrier-shuttle modules (bispecific antibody). Surprisingly, transcytosis does not rely on the release of the shuttle vehicle itself, because the payload becomes released even when applying shuttle modules that are not released.

Example 19

Haptenylated Payloads Separate from Blood Brain Barrier-Shuttle Modules within Vesicular Compartments Transcytosis assays with high affinity TfR binding site comprising blood brain barrier-shuttle modules that bind endothelial cells but are not released themselves from these cells (TfR1) showed a surprising result: haptenylated payloads were shuttled across cells and released into apical and basolateral compartments, even though the shuttle modules itself remained attached to cells/contained in the cell. Bispecific antibody mediated cell binding, uptake and distribution of payloads was analyzed by confocal microscopy. Therefore, brain endothelial cells (hCMEC/D3) were exposed to bispecific antibody-complexed haptenylated fluorescent payloads (hapten-Cy5 or hapten-DNA-Cy5) and analyzed by confocal fluorescence microscopy. Therefore, hCMEC/D3 cells were seeded onto microscopy grade glass coverslips and incubated with 50 nM bispecific antibody-complexed haptenylated fluorescent payloads for three hours at 37° C. in cell culture medium. Cells were then washed, fixed (4% paraformaldehyde) and the IgG part of the shuttle module was detected by counterstaining with anti-kappa light chain specific antibodies followed by secondary antibodies conjugated to ALEXA Fluor 488. Images were taken on a LEICA SP5× confocal microscope using a 100×/1.46NA objective lens using the appropriate band pass filter settings for ALEXAFluor488 (IgG) and CY5 (hapten-DNA-CY5 payload). The results of these analyses are shown in FIG. 13. Complexes of high affinity bispecific antibodies with fluorescent labeled haptenylated payloads (DNA-Cy5) bind to TfR and initially locate on cell surfaces. Subsequently, they become co-internalized with its cognate receptor and appear within cells in vesicular compartments, i.e. endosomes and lysosomes. Shortly after (three hours) internalization, we observed a substantial separation of the fluorescence signals attributable to the shuttle module from those attributable to the haptenylated payloads. Thus, non-covalent complexes of blood brain barrier-shuttle modules as reported herein and haptenylated payloads can dissociate into different vesicular compartments inside the cell. Thereby, the payload becomes released from the shuttle module and can exit via transcytosis from endothelial cells even when the shuttle module remains bound to cells/retained in the cell. Intracellular separation of non-covalently complexed haptenylated payload was observed for digoxigenin-binding as well as biotin-binding blood brain barrier-shuttle modules (bispecific antibodies) and the corresponding haptenylated payloads. Thus, different haptens can be used to design non-covalent complexes of haptenylated payloads and blood brain barrier-shuttle modules that enable payload transcytosis.

Example 20

HeliCar Motif Amino Acid Sequence Containing Peptide YY

Peptide YY is a short (36-amino acid) peptide released by cells in the ileum and colon in response to feeding. In humans it appears to reduce appetite. The most common form of circulating PYY is $PYY_{3-36}$, which binds to the Y2 receptor (Y2R) of the Y family of receptors. PYY is found in L cells in the mucosa of gastrointestinal tract, especially in ileum and colon. Also, a small amount of PYY, about 1-10%, is found in the esophagus, stomach, duodenum and jejunum. In the circulation, PYY concentration increases after food ingestion and decreases during fasting. PYY exerts its action through NPY receptors; it inhibits gastric motility and increases water and electrolyte absorption in the colon. PYY and PYY mimetics have been used to address obesity.

PYY was modified to comprise the HeliCar motif amino acid sequence and complexed by an anti-HeliCar motif amino acid sequence antibody in order to get advantage of the pharmacokinetic properties of the antibody and to avoid the intrinsic instability of the PYY.

Non-Covalent Complex Formation

The structural investigation of the $PYY_{3-36}$ peptide (Nygaard, R., et al., Biochem. 45 (2006) 8350-8357; SEQ ID NO: 143) reveals a helical motif (HeliCar-like motif amino acid sequence) for the central amino acids. As the N-terminal isoleucine and the modified C-terminus have been described as essential for the functional activity of the peptide, the central helix was modified in order to reflect the amino acids in the HeliCar motif amino acid sequence.

```
PYY(3-36)              3                                      36
(SEQ ID NO. 143)  IKPEAPGEDASPEELNRYYASLRHYLNLVTRQRYNH2
HeliCar motif                    AHLENEVARLKK
PYY_HeliCar       IKPEAPGEDASPEAHLANEVARLHYLNLVTRQRYNH2
(SEQ ID NO: 144)                 (YNH2 = tyrosine amide)
```

|                              | binding [K$_d$] | soluble in PBS |                              |
|------------------------------|---------------|----------------|------------------------------|
| PYY(3-36) (SEQ ID NO: 143)   | –             | +              | PYY wild-type                |
| PYY_HeliCar (SEQ ID NO: 144) | 12 nM         | +              | HeliCar motif engineered PYY |

The full IgG1 anti-HeliCar motif amino acid sequence antibody was produced in HEK293 cells by transfecting two plasmids containing the variable regions of the heavy and the light chain inserted in a vector containing the constant human IgG1 and the constant human lambda domain, respectively. The anti-HeliCar motif amino acid sequence antibody (0019) was purified by standard procedures using protein A chromatography. A mass spectroscopy experiment confirmed the identity of antibody 0019.

The complex between antibody 0019 and the modified PYY peptide PYY HeliCar was obtained in vitro by applying a small excess of the peptide to the antibody solution. The complex 0052 was formed. The stoichiometry of the complex was determined by SEC-MALLS analytical experiments to be 1.6 peptides complexed on one bivalent antibody.

The antibody 0019, the PYY(3-36) wild-type, the PYY HeliCar and the complex 0052 were tested for their effect on to the Y2Receptor family.

Covalent Complex Formation (Covalent Disulfide Bond)

In order to increase the in vitro and in vivo stability of the complex between the anti-HeliCar motif amino acid sequence antibody antibody and the HeliCar motif amino acid sequence containing compound, the formation of a disulfide bridge upon binding has been used.

The first step is a specific recognition step (high affinity interaction), i.e. the formation of the HeliCar motif amino acid sequence containing compound-anti-HeliCar motif amino acid sequence antibody complex. This is followed in the second step by a spontaneous shuffling of a disulfide bridge to form the stability improved covalent complex.

As the 12-mer peptide (HeliCar motif amino acid sequence) is a relatively rigid entity (at least when complexed by a specific anti-HeliCar motif amino acid sequence antibody) it has been found that a structurally specific design for the disulfide bridge has to be used. As the complex formation and the thereafter effected covalent coupling is between two recombinantly produced entities, the artificial cysteine residues introduced for the formation of a covalent disulfide bond are not produced necessarily as free cysteine residues but are expressed in a reduced from, i.e. conjugated to a free cysteine or homo cysteine amino acid.

The position in the amino acid sequence of the anti-HeliCar motif amino acid sequence antibody variable domain where the artificial free cysteine residue is introduced is critical. A non-exposed cysteine in the antibody

| | NPY2R | NPY1R | NPY4R | NPY5R |
|---|---|---|---|---|
| Ac-Ile-Lys-Pqa-Arg-His-Tyr-Leu-Asn-Trp-Val-Thr-Arg-Gln-(NMe)-Arg-Try-NH2 * 4 HOAc | 1.0 nM | inactive | inactive | inactive |
| PYY_HeliCar (IKPEAPGEDASPEAHLANEVARLH YLNLVTRQRYNH2)(SEQ ID NO: 144) | 6.38 nM | inactive | inactive | inactive |
| PYY(3-36) (IKPEAPGEDASPEELNRYYASLRHY LNLVTRQRYNH2)(SEQ ID NO: 143) charge 1 | 0.05 nM | 168 nM | 162 nM | 170 nM |
| PYY(3-36) (IKPEAPGEDASPEELNRYYASLRHY LNLVTRQRYNH2)(SEQ ID NO: 143) charge 2 | 0.05 nM | 160 nM | 131 nM | 202 nM |
| anti-HeliCar motif amino acid sequence antibody (0019) | inactive | inactive | inactive | inactive |
| anti-HeliCar motif amino acid sequence antibody-PYY_HeliCar complex (0052) | 0.93 nM | inactive | inactive | inactive |

As demonstrated (Hoffmann, E., et al., J. Cont. Rel. 171 (2013) 48-56.) the peptides complexed by an antibody have a prolonged half-life in vivo. Moreover and surprisingly, the complex demonstrates a slightly better affinity for the NPY2R receptor compared to the non-complexed peptide; the antibody stabilizes the polypeptide and presents the peptide in its fixed biologically active conformation.

variable domain amino acid sequence has more probability to be expressed as a free cysteine (not conjugated), whereas an exposed cysteine residue close to the binding pocket can abolish the binding of the 12-mer peptide (HeliCar motif amino acid sequence) due to a steric hindrance induced by the cysteine conjugation to an additional moiety like a free cysteine.

a) Complexes with a HeliCar Motif Amino Acid Sequence Containing Fluorescent Compound In order to identify a suitable position which has minimum risk of steric hindrance and strong affinity reduction, different positions for the introduction of the artificial cysteine residue in the HeliCar motif amino acid sequence have been tested. The cysteine residue has been introduced at the C-terminal end of the 12mer (HeliCar motif amino acid sequence) in order to have the major part of the paratope unchanged. The peptides have been synthesized and fused to a fluorescent motif.

```
wild-type:
                                    (SEQ ID NO: 145)
   AHLENEVARLKK cysteine variant 1:
                                    (SEQ ID NO: 146)
   AHLENEVARCKK
→ AHLENEVARCKK(5-Fluo)-OH cysteine variant 2:
                                    (SEQ ID NO: 147)
   AHLENEVARLCK
→ AHLENEVARLCK(5-Fluo)-OH x TFA
```

On the antibody, a structural design has been done to allow the formation of the disulfide bridge for both designed peptides including each a cysteine in different 3D environment.

The 12-mer helical peptide AHLENEVARLKK (SEQ ID NO: 145, HeliCar motif amino acid sequence) is modeled into the VH and the VH domains. At the C-terminus of the peptide the residues L10 and K11 are identified as possible position and in the light chain variable domain the positions N55 and G51 according to the light chain numbering of Kabat are identified.

The heavy chain variable domain of the anti-HeliCar motif amino acid sequence antibody (0019) has the amino acid sequence:

```
                                    (SEQ ID NO: 148)
QAVVTQEPSL TVSPGGTVTL TCGSSTGAVT TSNYASWVQQ

KPGQAFTGLI GGTNNRAPWT PARFSGSLLG GKAALTLSGA

QPEDEAEYYC ALWYSNHWVF GGGTKLTVL.
```

The light chain variable domain of the anti-HeliCar motif amino acid sequence antibody (0019) has the amino acid sequence:

```
                                    (SEQ ID NO: 149)
DAVVTQESAL TTSPGETVTL TCRSSTGAVT TSNYASWVQE

KPDHLFTGLI GGTNNRAPGV PARFSGSLIG DKAALTITGA

QTEDEAIYFC ALWYSNHWVF GGGTKLTVL.
```

The light chain variable domain N55C variant of the anti-HeliCar motif amino acid sequence antibody (0155) has the amino acid sequence:

```
                                    (SEQ ID NO: 150)
DAVVTQESAL TTSPGETVTL TCRSSTGAVT TSNYASWVQE

KPDHLFTGLI GGTNCRAPGV PARFSGSLIG DKAALTITGA

QTEDEAIYFC ALWYSNHWVF GGGTKLTVL.
```

The light chain variable domain N51C variant of the anti-HeliCar motif amino acid sequence antibody (0157) has the amino acid sequence:

```
                                    (SEQ ID NO: 151)
DAVVTQESAL TTSPGETVTL TCRSSTGAVT TSNYASWVQE

KPDHLFTGLI CGTNNRAPGV PARFSGSLIG DKAALTITGA

QTEDEAIYFC ALWYSNHWVF GGGTKLTVL.
``` i) Covalent Conjugate of HeliCar Motif Amino Acid Sequence Containing Compound with Antibody 0155

The bivalent antibody 0155 is expressed in HEK293 cells similarly to its parent molecule Y2R(bck)-0019 without free cysteine. The modified antibody is purified using the same protocol used for antibody 0019. The mass spectrometry analysis shows that the experimentally determined mass of the deglycosylated antibody is 142,001 Da. This exceeds the calculated mass by 259 Da. The reduced chains have the experimentally determined mass of 48,167 Da (complete heavy chain, calculated 48,168 Da, Cys=SH, C-Term=−K) and 22,720 Da (complete light chain, N55C, calculated 22,720 Da, Cys=SH). The sequences of the chains were confirmed after reduction.

Antibody 0155 was coupled to the HeliCar motif amino acid sequence cysteine variant 2 using a 2.5 molar excess of HeliCar motif amino acid sequence containing compound in 100% DMF to form the covalent complex 0156.

Figure 14:
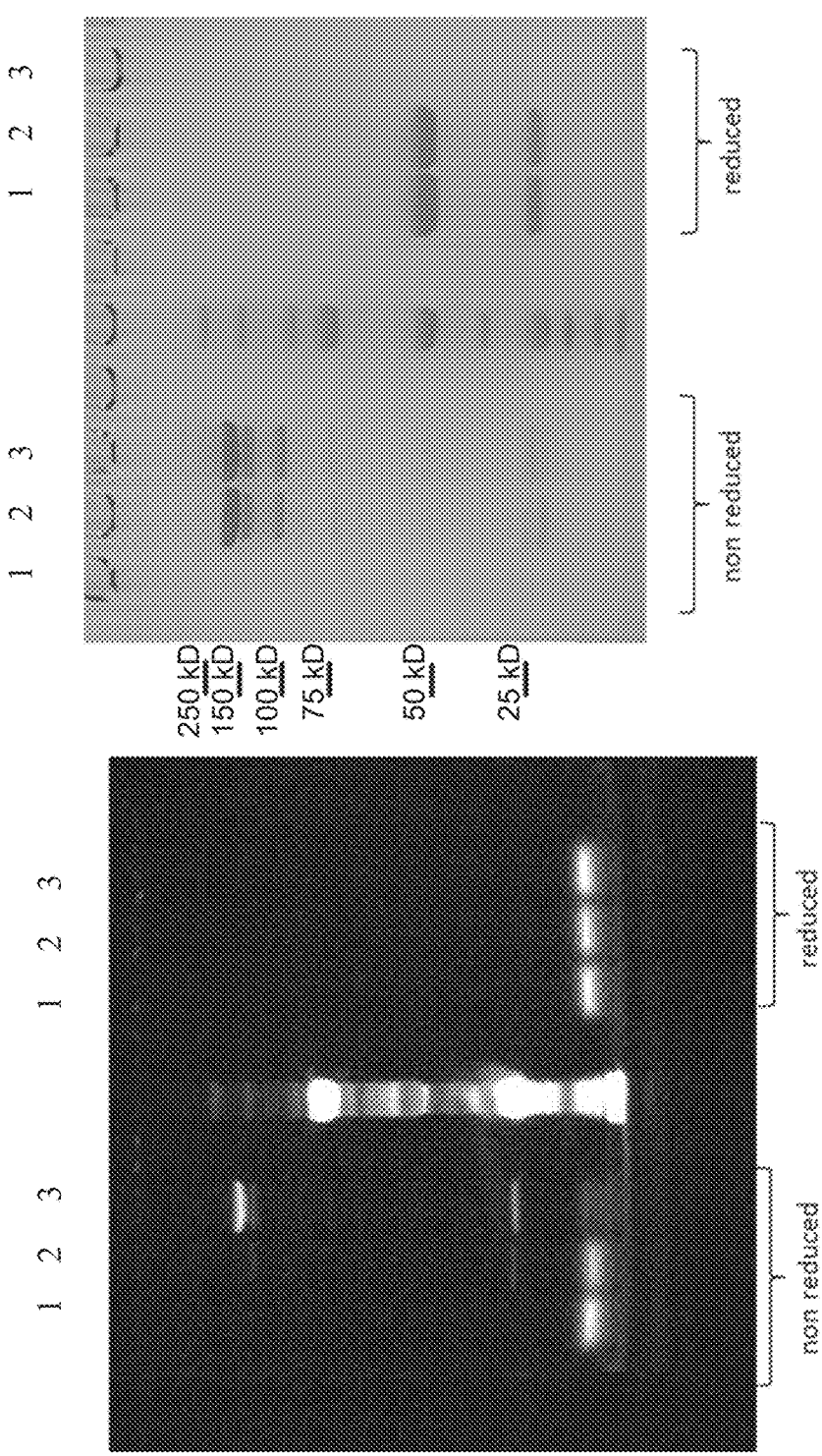

On the SDS page (denaturing condition, see FIG. 14) the fluorescence is seen only on the antibody 0155; in the reducing condition, only the small peptide is visible.

Results:

The covalent conjugation of the HeliCar motif amino acid sequence containing fluorescent compound to the anti-HeliCar motif amino acid sequence antibody was successful. A total of about 43% of the anti-HeliCar motif amino acid sequence antibody was covalently conjugated to two HeliCar motif amino acid sequences, about 40% of the anti-HeliCar motif amino acid sequence antibody was covalently conjugated to one HeliCar motif amino acid sequence, and about 17% of the anti-HeliCar motif amino acid sequence was not conjugated.

The conjugate comprising two HeliCar motif amino acid sequences is modified to about 50%. This species has not been taken into account for the quantification. As already determined for the starting material the antibody without HeliCar motif amino acid sequence contains two modifications of about 128 Da. The antibody conjugated to one HeliCar motif amino acid sequence has only one modification of about 128 Da.

ii) Covalent Conjugate of the HeliCar Motif Amino Acid Sequence Containing Compound with Antibody 0157

Similarly to antibody 0155 is antibody 0157 expressed mostly as a cysteinylated form. The mass spectrometry analysis shows that the experimentally determined mass of the deglycosylated antibody is 141,863 Da. This exceeds the calculated mass by 3 Da. The antibody is mainly present as single or double homocysteinylated form. The reduced chains have the experimentally determined mass of 48,168 Da (complete heavy chain, calculated 48,168 Da, Cys=SH, C-Term=−K) and 22,777 Da (complete light chain, N51C, calculated 22,777 Da, Cys=SH). The sequences of the chains were confirmed after reduction.

Figure 15:
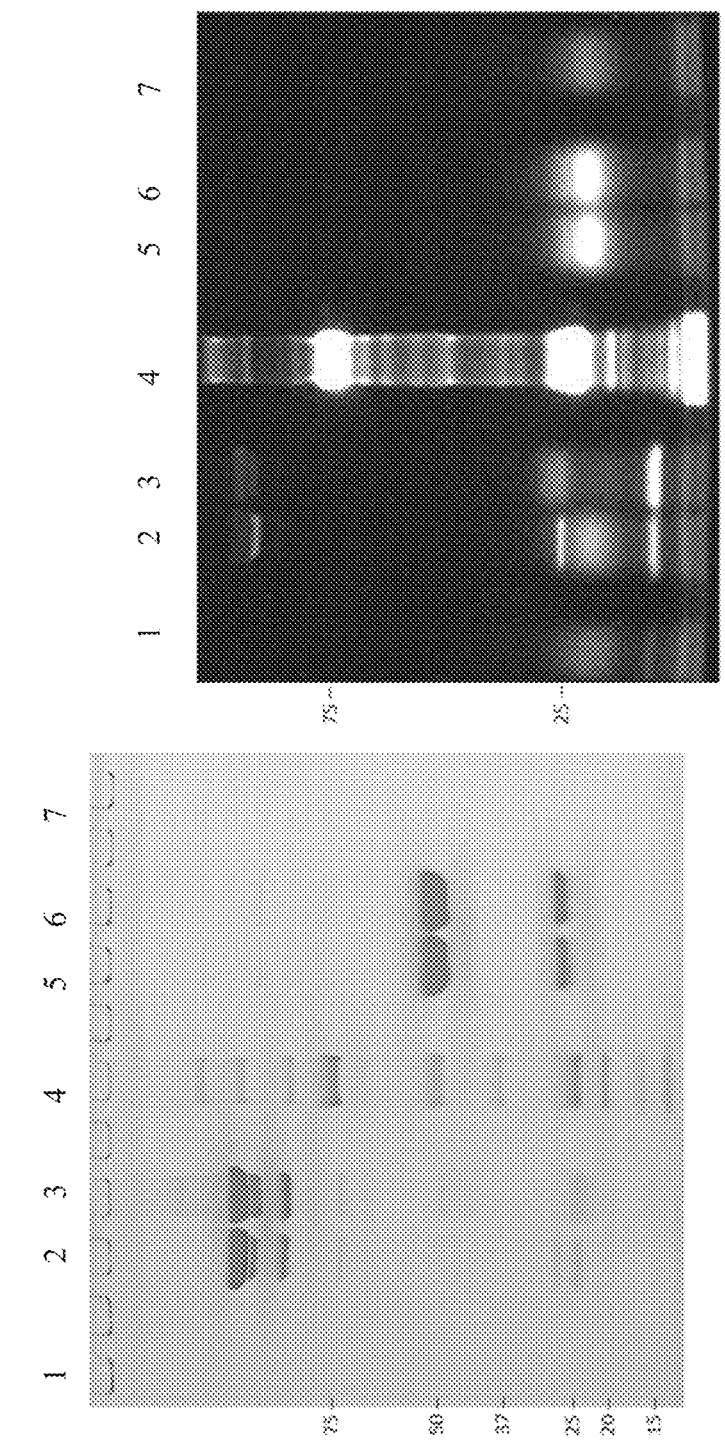
Figure 17:
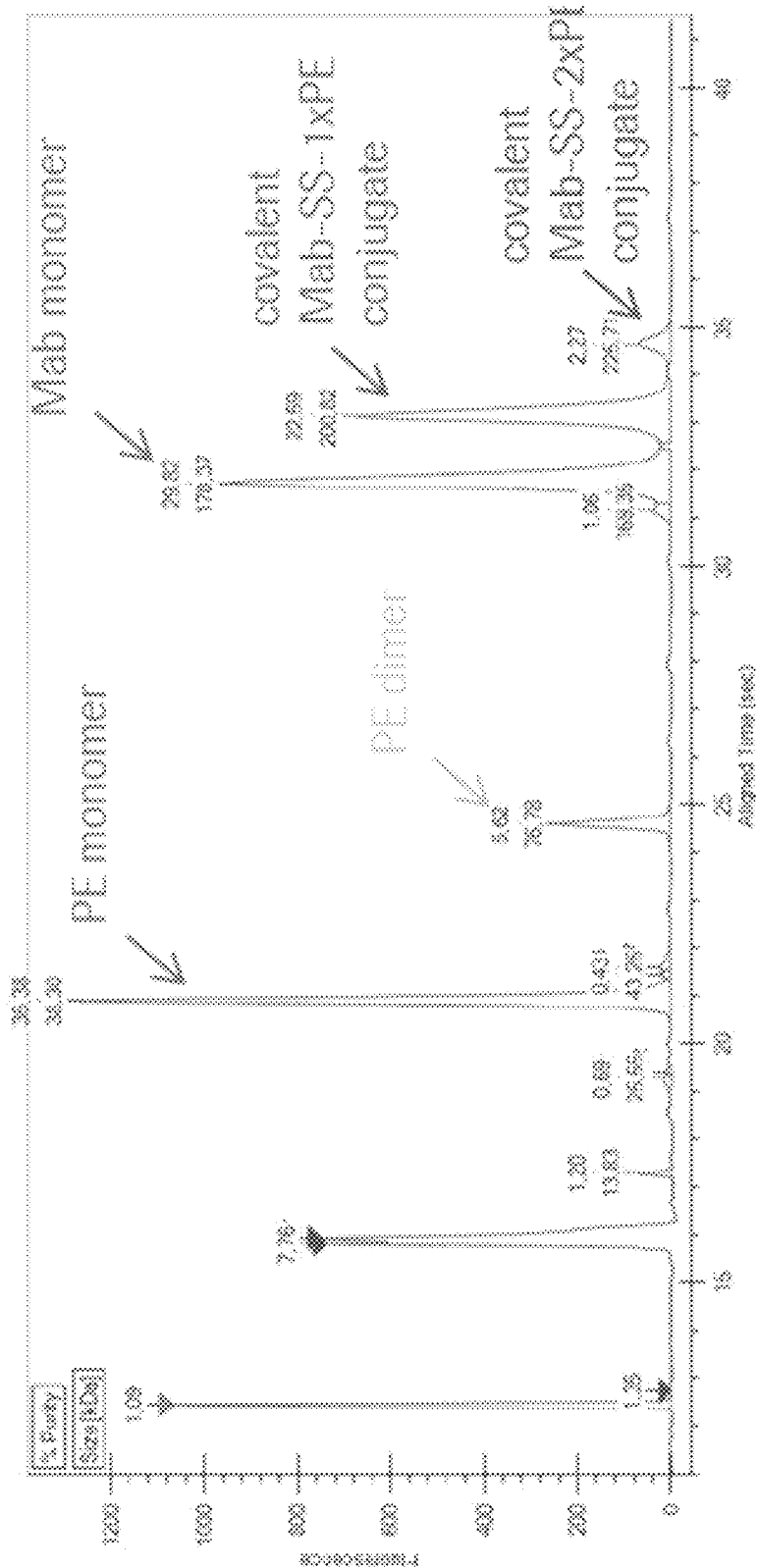
Figure 18:
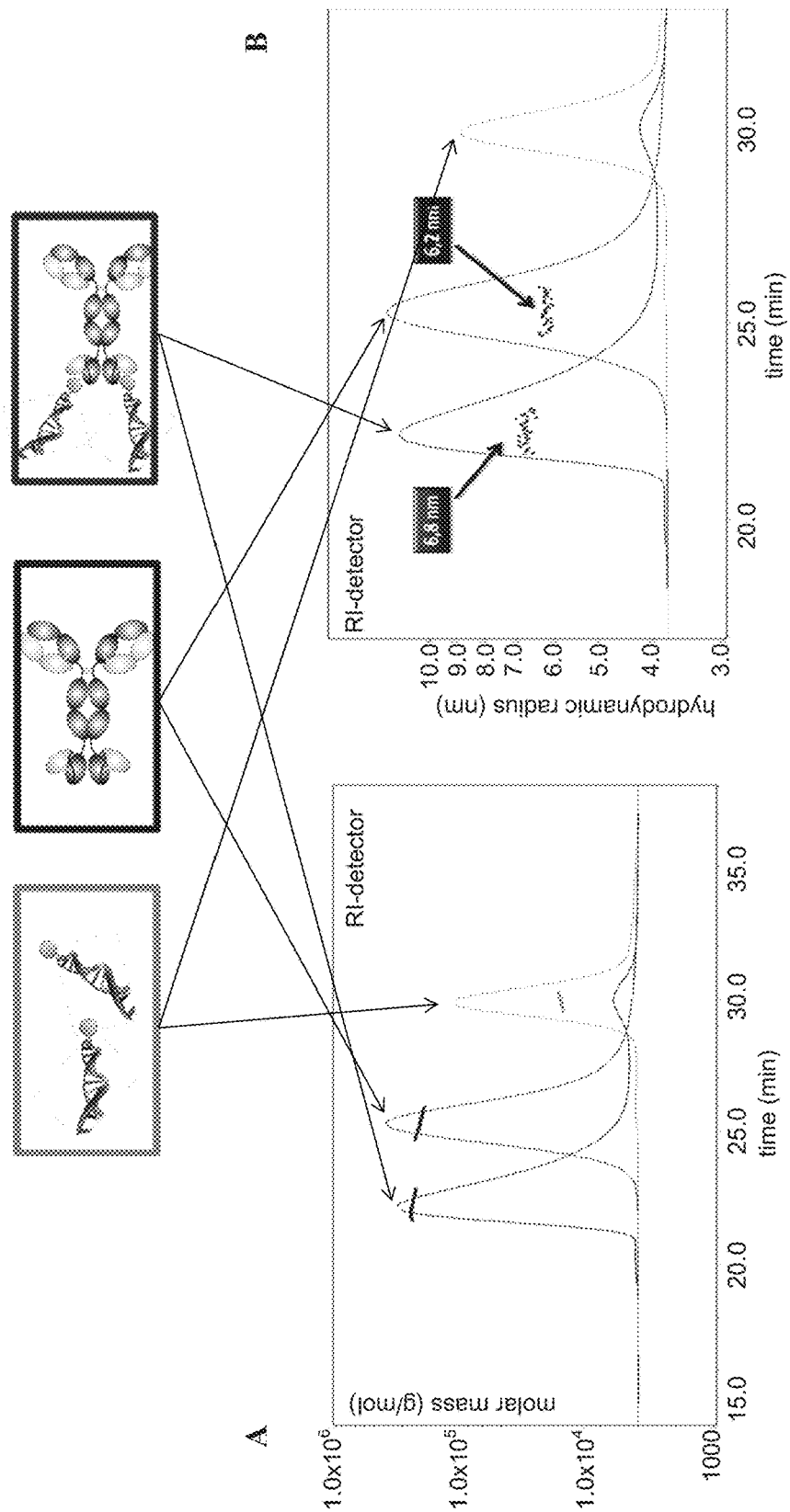

The coupling of antibody 0157 with the HeliCar motif amino acid sequence cysteine variant 1 was not resulting in the expected covalent complex. The fluorescence is not seen in the expected lane but on the reference which should be negative in this experiment (see FIG. 15).

Antibody 0157 was incubated with HeliCar motif amino acid sequence cysteine variant 1. As control antibody 0019 was incubated with the same HeliCar motif amino acid sequence cysteine variant 1.

Results:

The covalent conjugation of the HeliCar motif amino acid sequence containing fluorescent compound to the anti-HeliCar motif amino acid sequence antibody was not successful. Without being bound by this theory it is assumed that in this case the antibody cysteinylation is too deep in the binding pocket to allow the HeliCar motif amino acid sequence containing fluorescent compound to bind efficiently and deliver the nucleophilic thiol group in an appropriate position to attack the C51.

b) Complexes with HeliCar Motif Amino Acid Sequence Containing Recombinant Polypeptide The HeliCar based methodology becomes particularly attractive when considering the formation of a covalent complex with a recombinantly produced HeliCar motif amino acid sequence containing polypeptide.

As the conjugation of the antibody 0155 containing the VL-N55C mutation with the HeliCar motif amino acid sequence cysteine variant 1 (AHLENEVARLCK; SEQ ID NO: 146) has much better performed compared to the alternative (G51C on VL with HeliCar motif amino acid sequence cysteine variant 2 (AHLENEVARCKK; SEQ ID NO: 147)), the conjugation of 0155 with a HeliCar motif amino acid sequence cysteine variant 1 containing polypeptide was further investigated. The polypeptide contained the HeliCar motif amino acid sequence cysteine variant 1 (AHLENEVARLCK; SEQ ID NO: 146) fused to the N-terminus.

The HeliCar motif amino acid sequence cysteine variant 1 containing *Pseudomonas* exotoxin molecule LR8M with the C-terminal lysine residue deleted (0236; SEQ ID NO: 152) has been produced in *E. coli* and purified using a combination of anion exchange chromatography and SEC (see e.g. WO 2011/032022).

Antibody 0155 is covalently conjugated with the HeliCar motif amino acid sequence cysteine variant 1 containing *Pseudomonas* exotoxin molecule LR8M with the C-terminal lysine residue deleted of SEQ ID NO: 152. The SEC chromatogram is shown in FIG. 16. The conjugation efficiency is analyzed by SDS-CE, Caliper, for the non reduced samples (see FIG. 17).

A total of about 4% of the anti-HeliCar motif amino acid sequence antibody was covalently conjugated to two polypeptide of SEQ ID NO: 152, about 41% of the anti-HeliCar motif amino acid sequence antibody was covalently conjugated to one polypeptide of SEQ ID NO: 152, and about 55% of the anti-HeliCar motif amino acid sequence was not conjugated.

In conclusion, the anti-HeliCar motif amino acid sequence monoclonal antibody can be used to complex peptides, small molecules with peptidic linker, and recombinant proteins via a high affinity recognition of a 12-mer HeliCar motif amino acid sequence. Peptides with propensity to fold as helix can be modified to mimic the original 12-mer HeliCar motif amino acid sequence AHLENEVARLKK (SEQ ID NO: 145) and are thereafter complexable with the anti-HeliCar motif amino acid sequence monoclonal antibody. In addition to the high affinity complexation, covalent conjugation is enabled with a cysteine variant of SEQ ID NO: 145 containing a cysteine and a modified anti-HeliCar motif amino acid sequence antibody containing a cysteine in the CDRs via formation a stable disulfide bond. Recombinant proteins expressed by different system can be conjugated afterwards in vitro without particular reactions conditions but via spontaneous disulfide bridge shuffling.

Example 21

BrdU-Binding Bispecific Antibodies from Complexes with BrdU Containing Payloads SEC-MALLS analyses were applied to evaluate if and to what degree transferrin receptor (TfR)- and bromodeoxyuridine (BRDU)-binding bispecific antibody (bsAb) are capable of binding to BRDU containing payloads. Therefore, BRDU-DNA was added to TfR-BRDU bsAb at a 2:1 stoichiometric ratio (350 μg; 2.5 mg/ml) and incubated for 30 minutes at room temperature for formation of bsAb/payload-complexes. As control reagents we prepared free bispecific antibody (2.5 mg/ml) and free BRDU-DNA (3.2 mg/ml). BRDU-DNA (BRDU-ACC AAG CCT AGA GAG GAG CAA TAC AAC AGT ACA TAT CGC GTG GTA AGC GT; SEQ ID NO: 153) contained one BRDU per DNA molecule at the 5' end of the DNA. Complexes and control reagents were stored at −80° C. until analysis.

The hereby generated complexes and control reagents were subjected to SEC-MALLS analysis to identify and characterize free bispecific antibody, free payload and complexes of both. SEC-MALLS analysis was performed on a Dionex Ultimate 3000 HPLC equipped with Wyatt miniDawnTREOS/QELS and Optilab rEX detectors. Analytes were dissolved at 1 mg/ml in PBS buffer pH 7.4, applied to a Superdex200 10/300GL column at a flow rate of 0.5 ml/minute and eluted with PBS buffer pH 7.4 for 60 minutes.

The results of these analyses (shown in FIG. 18) indicate that BRDU-containing DNA forms defined complexes with the bispecific antibody. These complexes elute from the column at a MW of 244.9 kDa (FIG. 18, panel A) and display a hydrodynamic radius of 6.8 nm (FIG. 18, panel B), allowing the calculation of a stoichiometric ratio of approximately two (1.8) DNA molecules per bispecific antibody molecule. In comparison to that, free bispecific antibody was detected at a MW of 215.4 kDa and its hydrodynamic radius was determined at 6.2 nm. Free BRDU-DNA was detected at a MW of 16.4 kDa.

Thus, it was shown that BRDU-containing DNA is effectively and stoichiometrically bound by the anti-TfR/BRDU bispecific antibody, resulting in complexes in a 2:1 molar ratio.

Example 22

Biotin-Binding Bispecific Antibodies Bind to Biotin-Containing IgGs

To analyze if and to what degree the TfR/biotin bispecific antibody is capable of binding to mono-biotinylated full length IgG, mono-biotinylated antibody of the IgG isotype specifically binding to ptau (biotin-labeled anti-ptau antibody, BIO-ptau) was added to anti-TfR/biotin bispecific antibody at a 2:1 stoichiometric ratio (300 μg, 1.3 mg/ml), and the mixture was incubated for 30 minutes at room temperature (formation of bispecific antibody-payload complexes). Mono-biotinylated IgG was generated by producing IgG-derivatives with an Avi-tag at the C-terminus of one chain of a knob-into-hole heterodimeric antibody of the IgG isotype. The Avi-tag becomes enzymatically conjugated to one biotin in a defined manner.

As a control for the specificity of complex formation, an anti-TfR/digoxigenin bispecific antibody was mixed with BIO-ptau. As further control reagents aliquots of both free bispecific antibody and free BIO-ptau were prepared. Complexes and control reagents were stored at −80° C. until analysis.

The generated complexes were subjected to SEC-MALLS analysis to identify and characterize free bispecific antibody, free BIO-ptau and complexes thereof. SEC-MALLS analysis was performed on a Dionex Ultimate 3000 HPLC equipped with Wyatt miniDawnTREOS/QELS and Optilab rEX detectors. Analytes were dissolved at 1-2 mg/ml in PBS buffer pH 7.4, applied to a Superose 6 10/300GL column at a flow rate of 0.5 ml/minutes and eluted with PBS buffer pH 7.4 for 60 minutes.

Figure 19A:
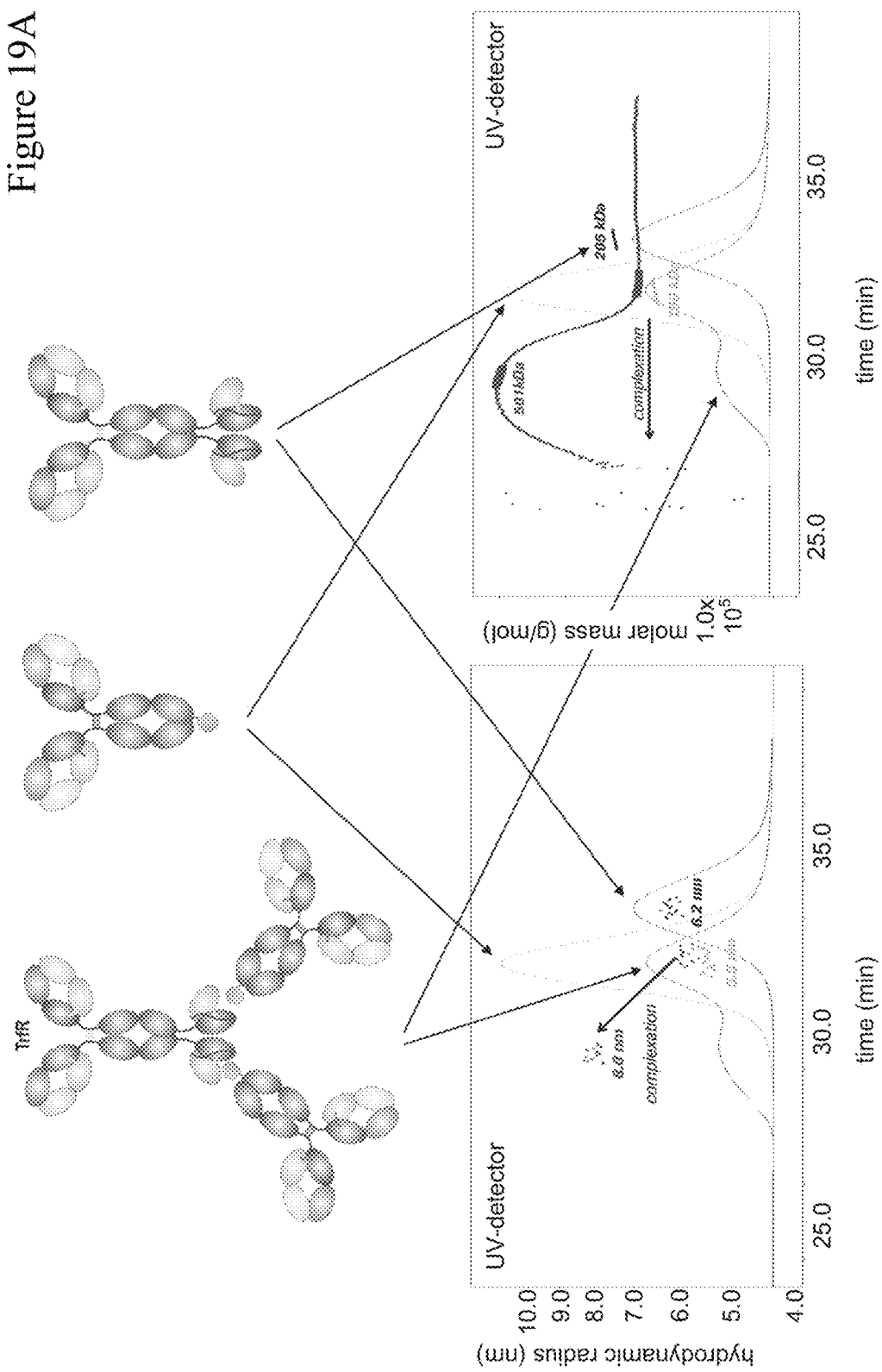
Figure 19B:
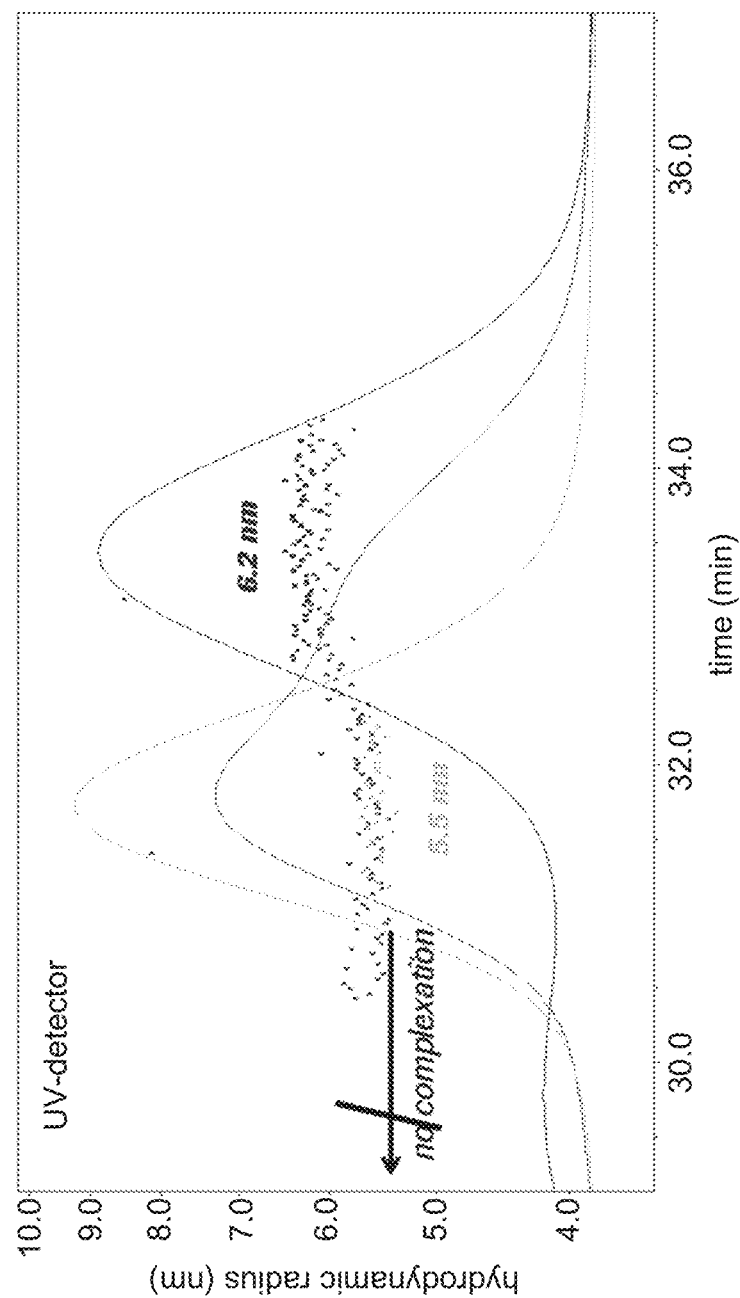

The results of these analyses (shown in FIG. 19A-FIG. 19B) indicate that BIO-ptau forms defined complexes with the bispecific antibody. These complexes elute from the column at a MW of 501 kDa (FIG. 19, right-hand panel B) and display a hydrodynamic radius of 8.0 nm (FIG. 19, left-hand panel A). In comparison to that, free bispecific antibody was detected at a MW of 205 kDa and its hydrodynamic radius was determined at 6.2 nm. Free BIO-ptau was detected at a MW of 150 kDa and its hydrodynamic radius was measured at 5.5 nm.

The complexes are specifically formed by interaction between biotin and the biotin-binding moiety of the bispecific antibody, because the digoxigenin-binding bispecific antibody does not form complexes with BIO-ptau. (See, e.g., FIG. 19B.)

Example 23

Transcytosis of Complex of Biotin-Labelled Anti-Ptau Antibody with Anti-TM/Biotin Bispecific Antibody To analyze if and to what degree the anti-TfR/biotin bispecific antibodies facilitate transcytosis of full length antibody payloads, complexes of anti-TfR/biotin bispecific antibody (anti-TfR/biotin bsAb-1 and anti-TfR/biotin bsAb-2) and BIO-ptau were formed as described in Example 22 and subjected to a transcytosis assay as described above e.g. in Example 18. As control for non-specific transcytosis, complexes of anti-CD33/biotin bispecific antibody and BIO-ptau as well as free BIO-ptau were tested in parallel. Samples of the apical and basolateral compartments, and of the cell lysates were taken at 0, 1, 2, 3, 4 and 5 hours after loading of the cells. Loading always with 3.8 µg/ml.

The amount of biotin-labelled anti-ptau antibody was measured by ELISA. Therefore ptau protein was coated onto NUNC Maxisorb White 384-well plates at 500 ng/ml, overnight at 2-8° C. or one hour at room temperature. Plates were blocked with PBS containing 2% BSA and 0.05 Tween 20 for at least one hour. Sample dilutions of up to 1/729 in PBS containing 0.5% BSA and 0.05% Tween 20 were applied for 1.5-2 hours, followed by Poly-HRP40-Streptavidin (Fitzgerald) for 30 minutes and Super Signal ELISA Pico substrate (Thermo Scientific) for 10 minutes, all at room temperature. Standard dilutions of BIO-ptau antibody (100 ng/ml-0.5 µg/ml) were assayed on the same plate. Plates were washed with PBS containing 0.1% Tween 20 between consecutive incubation steps.

Figure 20:
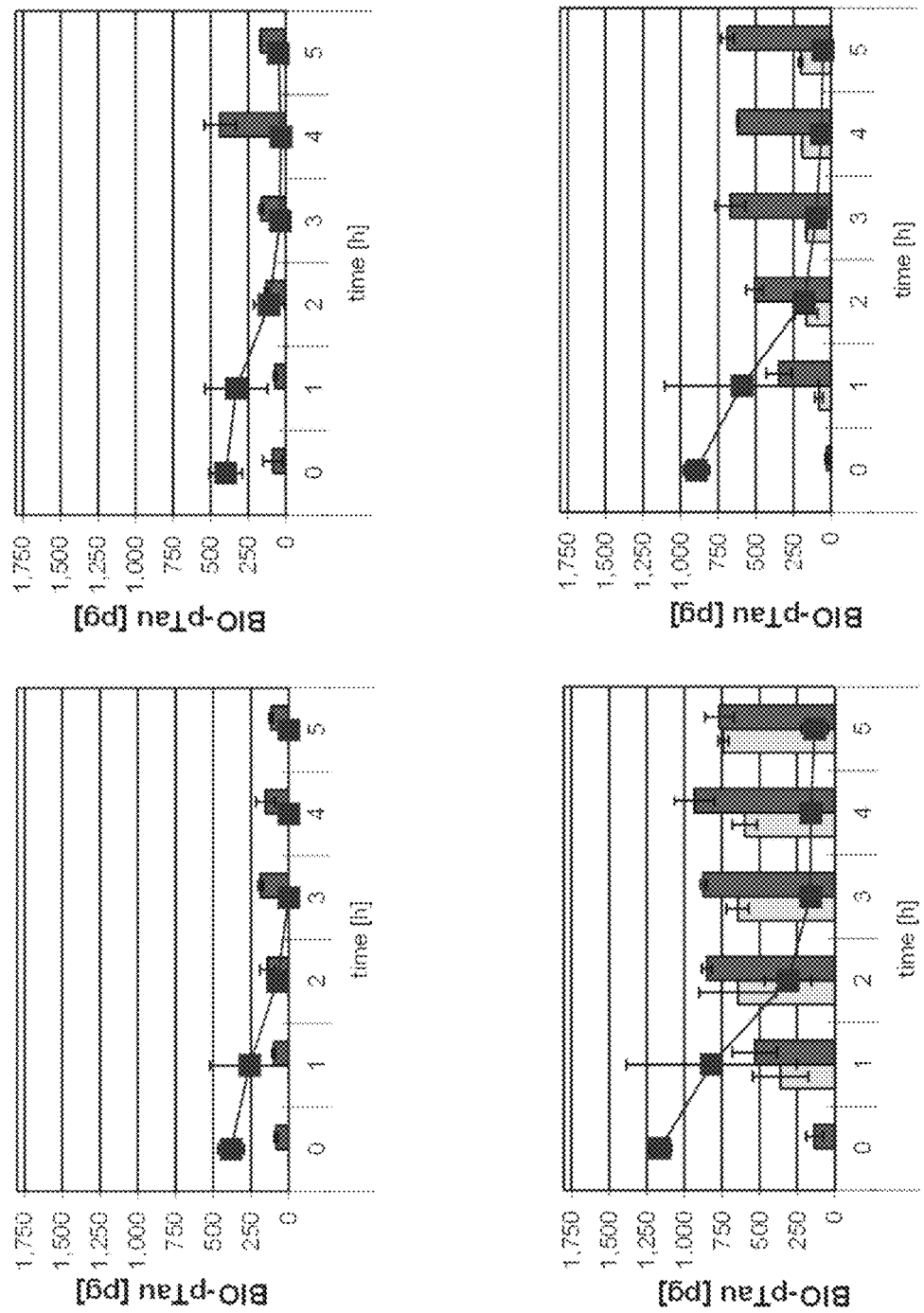

The results of these transcytosis assays (FIG. 20) show that complexing BIO-ptau to either anti-TfR/biotin bsAb-1 or anti-TfR/biotin bsAb-2 mediates effective endocytosis and subsequent transport of BIO-ptau into the basolateral as well as back into the apical compartment. In contrast, neither complexes of BIO-ptau to anti-CD33/biotin bispecific antibody nor free BIO-ptau are effectively endocytosed or transcytosed, indicating that the observed transcytosis is caused by specific binding of the anti-TfR/biotin bispecific antibody to the TfR on the surface of the cells.

Example 24

Figure 21:
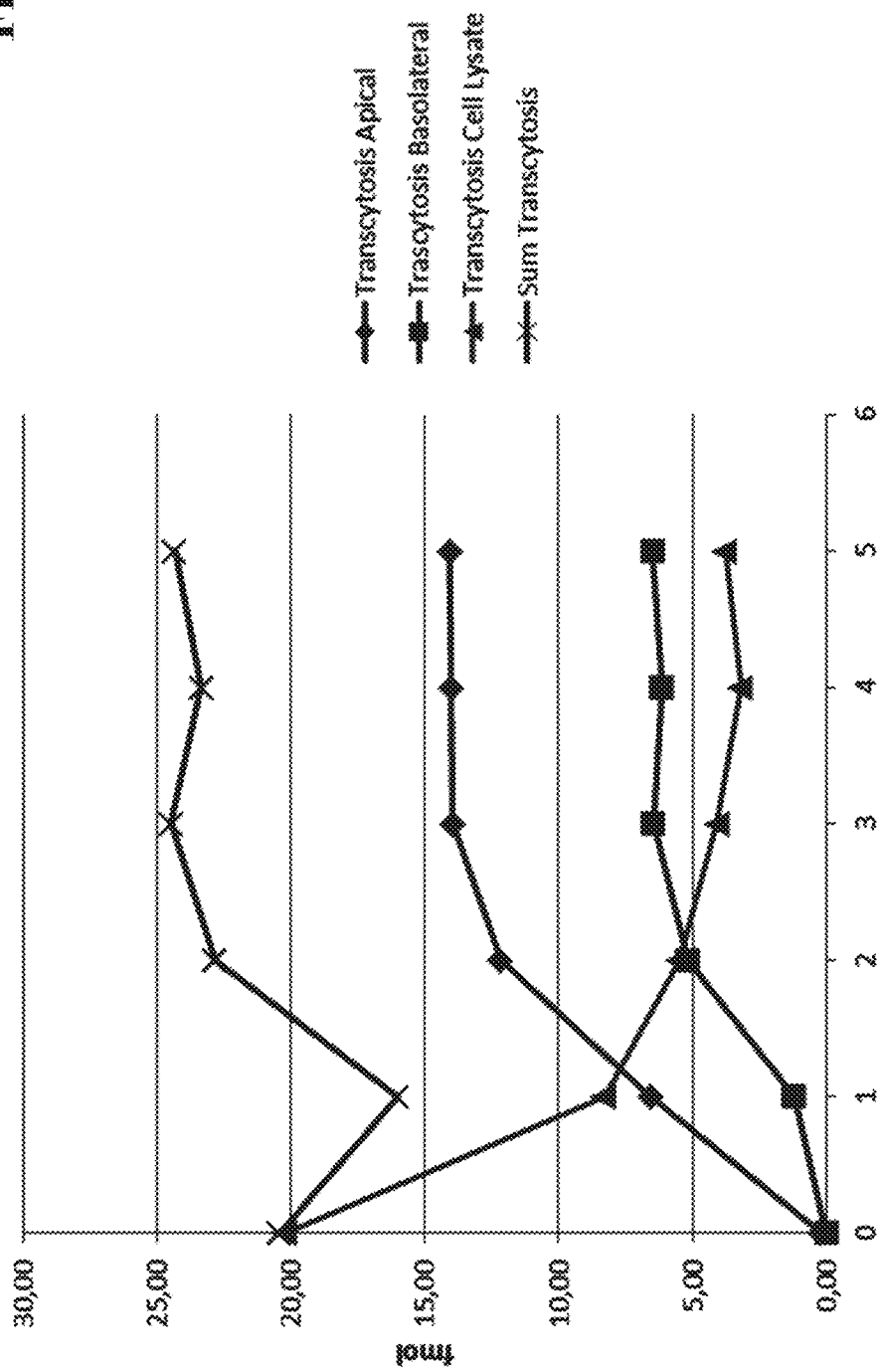

Transcytosis of Complex of Bispecific Anti-Human Tau (pS422)/Biotin Antibody and Biotinylated Anti-TfR Antibody Fab Fragment In analogy to the Examples presented above the transcytosis of a non-covalent complex of bispecific anti-human tau(pS422)/biotin antibody and biotinylated anti-TfR antibody Fab fragment has been elucidated. The results are presented in FIG. 21. For analysis human tau(pS422) was immobilized on the plate, an anti-human CH2 was used as secondary antibody, and detection was performed with an anti-digoxigenin antibody POD-conjugate.

All documents cited in this application are hereby incorporate by reference as if recited in full herein.

Although illustrative embodiments of the present invention have been described herein, it should be understood that the invention is not limited to those described, and that various other changes or modifications may be made by one skilled in the art without departing from the scope or spirit of the invention.

The invention claimed is:

1. A method for transport of an antibody that specifically binds to human tau(pS422) across the blood brain barrier in a subject comprising administering to the subject an effective amount of a non-covalent complex of a haptenylated antibody that specifically binds to human tau(pS422) and an anti-blood brain barrier receptor/hapten bispecific antibody,
   wherein the antibody that specifically binds to human tau(pS422) comprises:
   a) in the light chain variable domain the HVRs of SEQ ID NO: 13, 14 and 15, or
   b) in the light chain variable domain the HVRs of SEQ ID NO: 12, 05 and 15; and
   c) in the heavy chain variable domain the HVRs of SEQ ID NO: 08, 18 and 10, or
   d) in the heavy chain variable domain the HVRs of SEQ ID NO: 08, 09 and 10.

2. A method for transport of an antibody that specifically binds to human tau(pS422) across the blood brain barrier in a subject comprising administering to the subject an effective amount of a non-covalent complex of a bispecific antibody that specifically binds to human tau(pS422) and a hapten and a haptenylated anti-blood brain barrier receptor antibody,
   wherein the antibody that specifically binds to human tau(pS422) comprises:
   a) in the light chain variable domain the HVRs of SEQ ID NO: 13, 14 and 15, or
   b) in the light chain variable domain the HVRs of SEQ ID NO: 12, 05 and 15; and
   c) in the heavy chain variable domain the HVRs of SEQ ID NO: 08, 18 and 10, or
   d) in the heavy chain variable domain the HVRs of SEQ ID NO: 08, 09 and 10.

3. A method for transport of an antibody that specifically binds to human tau(pS422) across the blood brain barrier in a subject comprising administering to the subject an effective amount of a non-covalent complex comprising a haptenylated antibody that specifically binds to human tau (pS422) and bispecific antibody, which has a first binding specificity that specifically binds to the hapten of the haptenylated antibody that specifically binds to human tau (pS422) and a second binding specificity that specifically binds to a blood brain barrier receptor, wherein the haptenylated antibody that specifically binds to human tau (pS422) is specifically bound by the first binding specificity of the bispecific antibody,
   wherein the antibody that specifically binds to human tau(pS422) comprises:
   a) in the light chain variable domain the HVRs of SEQ ID NO: 13, 14 and 15, or
   b) in the light chain variable domain the HVRs of SEQ ID NO: 12, 05 and 15; and
   c) in the heavy chain variable domain the HVRs of SEQ ID NO: 08, 18 and 10, or
   d) in the heavy chain variable domain the HVRs of SEQ ID NO: 08, 09 and 10.

4. A method for transport of an antibody that specifically binds to human tau(pS422) across the blood brain barrier in a subject comprising administering to the subject an effective amount of a non-covalent complex comprising a haptenylated antibody, which specifically binds to a blood brain barrier receptor, and a bispecific antibody, which has a first binding specificity that specifically binds to human tau (pS422) and a second binding specificity that specifically binds to the hapten of the haptenylated antibody that specifically binds to a blood brain barrier receptor, wherein the haptenylated antibody that specifically binds to the blood brain barrier receptor is specifically bound by the first binding specificity of the bispecific antibody,
wherein the antibody that specifically binds to human tau(pS422) comprises:
a) in the light chain variable domain the HVRs of SEQ ID NO: 13, 14 and 15, or
b) in the light chain variable domain the HVRs of SEQ ID NO: 12, 05 and 15; and
c) in the heavy chain variable domain the HVRs of SEQ ID NO: 08, 18 and 10, or
d) in the heavy chain variable domain the HVRs of SEQ ID NO: 08, 09 and 10.

5. The method according to claim 1, wherein the haptenylated antibody is a biotinylated antibody or a digoxigenylated antibody.

6. The method according to claim 1, wherein the blood brain barrier receptor is the transferrin receptor (TfR) or the low density lipoprotein receptor-related protein 8 (LRP8).

7. The method according to claim 1, wherein the bispecific antibody comprises:
a) one binding site for the hapten of the haptenylated antibody and one binding site for the blood brain barrier receptor;
b) two binding sites for the hapten of the haptenylated antibody and one binding site for the blood brain barrier receptor;
c) one binding site for the hapten of haptenylated antibody and two binding sites for the blood brain barrier receptor;
d) two binding sites for the hapten of the haptenylated antibody and two binding sites for the blood brain barrier receptor;
e) one binding site for the hapten of the haptenylated antibody and one binding site for human tau(pS422);
f) two binding sites for the hapten of the haptenylated antibody and one binding site for human tau(pS4220);
g) one binding site for the hapten of haptenylated antibody and two binding sites for human tau(pS422), or
h) two binding sites for the hapten of the haptenylated antibody and two binding sites for human tau(pS422), wherein in cases b), c), f) and g) one heavy chain of the bispecific antibody comprises a hole mutation and the respective other chain comprises a knob mutation.

8. The method according to claim 1, wherein the bispecific antibody has two binding specificities that specifically bind to the hapten of the haptenylated antibody (two anti-hapten binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

9. The method according to claim 1, wherein the antibody that specifically binds to human tau(pS422) comprises:
a) in the heavy chain variable domain the HVRs of SEQ ID NO: 08, 18 and 10, and in the light chain variable domain the HVRs of SEQ ID NO: 13, 14 and 15;
b) in the heavy chain variable domain the HVRs of SEQ ID NO: 08, 09 and 10, and in the light chain variable domain the HVRs of SEQ ID NO: 12, 05 and 15, or
c) in the heavy chain variable domain the HVRs of SEQ ID NO: 08, 09 and 10, and in the light chain variable domain the HVRs of SEQ ID NO: 13, 14 and 15.

10. The method according to claim 1, wherein the antibody that specifically binds to human tau(pS422) comprises:
a) a heavy chain variable domain of SEQ ID NO: 20 and a light chain variable domain of SEQ ID NO: 17;
b) a heavy chain variable domain of SEQ ID NO: 19 and a light chain variable domain of SEQ ID NO: 16;
c) a heavy chain variable domain of SEQ ID NO: 19 and a light chain variable domain of SEQ ID NO: 17, or
d) a heavy chain variable domain of SEQ ID NO: 21 and a light chain variable domain of SEQ ID NO: 17.

11. A non-covalent complex of a haptenylated antibody that specifically binds to human tau(pS422) and an anti-blood brain barrier receptor/hapten bispecific antibody,
wherein the antibody that specifically binds to human tau(pS422) comprises:
a) in the light chain variable domain the HVRs of SEQ ID NO: 13, 14 and 15, or
b) in the light chain variable domain the HVRs of SEQ ID NO: 12, 05 and 15; and
c) in the heavy chain variable domain the HVRs of SEQ ID NO: 08, 18 and 10, or
d) in the heavy chain variable domain the HVRs of SEQ ID NO: 08, 09 and 10.

12. A non-covalent complex of a bispecific antibody that specifically binds to human tau(pS422) and a hapten and a haptenylated anti-blood brain barrier receptor antibody,
wherein the antibody that specifically binds to human tau(pS422) comprises:
a) in the light chain variable domain the HVRs of SEQ ID NO: 13, 14 and 15, or
b) in the light chain variable domain the HVRs of SEQ ID NO: 12, 05 and 15; and
c) in the heavy chain variable domain the HVRs of SEQ ID NO: 08, 18 and 10, or
d) in the heavy chain variable domain the HVRs of SEQ ID NO: 08, 09 and 10.

13. A non-covalent complex comprising a haptenylated antibody that specifically binds to human tau(pS422) and bispecific antibody, which has a first binding specificity that specifically binds to the hapten of the haptenylated antibody that specifically binds to human tau(pS422) and a second binding specificity that specifically binds to a blood brain barrier receptor, wherein the haptenylated antibody that specifically binds to human tau(pS422) is specifically bound by the first binding specificity of the bispecific antibody,
wherein the antibody that specifically binds to human tau(pS422) comprises:
a) in the light chain variable domain the HVRs of SEQ ID NO: 13, 14 and 15, or
b) in the light chain variable domain the HVRs of SEQ ID NO: 12, 05 and 15; and
c) in the heavy chain variable domain the HVRs of SEQ ID NO: 08, 18 and 10, or
d) in the heavy chain variable domain the HVRs of SEQ ID NO: 08, 09 and 10.

14. A non-covalent complex comprising a haptenylated antibody, which specifically binds to a blood brain barrier receptor, and a bispecific antibody, which has a first binding specificity that specifically binds to human tau(pS422) and a second binding specificity that specifically binds to the hapten of the haptenylated antibody that specifically binds to a blood brain barrier receptor, wherein the haptenylated antibody that specifically binds to the blood brain barrier receptor is specifically bound by the second binding specificity of the bispecific antibody, wherein the antibody that specifically binds to human tau(pS422) comprises:
a) in the light chain variable domain the HVRs of SEQ ID NO: 13, 14 and 15, or
b) in the light chain variable domain the HVRs of SEQ ID NO: 12, 05 and 15; and
c) in the heavy chain variable domain the HVRs of SEQ ID NO: 08, 18 and 10, or
d) in the heavy chain variable domain the HVRs of SEQ ID NO: 08, 09 and 10.

15. The non-covalent complex according to claim 11, wherein the haptenylated antibody is a biotinylated antibody or a digoxigenylated antibody.

16. The non-covalent complex according to claim 11, wherein the blood brain barrier receptor is the transferrin receptor (TfR).

17. The non-covalent complex according to claim 11, wherein the bispecific antibody comprises:
a) one binding site for the hapten of the haptenylated antibody and one binding site for the blood brain barrier receptor;
b) two binding sites for the hapten of the haptenylated antibody and one binding site for the blood brain barrier receptor;
c) one binding site for the hapten of haptenylated antibody and two binding sites for the blood brain barrier receptor;
d) two binding sites for the hapten of the haptenylated antibody and two binding sites for the blood brain barrier receptor;
e) one binding site for the hapten of the haptenylated antibody and one binding site for human tau(pS422);
f) two binding sites for the hapten of the haptenylated antibody and one binding site for human tau(pS422);
g) one binding site for the hapten of haptenylated antibody and two binding sites for human tau(pS422), or
h) two binding sites for the hapten of the haptenylated antibody and two binding sites for human tau(pS422), wherein in cases b), c), f) and g) one heavy chain of the bispecific antibody comprises a hole mutation and the respective other chain comprises a knob mutation.

18. The non-covalent complex according to claim 11, wherein the bispecific antibody has two binding specificities that specifically bind to the hapten of the haptenylated antibody (two anti-hapten binding specificities) and two binding specificities that specifically bind to the (human) transferrin receptor (two anti-(human) transferrin receptor binding specificities) or to low density lipoprotein receptor-related protein 8 (anti-low density lipoprotein receptor-related protein 8 binding specificity).

19. The non-covalent complex according to claim 11, wherein the antibody that specifically binds to human tau (pS422) comprises:
a) in the heavy chain variable domain the HVRs of SEQ ID NO: 08, 18 and 10, and in the light chain variable domain the HVRs of SEQ ID NO: 13, 14 and 15;
b) in the heavy chain variable domain the HVRs of SEQ ID NO: 08, 09 and 10, and in the light chain variable domain the HVRs of SEQ ID NO: 12, 05 and 15, or
c) in the heavy chain variable domain the HVRs of SEQ ID NO: 08, 09 and 10, and in the light chain variable domain the HVRs of SEQ ID NO: 13, 14 and 15.

20. The non-covalent complex according to claim 11, wherein the antibody that specifically binds to human tau (pS422) comprises:
a) a heavy chain variable domain of SEQ ID NO: 20 and a light chain variable domain of SEQ ID NO: 17;
b) a heavy chain variable domain of SEQ ID NO: 19 and a light chain variable domain of SEQ ID NO: 16;
c) a heavy chain variable domain of SEQ ID NO: 19 and a light chain variable domain of SEQ ID NO: 17, or
d) a heavy chain variable domain of SEQ ID NO: 21 and a light chain variable domain of SEQ ID NO: 17.

21. A medicament comprising the non-covalent complex according to any one of claims 11 to 18 and 19 to 20.

22. A method of treating a subject suffering from Alzheimer's disease, the method comprising administering to the subject an effective amount of the non-covalent complex according to any one of claims 11 to 18 and 19 to 20.

* * * * *

SEQUENCE LISTING

```
<160> NUMBER OF SEQ ID NOS: 153

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45
```

Gln Thr Pro Thr Glu Asp Gly Ser Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
<211> LENGTH: 441
<212> TYPE: PRT

```
<213> ORGANISM: Homo sapiens
<220> FEATURE:
<221> NAME/KEY: MISC_FEATURE
<222> LOCATION: (422)..(422)
<223> OTHER INFORMATION: X=phosphoserine

<400> SEQUENCE: 2
```

| | | | | | | | | | | | | | | |
|---|---|---|---|---|---|---|---|---|---|---|---|---|---|---|
| Met | Ala | Glu | Pro | Arg | Gln | Glu | Phe | Glu | Val | Met | Glu | Asp | His | Ala | Gly |
| 1 | | | | 5 | | | | | 10 | | | | | 15 | |
| Thr | Tyr | Gly | Leu | Gly | Asp | Arg | Lys | Asp | Gln | Gly | Gly | Tyr | Thr | Met | His |
| | | | 20 | | | | | 25 | | | | | 30 | | |
| Gln | Asp | Gln | Glu | Gly | Asp | Thr | Asp | Ala | Gly | Leu | Lys | Glu | Ser | Pro | Leu |
| | | 35 | | | | | 40 | | | | | 45 | | | |
| Gln | Thr | Pro | Thr | Glu | Asp | Gly | Ser | Glu | Glu | Pro | Gly | Ser | Glu | Thr | Ser |
| 50 | | | | | 55 | | | | | 60 | | | | | |
| Asp | Ala | Lys | Ser | Thr | Pro | Thr | Ala | Glu | Asp | Val | Thr | Ala | Pro | Leu | Val |
| 65 | | | | | 70 | | | | | 75 | | | | | 80 |
| Asp | Glu | Gly | Ala | Pro | Gly | Lys | Gln | Ala | Ala | Gln | Pro | His | Thr | Glu | |
| | | | | 85 | | | | | 90 | | | | | 95 | |
| Ile | Pro | Glu | Gly | Thr | Thr | Ala | Glu | Glu | Ala | Gly | Ile | Gly | Asp | Thr | Pro |
| | | | | 100 | | | | | 105 | | | | | 110 | |
| Ser | Leu | Glu | Asp | Glu | Ala | Ala | Gly | His | Val | Thr | Gln | Ala | Arg | Met | Val |
| | | | 115 | | | | | 120 | | | | | 125 | | |
| Ser | Lys | Ser | Lys | Asp | Gly | Thr | Gly | Ser | Asp | Asp | Lys | Lys | Ala | Lys | Gly |
| | 130 | | | | | 135 | | | | | 140 | | | | |
| Ala | Asp | Gly | Lys | Thr | Lys | Ile | Ala | Thr | Pro | Arg | Gly | Ala | Ala | Pro | Pro |
| 145 | | | | | 150 | | | | | 155 | | | | | 160 |
| Gly | Gln | Lys | Gly | Gln | Ala | Asn | Ala | Thr | Arg | Ile | Pro | Ala | Lys | Thr | Pro |
| | | | | 165 | | | | | 170 | | | | | 175 | |
| Pro | Ala | Pro | Lys | Thr | Pro | Ser | Ser | Gly | Glu | Pro | Pro | Lys | Ser | Gly |
| | | | 180 | | | | | 185 | | | | | 190 | | |
| Asp | Arg | Ser | Gly | Tyr | Ser | Ser | Pro | Gly | Ser | Pro | Gly | Thr | Pro | Gly | Ser |
| | | 195 | | | | | 200 | | | | | 205 | | | |
| Arg | Ser | Arg | Thr | Pro | Ser | Leu | Pro | Thr | Pro | Pro | Thr | Arg | Glu | Pro | Lys |
| 210 | | | | | 215 | | | | | 220 | | | | | |
| Lys | Val | Ala | Val | Val | Arg | Thr | Pro | Pro | Lys | Ser | Pro | Ser | Ser | Ala | Lys |
| 225 | | | | | 230 | | | | | 235 | | | | | 240 |
| Ser | Arg | Leu | Gln | Thr | Ala | Pro | Val | Pro | Met | Pro | Asp | Leu | Lys | Asn | Val |
| | | | | 245 | | | | | 250 | | | | | 255 | |
| Lys | Ser | Lys | Ile | Gly | Ser | Thr | Glu | Asn | Leu | Lys | His | Gln | Pro | Gly | Gly |
| | | | 260 | | | | | 265 | | | | | 270 | | |
| Gly | Lys | Val | Gln | Ile | Ile | Asn | Lys | Lys | Leu | Asp | Leu | Ser | Asn | Val | Gln |
| | | 275 | | | | | 280 | | | | | 285 | | | |
| Ser | Lys | Cys | Gly | Ser | Lys | Asp | Asn | Ile | Lys | His | Val | Pro | Gly | Gly | Gly |
| | 290 | | | | | 295 | | | | | 300 | | | | |
| Ser | Val | Gln | Ile | Val | Tyr | Lys | Pro | Val | Asp | Leu | Ser | Lys | Val | Thr | Ser |
| 305 | | | | | 310 | | | | | 315 | | | | | 320 |
| Lys | Cys | Gly | Ser | Leu | Gly | Asn | Ile | His | His | Lys | Pro | Gly | Gly | Gly | Gln |
| | | | | 325 | | | | | 330 | | | | | 335 | |
| Val | Glu | Val | Lys | Ser | Glu | Lys | Leu | Asp | Phe | Lys | Asp | Arg | Val | Gln | Ser |
| | | | 340 | | | | | 345 | | | | | 350 | | |
| Lys | Ile | Gly | Ser | Leu | Asp | Asn | Ile | Thr | His | Val | Pro | Gly | Gly | Gly | Asn |
| | | 355 | | | | | 360 | | | | | 365 | | | |
| Lys | Lys | Ile | Glu | Thr | His | Lys | Leu | Thr | Phe | Arg | Glu | Asn | Ala | Lys | Ala |
| | 370 | | | | | 375 | | | | | 380 | | | | |

```
Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Xaa Pro Gln Leu Ala Thr Leu Ala Asp Glu Val
            420                 425                 430

Ser Ala Ser Leu Ala Lys Gln Gly Leu
        435                 440

<210> SEQ ID NO 3
<211> LENGTH: 15
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: X=phosphoserine

<400> SEQUENCE: 3

Ser Ile Asp Met Val Asp Xaa Pro Gln Leu Ala Thr Leu Ala Asp
1               5                   10                  15

<210> SEQ ID NO 4
<211> LENGTH: 12
<212> TYPE: PRT
<213> ORGANISM: Oryctolagus cuniculus

<400> SEQUENCE: 4

Gln Ser Ser Gln Ser Val Arg Thr Asn Lys Leu Ala
1               5                   10

<210> SEQ ID NO 5
<211> LENGTH: 7
<212> TYPE: PRT
<213> ORGANISM: Oryctolagus cuniculus

<400> SEQUENCE: 5

Ser Ala Ser Thr Leu Asp Phe
1               5

<210> SEQ ID NO 6
<211> LENGTH: 13
<212> TYPE: PRT
<213> ORGANISM: Oryctolagus cuniculus

<400> SEQUENCE: 6

Leu Gly Tyr Phe Asp Cys Ser Ile Ala Asp Cys Val Ala
1               5                   10

<210> SEQ ID NO 7
<211> LENGTH: 112
<212> TYPE: PRT
<213> ORGANISM: Oryctolagus cuniculus

<400> SEQUENCE: 7

Ala Gln Val Leu Thr Gln Thr Thr Ser Pro Val Ser Ala Ala Val Gly
1               5                   10                  15

Ser Thr Val Thr Ile Ser Cys Gln Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
```

```
                       50                  55                  60

Ala Ser Gly Ser Gly Thr Gln Phe Thr Leu Thr Ile Ser Asp Val Gln
 65                  70                  75                  80

Cys Asp Asp Ala Ala Thr Tyr Tyr Cys Leu Gly Tyr Phe Asp Cys Ser
                 85                  90                  95

Ile Ala Asp Cys Val Ala Phe Gly Gly Gly Thr Glu Val Val Val Lys
            100                 105                 110

<210> SEQ ID NO 8
<211> LENGTH: 5
<212> TYPE: PRT
<213> ORGANISM: Oryctolagus cuniculus

<400> SEQUENCE: 8

Ser Asn Ala Ile Asn
1               5

<210> SEQ ID NO 9
<211> LENGTH: 16
<212> TYPE: PRT
<213> ORGANISM: Oryctolagus cuniculus

<400> SEQUENCE: 9

Tyr Ile Ala Val Ser Gly Asn Thr Tyr Tyr Ala Ser Trp Ala Lys Gly
1               5                  10                  15

<210> SEQ ID NO 10
<211> LENGTH: 3
<212> TYPE: PRT
<213> ORGANISM: Oryctolagus cuniculus

<400> SEQUENCE: 10

Ser Asn Ile
1

<210> SEQ ID NO 11
<211> LENGTH: 108
<212> TYPE: PRT
<213> ORGANISM: Oryctolagus cuniculus

<400> SEQUENCE: 11

Gln Ser Val Glu Glu Ser Gly Gly Arg Leu Val Thr Pro Gly Thr Pro
1               5                  10                  15

Leu Thr Leu Thr Cys Thr Val Ser Gly Phe Ser Leu Ser Ser Asn Ala
            20                  25                  30

Ile Asn Trp Val Arg Gln Ala Pro Gly Lys Gly Leu Glu Trp Ile Gly
        35                  40                  45

Tyr Ile Ala Val Ser Gly Asn Thr Tyr Tyr Ala Ser Trp Ala Lys Gly
    50                  55                  60

Arg Phe Thr Ile Ser Lys Ala Ser Thr Thr Val Asp Leu Lys Met Thr
65                  70                  75                  80

Ser Pro Thr Ala Glu Asp Thr Gly Thr Tyr Phe Cys Gly Lys Ser Asn
                85                  90                  95

Ile Trp Gly Pro Gly Thr Leu Val Thr Val Ser Leu
            100                 105

<210> SEQ ID NO 12
<211> LENGTH: 12
<212> TYPE: PRT
<213> ORGANISM: Artificial Sequence
<220> FEATURE:
```

```
<223> OTHER INFORMATION: humanized sequence

<400> SEQUENCE: 12

Arg Ser Ser Gln Ser Val Arg Thr Asn Lys Leu Ala
1               5                   10

<210> SEQ ID NO 13
<211> LENGTH: 12
<212> TYPE: PRT
<213> ORGANISM: Artificial Sequence
<220> FEATURE:
<223> OTHER INFORMATION: humanized sequence

<400> SEQUENCE: 13

Arg Ser Ser Gln Ser Val Arg Thr Asn Arg Leu Ala
1               5                   10

<210> SEQ ID NO 14
<211> LENGTH: 7
<212> TYPE: PRT
<213> ORGANISM: Artificial Sequence
<220> FEATURE:
<223> OTHER INFORMATION: humanized sequence

<400> SEQUENCE: 14

Ser Ala Ser Thr Leu Asp Tyr
1               5

<210> SEQ ID NO 15
<211> LENGTH: 12
<212> TYPE: PRT
<213> ORGANISM: Artificial Sequence
<220> FEATURE:
<223> OTHER INFORMATION: humanized sequence

<400> SEQUENCE: 15

Leu Gly Tyr Phe Asp Ser Ser Ala Asp Ile Val Ala
1               5                   10

<210> SEQ ID NO 16
<211> LENGTH: 111
<212> TYPE: PRT
<213> ORGANISM: Artificial Sequence
<220> FEATURE:
<223> OTHER INFORMATION: humanized sequence

<400> SEQUENCE: 16

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys
            100                 105                 110

<210> SEQ ID NO 17
```

```
<211> LENGTH: 111
<212> TYPE: PRT
<213> ORGANISM: Artificial Sequence
<220> FEATURE:
<223> OTHER INFORMATION: humanized sequence

<400> SEQUENCE: 17

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Tyr Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ala Asp Ile Val Ala Phe Gly Gly Gly Thr Lys Val Glu Ile Lys
            100                 105                 110

<210> SEQ ID NO 18
<211> LENGTH: 16
<212> TYPE: PRT
<213> ORGANISM: Artificial Sequence
<220> FEATURE:
<223> OTHER INFORMATION: humanized sequence

<400> SEQUENCE: 18

Tyr Ile Ala Val Ser Gly Asn Thr Tyr Tyr Ala Asp Ser Val Lys Gly
1               5                   10                  15

<210> SEQ ID NO 19
<211> LENGTH: 111
<212> TYPE: PRT
<213> ORGANISM: Artificial Sequence
<220> FEATURE:
<223> OTHER INFORMATION: humanized sequence

<400> SEQUENCE: 19

Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110

<210> SEQ ID NO 20
<211> LENGTH: 112
<212> TYPE: PRT
<213> ORGANISM: Artificial Sequence
<220> FEATURE:
```

<223> OTHER INFORMATION: humanized sequence

<400> SEQUENCE: 20

Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys
            100                 105                 110

<210> SEQ ID NO 21
<211> LENGTH: 112
<212> TYPE: PRT
<213> ORGANISM: Artificial Sequence
<220> FEATURE:
<223> OTHER INFORMATION: humanizes sequence

<400> SEQUENCE: 21

Ala Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys
            100                 105                 110

<210> SEQ ID NO 22
<211> LENGTH: 7
<212> TYPE: PRT
<213> ORGANISM: Artificial Sequence
<220> FEATURE:
<223> OTHER INFORMATION: humanized sequence

<400> SEQUENCE: 22

Ser Ala Ser Thr Leu Gln Ser
1               5

<210> SEQ ID NO 23
<211> LENGTH: 7
<212> TYPE: PRT
<213> ORGANISM: Artificial Sequence
<220> FEATURE:
<223> OTHER INFORMATION: humanized sequence

<400> SEQUENCE: 23

Ser Ala Ser Thr Leu Glu Ser
1               5

<210> SEQ ID NO 24
<211> LENGTH: 13
<212> TYPE: PRT
<213> ORGANISM: Artificial Sequence
<220> FEATURE:
<223> OTHER INFORMATION: humanized sequence

<400> SEQUENCE: 24

Leu Gly Tyr Phe Asp Ser Ser Ile Ala Asp Ser Val Ala
1               5                   10

<210> SEQ ID NO 25
<211> LENGTH: 13
<212> TYPE: PRT
<213> ORGANISM: Artificial Sequence
<220> FEATURE:
<223> OTHER INFORMATION: humanized sequence

<400> SEQUENCE: 25

Leu Gly Tyr Phe Asp Ser Ser Ile Ala Asp Arg Val Ala
1               5                   10

<210> SEQ ID NO 26
<211> LENGTH: 13
<212> TYPE: PRT
<213> ORGANISM: Artificial Sequence
<220> FEATURE:
<223> OTHER INFORMATION: humanized sequence

<400> SEQUENCE: 26

Leu Gly Tyr Phe Asp Pro Ser Ile Ala Asp Pro Val Ala
1               5                   10

<210> SEQ ID NO 27
<211> LENGTH: 13
<212> TYPE: PRT
<213> ORGANISM: Artificial Sequence
<220> FEATURE:
<223> OTHER INFORMATION: humanized sequence

<400> SEQUENCE: 27

Leu Gly Tyr Phe Asp Ser Ser Ile Ala Asp Ile Val Ala
1               5                   10

<210> SEQ ID NO 28
<211> LENGTH: 12
<212> TYPE: PRT
<213> ORGANISM: Artificial Sequence
<220> FEATURE:
<223> OTHER INFORMATION: humanized sequence

<400> SEQUENCE: 28

Leu Gly Tyr Phe Asp Pro Ser Ala Asp Pro Ile Ala
1               5                   10

<210> SEQ ID NO 29
<211> LENGTH: 12
<212> TYPE: PRT
<213> ORGANISM: Artificial Sequence
<220> FEATURE:
<223> OTHER INFORMATION: umanized sequence

<400> SEQUENCE: 29

Leu Gly Tyr Phe Asp Pro Ser Ala Asp Pro Val Ala

```
1               5                   10
```

<210> SEQ ID NO 30
<211> LENGTH: 12
<212> TYPE: PRT
<213> ORGANISM: Artificial Sequence
<220> FEATURE:
<223> OTHER INFORMATION: humanized sequence

<400> SEQUENCE: 30

```
Arg Ala Ser Gln Gly Val Arg Thr Asn Lys Leu Ala
1               5                   10
```

<210> SEQ ID NO 31
<211> LENGTH: 12
<212> TYPE: PRT
<213> ORGANISM: Artificial Sequence
<220> FEATURE:
<223> OTHER INFORMATION: humanized sequence

<400> SEQUENCE: 31

```
Arg Ala Ser Gln Ser Val Arg Thr Asn Lys Leu Ala
1               5                   10
```

<210> SEQ ID NO 32
<211> LENGTH: 112
<212> TYPE: PRT
<213> ORGANISM: Artificial Sequence
<220> FEATURE:
<223> OTHER INFORMATION: humanized sequence

<400> SEQUENCE: 32

```
Asp Ile Gln Met Thr Gln Ser Thr Ser Thr Leu Ser Ala Ser Val Gly
1               5                   10                  15

Asp Arg Val Thr Ile Thr Cys Gln Ser Ser Gln Ser Val Arg Thr Asn
                20                  25                  30

Lys Leu Ala Trp Phe Gln Gln Lys Pro Gly Lys Ala Pro Lys Arg Leu
            35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Tyr Phe Asp Cys Ser
                85                  90                  95

Ile Ala Asp Cys Val Ala Phe Gly Gly Gly Thr Lys Val Glu Ile Lys
            100                 105                 110
```

<210> SEQ ID NO 33
<211> LENGTH: 112
<212> TYPE: PRT
<213> ORGANISM: Artificial Sequence
<220> FEATURE:
<223> OTHER INFORMATION: humanized sequence

<400> SEQUENCE: 33

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Arg Thr Asn
                20                  25                  30

Lys Leu Ala Trp Tyr Gln Gln Lys Pro Gly Lys Ala Pro Lys Arg Leu
            35                  40                  45

Ile Tyr Ser Ala Ser Thr Leu Glu Ser Gly Val Pro Ser Arg Phe Ser
```

```
                50                  55                  60
Gly Ser Gly Ser Gly Thr Glu Phe Thr Leu Thr Ile Ser Ser Leu Gln
 65                  70                  75                  80

Pro Asp Asp Phe Ala Thr Tyr Tyr Cys Leu Gly Tyr Phe Asp Cys Ser
                     85                  90                  95

Ile Ala Asp Cys Val Ala Phe Gly Gly Gly Thr Lys Val Glu Ile Lys
                100                 105                 110

<210> SEQ ID NO 34
<211> LENGTH: 112
<212> TYPE: PRT
<213> ORGANISM: Artificial Sequence
<220> FEATURE:
<223> OTHER INFORMATION: humanized sequence

<400> SEQUENCE: 34

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Val Arg Thr Asn
                20                  25                  30

Lys Leu Ala Trp Phe Gln Gln Lys Pro Gly Gln Pro Pro Lys Arg Leu
                35                  40                  45

Ile Tyr Ser Ala Ser Thr Leu Gln Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Glu Asp Phe Ala Thr Tyr Tyr Cys Leu Gly Tyr Phe Asp Cys Ser
                     85                  90                  95

Ile Ala Asp Cys Val Ala Phe Gly Gly Gly Thr Lys Val Glu Ile Lys
                100                 105                 110

<210> SEQ ID NO 35
<211> LENGTH: 112
<212> TYPE: PRT
<213> ORGANISM: Artificial Sequence
<220> FEATURE:
<223> OTHER INFORMATION: humanized sequence

<400> SEQUENCE: 35

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Val Arg Thr Asn
                20                  25                  30

Lys Leu Ala Trp Phe Gln Gln Lys Pro Gly Gln Pro Pro Lys Arg Leu
                35                  40                  45

Ile Tyr Ser Ala Ser Thr Leu Gln Ser Gly Val Pro Ser Arg Phe Ser
 50                  55                  60

Gly Ser Gly Ser Gly Thr Glu Phe Thr Leu Thr Ile Ser Ser Leu Gln
 65                  70                  75                  80

Pro Glu Asp Phe Ala Thr Tyr Tyr Cys Leu Gly Tyr Phe Asp Ser Ser
                     85                  90                  95

Ile Ala Asp Ser Val Ala Phe Gly Gly Gly Thr Lys Val Glu Ile Lys
                100                 105                 110

<210> SEQ ID NO 36
<211> LENGTH: 112
<212> TYPE: PRT
<213> ORGANISM: Artificial Sequence
<220> FEATURE:
```

<223> OTHER INFORMATION: humanized sequence

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Gln Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Arg Val Ala Phe Gly Gly Gly Thr Lys Val Glu Ile Lys
            100                 105                 110
```

<210> SEQ ID NO 37
<211> LENGTH: 112
<212> TYPE: PRT
<213> ORGANISM: Artificial Sequence
<220> FEATURE:
<223> OTHER INFORMATION: humanized sequence

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Cys Ser
                85                  90                  95

Ile Ala Asp Cys Val Ala Phe Gly Gly Gly Thr Lys Val Glu Ile Lys
            100                 105                 110
```

<210> SEQ ID NO 38
<211> LENGTH: 112
<212> TYPE: PRT
<213> ORGANISM: Artificial Sequence
<220> FEATURE:
<223> OTHER INFORMATION: humanized sequence

<400> SEQUENCE: 38

```
Ala Gln Val Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Lys Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
```

```
                65                  70                  75                  80
Pro Glu Asp Phe Ala Thr Tyr Tyr Cys Leu Gly Tyr Phe Asp Cys Ser
                    85                  90                  95

Ile Ala Asp Cys Val Ala Phe Gly Gly Gly Thr Lys Val Glu Ile Lys
                100                 105                 110

<210> SEQ ID NO 39
<211> LENGTH: 111
<212> TYPE: PRT
<213> ORGANISM: Artificial Sequence
<220> FEATURE:
<223> OTHER INFORMATION: humanized sequence

<400> SEQUENCE: 39

Ala Ile Gln Met Thr Gln Ser Pro Ser Thr Leu Ser Ala Ser Val Gly
1               5                   10                  15

Asp Arg Val Thr Ile Thr Cys Arg Ser Ser Gln Ser Val Arg Thr Asn
                20                  25                  30

Arg Leu Ala Trp Phe Gln Gln Lys Pro Gly Lys Ala Pro Lys Arg Leu
            35                  40                  45

Ile Tyr Ser Ala Ser Thr Leu Asp Phe Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Leu Gly Tyr Phe Asp Pro Ser
                85                  90                  95

Ala Asp Pro Val Ala Phe Gly Gly Gly Thr Lys Val Glu Ile Lys
                100                 105                 110

<210> SEQ ID NO 40
<211> LENGTH: 112
<212> TYPE: PRT
<213> ORGANISM: Artificial Sequence
<220> FEATURE:
<223> OTHER INFORMATION: humanized sequence

<400> SEQUENCE: 40

Ala Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
                20                  25                  30

Arg Leu Ala Trp Phe Gln Gln Lys Pro Gly Gln Pro Pro Lys Arg Leu
            35                  40                  45

Ile Tyr Ser Ala Ser Thr Leu Asp Phe Gly Val Pro Ser Arg Phe Ser
50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys
                100                 105                 110

<210> SEQ ID NO 41
<211> LENGTH: 112
<212> TYPE: PRT
<213> ORGANISM: Artificial Sequence
<220> FEATURE:
<223> OTHER INFORMATION: humanized sequence

<400> SEQUENCE: 41
```

```
Ala Ile Gln Met Thr Gln Ser Thr Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Ser Ser
                85                  90                  95

Ile Ala Asp Ile Val Ala Phe Gly Gly Gly Thr Lys Val Glu Ile Lys
            100                 105                 110
```

<210> SEQ ID NO 42
<211> LENGTH: 112
<212> TYPE: PRT
<213> ORGANISM: Artificial Sequence
<220> FEATURE:
<223> OTHER INFORMATION: humanized sequence

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Pro Ser
                85                  90                  95

Ile Ala Asp Pro Val Ala Phe Gly Gly Gly Thr Lys Val Glu Ile Lys
            100                 105                 110
```

<210> SEQ ID NO 43
<211> LENGTH: 111
<212> TYPE: PRT
<213> ORGANISM: Artificial Sequence
<220> FEATURE:
<223> OTHER INFORMATION: humanized sequence

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Val Arg Thr Asn
            20                  25                  30

Arg Leu Ala Trp Phe Gln Gln Lys Pro Gly Gln Pro Pro Lys Arg Leu
        35                  40                  45

Ile Tyr Ser Ala Ser Thr Leu Asp Phe Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Pro Ser
```

```
                    85                  90                  95

Ala Asp Pro Val Ala Phe Gly Gly Gly Thr Lys Val Glu Ile Lys
                100                 105                 110

<210> SEQ ID NO 44
<211> LENGTH: 111
<212> TYPE: PRT
<213> ORGANISM: Artificial Sequence
<220> FEATURE:
<223> OTHER INFORMATION: humanized sequence

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Val Arg Thr Asn
                20                  25                  30

Arg Leu Ala Trp Phe Gln Gln Lys Pro Gly Gln Pro Pro Lys Arg Leu
            35                  40                  45

Ile Tyr Ser Ala Ser Thr Leu Asp Phe Gly Val Pro Ser Arg Phe Ser
        50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Pro Ser
                85                  90                  95

Ala Asp Pro Ile Ala Phe Gly Gly Gly Thr Lys Val Glu Ile Lys
                100                 105                 110

<210> SEQ ID NO 45
<211> LENGTH: 111
<212> TYPE: PRT
<213> ORGANISM: Artificial Sequence
<220> FEATURE:
<223> OTHER INFORMATION: humanized sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ser Gln Ser Val Arg Thr Asn
                20                  25                  30

Arg Leu Ala Trp Phe Gln Gln Lys Pro Gly Lys Ala Pro Lys Arg Leu
            35                  40                  45

Ile Tyr Ser Ala Ser Thr Leu Asp Phe Gly Val Pro Ser Arg Phe Ser
        50                  55                  60

Gly Ser Gly Ser Gly Thr Glu Phe Thr Leu Thr Ile Ser Ser Leu Gln
65                  70                  75                  80

Pro Glu Asp Phe Ala Thr Tyr Tyr Cys Leu Gly Tyr Phe Asp Pro Ser
                85                  90                  95

Ala Asp Pro Ile Ala Phe Gly Gly Gly Thr Lys Val Glu Ile Lys
                100                 105                 110

<210> SEQ ID NO 46
<211> LENGTH: 110
<212> TYPE: PRT
<213> ORGANISM: Artificial Sequence
<220> FEATURE:
<223> OTHER INFORMATION: humanized sequence

<400> SEQUENCE: 46

Gln Gln Leu Val Glu Ser Gly Gly Gly Leu Val Gln Pro Gly Gly Ser
1               5                   10                  15
```

```
Leu Arg Leu Ser Cys Ala Ala Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Gln Gly Thr Leu Val Thr Val Ser Ser
                100                 105                 110

<210> SEQ ID NO 47
<211> LENGTH: 110
<212> TYPE: PRT
<213> ORGANISM: Artificial Sequence
<220> FEATURE:
<223> OTHER INFORMATION: humanized sequence

<400> SEQUENCE: 47

Gln Ser Val Leu Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Pro Gly Thr Leu Val Thr Val Ser Ser
                100                 105                 110

<210> SEQ ID NO 48
<211> LENGTH: 110
<212> TYPE: PRT
<213> ORGANISM: Artificial Sequence
<220> FEATURE:
<223> OTHER INFORMATION: humanized sequence

<400> SEQUENCE: 48

Gln Ser Val Leu Glu Ser Gly Gly Gly Leu Val Gln Pro Gly Gly Ser
1               5                   10                  15

Leu Arg Leu Ser Cys Ala Val Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Pro Gly Thr Leu Val Thr Val Ser Ser
```

<210> SEQ ID NO 49
<211> LENGTH: 108
<212> TYPE: PRT
<213> ORGANISM: Artificial Sequence
<220> FEATURE:
<223> OTHER INFORMATION: humanized sequence

<400> SEQUENCE: 49

Gln Ser Val Leu Glu Ser Gly Gly Gly Leu Val Gln Pro Gly Gly Ser
1               5                   10                  15

Leu Arg Leu Ser Cys Ala Val Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
    50                  55                  60

Arg Phe Thr Ile Ser Arg Asp Ser Thr Thr Leu Tyr Leu Gln Met Asn
65                  70                  75                  80

Ser Leu Arg Ala Glu Asp Thr Ala Val Tyr Tyr Cys Gly Lys Ser Asn
                85                  90                  95

Ile Trp Gly Pro Gly Thr Leu Val Thr Val Ser Ser
            100                 105

<210> SEQ ID NO 50
<211> LENGTH: 110
<212> TYPE: PRT
<213> ORGANISM: Artificial Sequence
<220> FEATURE:
<223> OTHER INFORMATION: humanized sequence

<400> SEQUENCE: 50

Gln Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Pro Gly Thr Leu Val Thr Val Ser Ser
            100                 105                 110

<210> SEQ ID NO 51
<211> LENGTH: 110
<212> TYPE: PRT
<213> ORGANISM: Artificial Sequence
<220> FEATURE:
<223> OTHER INFORMATION: humanized sequence

<400> SEQUENCE: 51

Gln Ser Val Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
            20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Ser Trp Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Pro Gly Thr Leu Val Thr Val Ser Ser
            100                 105                 110

<210> SEQ ID NO 52
<211> LENGTH: 110
<212> TYPE: PRT
<213> ORGANISM: Artificial Sequence
<220> FEATURE:
<223> OTHER INFORMATION: humanized sequence

<400> SEQUENCE: 52

Gln Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
                20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Gln Gly Thr Leu Val Thr Val Ser Ser
            100                 105                 110

<210> SEQ ID NO 53
<211> LENGTH: 110
<212> TYPE: PRT
<213> ORGANISM: Artificial Sequence
<220> FEATURE:
<223> OTHER INFORMATION: humanized sequence

<400> SEQUENCE: 53

Gln Gln Leu Val Glu Ser Gly Gly Gly Leu Val Gln Pro Gly Gly Ser
1               5                   10                  15

Leu Arg Leu Ser Cys Ala Ala Ser Gly Phe Ser Leu Ser Ser Asn Ala
                20                  25                  30

Ile Asn Trp Val Arg Gln Ala Pro Gly Lys Gly Leu Glu Trp Val Gly
        35                  40                  45

Tyr Ile Ala Val Ser Gly Asn Thr Tyr Tyr Ala Asp Ser Val Lys Gly
    50                  55                  60

Arg Phe Thr Ile Ser Lys Asp Asn Ser Lys Asn Thr Leu Tyr Leu Gln
65                  70                  75                  80

Met Asn Ser Leu Arg Ala Glu Asp Thr Ala Val Tyr Tyr Cys Gly Lys
                85                  90                  95

Ser Asn Ile Trp Gly Gln Gly Thr Leu Val Thr Val Ser Ser
            100                 105                 110

<210> SEQ ID NO 54
<211> LENGTH: 111
<212> TYPE: PRT
<213> ORGANISM: Artificial Sequence
<220> FEATURE:
<223> OTHER INFORMATION: humanized sequence

<400> SEQUENCE: 54

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110
```

<210> SEQ ID NO 55
<211> LENGTH: 111
<212> TYPE: PRT
<213> ORGANISM: Artificial Sequence
<220> FEATURE:
<223> OTHER INFORMATION: humanized sequence

<400> SEQUENCE: 55

```
Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Ser Asn
            20                  25                  30

Ala Ile Asn Trp Val Arg Gln Ala Pro Gly Lys Gly Leu Glu Trp Val
        35                  40                  45

Gly Tyr Ile Ala Val Ser Gly Asn Thr Tyr Tyr Ala Asp Ser Val Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
            100                 105                 110
```

<210> SEQ ID NO 56
<211> LENGTH: 111
<212> TYPE: PRT
<213> ORGANISM: Artificial Sequence
<220> FEATURE:
<223> OTHER INFORMATION: humanized sequence

<400> SEQUENCE: 56

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Ser Ser Asn
            20                  25                  30

Ala Ile Asn Trp Val Arg Gln Ala Pro Gly Lys Gly Leu Glu Trp Val
        35                  40                  45
```

```
Gly Tyr Ile Ala Val Ser Gly Asn Thr Tyr Tyr Ala Asp Ser Val Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
                100                 105                 110

<210> SEQ ID NO 57
<211> LENGTH: 111
<212> TYPE: PRT
<213> ORGANISM: Artificial Sequence
<220> FEATURE:
<223> OTHER INFORMATION: humanized sequence

<400> SEQUENCE: 57

Glu Val Gln Val Leu Glu Ser Gly Gly Gly Leu Val Gln Pro Gly Gly
1               5                   10                  15

Ser Leu Arg Leu Ser Cys Ala Val Ser Gly Phe Ser Leu Ser Ser Asn
                20                  25                  30

Ala Ile Asn Trp Val Arg Gln Ala Pro Gly Lys Gly Leu Glu Trp Val
            35                  40                  45

Gly Tyr Ile Ala Val Ser Gly Asn Thr Tyr Tyr Ala Ser Trp Ala Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Gly
                85                  90                  95

Lys Ser Asn Ile Trp Gly Gln Gly Thr Leu Val Thr Val Ser Ser
                100                 105                 110

<210> SEQ ID NO 58
<211> LENGTH: 330
<212> TYPE: PRT
<213> ORGANISM: Homo sapiens

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 59
<211> LENGTH: 107
<212> TYPE: PRT
<213> ORGANISM: Homo sapiens

<400> SEQUENCE: 59

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 60
<211> LENGTH: 106
<212> TYPE: PRT
<213> ORGANISM: Homo sapiens

<400> SEQUENCE: 60

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

-continued

```
Phe Tyr Pro Gly Ala Val Thr Val Ala Trp Lys Ala Asp Ser Ser Pro
                35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 61
<211> LENGTH: 37
<212> TYPE: DNA
<213> ORGANISM: Artificial Sequence
<220> FEATURE:
<223> OTHER INFORMATION: rbHCfinal.up

<400> SEQUENCE: 61
aagcttgcca ccatggagac tgggctgcgc tggcttc         37

<210> SEQ ID NO 62
<211> LENGTH: 21
<212> TYPE: DNA
<213> ORGANISM: Artificial Sequence
<220> FEATURE:
<223> OTHER INFORMATION: rbHCfinal.do

<400> SEQUENCE: 62
ccattggtga gggtgcccga g         21

<210> SEQ ID NO 63
<211> LENGTH: 34
<212> TYPE: DNA
<213> ORGANISM: Artificial Sequence
<220> FEATURE:
<223> OTHER INFORMATION: rbLCfinal.up

<400> SEQUENCE: 63
aagcttgcca ccatggacay gagggccccc actc         34

<210> SEQ ID NO 64
<211> LENGTH: 26
<212> TYPE: DNA
<213> ORGANISM: Artificial Sequence
<220> FEATURE:
<223> OTHER INFORMATION: rbLCfinal.do

<400> SEQUENCE: 64
cagagtrctg ctgaggttgt aggtac         26

<210> SEQ ID NO 65
<211> LENGTH: 5
<212> TYPE: PRT
<213> ORGANISM: Mus musculus

<400> SEQUENCE: 65

Asp Tyr Ala Met Ser
 1               5

<210> SEQ ID NO 66
<211> LENGTH: 17
<212> TYPE: PRT
<213> ORGANISM: Mus musculus

```
<400> SEQUENCE: 66

Ser Ile Asn Ile Gly Ala Thr Tyr Ala Tyr Tyr Pro Asp Ser Val Lys
1               5                   10                  15

Gly

<210> SEQ ID NO 67
<211> LENGTH: 16
<212> TYPE: PRT
<213> ORGANISM: Mus musculus

<400> SEQUENCE: 67

Pro Gly Ser Pro Tyr Glu Tyr Asp Lys Ala Tyr Tyr Ser Met Ala Tyr
1               5                   10                  15

<210> SEQ ID NO 68
<211> LENGTH: 125
<212> TYPE: PRT
<213> ORGANISM: Mus musculus

<400> SEQUENCE: 68

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asp Tyr
                20                  25                  30

Ala Met Ser Trp Ile Arg Gln Thr Pro Glu Asn Arg Leu Glu Trp Val
            35                  40                  45

Ala Ser Ile Asn Ile Gly Ala Thr Tyr Ala Tyr Tyr Pro Asp Ser Val
        50                  55                  60

Lys Gly Arg Phe Thr Ile Ser Arg Asp Asn Ala Lys Asn Thr Leu Phe
65                  70                  75                  80

Leu Gln Met Ser Ser Leu Gly Ser Glu Asp Thr Ala Met Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Pro Gly Thr Ser Val Thr Val Ser Ser
        115                 120                 125

<210> SEQ ID NO 69
<211> LENGTH: 11
<212> TYPE: PRT
<213> ORGANISM: Mus musculus

<400> SEQUENCE: 69

Arg Ala Ser Gly Asn Ile His Asn Tyr Leu Ser
1               5                   10

<210> SEQ ID NO 70
<211> LENGTH: 7
<212> TYPE: PRT
<213> ORGANISM: Mus musculus

<400> SEQUENCE: 70

Ser Ala Lys Thr Leu Ala Asp
1               5

<210> SEQ ID NO 71
<211> LENGTH: 9
<212> TYPE: PRT
<213> ORGANISM: Mus musculus
```

<400> SEQUENCE: 71

Gln His Phe Trp Ser Ser Ile Tyr Thr
1               5

<210> SEQ ID NO 72
<211> LENGTH: 107
<212> TYPE: PRT
<213> ORGANISM: Mus musculus

<400> SEQUENCE: 72

Asp Val Gln Met Thr Gln Ser Thr Ser Ser Leu Ser Ala Ser Leu Gly
1               5                   10                  15

Asp Arg Val Thr Ile Ser Cys Arg Ala Ser Gln Asp Ile Lys Asn Tyr
            20                  25                  30

Leu Asn Trp Tyr Gln Gln Lys Pro Gly Gly Thr Val Lys Leu Leu Ile
        35                  40                  45

Tyr Tyr Ser Ser Thr Leu Leu Ser Gly Val Pro Ser Arg Phe Ser Gly
50                  55                  60

Arg Gly Ser Gly Thr Asp Phe Ser Leu Thr Ile Thr Asn Leu Glu Arg
65                  70                  75                  80

Glu Asp Ile Ala Thr Tyr Phe Cys Gln Gln Ser Ile Thr Leu Pro Pro
                85                  90                  95

Thr Phe Gly Gly Gly Thr Lys Leu Glu Ile Lys
            100                 105

<210> SEQ ID NO 73
<211> LENGTH: 5
<212> TYPE: PRT
<213> ORGANISM: Artificial Sequence
<220> FEATURE:
<223> OTHER INFORMATION: humanized anti-digoxigenin antibody HVR-H1

<400> SEQUENCE: 73

Asp Tyr Ala Met Ser
1               5

<210> SEQ ID NO 74
<211> LENGTH: 17
<212> TYPE: PRT
<213> ORGANISM: Artificial Sequence
<220> FEATURE:
<223> OTHER INFORMATION: humanized anti-digoxigenin antibody HVR-H2

<400> SEQUENCE: 74

Ser Ile Asn Ile Gly Ala Thr Tyr Ile Tyr Tyr Ala Asp Ser Val Lys
1               5                   10                  15

Gly

<210> SEQ ID NO 75
<211> LENGTH: 16
<212> TYPE: PRT
<213> ORGANISM: Artificial Sequence
<220> FEATURE:
<223> OTHER INFORMATION: humanized anti-digoxigenin antibody HVR-H3

<400> SEQUENCE: 75

Pro Gly Ser Pro Tyr Glu Tyr Asp Lys Ala Tyr Tyr Ser Met Ala Tyr
1               5                   10                  15

<210> SEQ ID NO 76
<211> LENGTH: 125
<212> TYPE: PRT

<210> SEQ ID NO 76
<211> LENGTH: 125
<212> TYPE: PRT
<213> ORGANISM: Artificial Sequence
<220> FEATURE:
<223> OTHER INFORMATION: humanized anti-digoxigenin antibody VH

<400> SEQUENCE: 76

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Ile Arg Gln Ala Pro Gly Lys Gly Leu Glu Trp Val
        35                  40                  45

Ser Ser Ile Asn Ile Gly Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Gly Ser Pro Tyr Glu Tyr Asp Lys Ala Tyr Tyr Ser Met
            100                 105                 110

Ala Tyr Trp Gly Gln Gly Thr Thr Val Thr Val Ser Ser
        115                 120                 125
```

<210> SEQ ID NO 77
<211> LENGTH: 11
<212> TYPE: PRT
<213> ORGANISM: Artificial Sequence
<220> FEATURE:
<223> OTHER INFORMATION: humanized anti-digoxigenin antibody HVR-L1

<400> SEQUENCE: 77

```
Arg Ala Ser Gln Asp Ile Lys Asn Tyr Leu Asn
1               5                   10
```

<210> SEQ ID NO 78
<211> LENGTH: 7
<212> TYPE: PRT
<213> ORGANISM: Artificial Sequence
<220> FEATURE:
<223> OTHER INFORMATION: humanized anti-digoxigenin antibody HVR-L2

<400> SEQUENCE: 78

```
Tyr Ser Ser Thr Leu Leu Ser
1               5
```

<210> SEQ ID NO 79
<211> LENGTH: 9
<212> TYPE: PRT
<213> ORGANISM: Artificial Sequence
<220> FEATURE:
<223> OTHER INFORMATION: humanized anti-digoxigenin antibody HVR-L3

<400> SEQUENCE: 79

```
Gln Gln Ser Ile Thr Leu Pro Pro Thr
1               5
```

<210> SEQ ID NO 80
<211> LENGTH: 108
<212> TYPE: PRT
<213> ORGANISM: Artificial Sequence
<220> FEATURE:
<223> OTHER INFORMATION: humanized anti-digoxigenin antibody VL

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Lys Asn Tyr
            20                  25                  30

Leu Asn Trp Tyr Gln Gln Lys Pro Gly Lys Ala Pro Lys Leu Leu Ile
        35                  40                  45

Tyr Tyr Ser Ser Thr Leu Leu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ile Thr Leu Pro Pro
                85                  90                  95

Thr Phe Gly Gly Gly Thr Lys Val Glu Ile Lys Arg
            100                 105

<210> SEQ ID NO 81
<211> LENGTH: 5
<212> TYPE: PRT
<213> ORGANISM: Mus musculus

<400> SEQUENCE: 81

Asp Thr Phe Phe Gln
1               5

<210> SEQ ID NO 82
<211> LENGTH: 17
<212> TYPE: PRT
<213> ORGANISM: Mus musculus

<400> SEQUENCE: 82

Arg Ile Asp Pro Ala Asn Gly Phe Thr Lys Tyr Asp Pro Lys Phe Gln
1               5                   10                  15

Gly

<210> SEQ ID NO 83
<211> LENGTH: 11
<212> TYPE: PRT
<213> ORGANISM: Mus musculus

<400> SEQUENCE: 83

Trp Asp Thr Tyr Gly Ala Ala Trp Phe Ala Tyr
1               5                   10

<210> SEQ ID NO 84
<211> LENGTH: 120
<212> TYPE: PRT
<213> ORGANISM: Mus musculus

<400> SEQUENCE: 84

Glu Val Gln Leu Gln Gln Ser Gly Ala Glu Leu Val Lys Pro Gly Ala
1               5                   10                  15

Ser Val Lys Leu Ser Cys Thr Ser Ser Gly Phe Asn Asn Lys Asp Thr
            20                  25                  30

Phe Phe Gln Trp Val Lys Gln Arg Pro Glu Glu Cys Leu Glu Trp Ile
        35                  40                  45

Gly Arg Ile Asp Pro Ala Asn Gly Phe Thr Lys Tyr Asp Pro Lys Phe
    50                  55                  60

Gln Gly Lys Ala Thr Ile Thr Val Asp Thr Ser Ser Asn Thr Ala Tyr
65                  70                  75                  80

```
Leu Gln Leu Asn Ser Leu Thr Ser Glu Asp Thr Ala Leu Tyr Tyr Cys
                85                  90                  95

Thr Arg Trp Asp Thr Tyr Gly Ala Ala Trp Phe Ala Tyr Trp Gly Gln
            100                 105                 110

Gly Thr Leu Val Thr Val Ser Ala
        115                 120

<210> SEQ ID NO 85
<211> LENGTH: 11
<212> TYPE: PRT
<213> ORGANISM: Mus musculus

<400> SEQUENCE: 85

Arg Ala Ser Gly Asn Ile His Asn Tyr Leu Ser
1               5                   10

<210> SEQ ID NO 86
<211> LENGTH: 7
<212> TYPE: PRT
<213> ORGANISM: Mus musculus

<400> SEQUENCE: 86

Ser Ala Lys Thr Leu Ala Asp
1               5

<210> SEQ ID NO 87
<211> LENGTH: 9
<212> TYPE: PRT
<213> ORGANISM: Mus musculus

<400> SEQUENCE: 87

Gln His Phe Trp Ser Ser Ile Tyr Thr
1               5

<210> SEQ ID NO 88
<211> LENGTH: 107
<212> TYPE: PRT
<213> ORGANISM: Mus musculus

<400> SEQUENCE: 88

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ser Trp Phe Gln Gln Lys Gln Gly Lys Ser Pro Gln Leu Leu Val
        35                  40                  45

Tyr Ser Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Ser Ile Tyr
                85                  90                  95

Thr Phe Gly Cys Gly Thr Lys Leu Glu Ile Lys
            100                 105

<210> SEQ ID NO 89
<211> LENGTH: 5
<212> TYPE: PRT
<213> ORGANISM: Artificial Sequence
<220> FEATURE:
<223> OTHER INFORMATION: humanized anti-biotin antibody HVR-H1
```

```
<400> SEQUENCE: 89

Asp Thr Phe Phe Gln
1               5

<210> SEQ ID NO 90
<211> LENGTH: 17
<212> TYPE: PRT
<213> ORGANISM: Artificial Sequence
<220> FEATURE:
<223> OTHER INFORMATION: humanized anti-biotin antibody HVR-H2

<400> SEQUENCE: 90

Arg Ile Asp Pro Ala Asn Gly Phe Thr Lys Tyr Ala Gln Lys Phe Gln
1               5                   10                  15

Gly

<210> SEQ ID NO 91
<211> LENGTH: 11
<212> TYPE: PRT
<213> ORGANISM: Artificial Sequence
<220> FEATURE:
<223> OTHER INFORMATION: humanized anti-biotin antibody HVR-H3

<400> SEQUENCE: 91

Trp Asp Thr Tyr Gly Ala Ala Trp Phe Ala Tyr
1               5                   10

<210> SEQ ID NO 92
<211> LENGTH: 120
<212> TYPE: PRT
<213> ORGANISM: Artificial Sequence
<220> FEATURE:
<223> OTHER INFORMATION: humanized anti-biotin antibody VH

<400> SEQUENCE: 92

Gln Val Gln Leu Val Gln Ser Gly Ala Glu Val Lys Lys Pro Gly Ser
1               5                   10                  15

Ser Val Lys Val Ser Cys Lys Ser Ser Gly Phe Asn Asn Lys Asp Thr
                20                  25                  30

Phe Phe Gln Trp Val Arg Gln Ala Pro Gly Gln Gly Leu Glu Trp Met
            35                  40                  45

Gly Arg Ile Asp Pro Ala Asn Gly Phe Thr Lys Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Trp Asp Thr Tyr Gly Ala Ala Trp Phe Ala Tyr Trp Gly Gln
            100                 105                 110

Gly Thr Leu Val Thr Val Ser Ser
        115                 120

<210> SEQ ID NO 93
<211> LENGTH: 11
<212> TYPE: PRT
<213> ORGANISM: Artificial Sequence
<220> FEATURE:
<223> OTHER INFORMATION: humanized anti-biotin antibody HVR-L1

<400> SEQUENCE: 93

Arg Ala Ser Gly Asn Ile His Asn Tyr Leu Ser
1               5                   10
```

```
<210> SEQ ID NO 94
<211> LENGTH: 7
<212> TYPE: PRT
<213> ORGANISM: Artificial Sequence
<220> FEATURE:
<223> OTHER INFORMATION: humanized anti-biotin antibody HVR-L2

<400> SEQUENCE: 94

Ser Ala Lys Thr Leu Ala Asp
1               5

<210> SEQ ID NO 95
<211> LENGTH: 9
<212> TYPE: PRT
<213> ORGANISM: Artificial Sequence
<220> FEATURE:
<223> OTHER INFORMATION: humanized anti-biotin antibody HVR-L3

<400> SEQUENCE: 95

Gln His Phe Trp Ser Ser Ile Tyr Thr
1               5

<210> SEQ ID NO 96
<211> LENGTH: 107
<212> TYPE: PRT
<213> ORGANISM: Artificial Sequence
<220> FEATURE:
<223> OTHER INFORMATION: humanized anti-biotin antibody VL

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ser Trp Tyr Gln Gln Lys Pro Gly Lys Val Pro Lys Leu Leu Ile
        35                  40                  45

Tyr Ser Ala Lys Thr Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Phe Trp Ser Ser Ile Tyr
                85                  90                  95

Thr Phe Gly Gln Gly Thr Lys Leu Glu Ile Lys
            100                 105

<210> SEQ ID NO 97
<211> LENGTH: 6
<212> TYPE: PRT
<213> ORGANISM: Mus musculus

<400> SEQUENCE: 97

Ser Asp Tyr Ala Trp Asn
1               5

<210> SEQ ID NO 98
<211> LENGTH: 16
<212> TYPE: PRT
<213> ORGANISM: Mus musculus

<400> SEQUENCE: 98

Tyr Ile Arg Tyr Ser Gly His Thr Gly Tyr Asn Pro Ser Leu Lys Ser
1               5                   10                  15
```

```
<210> SEQ ID NO 99
<211> LENGTH: 7
<212> TYPE: PRT
<213> ORGANISM: Mus musculus

<400> SEQUENCE: 99

Trp Val Asp Tyr Phe Asp Tyr
1               5

<210> SEQ ID NO 100
<211> LENGTH: 116
<212> TYPE: PRT
<213> ORGANISM: Mus musculus

<400> SEQUENCE: 100

Asp Val Gln Leu Gln Glu Ser Gly Pro Gly Leu Val Lys Pro Ser Gln
1               5                   10                  15

Ser Leu Ser Leu Thr Cys Ala Val Thr Gly Tyr Ser Ile Thr Ser Asp
            20                  25                  30

Tyr Ala Trp Asn Trp Ile Arg Gln Phe Pro Gly Asn Arg Leu Glu Trp
        35                  40                  45

Met Gly Tyr Ile Arg Tyr Ser Gly His Thr Gly Tyr Asn Pro Ser Leu
    50                  55                  60

Lys Ser Arg Ile Ser Ile Thr Arg Asp Thr Phe Lys Asn Gln Phe Phe
65                  70                  75                  80

Leu Gln Phe Asn Ser Val Thr Thr Glu Asp Thr Ala Thr Tyr Tyr Cys
                85                  90                  95

Ala Arg Trp Val Asp Tyr Phe Asp Tyr Trp Gly Gln Gly Thr Thr Leu
            100                 105                 110

Thr Val Ser Ser
        115

<210> SEQ ID NO 101
<211> LENGTH: 16
<212> TYPE: PRT
<213> ORGANISM: Mus musculus

<400> SEQUENCE: 101

Arg Ser Ser Gln Ser Ile Val Tyr Asn Asn Arg Tyr Thr Tyr Leu Glu
1               5                   10                  15

<210> SEQ ID NO 102
<211> LENGTH: 7
<212> TYPE: PRT
<213> ORGANISM: Mus musculus

<400> SEQUENCE: 102

Gly Val Ser Asn Arg Phe Ser
1               5

<210> SEQ ID NO 103
<211> LENGTH: 9
<212> TYPE: PRT
<213> ORGANISM: Mus musculus

<400> SEQUENCE: 103

Tyr Gln Gly Thr His Ala Pro Tyr Thr
1               5

<210> SEQ ID NO 104
```

```
<211> LENGTH: 112
<212> TYPE: PRT
<213> ORGANISM: Mus musculus

<400> SEQUENCE: 104

Asp Val Val Met Thr Gln Ser Pro Leu Ser Leu Pro Val Ser Leu Gly
1               5                   10                  15

Asp Gln Ala Ser Ile Ser Cys Arg Ser Gln Ser Ile Val Tyr Asn
            20                  25                  30

Asn Arg Tyr Thr Tyr Leu Glu Trp Phe Val Gln Lys Pro Gly Gln Ser
            35                  40                  45

Leu Lys Leu Leu Ile Tyr Gly Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Met Gly Val Tyr Tyr Cys Tyr Gln Gly
                85                  90                  95

Thr His Ala Pro Tyr Thr Phe Gly Gly Gly Thr Lys Leu Glu Ile Lys
            100                 105                 110

<210> SEQ ID NO 105
<211> LENGTH: 6
<212> TYPE: PRT
<213> ORGANISM: Artificial Sequence
<220> FEATURE:
<223> OTHER INFORMATION: humanized anti-theophylline antibody HVR-H1

<400> SEQUENCE: 105

Ser Asp Tyr Ala Trp Asn
1               5

<210> SEQ ID NO 106
<211> LENGTH: 16
<212> TYPE: PRT
<213> ORGANISM: Artificial Sequence
<220> FEATURE:
<223> OTHER INFORMATION: humanized anti-theophylline antibody HVR-H2

<400> SEQUENCE: 106

Tyr Ile Arg Tyr Ser Gly His Thr Gly Tyr Asn Pro Ser Leu Lys Ser
1               5                   10                  15

<210> SEQ ID NO 107
<211> LENGTH: 7
<212> TYPE: PRT
<213> ORGANISM: Artificial Sequence
<220> FEATURE:
<223> OTHER INFORMATION: humanized anti-theophylline antibody HVR-H3

<400> SEQUENCE: 107

Trp Val Asp Tyr Phe Asp Tyr
1               5

<210> SEQ ID NO 108
<211> LENGTH: 116
<212> TYPE: PRT
<213> ORGANISM: Artificial Sequence
<220> FEATURE:
<223> OTHER INFORMATION: humanized anti-theophylline antibody VH

<400> SEQUENCE: 108

Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Tyr Ser Ile Thr Ser Asp
        20                  25                  30

Tyr Ala Trp Asn Trp Ile Arg Gln His Pro Gly Lys Gly Leu Glu Trp
            35                  40                  45

Ile Gly Tyr Ile Arg Tyr Ser Gly His Thr Gly Tyr Asn Pro Ser Leu
50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Trp Val Asp Tyr Phe Asp Tyr Trp Gly Gln Gly Thr Leu Val
            100                 105                 110

Thr Val Ser Ser
        115

<210> SEQ ID NO 109
<211> LENGTH: 16
<212> TYPE: PRT
<213> ORGANISM: Artificial Sequence
<220> FEATURE:
<223> OTHER INFORMATION: humanized anti-theophylline antibody HVR-L1

<400> SEQUENCE: 109

Arg Ser Ser Gln Ser Ile Val Tyr Asn Asn Arg Tyr Thr Tyr Leu Glu
1               5                   10                  15

<210> SEQ ID NO 110
<211> LENGTH: 7
<212> TYPE: PRT
<213> ORGANISM: Artificial Sequence
<220> FEATURE:
<223> OTHER INFORMATION: humanized anti-theophylline antibody HVR-L2

<400> SEQUENCE: 110

Gly Val Ser Asn Arg Phe Ser
1               5

<210> SEQ ID NO 111
<211> LENGTH: 9
<212> TYPE: PRT
<213> ORGANISM: Artificial Sequence
<220> FEATURE:
<223> OTHER INFORMATION: humanized anti-theophylline antibody HVR-L3

<400> SEQUENCE: 111

Tyr Gln Gly Thr His Ala Pro Tyr Thr
1               5

<210> SEQ ID NO 112
<211> LENGTH: 112
<212> TYPE: PRT
<213> ORGANISM: Artificial Sequence
<220> FEATURE:
<223> OTHER INFORMATION: humanized anti-theophylline antibody VL

<400> SEQUENCE: 112

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val Tyr Asn
            20                  25                  30

Asn Arg Tyr Thr Tyr Leu Glu Trp Phe Gln Gln Arg Pro Gly Gln Ser
        35                  40                  45
```

```
Pro Arg Leu Leu Ile Tyr Gly Val Ser Asn Arg Phe Ser Gly Val Pro
 50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Tyr Gln Gly
                 85                  90                  95
Thr His Ala Pro Tyr Thr Phe Gly Gln Gly Thr Lys Leu Glu Ile Lys
            100                 105                 110
```

<210> SEQ ID NO 113
<211> LENGTH: 5
<212> TYPE: PRT
<213> ORGANISM: Mus musculus

<400> SEQUENCE: 113

```
His Tyr Trp Met Asn
 1               5
```

<210> SEQ ID NO 114
<211> LENGTH: 19
<212> TYPE: PRT
<213> ORGANISM: Mus musculus

<400> SEQUENCE: 114

```
Gln Phe Arg Asn Lys Pro Tyr Asn Tyr Glu Thr Tyr Tyr Ser Asp Ser
 1               5                  10                  15
Val Lys Gly
```

<210> SEQ ID NO 115
<211> LENGTH: 7
<212> TYPE: PRT
<213> ORGANISM: Mus musculus

<400> SEQUENCE: 115

```
Ala Ser Tyr Gly Met Glu Tyr
 1               5
```

<210> SEQ ID NO 116
<211> LENGTH: 118
<212> TYPE: PRT
<213> ORGANISM: Mus musculus

<400> SEQUENCE: 116

```
Gly Val Lys Leu Asp Glu Thr Gly Gly Gly Leu Val Gln Pro Gly Gly
 1               5                  10                  15
Ala Met Lys Leu Ser Cys Val Thr Ser Gly Phe Thr Phe Gly His Tyr
                20                  25                  30
Trp Met Asn Trp Val Arg Gln Ser Pro Glu Lys Gly Leu Glu Trp Val
            35                  40                  45
Ala Gln Phe Arg Asn Lys Pro Tyr Asn Tyr Glu Thr Tyr Tyr Ser Asp
 50                  55                  60
Ser Val Lys Gly Arg Phe Thr Ile Ser Arg Asp Asp Ser Lys Ser Ser
 65                  70                  75                  80
Val Tyr Leu Gln Met Asn Asn Leu Arg Val Glu Asp Thr Gly Ile Tyr
                 85                  90                  95
Tyr Cys Thr Gly Ala Ser Tyr Gly Met Glu Tyr Leu Gly Gln Gly Thr
            100                 105                 110
Ser Val Thr Val Ser Ser
            115
```

-continued

```
<210> SEQ ID NO 117
<211> LENGTH: 16
<212> TYPE: PRT
<213> ORGANISM: Mus musculus

<400> SEQUENCE: 117

Arg Ser Ser Gln Ser Leu Val His Ser Asn Gly Asn Thr Tyr Leu Arg
1               5                   10                  15

<210> SEQ ID NO 118
<211> LENGTH: 7
<212> TYPE: PRT
<213> ORGANISM: Mus musculus

<400> SEQUENCE: 118

Lys Val Ser Asn Arg Val Ser
1               5

<210> SEQ ID NO 119
<211> LENGTH: 9
<212> TYPE: PRT
<213> ORGANISM: Mus musculus

<400> SEQUENCE: 119

Ser Gln Ser Thr His Val Pro Trp Thr
1               5

<210> SEQ ID NO 120
<211> LENGTH: 120
<212> TYPE: PRT
<213> ORGANISM: Mus musculus

<400> SEQUENCE: 120

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Arg Trp Tyr Leu Gln Lys Pro Gly Gln Ser
        35                  40                  45

Pro Lys Val Leu Ile Tyr Lys Val Ser Asn Arg Val Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

Arg Thr Val Ala Ala Pro Ser Val
        115                 120

<210> SEQ ID NO 121
<211> LENGTH: 5
<212> TYPE: PRT
<213> ORGANISM: Mus musculus

<400> SEQUENCE: 121

Glu Tyr Pro Ile His
1               5

<210> SEQ ID NO 122
<211> LENGTH: 10
```

```
<212> TYPE: PRT
<213> ORGANISM: Mus musculus

<400> SEQUENCE: 122

Gly Tyr Thr Phe Pro Glu Tyr Pro Ile His
1               5                   10

<210> SEQ ID NO 123
<211> LENGTH: 17
<212> TYPE: PRT
<213> ORGANISM: Artificial Sequence
<220> FEATURE:
<223> OTHER INFORMATION: humanized CDR-H2

<400> SEQUENCE: 123

Gly Ile Val Pro Asn Asn Gly Phe Thr Phe Tyr Ala Gln Lys Leu Gln
1               5                   10                  15

Gly

<210> SEQ ID NO 124
<211> LENGTH: 6
<212> TYPE: PRT
<213> ORGANISM: Mus musculus

<400> SEQUENCE: 124

Val Pro Asn Asn Gly Phe
1               5

<210> SEQ ID NO 125
<211> LENGTH: 10
<212> TYPE: PRT
<213> ORGANISM: Mus musculus

<400> SEQUENCE: 125

Lys Asn Leu Gly Ser Ser Pro Leu Asp Tyr
1               5                   10

<210> SEQ ID NO 126
<211> LENGTH: 11
<212> TYPE: PRT
<213> ORGANISM: Mus musculus

<400> SEQUENCE: 126

Arg Ala Ser Gln Ser Ile Gly Thr Ser Ile His
1               5                   10

<210> SEQ ID NO 127
<211> LENGTH: 7
<212> TYPE: PRT
<213> ORGANISM: Mus musculus

<400> SEQUENCE: 127

Tyr Ala Ser Glu Ser Ile Ser
1               5

<210> SEQ ID NO 128
<211> LENGTH: 9
<212> TYPE: PRT
<213> ORGANISM: Mus musculus

<400> SEQUENCE: 128

Gln Gln Ser Asn Arg Trp Pro Leu Thr
1               5
```

<210> SEQ ID NO 129
<211> LENGTH: 119
<212> TYPE: PRT
<213> ORGANISM: Artificial Sequence
<220> FEATURE:
<223> OTHER INFORMATION: humanized heavy chain variable domain

<400> SEQUENCE: 129

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Pro Glu Tyr
                20                  25                  30

Pro Ile His Trp Val Arg Gln Ala Pro Gly Gln Gly Leu Glu Trp Met
            35                  40                  45

Gly Gly Ile Val Pro Asn Asn Gly Phe Thr Phe Tyr Ala Gln Lys Leu
    50                  55                  60

Gln Gly Arg Val Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Asn Leu Gly Ser Ser Pro Leu Asp Tyr Trp Gly Gln Gly
                100                 105                 110

Thr Thr Val Thr Val Ser Ser
            115
```

<210> SEQ ID NO 130
<211> LENGTH: 107
<212> TYPE: PRT
<213> ORGANISM: Artificial Sequence
<220> FEATURE:
<223> OTHER INFORMATION: humanized light chain variable domain

<400> SEQUENCE: 130

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser
                20                  25                  30

Ile His Trp Tyr Gln Gln Lys Pro Gly Gln Ala Pro Arg Leu Leu Ile
            35                  40                  45

Lys Tyr Ala Ser Glu Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Arg Trp Pro Leu
                85                  90                  95

Thr Leu Gly Gln Gly Thr Lys Leu Glu Ile Lys
            100                 105
```

<210> SEQ ID NO 131
<211> LENGTH: 119
<212> TYPE: PRT
<213> ORGANISM: Mus musculus

<400> SEQUENCE: 131

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Pro Glu Tyr
                20                  25                  30

Pro Ile His Trp Val Lys Gln Ser His Gly Lys Ser Leu Glu Trp Ile
```

```
                35                  40                  45
Gly Gly Ile Val Pro Asn Asn Gly Phe Thr Phe Tyr Asn Gln Lys Phe
        50                  55                  60
Lys Gly Lys Ala Ser Leu Thr Val Asp Lys Ser Ser Thr Ala Tyr
 65                  70                  75                  80
Val Glu Val Arg Ser Leu Thr Ser Asp Asp Ser Ala Val Tyr Tyr Cys
                 85                  90                  95
Ala Arg Lys Asn Leu Gly Ser Ser Pro Leu Asp Tyr Trp Gly Gln Gly
                100                 105                 110
Thr Thr Leu Thr Val Ser Ser
            115

<210> SEQ ID NO 132
<211> LENGTH: 107
<212> TYPE: PRT
<213> ORGANISM: Mus musculus

<400> SEQUENCE: 132

Asp Ile Leu Leu Thr Gln Ser Pro Ala Ile Leu Ser Val Ser Pro Gly
 1               5                   10                  15
Glu Arg Val Ser Phe Ser Cys Arg Ala Ser Gln Ser Ile Gly Thr Ser
                20                  25                  30
Ile His Trp Tyr Gln His Arg Thr Asn Gly Ser Pro Arg Leu Leu Ile
            35                  40                  45
Lys Tyr Ala Ser Glu Ser Ile Ser Gly Ile Pro Ser Arg Phe Ser Gly
        50                  55                  60
Ser Gly Ser Gly Thr Asp Phe Thr Leu Ser Ile Asn Ser Val Glu Ser
 65                 70                  75                  80
Glu Asp Ile Ala Asp Tyr Tyr Cys Gln Gln Ser Asn Arg Trp Pro Leu
                 85                  90                  95
Thr Leu Gly Ala Gly Thr Lys Leu Glu Leu Lys
                100                 105

<210> SEQ ID NO 133
<211> LENGTH: 5
<212> TYPE: PRT
<213> ORGANISM: Mus musculus

<400> SEQUENCE: 133

Asp Tyr Ala Met Ser
 1               5

<210> SEQ ID NO 134
<211> LENGTH: 213
<212> TYPE: PRT
<213> ORGANISM: Artificial Sequence
<220> FEATURE:
<223> OTHER INFORMATION: LC anti-TfR1 antibody

<400> SEQUENCE: 134

Gln Ile Val Leu Thr Gln Ser Pro Ala Ile Met Ser Ala Ser Pro Gly
 1               5                   10                  15
Glu Lys Val Thr Met Thr Cys Ser Ala Ser Ser Ser Ile Arg Tyr Ile
                20                  25                  30
His Trp Tyr Gln Gln Arg Pro Gly Thr Ser Pro Lys Arg Trp Ile Tyr
            35                  40                  45
Asp Thr Ser Asn Leu Ala Ser Gly Val Pro Ala Arg Phe Ser Gly Ser
        50                  55                  60
```

```
Gly Ser Gly Thr Ser Tyr Ser Leu Thr Ile Ser Ser Met Glu Ala Glu
65                  70                  75                  80

Asp Ala Ala Thr Tyr Tyr Cys His Gln Arg Asn Ser Tyr Pro Trp Thr
                85                  90                  95

Phe Gly Gly Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 135
<211> LENGTH: 705
<212> TYPE: PRT
<213> ORGANISM: Artificial Sequence
<220> FEATURE:
<223> OTHER INFORMATION: HC anti-TfR1 antibody conjugated to scFv anti- digoxigenin antibody fragment

<400> SEQUENCE: 135

```
Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Glu Asn Leu Glu Trp Ile
        35                  40                  45

Gly Arg Ile Asn Pro His Asn Gly Gly Thr Asp Tyr Asn Gln Lys Phe
50                  55                  60

Lys Asp Lys Ala Pro Leu Thr Val Asp Lys Ser Ser Asn Thr Ala Tyr
65                  70                  75                  80

Met Glu Leu Leu Ser Leu Thr Ser Glu Asp Ser Ala Val Tyr Tyr Cys
                85                  90                  95

Ala Arg Gly Tyr Tyr Tyr Tyr Ser Leu Asp Tyr Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

-continued

```
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
Gly Gly Gly Gly Ser Gly Gly Gly Ser Gln Val Gln Leu Val Glu
        450                 455                 460
Ser Gly Gly Gly Leu Val Lys Pro Gly Gly Ser Leu Arg Leu Ser Cys
465                 470                 475                 480
Ala Ala Ser Gly Phe Thr Phe Ser Asp Tyr Ala Met Ser Trp Ile Arg
                485                 490                 495
Gln Ala Pro Gly Lys Cys Leu Glu Trp Val Ser Ser Ile Asn Ile Gly
            500                 505                 510
Ala Thr Tyr Ile Tyr Tyr Ala Asp Ser Val Lys Gly Arg Phe Thr Ile
        515                 520                 525
Ser Arg Asp Asn Ala Lys Asn Ser Leu Tyr Leu Gln Met Asn Ser Leu
530                 535                 540
Arg Ala Glu Asp Thr Ala Val Tyr Tyr Cys Ala Arg Pro Gly Ser Pro
545                 550                 555                 560
Tyr Glu Tyr Asp Lys Ala Tyr Tyr Ser Met Ala Tyr Trp Gly Gln Gly
                565                 570                 575
Thr Thr Val Thr Val Ser Ser Gly Gly Gly Ser Gly Gly Gly Gly
            580                 585                 590
Ser Gly Gly Gly Gly Ser Asp Ile Gln Met Thr Gln Ser Pro Ser Ser
        595                 600                 605
Leu Ser Ala Ser Val Gly Asp Arg Val Thr Ile Thr Cys Arg Ala Ser
        610                 615                 620
Gln Asp Ile Lys Asn Tyr Leu Asn Trp Tyr Gln Gln Lys Pro Gly Lys
```

```
                        625                 630                 635                 640
Ala Pro Lys Leu Leu Ile Tyr Tyr Ser Ser Thr Leu Leu Ser Gly Val
                645                 650                 655

Pro Ser Arg Phe Ser Gly Ser Gly Ser Gly Thr Asp Phe Thr Leu Thr
                660                 665                 670

Ile Ser Ser Leu Gln Pro Glu Asp Phe Ala Thr Tyr Tyr Cys Gln Gln
                675                 680                 685

Ser Ile Thr Leu Pro Pro Thr Phe Gly Cys Gly Thr Lys Val Glu Ile
                690                 695                 700

Lys
705

<210> SEQ ID NO 136
<211> LENGTH: 706
<212> TYPE: PRT
<213> ORGANISM: Artificial Sequence
<220> FEATURE:
<223> OTHER INFORMATION: HC anti-TfR1 antibody conjugated to scFv anti-     biotin antibody fragment

<400> SEQUENCE: 136

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met

-continued

```
                275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445
Gly Gly Gly Gly Ser Gly Gly Gly Ser Asp Ile Gln Met Thr Gln
450                 455                 460
Ser Pro Ser Ser Leu Ser Ala Ser Val Gly Asp Arg Val Thr Ile Thr
465                 470                 475                 480
Cys Arg Ala Ser Gly Asn Ile His Asn Tyr Leu Ser Trp Tyr Gln Gln
                485                 490                 495
Lys Pro Gly Lys Val Pro Lys Leu Leu Ile Tyr Ser Ala Lys Thr Leu
                500                 505                 510
Ala Asp Gly Val Pro Ser Arg Phe Ser Gly Ser Gly Ser Gly Thr Asp
                515                 520                 525
Phe Thr Leu Thr Ile Ser Ser Leu Gln Pro Glu Asp Val Ala Thr Tyr
530                 535                 540
Tyr Cys Gln His Phe Trp Ser Ser Ile Tyr Thr Phe Gly Cys Gly Thr
545                 550                 555                 560
Lys Leu Glu Ile Lys Arg Gly Gly Gly Ser Gly Gly Gly Gly Ser
                565                 570                 575
Gly Gly Gly Gly Ser Gly Gly Gly Gly Ser Gln Val Gln Leu Val Gln
                580                 585                 590
Ser Gly Ala Glu Val Lys Lys Pro Gly Ser Ser Val Lys Val Ser Cys
                595                 600                 605
Lys Ser Ser Gly Phe Asn Asn Lys Asp Thr Phe Gln Trp Val Arg
610                 615                 620
Gln Ala Pro Gly Gln Cys Leu Glu Trp Met Gly Arg Ile Asp Pro Ala
625                 630                 635                 640
Asn Gly Phe Thr Lys Tyr Ala Gln Lys Phe Gln Gly Arg Val Thr Ile
                645                 650                 655
Thr Ala Asp Thr Ser Thr Ser Thr Ala Tyr Met Glu Leu Ser Ser Leu
                660                 665                 670
Arg Ser Glu Asp Thr Ala Val Tyr Tyr Cys Ala Arg Trp Asp Thr Tyr
                675                 680                 685
Gly Ala Ala Trp Phe Ala Tyr Trp Gly Gln Gly Thr Leu Val Thr Val
690                 695                 700
```

Ser Ser
705

<210> SEQ ID NO 137
<211> LENGTH: 213
<212> TYPE: PRT
<213> ORGANISM: Artificial Sequence
<220> FEATURE:
<223> OTHER INFORMATION: LC anti-TfR2 antibody

<400> SEQUENCE: 137

Gln Ile Val Leu Thr Gln Ser Pro Ala Ile Met Ser Ala Ser Pro Gly
1               5                   10                  15

Glu Lys Val Thr Val Thr Cys Ser Ala Ser Ser Ser Ile Arg Tyr Met
            20                  25                  30

His Trp Tyr Gln Gln Lys Pro Gly Thr Ser Pro Lys Arg Trp Ile Tyr
        35                  40                  45

Asp Thr Ser Glu Leu Ala Ser Gly Val Pro Ala Arg Phe Ser Gly Ser
    50                  55                  60

Gly Ser Gly Thr Ser Tyr Ser Leu Thr Ile Asn Ser Met Glu Ala Glu
65                  70                  75                  80

Asp Ala Ala Thr Tyr Tyr Cys His Gln Arg Ser Ser Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 138
<211> LENGTH: 705
<212> TYPE: PRT
<213> ORGANISM: Artificial Sequence
<220> FEATURE:
<223> OTHER INFORMATION: HC anti-TfR2 antibody conjugated to scFv anti-digoxigenin antibody fragment

<400> SEQUENCE: 138

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Val Asn Pro Tyr Asn Asp Asp Thr Lys Tyr Asn Glu Lys Phe
    50                  55                  60

Arg Gly Lys Ala Thr Leu Thr Ser Asp Lys Ser Ser Ser Thr Ala Tyr

-continued

```
            65                  70                  75                  80
Met Glu Leu Ser Ser Leu Thr Ser Glu Asp Ser Ala Val Tyr Tyr Cys
                    85                  90                  95

Ala Arg Ser Tyr Tyr Tyr Ser Met Asp Asn Trp Gly Gln Gly Thr
                100                 105                 110

Ser Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

Gly Gly Gly Gly Ser Gly Gly Gly Ser Gln Val Gln Leu Val Glu
            450                 455                 460

Ser Gly Gly Gly Leu Val Lys Pro Gly Gly Ser Leu Arg Leu Ser Cys
465                 470                 475                 480

Ala Ala Ser Gly Phe Thr Phe Ser Asp Tyr Ala Met Ser Trp Ile Arg
                485                 490                 495
```

Gln Ala Pro Gly Lys Cys Leu Glu Trp Val Ser Ser Ile Asn Ile Gly
            500                 505                 510

Ala Thr Tyr Ile Tyr Tyr Ala Asp Ser Val Lys Gly Arg Phe Thr Ile
            515                 520                 525

Ser Arg Asp Asn Ala Lys Asn Ser Leu Tyr Leu Gln Met Asn Ser Leu
    530                 535                 540

Arg Ala Glu Asp Thr Ala Val Tyr Tyr Cys Ala Arg Pro Gly Ser Pro
545                 550                 555                 560

Tyr Glu Tyr Asp Lys Ala Tyr Tyr Ser Met Ala Tyr Trp Gly Gln Gly
                565                 570                 575

Thr Thr Val Thr Val Ser Ser Gly Gly Gly Ser Gly Gly Gly
            580                 585                 590

Ser Gly Gly Gly Ser Asp Ile Gln Met Thr Gln Ser Pro Ser Ser
        595                 600                 605

Leu Ser Ala Ser Val Gly Asp Arg Val Thr Ile Thr Cys Arg Ala Ser
    610                 615                 620

Gln Asp Ile Lys Asn Tyr Leu Asn Trp Tyr Gln Gln Lys Pro Gly Lys
625                 630                 635                 640

Ala Pro Lys Leu Leu Ile Tyr Tyr Ser Ser Thr Leu Leu Ser Gly Val
                645                 650                 655

Pro Ser Arg Phe Ser Gly Ser Gly Ser Gly Thr Asp Phe Thr Leu Thr
            660                 665                 670

Ile Ser Ser Leu Gln Pro Glu Asp Phe Ala Thr Tyr Tyr Cys Gln Gln
        675                 680                 685

Ser Ile Thr Leu Pro Pro Thr Phe Gly Cys Gly Thr Lys Val Glu Ile
    690                 695                 700

Lys
705

<210> SEQ ID NO 139
<211> LENGTH: 725
<212> TYPE: PRT
<213> ORGANISM: Artificial Sequence
<220> FEATURE:
<223> OTHER INFORMATION: HC anti-TfR2 antibody conjugated to scFv anti-     biotin antibody fragment

<400> SEQUENCE: 139

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Glu Leu Val Lys
            20                  25                  30

Pro Gly Ala

```
Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
            450                 455                 460

Pro Gly Lys Gly Gly Gly Gly Ser Gly Gly Gly Gly Ser Asp Ile Gln
465                 470                 475                 480

Met Thr Gln Ser Pro Ser Ser Leu Ser Ala Ser Val Gly Asp Arg Val
            485                 490                 495

Thr Ile Thr Cys Arg Ala Ser Gly Asn Ile His Asn Tyr Leu Ser Trp
            500                 505                 510

Tyr Gln Gln Lys Pro Gly Lys Val Pro Lys Leu Leu Ile Tyr Ser Ala
            515                 520                 525

Lys Thr Leu Ala Asp Gly Val Pro Ser Arg Phe Ser Gly Ser Gly Ser
            530                 535                 540

Gly Thr Asp Phe Thr Leu Thr Ile Ser Ser Leu Gln Pro Glu Asp Val
545                 550                 555                 560
```

Ala Thr Tyr Tyr Cys Gln His Phe Trp Ser Ser Ile Tyr Thr Phe Gly
                565                 570                 575

Cys Gly Thr Lys Leu Glu Ile Lys Arg Gly Gly Gly Ser Gly Gly
            580                 585                 590

Gly Gly Ser Gly Gly Gly Gly Ser Gly Gly Gly Ser Gln Val Gln
        595                 600                 605

Leu Val Gln Ser Gly Ala Glu Val Lys Lys Pro Gly Ser Val Lys
    610                 615                 620

Val Ser Cys Lys Ser Ser Gly Phe Asn Asn Lys Asp Thr Phe Gln
625                 630                 635                 640

Trp Val Arg Gln Ala Pro Gly Gln Cys Leu Glu Trp Met Gly Arg Ile
                645                 650                 655

Asp Pro Ala Asn Gly Phe Thr Lys Tyr Ala Gln Lys Phe Gln Gly Arg
                660                 665                 670

Val Thr Ile Thr Ala Asp Thr Ser Thr Ser Thr Ala Tyr Met Glu Leu
            675                 680                 685

Ser Ser Leu Arg Ser Glu Asp Thr Ala Val Tyr Tyr Cys Ala Arg Trp
            690                 695                 700

Asp Thr Tyr Gly Ala Ala Trp Phe Ala Tyr Trp Gly Gln Gly Thr Leu
705                 710                 715                 720

Val Thr Val Ser Ser
                725

<210> SEQ ID NO 140
<211> LENGTH: 51
<212> TYPE: DNA
<213> ORGANISM: Artificial Sequence
<220> FEATURE:
<223> OTHER INFORMATION: terminally mono-biotinylated or mono-     digoxigeninylated double-
stranded DNA 50 mer payload
<220> FEATURE:
<221> NAME/KEY: misc_structure
<222> LOCATION: (1)..(1)
<223> OTHER INFORMATION: n=biotin or digoxigenin
<220> FEATURE:
<221> NAME/KEY: misc_feature
<222> LOCATION: (1)..(1)
<223> OTHER INFORMATION: n is a, c, g, or t

<400> SEQUENCE: 140
naccaagcct agagaggagc aatacaacag tacatatcgc gtggtaagcg t         51

<210> SEQ ID NO 141
<211> LENGTH: 20
<212> TYPE: DNA
<213> ORGANISM: Artificial Sequence
<220> FEATURE:
<223> OTHER INFORMATION: PrFor

<400> SEQUENCE: 141
accaagccta gagaggagca                                            20

<210> SEQ ID NO 142
<211> LENGTH: 20
<212> TYPE: DNA
<213> ORGANISM: Artificial Sequence
<220> FEATURE:
<223> OTHER INFORMATION: PrRev

<400> SEQUENCE: 142
acgcttacca cgcgatatgt                                            20

<210> SEQ ID NO 143

```
<211> LENGTH: 34
<212> TYPE: PRT
<213> ORGANISM: Homo sapiens
<220> FEATURE:
<221> NAME/KEY: MISC_FEATURE
<222> LOCATION: (34)..(34)
<223> OTHER INFORMATION: X=tyrosine amide

<400> SEQUENCE: 143

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Xaa

<210> SEQ ID NO 144
<211> LENGTH: 34
<212> TYPE: PRT
<213> ORGANISM: Artificial Sequence
<220> FEATURE:
<223> OTHER INFORMATION: PYY3-36 helicar
<220> FEATURE:
<221> NAME/KEY: MISC_FEATURE
<222> LOCATION: (34)..(34)
<223> OTHER INFORMATION: X=thyrosine amide

<400> SEQUENCE: 144

Ile Lys Pro Glu Ala Pro Gly Glu Asp Ala Ser Pro Glu Ala His Leu
1               5                   10                  15

Ala Asn Glu Val Ala Arg Leu His Tyr Leu Asn Leu Val Thr Arg Gln
            20                  25                  30

Arg Xaa

<210> SEQ ID NO 145
<211> LENGTH: 12
<212> TYPE: PRT
<213> ORGANISM: Saccharomyces cerevisiae

<400> SEQUENCE: 145

Ala His Leu Glu Asn Glu Val Ala Arg Leu Lys Lys
1               5                   10

<210> SEQ ID NO 146
<211> LENGTH: 12
<212> TYPE: PRT
<213> ORGANISM: Artificial Sequence
<220> FEATURE:
<223> OTHER INFORMATION: helicar motif variant 1

<400> SEQUENCE: 146

Ala His Leu Glu Asn Glu Val Ala Arg Cys Lys Lys
1               5                   10

<210> SEQ ID NO 147
<211> LENGTH: 12
<212> TYPE: PRT
<213> ORGANISM: Artificial Sequence
<220> FEATURE:
<223> OTHER INFORMATION: helicar motif variant 2

<400> SEQUENCE: 147

Ala His Leu Glu Asn Glu Val Ala Arg Leu Cys Lys
1               5                   10

<210> SEQ ID NO 148
```

<211> LENGTH: 109
<212> TYPE: PRT
<213> ORGANISM: Artificial Sequence
<220> FEATURE:
<223> OTHER INFORMATION: anti-helicar antibody VH

<400> SEQUENCE: 148

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Ser Trp Val Gln Gln Lys Pro Gly Gln Ala Phe Thr Gly
        35                  40                  45

Leu Ile Gly Gly Thr Asn Asn Arg Ala Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 149
<211> LENGTH: 109
<212> TYPE: PRT
<213> ORGANISM: Artificial Sequence
<220> FEATURE:
<223> OTHER INFORMATION: anti-helicar antibody VL

<400> SEQUENCE: 149

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
            100                 105

<210> SEQ ID NO 150
<211> LENGTH: 109
<212> TYPE: PRT
<213> ORGANISM: Artificial Sequence
<220> FEATURE:
<223> OTHER INFORMATION: anti-helicar antibody VL55C

<400> SEQUENCE: 150

Asp Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Ser Trp Val Gln Glu Lys Pro Asp His Leu Phe Thr Gly
        35                  40                  45

```
Leu Ile Gly Gly Thr Asn Cys Arg Ala Pro Gly Val Pro Ala Arg Phe
50 55 60
```
```
Ser Gly Ser Leu Ile Gly Asp Lys Ala Ala Leu Thr Ile Thr Gly Ala
65 70 75 80
```
```
Gln Thr Glu Asp Glu Ala Ile Tyr Phe Cys Ala Leu Trp Tyr Ser Asn
85 90 95
```
```
His Trp Val Phe Gly Gly Gly Thr Lys Leu Thr Val Leu
100 105
```

<210> SEQ ID NO 151
<211> LENGTH: 109
<212> TYPE: PRT
<213> ORGANISM: Artificial Sequence
<220> FEATURE:
<223> OTHER INFORMATION: anti-helicar antibody VL51C

<400> SEQUENCE: 151

```
Asp Ala Val Val Thr Gln Glu Ser Ala Leu Thr Thr Ser Pro Gly Glu
1 5 10 15
```
```
Thr Val Thr Leu Thr Cys Arg Ser Ser Thr Gly Ala Val Thr Thr Ser
20 25 30
```
```
Asn Tyr Ala Ser Trp Val Gln Glu Lys Pro Asp His Leu Phe Thr Gly
35 40 45
```
```
Leu Ile Cys Gly Thr Asn Asn Arg Ala Pro Gly Val Pro Ala Arg Phe
50 55 60
```
```
Ser Gly Ser Leu Ile Gly Asp Lys Ala Ala Leu Thr Ile Thr Gly Ala
65 70 75 80
```
```
Gln Thr Glu Asp Glu Ala Ile Tyr Phe Cys Ala Leu Trp Tyr Ser Asn
85 90 95
```
```
His Trp Val Phe Gly Gly Gly Thr Lys Leu Thr Val Leu
100 105
```

<210> SEQ ID NO 152
<211> LENGTH: 244
<212> TYPE: PRT
<213> ORGANISM: Artificial Sequence
<220> FEATURE:
<223> OTHER INFORMATION: helicar motif amino acid sequence cystein vari-
ant 1 fused to pseudomonas exotoxin LR8M with a GGG-peptidic linker and the C-terminal K deleted

<400> SEQUENCE: 152

```
Ala His Leu Glu Asn Glu Val Ala Arg Leu Cys Lys Gly Gly Gly Arg
1 5 10 15

His Arg Gln Pro Arg Gly Trp Glu Gln Leu Pro Thr Gly Ala Glu Phe
20 25 30

Leu Gly Asp Gly Gly Ala Val Ser Phe Ser Thr Arg Gly Thr Gln Asn
35 40 45

Trp Thr Val Glu Arg Leu Leu Gln Ala His Arg Gln Leu Glu Glu Gly
50 55 60

Gly Tyr Val Phe Val Gly Tyr His Gly Thr Phe Leu Glu Ala Ala Gln
65 70 75 80

Ser Ile Val Phe Gly Gly Val Arg Ala Arg Ser Gln Asp Leu Asp Ala
85 90 95

Ile Trp Ala Gly Phe Tyr Ile Ala Gly Asp Pro Ala Leu Ala Tyr Gly
100 105 110

Tyr Ala Gln Asp Gln Glu Pro Asp Ala Ala Gly Arg Ile Arg Asn Gly
115 120 125

Ala Leu Leu Arg Val Tyr Val Pro Arg Ser Ser Leu Pro Gly Phe Tyr
130 135 140

```
Ala Thr Ser Leu Thr Leu Ala Ala Pro Glu Ala Ala Gly Glu Val Glu
145                 150                 155                 160

Arg Leu Ile Gly His Pro Leu Pro Leu Arg Leu Asp Ala Ile Thr Gly
                165                 170                 175

Pro Glu Glu Ser Gly Gly Arg Leu Glu Thr Ile Leu Gly Trp Pro Leu
            180                 185                 190

Ala Glu Arg Thr Val Val Ile Pro Ser Ala Ile Pro Thr Asp Pro Arg
        195                 200                 205

Asn Val Gly Gly Asp Leu Asp Pro Ser Ser Ile Pro Asp Ser Glu Ala
    210                 215                 220

Ala Ile Ser Ala Leu Pro Asp Tyr Ala Ser Gln Pro Gly Lys Pro Pro
225                 230                 235                 240

Arg Glu Asp Leu

<210> SEQ ID NO 153
<211> LENGTH: 51
<212> TYPE: DNA
<213> ORGANISM: Artificial Sequence
<220> FEATURE:
<223> OTHER INFORMATION: BRDU-DNA conjugate
<220> FEATURE:
<221> NAME/KEY: misc_RNA
<222> LOCATION: (1)..(1)
<223> OTHER INFORMATION: BRDU
<220> FEATURE:
<221> NAME/KEY: misc_feature
<222> LOCATION: (1)..(1)
<223> OTHER INFORMATION: n is a, c, g, or t

<400> SEQUENCE: 153
naccaagcct agagaggagc aatacaacag tacatatcgc gtggtaagcg t          51
```